US011136567B2

(12) United States Patent
Behlke et al.

(10) Patent No.: US 11,136,567 B2
(45) Date of Patent: Oct. 5, 2021

(54) CRISPR/CPF1 SYSTEMS AND METHODS

(71) Applicant: Integrated DNA Technologies, Inc., Coralville, IA (US)

(72) Inventors: Mark Aaron Behlke, Coralville, IA (US); Michael Allen Collingwood, North Liberty, IA (US); Rolf Turk, Iowa City, IA (US); Christopher Anthony Vakulskas, North Liberty, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 340 days.

(21) Appl. No.: 15/821,736

(22) Filed: Nov. 22, 2017

(65) Prior Publication Data
US 2018/0187176 A1 Jul. 5, 2018

Related U.S. Application Data

(60) Provisional application No. 62/482,896, filed on Apr. 7, 2017, provisional application No. 62/425,307, filed on Nov. 22, 2016.

(51) Int. Cl.
*C12N 9/22* (2006.01)
*C12N 15/63* (2006.01)
*C12N 15/90* (2006.01)
*C12N 15/11* (2006.01)
*C12N 15/113* (2010.01)
*C12N 15/10* (2006.01)
*C12N 15/85* (2006.01)

(52) U.S. Cl.
CPC ............. *C12N 9/22* (2013.01); *C12N 15/102* (2013.01); *C12N 15/111* (2013.01); *C12N 15/113* (2013.01); *C12N 15/63* (2013.01); *C12N 15/8509* (2013.01); *C12N 15/90* (2013.01); *C12N 2310/20* (2017.05); *C12Y 301/30* (2013.01)

(58) Field of Classification Search
CPC .......... C12N 9/22; C12N 15/63; C12N 15/90; C12N 15/111; C12N 15/113; C12N 15/102; C12N 15/8509; C12N 2310/20; C12Y 301/30
See application file for complete search history.

(56) References Cited

U.S. PATENT DOCUMENTS

| | | | |
|---|---|---|---|
| 5,672,695 | A | 9/1997 | Eckstein et al. |
| 6,248,878 | B1 | 6/2001 | Matulic-Adamic et al. |
| 8,697,359 | B1 | 4/2014 | Zhang |
| 9,840,702 | B2 | 12/2017 | Collingwood et al. |
| 10,369,232 | B2 | 8/2019 | Chivukula et al. |
| 2014/0273226 | A1 | 9/2014 | Wu |
| 2014/0273232 | A1 | 9/2014 | Zhang et al. |
| 2014/0295557 | A1 | 10/2014 | Joung et al. |
| 2015/0059010 | A1 | 2/2015 | Cigan et al. |
| 2015/0067922 | A1 | 3/2015 | Yang et al. |
| 2015/0073041 | A1 | 3/2015 | Saltzman |
| 2016/0024524 | A1 | 1/2016 | Joung et al. |
| 2016/0208241 | A1 | 7/2016 | Tsai et al. |
| 2016/0208243 | A1 | 7/2016 | Zhang et al. |
| 2016/0215300 | A1 | 7/2016 | May et al. |
| 2016/0289675 | A1 | 10/2016 | Ryan et al. |
| 2016/0362667 | A1 | 12/2016 | Donohoue et al. |

FOREIGN PATENT DOCUMENTS

| | | |
|---|---|---|
| CN | 106244591 | 8/2016 |
| WO | 2014065596 A1 | 5/2014 |
| WO | 2014124226 A1 | 8/2014 |
| WO | 2014144592 A2 | 9/2014 |
| WO | 2016080097 A1 | 5/2016 |
| WO | 2016089433 A1 | 6/2016 |
| WO | 2016115179 A1 | 7/2016 |
| WO | 2016161207 A1 | 10/2016 |
| WO | 2016164356 | 10/2016 |
| WO | 2017147432 A1 | 8/2017 |
| WO | 2017/184768 A1 | 10/2017 |
| WO | 2017/184786 A1 | 10/2017 |
| WO | 2017184799 A1 | 10/2017 |
| WO | 2017/189308 A1 | 11/2017 |

OTHER PUBLICATIONS

Kim et al. "Genome-wide analysis reveals specificities of Cpf1 endonucleases in human cells." Nature Biotechnology vol. 34, pp. 863-868 (Jun. 2016 (Year: 2016).*
Behlke, M.A., "Chemical Modification of siRNAs for In Vivo Use" Oligonucleotides (2008) 18:305-320.
Briner, A.E. et al., "Guide RNA Functional Modules Direct Cas9 Activity and Orthogonality." Molecular Cell (2014) 56:333-339.
Eder, P.S. et al., "Substrate Specificity and Kinetics of Degradation of Antisense Oligonucleotides by a 3' Exonuclease in Plasma." Antisense Research and Development (1991) 1:141-151.

(Continued)

*Primary Examiner* — Titilayo Moloye
(74) *Attorney, Agent, or Firm* — Klintworth & Rozenblat IP LLP

(57) ABSTRACT

This invention pertains to recombinant AsCpf1 and LbCpf1 nucleic acids and polypeptides for use in CRISPR/Cpf1 endonuclease systems and mammalian cell lines encoding recombinant AsCpf1 or LbCpf1 polypeptides. The invention includes recombinant ribonucleoprotein complexes and CRSPR/Cpf1 endonuclease systems having a suitable AsCpf1 crRNA is selected from a length-truncated AsCpf1 crRNA, a chemically-modified AsCpf1 crRNA, or an AsCpf1 crRNA comprising both length truncations and chemical modifications. Methods of performing gene editing using these systems and reagents are also provided.

11 Claims, 9 Drawing Sheets

Specification includes a Sequence Listing.

(56) References Cited

OTHER PUBLICATIONS

Gasiunas, G. et al., "Cas9-crRNA ribonucleoprotein complex mediates specific DNA cleavage for adaptive immunity in bacteria." Proc Natl Acad Sci USA (2012) 109(39):E2579-86.
Jinek, M. et al., "A Programmable Dual-RNA-Guided DNA Endonuclease in Adaptive Bacterial Immunity." Science (2012) 337(6096):816-21.
Jinek, M. et al., "Structures of Cas9 Endonucleases Reveal RNA-Mediated Conformational Activation." Science (2014) 343:1215-26.
Kurreck, J., "Antisense technologies Improvement through novel chemical modifications." Eur. J. Biochem. (2003) 270:1628-1644.
Lennox, K.A. et al., "Chemical modification and design of anti-miRNA oligonucleotides." Gene Therapy (2011) 18:1111-1120.
Nishimasu, H. et al., "Crystal Structure of Cas9 in Complex with Guide RNA and Target DNA" Cell (2014) 156 (5):935-949.
O'Connell, M.R. et al., "Programmable RNA recognition and cleavage by CRISPR/Cas9." Nature (2014) 516:263-278.
Sahin, U. et al., "mRNA-based therapeutics—developing a new class of drugs." Nat Rev Drug Discov (2014) 13:759-780.
Xu, T. et al., "Cas9-Based Tools for Targeted Genome Editing and Transcriptional Control." Applied Environmental Microbiology (2014) 80(6):1544-1552.
Fu et al., "IMproving CRISPR-Cas nuclease specificity using truncated guide RNAs," Nature Biotechnol. 32(3):279-284 (2014).
Cencic et al., "Protospacer Adjacent Motif (PAM)-Distal Sequences Engage CRISPR Cas9 DNA Target Cleavage", PLOS One 9(10):e109213 (2014).
Hendel et al., "Chemically modified guide RNAs enhance CRISPR-Cas genome editing in human primary cells", Nat. Biotech. 33(9):985 (2015).
Jinek et al., Supplementary Materials for "A Programmable Dual-RNA-Guided DNA Endonuclease in Adaptive Bacterial Immunity", Science 337 (2012).
Rahdar et al., "Synthetic CRISPR RNA-Cas9-guided genome editing in human cells," Proc. Natl. Acad. Sci. (pub. Nov. 16, 2015).
International Search Report and Written Opinion for PCT/US2015/066942 dated Aug. 25, 2016, 25 pages.
Notification of Transmittal of the International Search Report and the Written Opinion of the International Searching Authority, or the Declaration, for PCT/US2017/065923, dated Apr. 12, 2018, 15 pages.
Nelles, David A., et al., "Programmable RNA Tracking in Live Cells with CRISPR/Cas9" Cell, Cell Press, vol. 165, No. 2, Mar. 17, 2016 (Mar. 17, 2016), pp. 488-496, XP029496630, ISSN: 0092-8674, DOI: 10.1016/J.CELL.2016.02.054 figure 1.
Xiaoxiao, Zhu et al., "An Efficient Genotyping Method for Genome-modified Animals and Human Cells Generated with CRISPR/Cas9 System", Scientific Reports, vol. 4, No. 1, Sep. 19, 2014 (Sep. 19, 2014), XP055461892, doi: 10.1038/SREP06420 (p. 2, col. 1, Last Para); Figure 1.
Notification of Transmittal of the International Search Report and the Written Opinion of the International Searching Authority, or the Declaration, for PCT/US2017/63161, dated Apr. 24, 2018, 16 pages.
Zutsche, B., et al., Cpf1 is a Single RNA-Guided Endonuclease of a Class 2 CRISPR-Cas System, Cell. Oct. 22, 2015, Epub Sep. 25, 2015, vol. 163, No. 3; pp. 789-771; p. 760, 2nd column, 1st paragraph; p. 765, 2nd column, 1st paragraph; p. 769, 1st column, 6th paragraph—2nd Column, 1st paragraph; Figure 7, pp. S2-S8; Table S1; DOI 10.1016/j.cell.2015.09.038.
Kleinstiver, B., et al., Genome-wide specificities of CRISPR-Cas Cpf1 nucleases in human cells. Nature Biotechnology. Aug. 2015, Epub Jun. 27, 2016, vol. 34, No. 8; pp. 869-874; abstract; p. 870, 1st column, 1st-2nd paragraphs; Figure 2; DOI: 10.1038/nbt.3620.
Notification of Transmittal of the International Search Report and the Written Opinion of the International Searching Authority, or the Declaration, for PCT/US17/55952, dated Apr. 6, 2018, 17 pages.
Makarova, K.S., et al., A putative RNA-interference-based immune system in prokaryotes: computational analysis of the predicted enzymatic machinery, functional analogies with eukaryotic RNAi, and hypothetical mechanisms of action. Biol Direct, 2006. 1: p. 7.
Tsai, S.Q., et al., GUIDE-seq enables genome-wide profiling of off-target cleavage by CRISPR-Cas nucleases. Nat Biotechnol, 2015. 33(2): p. 187-97.
Slaymaker, I.M., et al., Rationally engineered Cas9 nucleases with improved specificity. Science, 2016.351(6268): p. 84-8.
Kleinstiver, B.P., et al., High-fidelity CRISPR-Cas9 nucleases with no detectable genome-wide off-target effects. Nature, 2016. 529(7587): p. 490-495.
Anders et al., Nature 2014, 513(7519) p. 569-73, "Structural basis of PAM-dependent target DNA recognition by the Cas9 endonuclease."
Chen, et al., Nature 2017, http://dx.doi.org/10.1038/nature24268 (2017), "The chemistry of Cas9 and its CRIPSR colleagues."
Cong, et al., Science 2013, 339 p. 819-823, "Multiplex Genome Engineereing Using CRISPR/Cas Systems."
Mali et al, Science, 2013, 339 p. 823-826, "CAS9 transcriptional activators for target specificity screening and paired nickases for cooperative genome engineereing."
Cho et al., Genome Research, 2014, 24 p. 132-141, "Analysis off=target effects of CRIPSR/CAs-derived RNA-guided endonucleases and nickases."
Aida et al., Genome Biology, 2015, 16 p. 87-98, "Cloning-free CRISPR/Cas system faciliates functional cassette knock-in mice."
Non-Final Office Action for U.S. Appl. No. 14/975,709, dated Feb. 21, 2017, 13 pages.
Final Office Action for U.S. Appl. No. 14/975,709, dated Jul. 25, 2016, 9 pages.
Non-Final Office Action for U.S. Appl. No. 14/975,709 dated Mar. 25, 2016, 14 pages.
Kleinstiver et al. "Engineered CRISPR-Cas9 nucleases with altered PAM specificities," Nature, vol. 523, No. 7561, 2015, pp. 481-485, 17 pages.
European Communication and Supplementary European Search Report for EP 17859322 dated Apr. 21, 2020, 11 pages.
Official Communication dated Jun. 20, 2020 with Supplemental Partial European Search Report dated Jun. 16, 2020 for corresponding European Patent Application No. 17873549.4, 24 pages.
Moreno-Mateosi, et al. "CRISPR-Cpfl mediates efficient homology-directed repair and temperature controlled genome editing," Nature Communications, vol. 8, No. 2024, 2017, 9 pages.
Yamano et al. "Crystal Structure of Cpfl in Complex with Guide RNA and Target DNA," Cell, Elsevier, Amsterdam, NL, vol. 165, No. 4, 2016, 24 pages.
Kim A. Lennox et al. "Improved Performance of Anti-miRNA Oligonucleotides Using a Novel Non-Nucleotide Modifier" Molecular Therapy—Nucleic Acids (2013) 2, e117; doi:10.1038/mtna.2013.46; published online Aug. 27, 2013.
Kurreck et al. "Design of antisense oligonucleotides stabilized by locked nucleic acids," Nucleic Acids Research, 30, 2002, pp. 1911-1918.
Final Office Action for U.S. Appl. No. 15/299,593 dated Jun. 24, 2020.

* cited by examiner

Universal Loop Domain    Target-specific Protospacer Domain

X-uaauuucuacucuuguaguunnnnnnnnnnnnnnnnnnnn-X

U*a*auuucuacucuuguaguunnnnnnnnnnnnnnnnnnnnN*N*N

U*a*a*uUUCUACuCUUgUAGAunnnnnnnnnnnnnnnnnnn*n*n*n

U*a*auUUCUACuCUUgUAGAunnnnnnnnnnnnnnnnnnnn*n*n

X-UaauUUCUACuCUUgUAGAunnnnnnnnnnnnnnnnnnnnn-X

FIG. 8

SEQUENCE LISTING

<160> NUMBER OF SEQ ID NOS: 395

<210> SEQ ID NO 1
<211> LENGTH: 3924
<212> TYPE: DNA
<213> ORGANISM: Acidaminococcus sp. BV3L6

<400> SEQUENCE: 1

```
atgacccaat ttgaaggttt taccaattta taccaagttt cgaagaccct tcgttttgaa      60
ctgattcccc aaggaaaaac actcaaacat atccaggagc aagggttcat tgaggaggat     120
aaagctcgca atgaccatta caaagagtta aaaccaatca ttgaccgcat ctataagact     180
tatgctgatc aatgtctcca actggtacag cttgactggg agaatctatc tgcagccata     240
gactcctatc gtaaggaaaa aaccgaagaa acacgaaatg cgctgattga ggagcaagca     300
acatatagaa atgcgattca tgactacttt ataggtcgga cggataatct gacagatgcc     360
ataaataagc gccatgctga aatctataaa ggactttta aagctgaact tttcaatgga     420
aaagttttaa agcaattagg gaccgtaacc acgacagaac atgaaaatgc tctactccgt     480
tcgtttgaca aatttacgac ctatttttcc ggctttatg aaaaccgaaa aaatgtcttt     540
```

```
agcgctgaag atatcagcac ggcaattccc catcgaatcg tccaggacaa tttccctaaa    600
tttaaggaaa actgccatat ttttacaaga ttgataaccg cagttccttc tttgcgggag    660
cattttgaaa atgtcaaaaa ggccattgga atctttgtta gtacgtctat tgaagaagtc    720
ttttcctttc cctttttataa tcaacttcta acccaaacgc aaattgatct ttataatcaa    780
cttctcggcg gcatatctag ggaagcaggc acagaaaaaa tcaagggact taatgaagtt    840
ctcaatctgg ctatccaaaa aaatgatgaa acagcccata taatcgcgtc cctgccgcat    900
cgttttattc ctcttttaa acaaattctt tccgatcgaa atacgttatc ctttattttg     960
gaagaattca aaagcgatga ggaagtcatc caatccttct gcaaatataa aaccctcttg   1020
agaaacgaaa atgtactgga gactgcagaa gcccttttca atgaattaaa ttccattgat   1080
ttgactcata tctttatttc ccataaaaag ttagaaacca tctcttcagc gctttgtgac   1140
cattgggata ccttgcgcaa tgcactttac gaaagacgga tttctgaact cactggcaaa   1200
ataacaaaaa gtgccaaaga aaagttcaa aggtcattaa acatgagga tataaatctc     1260 caagaaatta tttctgctgc aggaaaagaa ctatcagaag cattcaaaca aaaaacaagt   1320
gaaattcttt cccatgccca tgctgcactt gaccagcctc ttcccacaac attaaaaaaa   1380
caggaagaaa aagaaatcct caaatcacag ctcgattcgc ttttaggcct ttatcatctt   1440
cttgattggt ttgctgtcga tgaaagcaat gaagtcgacc cagaattctc agcacggctg   1500
acaggcatta aactagaaat ggaaccaagc ctttcgtttt ataataaagc aagaaattat   1560
gcgacaaaaa agcccctattc ggtggaaaaa tttaaattga atttcaaat gccaaccctt    1620 gcctctggtt gggatgtcaa taagaaaaa ataatggag ctattttatt cgtaaaaaat      1680
ggtctctatt accttggtat catgcctaaa cagaagggc gctataaagc cctgtctttt     1740
gagccgacag aaaaaacatc agaaggattc gataagatgt actatgacta cttcccagat   1800
gccgcaaaaa tgattcctaa gtgttccact cagctaaagg ctgtaaccgc tcattttcaa   1860
actcatacca cccccattct tctctcaaat aatttcattg aacctcttga atcacaaaa    1920 gaaatttatg acctgaacaa tcctgaaaag gagcctaaaa agtttcaaac ggcttatgca   1980
aagaagacag gcgatcaaaa aggctataga gaagcgcttt gcaaatggat tgactttacg   2040
cgggattttc tctctaaata tacgaaaaca acttcaatcg atttatcttc actccgccct   2100
tcttcgcaat ataaagattt aggggaatat acgccgaac tgaatccgct tctctatcat    2160
atctccttcc aacgaattgc tgaaaaggaa atcatggatg ctgtagaaac gggaaaattg   2220
tatctgttcc aaatctacaa taaggatttt gcgaagggcc atcacgggaa accaaatctc   2280
cacaccctgt attggacagg tctcttcagt cctgaaaacc ttgcgaaaac cagcatcaaa   2340
cttaatggtc aagcagaatt gttctatcga cctaaaagcc gcatgaagcg gatggcccat   2400
cgtcttgggg aaaaaatgct gaacaaaaaa ctaaggacc agaagacacc gattccagat    2460
accctctacc aagaactgta cgattatgtc aaccaccggc taagccatga tctttccgat   2520
gaagcaaggg ccctgcttcc aaatgttatc accaaagaag tctcccatga aattataaag   2580
gatcggcggt ttacttccga taaatttttc ttccatgttc ccattacact gaattatcaa   2640
gcagccaata gtcccagtaa attcaaccag cgtgtcaatg cctaccttaa ggagcatccg   2700
gaaacgccca tcattggtat cgatcgtgga gaacgcaatc taatctatat taccgtcatt   2760
gacagtactg ggaaaatttt ggagcagcgt tccctgaata ccatccagca atttgactac   2820
caaaaaaaat tggacaacag ggaaaagag cgtgttgccg cccgtcaagc ctggtccgtc     2880
gtcggaacga tcaaagacct taaacaaggc tacttgtcac aggtcatcca tgaaattgta   2940
```

```
gacctgatga ttcattacca agctgttgtc gtccttgaaa acctcaactt cggatttaaa   3000
tcaaaacgga caggcattgc cgaaaaagca gtctaccaac aatttgaaaa gatgctaata   3060
gataaactca actgtttggt tctcaaagat tatcctgctg agaaagtggg aggcgtctta   3120
aacccgtatc aacttacaga tcagttcacg agctttgcaa aaatgggcac gcaaagcggc   3180
ttccttttct atgtaccggc cccttatacc tcaaagattg atcccctgac tggttttgtc   3240 gatcccttg tatggaagac cattaaaaat catgaaagtc ggaagcattt cctagaagga    3300
tttgatttcc tgcattatga tgtcaaaaca ggtgatttta tcctccattt taaaatgaat   3360
cggaatctct ctttccagag agggcttcct ggcttcatgc agcttggga tattgttttc    3420 gaaaagaatg aaacccaatt tgatgcaaaa gggacgccct tcattgcagg aaaacgaatt   3480
gttcctgtaa tcgaaaatca tcgttttacg ggtcgttaca gagacctcta tcccgctaat   3540
gaactcattg cccttctgga agaaaaggc attgtcttta gagacggaag taatatatta    3600
cccaaacttt tagaaaatga tgattctcat gcaattgata cgatggtcgc cttgattcgc   3660
agtgtactcc aaatgagaaa cagcaatgcc gcaacggggg aagactacat caactctccc   3720
gttagggatc tgaacggggt gtgtttcgac agtcgattcc aaaatccaga atggccaatg   3780
gatgcggatg ccaacggagc ttatcatatt gccttaaaag ggcagcttct tctgaaccac   3840
ctcaaagaaa gcaaagatct gaaattacaa aacggcatca gcaaccaaga ttggctggcc   3900
tacattcagg aactgagaaa ctga                                          3924

<210> SEQ ID NO 2
<211> LENGTH: 1307
<212> TYPE: PRT
<213> ORGANISM: Acidaminococcus sp. BV3L6

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190
```

```
Ile Val Gln Asp Asn Phe Pro Lys Phe Lys Glu Asn Cys His Ile Phe
            195                 200                 205
Thr Arg Leu Ile Thr Ala Val Pro Ser Leu Arg Glu His Phe Glu Asn
210                 215                 220
Val Lys Lys Ala Ile Gly Ile Phe Val Ser Thr Ser Ile Glu Glu Val
225                 230                 235                 240
Phe Ser Phe Pro Phe Tyr Asn Gln Leu Leu Thr Gln Thr Gln Ile Asp
                245                 250                 255
Leu Tyr Asn Gln Leu Leu Gly Gly Ile Ser Arg Glu Ala Gly Thr Glu
            260                 265                 270
Lys Ile Lys Gly Leu Asn Glu Val Leu Asn Leu Ala Ile Gln Lys Asn
            275                 280                 285
Asp Glu Thr Ala His Ile Ile Ala Ser Leu Pro His Arg Phe Ile Pro
            290                 295                 300
Leu Phe Lys Gln Ile Leu Ser Asp Arg Asn Thr Leu Ser Phe Ile Leu
305                 310                 315                 320
Glu Glu Phe Lys Ser Asp Glu Glu Val Ile Gln Ser Phe Cys Lys Tyr
                325                 330                 335
Lys Thr Leu Leu Arg Asn Glu Asn Val Leu Glu Thr Ala Glu Ala Leu
            340                 345                 350
Phe Asn Glu Leu Asn Ser Ile Asp Leu Thr His Ile Phe Ile Ser His
            355                 360                 365
Lys Lys Leu Glu Thr Ile Ser Ser Ala Leu Cys Asp His Trp Asp Thr
            370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
                405                 410                 415
Asp Ile Asn Leu Gln Glu Ile Ile Ser Ala Ala Gly Lys Glu Leu Ser
            420                 425                 430
Glu Ala Phe Lys Gln Lys Thr Ser Glu Ile Leu Ser His Ala His Ala
            435                 440                 445
Ala Leu Asp Gln Pro Leu Pro Thr Thr Leu Lys Lys Gln Glu Glu Lys
450                 455                 460
Glu Ile Leu Lys Ser Gln Leu Asp Ser Leu Leu Gly Leu Tyr His Leu
465                 470                 475                 480
Leu Asp Trp Phe Ala Val Asp Glu Ser Asn Glu Val Asp Pro Glu Phe
                485                 490                 495
Ser Ala Arg Leu Thr Gly Ile Lys Leu Glu Met Glu Pro Ser Leu Ser
            500                 505                 510
Phe Tyr Asn Lys Ala Arg Asn Tyr Ala Thr Lys Lys Pro Tyr Ser Val
            515                 520                 525
Glu Lys Phe Lys Leu Asn Phe Gln Met Pro Thr Leu Ala Ser Gly Trp
            530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
                565                 570                 575
Ala Leu Ser Phe Glu Pro Thr Glu Lys Thr Ser Glu Gly Phe Asp Lys
                580                 585                 590
Met Tyr Tyr Asp Tyr Phe Pro Asp Ala Ala Lys Met Ile Pro Lys Cys
            595                 600                 605
Ser Thr Gln Leu Lys Ala Val Thr Ala His Phe Gln Thr His Thr Thr
```

```
            610                 615                 620
Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035
```

| Val | Leu | Asn | Pro | Tyr | Gln | Leu | Thr | Asp | Gln | Phe | Thr | Ser | Phe | Ala |
|     | 1040|     |     |     | 1045|     |     |     | 1050|     |     |     |     |     |

Lys Met Gly Thr Gln Ser Gly Phe Leu Phe Tyr Val Pro Ala Pro
    1055            1060                1065

Tyr Thr Ser Lys Ile Asp Pro Leu Thr Gly Phe Val Asp Pro Phe
    1070            1075                1080

Val Trp Lys Thr Ile Lys Asn His Glu Ser Arg Lys His Phe Leu
    1085            1090                1095

Glu Gly Phe Asp Phe Leu His Tyr Asp Val Lys Thr Gly Asp Phe
    1100            1105                1110

Ile Leu His Phe Lys Met Asn Arg Asn Leu Ser Phe Gln Arg Gly
    1115            1120                1125

Leu Pro Gly Phe Met Pro Ala Trp Asp Ile Val Phe Glu Lys Asn
    1130            1135                1140

Glu Thr Gln Phe Asp Ala Lys Gly Thr Pro Phe Ile Ala Gly Lys
    1145            1150                1155

Arg Ile Val Pro Val Ile Glu Asn His Arg Phe Thr Gly Arg Tyr
    1160            1165                1170

Arg Asp Leu Tyr Pro Ala Asn Glu Leu Ile Ala Leu Leu Glu Glu
    1175            1180                1185

Lys Gly Ile Val Phe Arg Asp Gly Ser Asn Ile Leu Pro Lys Leu
    1190            1195                1200

Leu Glu Asn Asp Asp Ser His Ala Ile Asp Thr Met Val Ala Leu
    1205            1210                1215

Ile Arg Ser Val Leu Gln Met Arg Asn Ser Asn Ala Ala Thr Gly
    1220            1225                1230

Glu Asp Tyr Ile Asn Ser Pro Val Arg Asp Leu Asn Gly Val Cys
    1235            1240                1245

Phe Asp Ser Arg Phe Gln Asn Pro Glu Trp Pro Met Asp Ala Asp
    1250            1255                1260

Ala Asn Gly Ala Tyr His Ile Ala Leu Lys Gly Gln Leu Leu Leu
    1265            1270                1275

Asn His Leu Lys Glu Ser Lys Asp Leu Lys Leu Gln Asn Gly Ile
    1280            1285                1290

Ser Asn Gln Asp Trp Leu Ala Tyr Ile Gln Glu Leu Arg Asn
    1295            1300                1305

<210> SEQ ID NO 3
<211> LENGTH: 3714
<212> TYPE: DNA
<213> ORGANISM: Lachnospiraceae bacterium ND2006

<400> SEQUENCE: 3
atgagcaaac tggaaaaatt tacgaattgt tatagcctgt ccaagaccct gcgtttcaaa     60 gccatcccccg ttggcaaaac ccaggagaat attgataata acgtctgct ggttgaggat    120 gaaaaaagag cagaagacta aagggagtc aaaaaactgc tggatcggta ctacctgagc    180
tttataaatg acgtgctgca tagcattaaa ctgaaaaatc tgaataacta tattagtctg    240
ttccgcaaga aacccgaac agagaaagaa ataaagagc tggaaaacct ggagatcaat    300
ctgcgtaaag agatcgcaaa agctttaaa ggaaatgaag gttataaaag cctgttcaaa    360
aaagacatta ttgaaaccat cctgccggaa tttctggatg ataaagacga gatagcgctc    420
gtgaacagct tcaacggtt cacgaccgcc ttcacgggct ttttcgataa cagggaaaat    480

-continued

```
atgttttcag aggaagccaa aagcacctcg atagcgttcc gttgcattaa tgaaaatttg    540
acaagatata tcagcaacat ggatattttc gagaaagttg atgcgatctt tgacaaacat    600
gaagtgcagg agattaagga aaaaattctg aacagcgatt atgatgttga ggattttttc    660
gagggggaat tttttaactt tgtactgaca caggaaggta tagatgtgta taatgctatt    720
atcggcgggt tcgttaccga atccggcgag aaaattaagg gtctgaatga gtacatcaat    780
ctgtataacc aaaagaccaa acagaaactg ccaaaattca aaccgctgta caagcaagtc    840
ctgagcgatc gggaaagctt gagcttttac ggtgaaggtt ataccagcga cgaggaggta    900
ctggaggtct ttcgcaatac cctgaacaag aacagcgaaa ttttcagctc cattaaaaag    960
ctggagaaac tgtttaagaa ttttgacgag tacagcagcg caggtatttt tgtgaagaac   1020
ggacctgcca taagcaccat tagcaaggat attttttggag agtggaatgt tatccgtgat   1080
aaatggaacg cggaatatga tgacatacac ctgaaaaaga aggctgtggt aactgagaaa   1140
tatgaagacg atcgccgcaa aagctttaaa aaaatcggca gctttagcct ggagcagctg   1200
caggaatatg cggacgccga cctgagcgtg gtcgagaaac tgaaggaaat tattatccaa   1260
aaagtggatg agatttacaa ggtatatggt agcagcgaaa aactgtttga tgcggacttc   1320
gttctggaaa aaagcctgaa aaaaaatgat gctgttgttg cgatcatgaa agacctgctc   1380
gatagcgtta agagctttga aaattacatt aaagcattct ttggcgaggg caaagaaaca   1440
aacagagacg aaagcttttta tggcgacttc gtcctggctt atgacatcct gttgaaggta   1500
gatcatatat atgatgcaat tcgtaattac gtaacccaaa agccgtacag caaagataag   1560
ttcaaactgt atttccagaa cccgcagttt atgggtggct gggacaaaga caaggagaca   1620
gactatcgcg ccactattct gcgttacggc agcaagtact atctcgccat catggacaaa   1680
aaatatgcaa agtgtctgca gaaaatcgat aaagacgacg tgaacggaaa ttacgaaaag   1740
attaattata agctgctgcc agggcccaac aagatgttac cgaaagtatt ttttttccaaa   1800 aaatggatgg catactataa cccgagcgag gatatacaga agatttacaa aaatgggacc   1860
ttcaaaaagg gggatatgtt caatctgaat gactgccaca aactgatcga ttttttttaaa   1920 gatagcatca gccgttatcc taaatggtca aacgcgtatg attttaattt ctccgaaacg   1980
gagaaatata aagacattgc tggtttctat cgcgaagtcg aagaacaggg ttataaagtt   2040
agctttgaat cggccagcaa gaaagaggtt gataaactgg tggaggaggg taagctgtat   2100 atgttttcaga tttataacaa agactttagc gacaaaagcc acggtactcc taatctgcat   2160
acgatgtact ttaaactgct gtttgatgag aataaccacg gccaaatccg tctctccggt   2220
ggagcagaac ttttttatgcg gcgtgcgagc ctaaaaaagg aagaactggt ggtgcatccc   2280
gccaacagcc cgattgctaa caaaaatcca gataatccta agaagaccac cacactgtcg   2340
tacgatgtct ataaggataa acgtttctcg gaagaccagt atgaattgca tataccgata   2400
gcaattaata aatgcccaaa aaacattttc aaaatcaaca ctgaagttcg tgtgctgctg   2460
aaacatgatg ataatccgta tgtgatcgga attgaccgtg gggagagaaa tctgctgtat   2520
attgtagtcg ttgatggcaa gggcaacatc gttgagcagt atagcctgaa tgaaataatt   2580 aataattttta acggtatacg tattaaaacc gactatcata gcctgctgga taaaaggag   2640 aaagagcgtt ttgaggcacg ccaaaattgg acgagcatcg aaaacatcaa ggaactgaag   2700
gcaggatata tcagccaagt agtccataaa atctgtgaac tggtggagaa gtacgacgct   2760
gtcattgccc tggaagacct caatagcggc tttaaaaaca gccgggtgaa ggtggagaaa   2820
caggtatacc aaaagtttga aaagatgctc attgataagc tgaactatat ggttgataaa   2880
```

-continued

```
aagagcaacc cgtgcgccac tggcggtgca ctgaaagggt accaaattac caataaattt    2940
gaaagcttta aaagcatgag cacgcagaat gggtttattt tttatatacc agcatggctg    3000
acgagcaaga ttgaccccag cactggtttt gtcaatctgc tgaaaaccaa atacacaagc    3060 attgcgata gcaaaaaatt tatttcgagc ttcgaccgta ttatgtatgt tccggaggaa    3120
gatctgtttg aatttgccct ggattataaa aacttcagcc gcaccgatgc agattatatc    3180
aaaaaatgga agctgtacag ttatggtaat cgtatacgta tcttccgtaa tccgaagaaa    3240
aacaatgtgt tcgattggga agaggtctgt ctgaccagcg cgtataaaga actgttcaac    3300
aagtacggaa taaattatca gcaaggtgac attcgcgcac tgctgtgtga acagtcagat    3360
aaagcatttt atagcagctt tatggcgctg atgagcctga tgctccagat gcgcaacagc    3420
ataaccggtc gcacagatgt tgactttctg atcagccctg tgaagaatag cgacggcatc    3480
ttctacgatt ccaggaacta tgaagcacag gaaaacgcta ttctgcctaa aaatgccgat    3540
gccaacggcg cctataatat tgcacggaag gttctgtggg cgattggaca gttcaagaaa    3600
gcggaagatg agaagctgga taaggtaaaa attgctatta gcaataagga atggctggag    3660
tacgcacaga catcggttaa acacgcggcc gcttccctgc aggtaattaa ataa          3714
```

<210> SEQ ID NO 4
<211> LENGTH: 1246
<212> TYPE: PRT
<213> ORGANISM: Lachnospiraceae bacterium ND2006

<400> SEQUENCE: 4

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220
```

```
Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
            245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
            275                 280                 285

Pro Lys Phe Lys Pro Leu Tyr Lys Gln Val Leu Ser Asp Arg Glu Ser
            290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
            325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
            355                 360                 365

Ile Phe Gly Glu Trp Asn Val Ile Arg Asp Lys Trp Asn Ala Glu Tyr
            370                 375                 380

Asp Asp Ile His Leu Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
            405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
            435                 440                 445

Ser Ser Glu Lys Leu Phe Asp Ala Asp Phe Val Leu Glu Lys Ser Leu
450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
            485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
            515                 520                 525

Val Thr Gln Lys Pro Tyr Ser Lys Asp Lys Phe Lys Leu Tyr Phe Gln
            530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
            565                 570                 575

Asp Lys Lys Tyr Ala Lys Cys Leu Gln Lys Ile Asp Lys Asp Asp Val
            580                 585                 590

Asn Gly Asn Tyr Glu Lys Ile Asn Tyr Lys Leu Leu Pro Gly Pro Asn
            595                 600                 605

Lys Met Leu Pro Lys Val Phe Phe Ser Lys Trp Met Ala Tyr Tyr
            610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
```

```
              645                 650                 655
Phe Lys Asp Ser Ile Ser Arg Tyr Pro Lys Trp Ser Asn Ala Tyr Asp
            660                 665                 670
Phe Asn Phe Ser Glu Thr Glu Lys Tyr Lys Asp Ile Ala Gly Phe Tyr
            675                 680                 685
Arg Glu Val Glu Glu Gln Gly Tyr Lys Val Ser Phe Glu Ser Ala Ser
            690                 695                 700
Lys Lys Glu Val Asp Lys Leu Val Glu Gly Lys Leu Tyr Met Phe
705                 710                 715                 720
Gln Ile Tyr Asn Lys Asp Phe Ser Asp Lys Ser His Gly Thr Pro Asn
            725                 730                 735
Leu His Thr Met Tyr Phe Lys Leu Leu Phe Asp Glu Asn Asn His Gly
            740                 745                 750
Gln Ile Arg Leu Ser Gly Gly Ala Glu Leu Phe Met Arg Arg Ala Ser
            755                 760                 765
Leu Lys Lys Glu Glu Leu Val Val His Pro Ala Asn Ser Pro Ile Ala
770                 775                 780
Asn Lys Asn Pro Asp Asn Pro Lys Lys Thr Thr Thr Leu Ser Tyr Asp
785                 790                 795                 800
Val Tyr Lys Asp Lys Arg Phe Ser Glu Asp Gln Tyr Glu Leu His Ile
            805                 810                 815
Pro Ile Ala Ile Asn Lys Cys Pro Lys Asn Ile Phe Lys Ile Asn Thr
            820                 825                 830
Glu Val Arg Val Leu Leu Lys His Asp Asp Asn Pro Tyr Val Ile Gly
            835                 840                 845
Ile Asp Arg Gly Glu Arg Asn Leu Leu Tyr Ile Val Val Asp Gly
            850                 855                 860
Lys Gly Asn Ile Val Glu Gln Tyr Ser Leu Asn Glu Ile Ile Asn Asn
865                 870                 875                 880
Phe Asn Gly Ile Arg Ile Lys Thr Asp Tyr His Ser Leu Leu Asp Lys
            885                 890                 895
Lys Glu Lys Glu Arg Phe Glu Ala Arg Gln Asn Trp Thr Ser Ile Glu
            900                 905                 910
Asn Ile Lys Glu Leu Lys Ala Gly Tyr Ile Ser Gln Val Val His Lys
            915                 920                 925
Ile Cys Glu Leu Val Glu Lys Tyr Asp Ala Val Ile Ala Leu Glu Asp
            930                 935                 940
Leu Asn Ser Gly Phe Lys Asn Ser Arg Val Lys Val Glu Lys Gln Val
945                 950                 955                 960
Tyr Gln Lys Phe Glu Lys Met Leu Ile Asp Lys Leu Asn Tyr Met Val
            965                 970                 975
Asp Lys Lys Ser Asn Pro Cys Ala Thr Gly Gly Ala Leu Lys Gly Tyr
            980                 985                 990
Gln Ile Thr Asn Lys Phe Glu Ser Phe Lys Ser Met Ser Thr Gln Asn
            995                1000                1005
Gly Phe Ile Phe Tyr Ile Pro Ala Trp Leu Thr Ser Lys Ile Asp
            1010                1015                1020
Pro Ser Thr Gly Phe Val Asn Leu Leu Lys Thr Lys Tyr Thr Ser
            1025                1030                1035
Ile Ala Asp Ser Lys Lys Phe Ile Ser Ser Phe Asp Arg Ile Met
            1040                1045                1050
Tyr Val Pro Glu Glu Asp Leu Phe Glu Phe Ala Leu Asp Tyr Lys
            1055                1060                1065
```

| | | | | | | | | | | |
|---|---|---|---|---|---|---|---|---|---|---|
| Asn | Phe | Ser | Arg | Thr | Asp | Ala | Asp | Tyr | Ile | Lys | Lys | Trp | Lys | Leu |
| | 1070 | | | | 1075 | | | | 1080 | | |

| Tyr | Ser | Tyr | Gly | Asn | Arg | Ile | Arg | Ile | Phe | Arg | Asn | Pro | Lys | Lys |
|---|---|---|---|---|---|---|---|---|---|---|---|---|---|---|
| | 1085 | | | | 1090 | | | | 1095 | | |

| Asn | Asn | Val | Phe | Asp | Trp | Glu | Glu | Val | Cys | Leu | Thr | Ser | Ala | Tyr |
|---|---|---|---|---|---|---|---|---|---|---|---|---|---|---|
| 1100 | | | | | 1105 | | | | 1110 | | |

| Lys | Glu | Leu | Phe | Asn | Lys | Tyr | Gly | Ile | Asn | Tyr | Gln | Gln | Gly | Asp |
|---|---|---|---|---|---|---|---|---|---|---|---|---|---|---|
| 1115 | | | | | 1120 | | | | 1125 | | |

| Ile | Arg | Ala | Leu | Leu | Cys | Glu | Gln | Ser | Asp | Lys | Ala | Phe | Tyr | Ser |
|---|---|---|---|---|---|---|---|---|---|---|---|---|---|---|
| 1130 | | | | | 1135 | | | | 1140 | | |

| Ser | Phe | Met | Ala | Leu | Met | Ser | Leu | Met | Leu | Gln | Met | Arg | Asn | Ser |
|---|---|---|---|---|---|---|---|---|---|---|---|---|---|---|
| 1145 | | | | | 1150 | | | | 1155 | | |

| Ile | Thr | Gly | Arg | Thr | Asp | Val | Asp | Phe | Leu | Ile | Ser | Pro | Val | Lys |
|---|---|---|---|---|---|---|---|---|---|---|---|---|---|---|
| 1160 | | | | | 1165 | | | | 1170 | | |

| Asn | Ser | Asp | Gly | Ile | Phe | Tyr | Asp | Ser | Arg | Asn | Tyr | Glu | Ala | Gln |
|---|---|---|---|---|---|---|---|---|---|---|---|---|---|---|
| 1175 | | | | | 1180 | | | | 1185 | | |

| Glu | Asn | Ala | Ile | Leu | Pro | Lys | Asn | Ala | Asp | Ala | Asn | Gly | Ala | Tyr |
|---|---|---|---|---|---|---|---|---|---|---|---|---|---|---|
| 1190 | | | | | 1195 | | | | 1200 | | |

| Asn | Ile | Ala | Arg | Lys | Val | Leu | Trp | Ala | Ile | Gly | Gln | Phe | Lys | Lys |
|---|---|---|---|---|---|---|---|---|---|---|---|---|---|---|
| 1205 | | | | | 1210 | | | | 1215 | | |

| Ala | Glu | Asp | Glu | Lys | Leu | Asp | Lys | Val | Lys | Ile | Ala | Ile | Ser | Asn |
|---|---|---|---|---|---|---|---|---|---|---|---|---|---|---|
| 1220 | | | | | 1225 | | | | 1230 | | |

| Lys | Glu | Trp | Leu | Glu | Tyr | Ala | Gln | Thr | Ser | Val | Lys | His |
|---|---|---|---|---|---|---|---|---|---|---|---|---|
| 1235 | | | | | 1240 | | | | 1245 | | |

<210> SEQ ID NO 5
<211> LENGTH: 3924
<212> TYPE: DNA
<213> ORGANISM: Artificial Sequence
<220> FEATURE:
<223> OTHER INFORMATION: Synthetic DNA

<400> SEQUENCE: 5

| | |
|---|---|
| atgacccagt tgaaggtttt caccaatctg tatcaggtta gcaaaaccct gcgttttgaa | 60 |
| ctgattccgc agggtaaaac cctgaaacat attcaagaac agggcttcat cgaagaggat | 120 |
| aaagcacgta acgatcacta caaagaactg aaaccgatta tcgaccgcat ctataaaacc | 180 |
| tatgcagatc agtgtctgca gctggttcag ctggattggg aaaatctgag cgcagcaatt | 240 |
| gatagttatc gcaaagaaaa aaccgaagaa acccgtaatg cactgattga agaacaggca | 300 |
| acctatcgta tgccatcca tgattatttc attggtcgta ccgataatct gaccgatgca | 360 |
| attaacaaac gtcacgccga atctataaa ggcctgttta agccgaact gtttaatggc | 420 |
| aaagttctga acagctggg caccgttacc accaccgaac atgaaaatgc actgctgcgt | 480 |
| agctttgata aattcaccac ctatttcagc ggcttttatg agaatcgcaa aaacgtgttt | 540 |
| agcgcagaag atattagcac cgcaattccg catcgtattg tgcaggataa tttcccgaaa | 600 |
| ttcaaagaga actgccacat ttttacccgt ctgattaccg cagttccgag cctgcgtgaa | 660 |
| cattttgaaa acgttaaaaa agccatcggc atctttgtta gcaccagcat tgaagaagtt | 720 |
| tttagcttcc cgtttttacaa tcagctgctg acccagaccc agattgatct gtataaccaa | 780 |
| ctgctgggtg gtattagccg tgaagcaggc accgaaaaaa tcaaaggtct gaatgaagtg | 840 |
| ctgaatctgg ccattcagaa aaatgatgaa accgcacata ttattgcaag cctgccgcat | 900 |
| cgttttattc cgctgttcaa acaaattctg agcgatcgta atacccctgag ctttattctg | 960 |

```
gaagaattca atccgatga agaggtgatt cagagctttt gcaaatacaa aacgctgctg    1020
cgcaatgaaa atgttctgga aactgccgaa gcactgttta acgaactgaa tagcattgat    1080
ctgacccaca tctttatcag ccacaaaaaa ctggaaacca tttcaagcgc actgtgtgat    1140
cattgggata ccctgcgtaa tgccctgtat aacgtcgta ttagcgaact gaccggtaaa     1200
attaccaaaa gcgcgaaaga aaagttcag cgcagtctga acatgagga tattaatctg      1260 caagagatta ttagcgcagc cggtaaagaa ctgtcagaag catttaaaca gaaaaccagc    1320
gaaattctgt cacatgcaca tgcagcactg gatcagccgc tgccgaccac cctgaaaaaa    1380
caagaagaaa aagaaatcct gaaaagccag ctggatagcc tgctgggtct gtatcatctg    1440
ctggactggt ttgcagttga tgaaagcaat gaagttgatc cggaatttag cgcacgtctg    1500
accggcatta aactggaaat ggaaccgagc ctgagctttt ataacaaagc ccgtaattat    1560
gccaccaaaa aaccgtatag cgtcgaaaaa ttcaaactga actttcagat gccgaccctg    1620
gcaagcggtt gggatgttaa taagaaaaa aacaacggtg ccatcctgtt cgtgaaaaat     1680
ggcctgtatt atctgggtat tatgccgaaa cagaaaggtc gttataaagc gctgagcttt    1740
gaaccgacgg aaaaaaccag tgaaggtttt gataaaatgt actacgacta ttttccggat    1800
gcagccaaaa tgattccgaa atgtagcacc cagctgaaag cagttaccgc acattttcag    1860
acccatacca ccccgattct gctgagcaat aactttattg aaccgctgga atcaccaaa     1920 gagatctaca atctgaataa cccggaaaaa gagccgaaaa aattccagac cgcatatgca    1980
aaaaaaaccg gtgatcagaa aggttatcgt gaagcgctgt gtaaatggat tgatttcacc    2040 cgtgatttc tgagcaaata caccaaaacc accagtatcg atctgagcag cctgcgtccg     2100
agcagccagt ataaagatct gggcgaatat tatgcagaac tgaatccgct gctgtatcat    2160
attagctttc agcgtattgc cgagaaagaa atcatggacg cagttgaaac cggtaaactg    2220
tacctgttcc agatctacaa taaagatttt gccaaaggcc atcatggcaa accgaatctg    2280 catacctgt attggaccgg tctgtttagc cctgaaaatc tggcaaaaac ctcgattaaa     2340
ctgaatggtc aggcggaact gttttatcgt ccgaaaagcc gtatgaaacg tatggcacat    2400
cgtctgggtg aaaaaatgct gaacaaaaaa ctgaaagacc agaaaacccc gatcccggat    2460
acactgtatc aagaactgta tgattatgtg aaccatcgtc tgagccatga tctgagtgat    2520
gaagcacgtg ccctgctgcc gaatgttatt accaagaag ttagccacga gatcattaaa     2580
gatcgtcgtt ttaccagcga caaattcttt tttcatgtgc cgattaccct gaattatcag    2640
gcagcaaata gcccgagcaa atttaaccag cgtgttaatg catatctgaa agaacatcca    2700
gaaacgccga ttattggtat tgatcgtggt gaacgtaacc tgatttatat caccgttatt    2760
gatagcaccg gcaaaatcct ggaacagcgt agcctgaata ccattcagca gtttgattac    2820
cagaaaaaac tggataatcg cgagaaagaa cgtgttgcag cacgtcaggc atggtcagtt    2880
gttggtacaa ttaaagacct gaaacagggt tatctgagcc aggttattca tgaaattgtg    2940
gatctgatga ttcactatca ggccgttgtt gtgctggaaa acctgaattt tggctttaaa    3000
agcaaacgta ccggcattgc agaaaaagca gtttatcagc agttcgagaa aatgctgatt    3060
gacaaactga attgcctggt gctgaaagat tatccggctg aaaagttgg tggtgttctg     3120 aatccgtatc agctgaccga tcagtttacc agctttgcaa aaatgggcac ccagagcgga    3180
tttctgtttt atgttccggc accgtatacg agcaaaattg atccgctgac cggttttgtt    3240
gatccgtttg tttggaaaac catcaaaaac catgaaagcc gcaaacattt tctggaaggt    3300
ttcgattttc tgcattacga cgttaaaacg ggtgatttca tcctgcactt taaaatgaat    3360
```

```
cgcaatctga gttttcagcg tggcctgcct ggtttatgc ctgcatggga tattgtgttt    3420
gagaaaaacg aaacacagtt cgatgcaaaa ggcacccccgt ttattgcagg taaacgtatt    3480
gttccggtga ttgaaaatca tcgtttcacc ggtcgttatc gcgatctgta tccggcaaat    3540
gaactgatcg cactgctgga agagaaaggt attgttttc gtgatggctc aaacattctg    3600
ccgaaactgc tggaaaatga tgatagccat gcaattgata ccatggttgc actgattcgt    3660
agcgttctgc agatgcgtaa tagcaatgca gcaaccggtg aagattacat taatagtccg    3720
gttcgtgatc tgaatggtgt ttgttttgat agccgttttc agaatccgga atggccgatg    3780
gatgcagatg caaatggtgc atatcatatt gcactgaaag acagctgct gctgaaccac    3840 ctgaaagaaa gcaaagatct gaaactgcaa acggcatta gcaatcagga ttggctggca    3900
tatatccaag aactgcgtaa ctga                                           3924
```

<210> SEQ ID NO 6
<211> LENGTH: 3741
<212> TYPE: DNA
<213> ORGANISM: Artificial Sequence
<220> FEATURE:
<223> OTHER INFORMATION: Synthetic DNA

<400> SEQUENCE: 6

```
atgctgaaaa acgtgggtat tgatcgtctg gatgttgaaa aaggtcgcaa aaatatgagc      60
aaactggaaa agttcaccaa ctgttatagc ctgagcaaaa ccctgcgttt taaagcaatt     120
ccggttggta aaacccaaga gaacattgat aataaacgcc tgctggtcga agatgaaaaa     180
cgcgctgaag attataaagg cgtgaaaaaa ctgctggatc gctattatct gagcttcatt     240
aacgatgtgc tgcacagcat taaactgaag aacctgaaca actatatcag cctgtttcgt     300
aaaaaaaccc gcaccgaaaa agaaaacaaa gagctggaaa acctggaaat caatctgcgt     360
aaagaaatcg ccaaagcgtt taaggtaac gagggttata aaagcctgtt caagaaagac     420
atcatcgaaa ccattctgcc ggaatttctg gatgataaag atgaaattgc cctggtgaat     480
agctttaatg gctttaccac cgcatttacc ggctttttg ataatcgcga aaacatgttc     540
agcgaagaag caaaaagcac cagcattgca tttcgctgca ttaatgaaaa tctgacccgc     600
tacattagca acatggatat ctttgaaaaa gtggacgcga tcttcgataa acacgaagtg     660
caagagatca aagagaaaat cctgaacagc gattatgacg tcgaagattt ttttgaaggc     720
gagttcttta acttcgttct gacccaagaa ggtatcgacg tttataacgc aattattggt     780
ggttttgtta ccgaaagcgg tgagaaaatc aaaggcctga tgaatatat caacctgtat     840 aaccagaaaa ccaaacagaa actgccgaaa ttcaaaccgc tgtataaaca ggttctgagc     900
gatcgtgaaa gcctgagctt ttatggtgaa ggttatacca gtgatgaaga ggttctggaa     960
gtttttcgta cacccctgaa taaaaacagc gagatcttta gcagcatcaa aaagcttgag    1020
aaactgttca aaaactttga tgagtatagc agcgcaggca tctttgttaa aatggtccg    1080 gcaattagca ccatcagcaa agatattttt ggcgaatgga atgtgatccg cgataaatgg    1140
aatgccgaat atgatgatat ccacctgaaa aaaaaggccg tggtgaccga gaaatatgaa    1200
gatgatcgtc gtaaaagctt caagaaaatt ggtagcttta gcctggaaca gctgcaagaa    1260
tatgcagatg cagatctgag cgttgtggaa aaactgaaag aaatcatcat tcagaaggtg    1320
gacgagatct ataagttta tggtagcagc gaaaaactgt tcgatgcaga ttttgttctg    1380 gaaaaagcc tgaaaagaa tgatgccgtt gtggccatta tgaaagatct gctggatagc    1440
```

```
gttaagagct tcgagaatta catcaaagcc tttttggtg agggcaaaga aaccaatcgt    1500
gatgaaagtt tctatggcga ttttgtgctg gcctatgata ttctgctgaa agtggaccat   1560
atttatgatg ccattcgcaa ttatgttacc cagaaaccgt atagcaaaga caagttcaaa   1620
ctgtactttc agaacccgca gtttatgggt ggttgggata agataaaga aaccgattat    1680 cgtgccacca tcctgcgtta tggtagtaaa tactatctgg ccatcatgga caaaaaatac   1740
gcaaaatgcc tgcagaaaat cgacaaagat gatgtgaatg caactatga aaaaatcaac    1800 tacaaactgc tgcctggtcc gaataaaatg ctgccgaaag tgttctttag caagaaatgg   1860
atggcctatt ataacccgag cgaggatatt caaaagatct acaaaaatgg cacctttaaa   1920
aagggcgaca tgttcaatct gaacgattgc cacaaactga tcgatttctt caaagattca   1980
atttcgcgtt atccgaaatg gtccaatgcc tatgattta actttagcga aaccgaaaaa    2040
tacaaagaca ttgccggttt ttatcgcgaa gtggaagaac agggctataa agtgagcttt   2100
gaaagcgcaa gcaaaaaga ggttgataag ctggttgaag agggcaaact gtatatgttc    2160
cagatttaca acaaagattt tagcgacaaa agccatggca ccccgaatct gcataccatg   2220
tactttaaac tgctgttcga cgaaaataac catggtcaga ttcgtctgag cggtggtgcc   2280
gaactgttta tgcgtcgtgc aagtctgaaa aaagaagaac tggttgttca tccggcaaat   2340
agcccgattg caacaaaaa tccggacaat ccgaaaaaaa ccacgacact gagctatgat    2400
gtgtataaag acaaacgttt tagcgaggat cagtatgaac tgcatatccc gattgccatc   2460
aataaatgcc gaaaaacat ctttaagatc aacaccgaag ttcgcgtgct gctgaaacat    2520
gatgataatc cgtatgtgat tggcattgat cgtggtgaac gtaacctgct gtatattgtt   2580
gttgttgatg gtaaaggcaa catcgtggaa cagtatagtc tgaacgaaat tatcaacaac   2640
tttaacggca tccgcatcaa aaccgactat catagcctgc tggacaagaa agaaaaagaa   2700
cgttttgaag cacgtcagaa ctggaccagt attgaaaaca tcaaagaact gaaagccggt   2760
tatattagca aggtggttca taaaatctgt gagctggtag aaaaatacga tgcagttatt   2820
gcactggaag atctgaatag cggtttcaaa aatagccgtg tgaaagtcga aaaacaggtg   2880
tatcagaaat tcgagaaaat gctgatcgac aaactgaact acatggtcga caaaaaaagc   2940
aatccgtgtg caaccggtgg tgcactgaaa ggttatcaga ttaccaacaa atttgaaagc   3000
tttaaaagca tgagcaccca gaacggcttt atcttctata ttccggcatg gctgaccagc   3060
aaaattgatc cgagcaccgg ttttgtgaac ctgctgaaaa caaatatac ctccattgcc    3120 gacagcaaga agtttattag cagctttgat cgcattatgt atgttccgga gaggacctg    3180 tttgaattcg cactggatta caaaaatttc agccgtaccg atgccgacta catcaaaaaa   3240
tggaaactgt acagctatgg taaccgcatt cgcattttc gcaacccgaa gaaaaacaat    3300
gtgttcgatt gggaagaagt ttgtctgacc agcgcatata aagaactttt caacaaatac   3360
ggcatcaact atcagcaggg tgatattcgt gcactgctgt gtgaacagag cgataaagcg   3420
ttttatagca gttttatggc actgatgagc ctgatgctgc agatgcgtaa tagcattacc   3480
ggtcgcaccg atgtggattt tctgattagt ccggtgaaaa attccgatgg catctttat    3540 gatagccgca attacgaagc acaagaaaat gcaattctgc cgaaaaacgc agatgcaaat   3600
ggtgcatata acattgcacg taaagttctg tgggcaattg ccagtttaa gaaagcagaa    3660 gatgagaagc tggacaaagt gaaaattgcg atcagcaata agagtggct ggaatacgca    3720 cagaccagcg ttaaacattg a                                            3741
```

<210> SEQ ID NO 7
<211> LENGTH: 1246
<212> TYPE: PRT
<213> ORGANISM: Artificial Sequence
<220> FEATURE:
<223> OTHER INFORMATION: Synthetic Amino Acid sequence

<400> SEQUENCE: 7

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
    290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
```

```
            370                 375                 380
Asp Asp Ile His Leu Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
                420                 425                 430

Lys Glu Ile Ile Ile Gln Lys Val Asp Glu Ile Tyr Lys Val Tyr Gly
                435                 440                 445

Ser Ser Glu Lys Leu Phe Asp Ala Asp Phe Val Leu Glu Lys Ser Leu
                450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
                500                 505                 510

Asp Ile Leu Leu Lys Val Asp His Ile Tyr Asp Ala Ile Arg Asn Tyr
                515                 520                 525

Val Thr Gln Lys Pro Tyr Ser Lys Asp Lys Phe Lys Leu Tyr Phe Gln
                530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
                580                 585                 590

Asn Gly Asn Tyr Glu Lys Ile Asn Tyr Lys Leu Leu Pro Gly Pro Asn
                595                 600                 605

Lys Met Leu Pro Lys Val Phe Phe Ser Lys Lys Trp Met Ala Tyr Tyr
                610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
                660                 665                 670

Phe Asn Phe Ser Glu Thr Glu Lys Tyr Lys Asp Ile Ala Gly Phe Tyr
                675                 680                 685

Arg Glu Val Glu Glu Gln Gly Tyr Lys Val Ser Phe Glu Ser Ala Ser
                690                 695                 700

Lys Lys Glu Val Asp Lys Leu Val Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
                755                 760                 765

Leu Lys Lys Glu Glu Leu Val Val His Pro Ala Asn Ser Pro Ile Ala
                770                 775                 780

Asn Lys Asn Pro Asp Asn Pro Lys Lys Thr Thr Thr Leu Ser Tyr Asp
785                 790                 795                 800
```

```
Val Tyr Lys Asp Lys Arg Phe Ser Glu Asp Gln Tyr Glu Leu His Ile
            805                 810                 815
Pro Ile Ala Ile Asn Lys Cys Pro Lys Asn Ile Phe Lys Ile Asn Thr
            820                 825                 830
Glu Val Arg Val Leu Lys His Asp Asp Asn Pro Tyr Val Ile Gly
            835                 840                 845
Ile Asp Arg Gly Glu Arg Asn Leu Leu Tyr Ile Val Val Asp Gly
        850                 855                 860
Lys Gly Asn Ile Val Glu Gln Tyr Ser Leu Asn Glu Ile Asn Asn
865                 870                 875                 880
Phe Asn Gly Ile Arg Ile Lys Thr Asp Tyr His Ser Leu Leu Asp Lys
                885                 890                 895
Lys Glu Lys Glu Arg Phe Glu Ala Arg Gln Asn Trp Thr Ser Ile Glu
            900                 905                 910
Asn Ile Lys Glu Leu Lys Ala Gly Tyr Ile Ser Gln Val Val His Lys
            915                 920                 925
Ile Cys Glu Leu Val Glu Lys Tyr Asp Ala Val Ile Ala Leu Glu Asp
            930                 935                 940
Leu Asn Ser Gly Phe Lys Asn Ser Arg Val Lys Val Glu Lys Gln Val
945                 950                 955                 960
Tyr Gln Lys Phe Glu Lys Met Leu Ile Asp Lys Leu Asn Tyr Met Val
                965                 970                 975
Asp Lys Lys Ser Asn Pro Cys Ala Thr Gly Gly Ala Leu Lys Gly Tyr
                980                 985                 990
Gln Ile Thr Asn Lys Phe Glu Ser Phe Lys Ser Met Ser Thr Gln Asn
            995                 1000                1005
Gly Phe Ile Phe Tyr Ile Pro Ala Trp Leu Thr Ser Lys Ile Asp
    1010                1015                1020
Pro Ser Thr Gly Phe Val Asn Leu Leu Lys Thr Lys Tyr Thr Ser
    1025                1030                1035
Ile Ala Asp Ser Lys Lys Phe Ile Ser Ser Phe Asp Arg Ile Met
    1040                1045                1050
Tyr Val Pro Glu Glu Asp Leu Phe Glu Phe Ala Leu Asp Tyr Lys
    1055                1060                1065
Asn Phe Ser Arg Thr Asp Ala Asp Tyr Ile Lys Lys Trp Lys Leu
    1070                1075                1080
Tyr Ser Tyr Gly Asn Arg Ile Arg Ile Phe Arg Asn Pro Lys Lys
    1085                1090                1095
Asn Asn Val Phe Asp Trp Glu Glu Val Cys Leu Thr Ser Ala Tyr
    1100                1105                1110
Lys Glu Leu Phe Asn Lys Tyr Gly Ile Asn Tyr Gln Gln Gly Asp
    1115                1120                1125
Ile Arg Ala Leu Leu Cys Glu Gln Ser Asp Lys Ala Phe Tyr Ser
    1130                1135                1140
Ser Phe Met Ala Leu Met Ser Leu Met Leu Gln Met Arg Asn Ser
    1145                1150                1155
Ile Thr Gly Arg Thr Asp Val Asp Phe Leu Ile Ser Pro Val Lys
    1160                1165                1170
Asn Ser Asp Gly Ile Phe Tyr Asp Ser Arg Asn Tyr Glu Ala Gln
    1175                1180                1185
Glu Asn Ala Ile Leu Pro Lys Asn Ala Asp Ala Asn Gly Ala Tyr
    1190                1195                1200
```

| | | | | | | | | | | |
|---|---|---|---|---|---|---|---|---|---|---|
| Asn | Ile | Ala | Arg | Lys | Val | Leu | Trp | Ala | Ile | Gly | Gln | Phe | Lys | Lys |
| | 1205 | | | | 1210 | | | | 1215 | |

| | | | | | | | | | | |
|---|---|---|---|---|---|---|---|---|---|---|
| Ala | Glu | Asp | Glu | Lys | Leu | Asp | Lys | Val | Lys | Ile | Ala | Ile | Ser | Asn |
| 1220 | | | | | 1225 | | | | | 1230 |

| | | | | | | | | | | |
|---|---|---|---|---|---|---|---|---|---|---|
| Lys | Glu | Trp | Leu | Glu | Tyr | Ala | Gln | Thr | Ser | Val | Lys | His |
| 1235 | | | | | 1240 | | | | | 1245 |

<210> SEQ ID NO 8
<211> LENGTH: 3924
<212> TYPE: DNA
<213> ORGANISM: Artificial Sequence
<220> FEATURE:
<223> OTHER INFORMATION: Synthetic DNA

<400> SEQUENCE: 8

| | | | | | |
|---|---|---|---|---|---|
| atgacccagt | tcgagggctt | caccaacctg | taccaggtgt | ccaagaccct | gagattcgag | 60 |
| ctgatccccc | agggcaagac | actgaagcac | atccaggaac | agggcttcat | cgaagaggac | 120 |
| aaggcccgga | cgaccacta | caaagagctg | aagcccatca | tcgaccggat | ctacaagacc | 180 |
| tacgccgacc | agtgcctgca | gctggtgcag | ctggactggg | agaatctgag | cgccgccatc | 240 |
| gacagctacc | ggaaagagaa | aaccgaggaa | acccggaacg | ccctgatcga | ggaacaggcc | 300 |
| acctacagaa | acgccatcca | cgactacttc | atcggccgga | ccgacaacct | gaccgacgcc | 360 |
| atcaacaagc | ggcacgccga | gatctataag | ggcctgttca | aggccgagct | gttcaacggc | 420 |
| aaggtgctga | agcagctggg | caccgtgacc | accaccgagc | acgaaaacgc | cctgctgcgg | 480 |
| agcttcgaca | agttcaccac | ctacttcagc | ggcttctacg | agaaccggaa | gaacgtgttc | 540 |
| agcgccgagg | acatcagcac | cgccatcccc | cacagaatcg | tgcaggacaa | cttccccaag | 600 |
| ttcaaagaga | actgccacat | cttcacccgg | ctgatcaccg | ccgtgcccag | cctgagagaa | 660 |
| cacttcgaga | acgtgaagaa | ggccatcggc | atcttcgtgt | ccaccagcat | cgaggaagtg | 720 |
| ttcagcttcc | cattctacaa | ccagctgctg | acccagaccc | agatcgacct | gtataatcag | 780 |
| ctgctgggcg | gcatcagcag | agaggccggc | accgagaaga | tcaagggcct | gaacgaagtg | 840 |
| ctgaacctgg | ccatccagaa | gaacgacgag | acagcccaca | tcattgccag | cctgccccac | 900 |
| cggttcatcc | ctctgttcaa | gcagatcctg | agcgacagaa | acaccctgag | cttcatcctg | 960 |
| gaagagttca | gtccgatga | ggaagtgatc | cagagcttct | gcaagtataa | gaccctgctg | 1020 |
| aggaacgaga | atgtgctgga | aaccgccgag | gccctgttca | atgagctgaa | cagcatcgac | 1080 |
| ctgacccaca | tctttatcag | ccacaagaag | ctggaaacaa | tcagcagcgc | cctgtgcgac | 1140 |
| cactgggaca | cactgcggaa | tgccctgtac | gagcggcgga | tctctgagct | gaccggcaag | 1200 |
| atcaccaaga | gcgccaaaga | aaaggtgcag | cggagcctga | agcacgagga | tatcaacctg | 1260 |
| caggaaatca | tcagcgccgc | tggcaaagaa | ctgagcgagg | cctttaagca | gaaaaccagc | 1320 |
| gagatcctgt | cccacgccca | cgccgcactg | gatcagcctc | tgcctaccac | cctgaagaag | 1380 |
| caggaagaga | aagagatcct | gaagtcccag | ctggacagcc | tgctgggcct | gtaccatctg | 1440 |
| ctggattggt | tcgccgtgga | cgagagcaac | gaggtggacc | ccgagttctc | cgccagactg | 1500 |
| acaggcatca | aactggaaat | ggaacccagc | ctgtccttct | acaacaaggc | cagaaactac | 1560 |
| gccaccaaga | aaccctacag | cgtggaaaag | tttaagctga | acttccagat | gcccaccctg | 1620 |
| gccagcggct | gggacgtgaa | caaagagaag | aacaacggcg | ccatcctgtt | cgtgaagaac | 1680 |
| ggactgtact | acctgggcat | catgcctaag | cagaagggca | gatacaaggc | cctgtccttt | 1740 |
| gagcccaccg | aaaagaccag | cgagggcttt | gacaagatgt | actacgatta | cttccccgac | 1800 |

```
gccgccaaga tgatccccaa gtgcagcacc cagctgaagg ccgtgaccgc ccactttcag    1860
acccacacca cccccatcct gctgagcaac aacttcatcg agcccctgga aatcaccaaa    1920
gagatctacg acctgaacaa ccccgagaaa gagcccaaga agttccagac cgcctacgcc    1980
aagaaaaccg gcgaccagaa gggctaccgc gaggctctgt gcaagtggat cgactttacc    2040
cgggacttcc tgagcaagta caccaagacc acctccatcg atctgagcag cctgcggccc    2100
agctcccagt acaaggatct gggcgagtac tacgccgagc tgaaccctct gctgtaccac    2160
atcagcttcc agcggatcgc cgaaaaagaa atcatggacg ccgtggaaac cggcaagctg    2220
tacctgttcc agatctataa caaggacttc gccaagggcc accacggcaa gcccaatctg    2280
cacaccctgt actggaccgg cctgtttagc cccgagaatc tggccaagac cagcatcaag    2340
ctgaacggcc aggccgaact gttttaccgg cccaagagcc ggatgaagcg gatggcccat    2400
agactgggcg agaagatgct gaacaagaaa ctgaaggacc agaaaccccc tatccccgac    2460
acactgtatc aggaactgta cgactacgtg aaccaccggc tgagccacga cctgtccgac    2520
gaagctagag cactgctgcc caacgtgatc acaaaagagg tgtcccacga gatcatcaag    2580
gaccggcggt ttacctccga taagttcttc ttccacgtgc ccatcaccct gaactaccag    2640
gccgccaaca gccccagcaa gttcaaccag agagtgaacg cctacctgaa agagcacccc    2700
gagacaccca tcattggcat cgacagaggc gagcggaacc tgatctacat caccgtgatc    2760
gacagcacag gcaaaatcct ggaacagaga gcctgaaca ccatccagca gttcgactac    2820
cagaagaaac tggacaaccg ggaaaaagaa cgggtggccg ccagacaggc ttggagcgtc    2880
gtgggcacca ttaaggacct gaagcagggc tacctgagcc aagtgattca cgagatcgtg    2940
gacctgatga tccactatca ggctgtggtg gtgctggaaa acctgaactt cggcttcaag    3000
agcaagcgga ccggaatcgc cgagaaagcc gtgtaccagc agtttgagaa aatgctgatc    3060
gacaagctga attgcctggt gctgaaagac taccccgctg agaaagtggg aggcgtgctg    3120
aatccctacc agctgaccga ccagttcacc tcctttgcca agatgggaac ccagagcggc    3180
ttcctgtttc tacgtgccagc cccctacacc agcaagatcg accctctgac cggcttcgtg    3240 gacccccttcg tgtggaaaac catcaagaac cacgagtccc ggaagcactt cctggaaggc    3300
tttgacttcc tgcactacga cgtgaaaaca ggcgatttca tcctgcactt caagatgaat    3360
cggaatctgt ccttccagag gggcctgccc ggcttcatgc ctgcctggga tatcgtgttc    3420
gagaagaatg agacacagtt cgacgccaag ggaaccccct ttatcgccgg caagaggatc    3480
gtgcctgtga tcgagaacca cagattcacc ggcagatacc gggacctgta ccccgccaac    3540
gagctgattg ccctgctgga agagaagggc atcgtgttcc gggacggcag caacatcctg    3600
cccaagctgc tggaaaatga cgacagccac gccatcgata ccatggtggc actgatccgc    3660
agcgtgctgc agatgcggaa cagcaatgcc gccaccggcg aggactacat caatagccca    3720
gtgcgggacc tgaacggcgt gtgcttcgac agcagattcc agaaccccga gtggcccatg    3780
gatgccgacg ccaatggcgc ctaccacatt gccctgaagg acagctgct gctgaaccat    3840 ctgaaagaga gcaaagacct gaaactgcag aacggcatct ccaaccagga ctggctggcc    3900
tatatccagg aactgcggaa ctga                                           3924

<210> SEQ ID NO 9
<211> LENGTH: 683
<212> TYPE: DNA
<213> ORGANISM: Artificial Sequence
<220> FEATURE:
<223> OTHER INFORMATION: Synthetic DNA
```

<400> SEQUENCE: 9

```
ccagcaagat cgatcctagc accggattcg tgaacctgct caagaccaag tacaccagca    60
ttgccgacag caagaagttc atctccagct tcgaccggat tatgtacgtg cccgaagagg   120
acctgttcga attcgccctg gattacaaga acttcagccg gaccgatgcc gactatatca   180
agaagtggaa gctgtatagc tacggcaacc gcatccgcat cttcagaaac ccgaagaaaa   240
acaacgtgtt cgactgggaa gaagtgtgcc tgaccagcgc ctacaaagaa ctcttcaaca   300
aatacggcat caactaccag cagggcgaca tcagagccct gctgtgcgag cagagcgaca   360
aggccttttta cagctccttc atggccctga tgtccctgat gctgcagatg cggaatagca   420
tcaccggcag gaccgacgtg gacttcctga tcagccctgt gaagaattcc gacgggatct   480
tctacgacag cagaaactac gaggctcaag agaacgccat cctgcctaag aacgccgatg   540
ccaacggcgc ctataatatc gccagaaagg tgctgtgggc catcggccag tttaagaagg   600
ccgaggacga gaaactggac aaagtgaaga tcgccatctc taacaaagag tggctggaat   660
acgcccagac cagcgtgaaa cac                                            683
```

<210> SEQ ID NO 10
<211> LENGTH: 1246
<212> TYPE: PRT
<213> ORGANISM: Artificial Sequence
<220> FEATURE:
<223> OTHER INFORMATION: Synthetic Amino Acid Sequence

<400> SEQUENCE: 10

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220
```

```
Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
            245                 250                 255

Ala Ile Ile Gly Gly Phe Val Thr Glu Ser Gly Glu Lys Ile Lys Gly
                260                 265                 270

Leu Asn Glu Tyr Ile Asn Leu Tyr Asn Gln Lys Thr Lys Gln Lys Leu
            275                 280                 285

Pro Lys Phe Lys Pro Leu Tyr Lys Gln Val Leu Ser Asp Arg Glu Ser
            290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
                340                 345                 350

Gly Ile Phe Val Lys Asn Gly Pro Ala Ile Ser Thr Ile Ser Lys Asp
                355                 360                 365

Ile Phe Gly Glu Trp Asn Val Ile Arg Asp Lys Trp Asn Ala Glu Tyr
            370                 375                 380

Asp Asp Ile His Leu Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
            435                 440                 445

Ser Ser Glu Lys Leu Phe Asp Ala Asp Phe Val Leu Glu Lys Ser Leu
450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
            515                 520                 525

Val Thr Gln Lys Pro Tyr Ser Lys Asp Lys Phe Lys Leu Tyr Phe Gln
            530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
            580                 585                 590

Asn Gly Asn Tyr Glu Lys Ile Asn Tyr Lys Leu Leu Pro Gly Pro Asn
            595                 600                 605

Lys Met Leu Pro Lys Val Phe Phe Ser Lys Lys Trp Met Ala Tyr Tyr
            610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
```

```
                    645                 650                 655
Phe Lys Asp Ser Ile Ser Arg Tyr Pro Lys Trp Ser Asn Ala Tyr Asp
                660                 665                 670

Phe Asn Phe Ser Glu Thr Glu Lys Tyr Lys Asp Ile Ala Gly Phe Tyr
                675                 680                 685

Arg Glu Val Glu Glu Gln Gly Tyr Lys Val Ser Phe Glu Ser Ala Ser
                690                 695                 700

Lys Lys Glu Val Asp Lys Leu Val Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
                740                 745                 750

Gln Ile Arg Leu Ser Gly Gly Ala Glu Leu Phe Met Arg Arg Ala Ser
                755                 760                 765

Leu Lys Lys Glu Glu Leu Val Val His Pro Ala Asn Ser Pro Ile Ala
770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
                820                 825                 830

Glu Val Arg Val Leu Leu Lys His Asp Asp Asn Pro Tyr Val Ile Gly
                835                 840                 845

Ile Asp Arg Gly Glu Arg Asn Leu Leu Tyr Ile Val Val Val Asp Gly
                850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
                900                 905                 910

Asn Ile Lys Glu Leu Lys Ala Gly Tyr Ile Ser Gln Val Val His Lys
                915                 920                 925

Ile Cys Glu Leu Val Glu Lys Tyr Asp Ala Val Ile Ala Leu Glu Asp
                930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
                980                 985                 990

Gln Ile Thr Asn Lys Phe Glu Ser Phe Lys Ser Met Ser Thr Gln Asn
                995                 1000                1005

Gly Phe Ile Phe Tyr Ile Pro Ala Trp Leu Thr Ser Lys Ile Asp
                1010                1015                1020

Pro Ser Thr Gly Phe Val Asn Leu Leu Lys Thr Lys Tyr Thr Ser
                1025                1030                1035

Ile Ala Asp Ser Lys Lys Phe Ile Ser Ser Phe Asp Arg Ile Met
                1040                1045                1050

Tyr Val Pro Glu Glu Asp Leu Phe Glu Phe Ala Leu Asp Tyr Lys
                1055                1060                1065
```

```
Asn Phe Ser Arg Thr Asp Ala Asp Tyr Ile Lys Lys Trp Lys Leu
    1070            1075                1080

Tyr Ser Tyr Gly Asn Arg Ile Arg Ile Phe Arg Asn Pro Lys Lys
    1085            1090                1095

Asn Asn Val Phe Asp Trp Glu Glu Val Cys Leu Thr Ser Ala Tyr
    1100            1105                1110

Lys Glu Leu Phe Asn Lys Tyr Gly Ile Asn Tyr Gln Gln Gly Asp
    1115            1120                1125

Ile Arg Ala Leu Leu Cys Glu Gln Ser Asp Lys Ala Phe Tyr Ser
    1130            1135                1140

Ser Phe Met Ala Leu Met Ser Leu Met Leu Gln Met Arg Asn Ser
    1145            1150                1155

Ile Thr Gly Arg Thr Asp Val Asp Phe Leu Ile Ser Pro Val Lys
    1160            1165                1170

Asn Ser Asp Gly Ile Phe Tyr Asp Ser Arg Asn Tyr Glu Ala Gln
    1175            1180                1185

Glu Asn Ala Ile Leu Pro Lys Asn Ala Asp Ala Asn Gly Ala Tyr
    1190            1195                1200

Asn Ile Ala Arg Lys Val Leu Trp Ala Ile Gly Gln Phe Lys Lys
    1205            1210                1215

Ala Glu Asp Glu Lys Leu Asp Lys Val Lys Ile Ala Ile Ser Asn
    1220            1225                1230

Lys Glu Trp Leu Glu Tyr Ala Gln Thr Ser Val Lys His
    1235            1240                1245

<210> SEQ ID NO 11
<211> LENGTH: 4086
<212> TYPE: DNA
<213> ORGANISM: Artificial Sequence
<220> FEATURE:
<223> OTHER INFORMATION: Synthetic DNA

<400> SEQUENCE: 11
atgggtcggg atccaggtaa accgattccg aatccgctgc tgggtctgga tagcaccgca      60
ccgaaaaaaa aacgtaaagt tggtattcat ggtgttccgg cagcaaccca gtttgaaggt     120
ttcaccaatc tgtatcaggt tagcaaaacc ctgcgttttg aactgattcc gcagggtaaa     180
accctgaaac atattcaaga cagggcttc atcgaagagg ataaagcacg taacgatcac      240
tacaaagaac tgaaaccgat tatcgaccgc atctataaaa cctatgcaga tcagtgtctg     300
cagctggttc agctggattg ggaaaatctg agcgcagcaa ttgatagtta tcgcaaagaa     360
aaaaccgaag aaacccgtaa tgcactgatt gaagaacagg caacctatcg taatgccatc     420
catgattatt tcattggtcg taccgataat ctgaccgatg caattaacaa cgtcacgcc     480 gaaatctata aaggcctgtt taaagccgaa ctgtttaatg caaagttct gaaacagctg      540 ggcaccgtta ccaccaccga acatgaaaat gcactgctgc gtagctttga taaattcacc     600
acctatttca gcggctttta tgagaatcgc aaaaacgtgt ttagcgcaga agatattagc     660
accgcaattc gcatcgtat tgtgcaggat aatttcccga attcaaaga gaactgccac       720 atttttaccc gtctgattac cgcagttccg agcctgcgtg aacattttga aaacgttaaa     780
aaagccatcg gcatctttgt tagcaccagc attgaagaag ttttagctt cccgtttttac    840 aatcagctgc tgacccagac ccagattgat ctgtataacc aactgctggg tggtattagc     900
cgtgaagcag gcaccgaaaa aatcaaaggt ctgaatgaag tgctgaatct ggccattcag     960
```

```
aaaaatgatg aaaccgcaca tattattgca agcctgccgc atcgttttat tccgctgttc    1020
aaacaaattc tgagcgatcg taatacccctg agctttattc tggaagaatt caaatccgat    1080
gaagaggtga ttcagagctt ttgcaaatac aaaacgctgc tgcgcaatga aaatgttctg    1140
gaaactgccg aagcactgtt taacgaactg aatagcattg atctgaccca catctttatc    1200
agccacaaaa aactggaaac catttcaagc gcactgtgtg atcattggga taccctgcgt    1260
aatgccctgt atgaacgtcg tattagcgaa ctgaccggta aaattaccaa agcgcgaaa     1320 gaaaaagttc agcgcagtct gaaacatgag gatattaatc tgcaagagat tattagcgca    1380
gccggtaaag aactgtcaga agcatttaaa cagaaaacca gcgaaattct gtcacatgca    1440
catgcagcac tggatcagcc gctgccgacc accctgaaaa acaagaaga aaagaaatc     1500 ctgaaaagcc agctggatag cctgctgggt ctgtatcatc tgctggactg gtttgcagtt    1560
gatgaaagca atgaagttga tccggaattt agcgcacgtc tgaccggcat taaactggaa    1620
atggaaccga gcctgagctt ttataacaaa gcccgtaatt atgccaccaa aaaaccgtat    1680
agcgtcgaaa aattcaaact gaactttcag atgccgaccc tggcaagcgg ttgggatgtt    1740 aataagaaa aaaacaacgg tgccatcctg ttcgtgaaaa atggcctgta ttatctgggt    1800
attatgccga aacagaaagg tcgttataaa gcgctgagct tgaaccgac ggaaaaaacc     1860 agtgaaggtt ttgataaaat gtactacgac tattttccgg atgcagccaa aatgattccg    1920
aaatgtagca cccagctgaa agcagttacc gcacattttc agacccatac cacccccgatt    1980 ctgctgagca taactttat tgaaccgctg gaaatcacca agagatcta cgatctgaat     2040 aacccggaaa aagagccgaa aaaattccag accgcatatg caaaaaaaac cggtgatcag    2100
aaaggttatc gtgaagcgct gtgtaaatgg attgatttca cccgtgattt tctgagcaaa    2160
tacaccaaaa ccaccagtat cgatctgagc agcctgcgtc cgagcagcca gtataaagat    2220
ctgggcgaat attatgcaga actgaatccg ctgctgtatc atattagctt tcagcgtatt    2280
gccgagaaag aaaatcatgga cgcagttgaa accggtaaac tgtacctgtt ccagatctac    2340
aataaagatt ttgccaaagg ccatcatggc aaaccgaatc tgcatacccct gtattggacc    2400 ggtctgttta gccctgaaaa tctggcaaaa acctcgatta aactgaatgg tcaggcggaa    2460
ctgttttatc gtccgaaaag ccgtatgaaa cgtatggcac atcgtctggg tgaaaaaatg    2520
ctgaacaaaa aactgaaaga ccagaaaacc ccgatcccgg atacactgta tcaagaactg    2580
tatgattatg tgaaccatcg tctgagccat gatctgagtg atgaagcacg tgccctgctg    2640
ccgaatgtta ttaccaaaga agttagccac gagatcatta aagatcgtcg ttttaccagc    2700
gacaaattct tttttcatgt gccgattacc ctgaattatc aggcagcaaa tagcccgagc    2760
aaatttaacc agcgtgttaa tgcatatctg aaagaacatc cagaaacgcc gattattggt    2820
attgatcgtg gtgaacgtaa cctgatttat atcaccgtta ttgatagcac cggcaaaatc    2880
ctggaacagc gtagcctgaa taccattcag cagtttgatt accagaaaaa actggataat    2940
cgcgagaaag aacgtgttgc agcacgtcag gcatggtcag ttgttggtac aattaaagac    3000
ctgaaacagg gttatctgag ccaggttatt catgaaattg tggatctgat gattcactat    3060
caggccgttg ttgtgctgga aaacctgaat tttggcttta aaagcaaacg taccggcatt    3120
gcagaaaaag cagtttatca gcagttcgag aaaatgctga ttgacaaact gaattgcctg    3180
gtgctgaaag attatccggc tgaaaaagtt ggtggtgttc tgaatccgta tcagctgacc    3240
gatcagttta ccagctttgc aaaaatgggc acccagagcg gatttctgtt ttatgttccg    3300
gcaccgtata cgagcaaaat tgatccgctg accggttttg ttgatccgtt tgtttggaaa    3360
```

-continued

```
accatcaaaa accatgaaag ccgcaaacat tttctggaag gtttcgattt tctgcattac    3420
gacgttaaaa cgggtgattt catcctgcac tttaaaatga atcgcaatct gagttttcag    3480
cgtggcctgc ctggttttat gcctgcatgg gatattgtgt ttgagaaaaa cgaaacacag    3540
ttcgatgcaa aaggcacccc gtttattgca ggtaaacgta ttgttccggt gattgaaaat    3600
catcgtttca ccggtcgtta tcgcgatctg tatccggcaa atgaactgat cgcactgctg    3660
gaagagaaag gtattgtttt tcgtgatggc tcaaacattc tgccgaaact gctggaaaat    3720
gatgatagcc atgcaattga taccatggtt gcactgattc gtagcgttct gcagatgcgt    3780
aatagcaatg cagcaaccgg tgaagattac attaatagtc cggttcgtga tctgaatggt    3840
gtttgttttg atagccgttt tcagaatccg gaatggccga tggatgcaga tgcaaatggt    3900
gcatatcata ttgcactgaa aggacagctg ctgctgaacc acctgaaaga aagcaaagat    3960
ctgaaactgc aaaacggcat tagcaatcag gattggctgg catatatcca agaactgcgt    4020
aaccctaaaa aaaaacgcaa agtgaagctt gcggccgcac tcgagcacca ccaccaccac    4080
cactga                                                                4086
```

<210> SEQ ID NO 12
<211> LENGTH: 1361
<212> TYPE: PRT
<213> ORGANISM: Artificial Sequence
<220> FEATURE:
<223> OTHER INFORMATION: Synthetic Amino Acid Sequence

<400> SEQUENCE: 12

```
Met Gly Arg Asp Pro Gly Lys Pro Ile Pro Asn Pro Leu Leu Gly Leu
 1               5                  10                  15

Asp Ser Thr Ala Pro Lys Lys Arg Lys Val Gly Ile His Gly Val
            20                  25                  30

Pro Ala Ala Thr Gln Phe Glu Gly Phe Thr Asn Leu Tyr Gln Val Ser
        35                  40                  45

Lys Thr Leu Arg Phe Glu Leu Ile Pro Gln Gly Lys Thr Leu Lys His
    50                  55                  60

Ile Gln Glu Gln Gly Phe Ile Glu Glu Asp Lys Ala Arg Asn Asp His
65                  70                  75                  80

Tyr Lys Glu Leu Lys Pro Ile Ile Asp Arg Ile Tyr Lys Thr Tyr Ala
                85                  90                  95

Asp Gln Cys Leu Gln Leu Val Gln Leu Asp Trp Glu Asn Leu Ser Ala
            100                 105                 110

Ala Ile Asp Ser Tyr Arg Lys Glu Lys Thr Glu Glu Thr Arg Asn Ala
        115                 120                 125

Leu Ile Glu Glu Gln Ala Thr Tyr Arg Asn Ala Ile His Asp Tyr Phe
    130                 135                 140

Ile Gly Arg Thr Asp Asn Leu Thr Asp Ala Ile Asn Lys Arg His Ala
145                 150                 155                 160

Glu Ile Tyr Lys Gly Leu Phe Lys Ala Glu Leu Phe Asn Gly Lys Val
                165                 170                 175

Leu Lys Gln Leu Gly Thr Val Thr Thr Thr Glu His Glu Asn Ala Leu
            180                 185                 190

Leu Arg Ser Phe Asp Lys Phe Thr Thr Tyr Phe Ser Gly Phe Tyr Glu
        195                 200                 205

Asn Arg Lys Asn Val Phe Ser Ala Glu Asp Ile Ser Thr Ala Ile Pro
    210                 215                 220
```

```
His Arg Ile Val Gln Asp Asn Phe Pro Lys Phe Lys Glu Asn Cys His
225                 230                 235                 240

Ile Phe Thr Arg Leu Ile Thr Ala Val Pro Ser Leu Arg Glu His Phe
            245                 250                 255

Glu Asn Val Lys Lys Ala Ile Gly Ile Phe Val Ser Thr Ser Ile Glu
        260                 265                 270

Glu Val Phe Ser Phe Pro Phe Tyr Asn Gln Leu Leu Thr Gln Thr Gln
    275                 280                 285

Ile Asp Leu Tyr Asn Gln Leu Leu Gly Gly Ile Ser Arg Glu Ala Gly
290                 295                 300

Thr Glu Lys Ile Lys Gly Leu Asn Glu Val Leu Asn Leu Ala Ile Gln
305                 310                 315                 320

Lys Asn Asp Glu Thr Ala His Ile Ile Ala Ser Leu Pro His Arg Phe
                325                 330                 335

Ile Pro Leu Phe Lys Gln Ile Leu Ser Asp Arg Asn Thr Leu Ser Phe
                340                 345                 350

Ile Leu Glu Glu Phe Lys Ser Asp Glu Val Ile Gln Ser Phe Cys
                355                 360                 365

Lys Tyr Lys Thr Leu Leu Arg Asn Glu Asn Val Leu Glu Thr Ala Glu
370                 375                 380

Ala Leu Phe Asn Glu Leu Asn Ser Ile Asp Leu Thr His Ile Phe Ile
385                 390                 395                 400

Ser His Lys Lys Leu Glu Thr Ile Ser Ser Ala Leu Cys Asp His Trp
                405                 410                 415

Asp Thr Leu Arg Asn Ala Leu Tyr Glu Arg Arg Ile Ser Glu Leu Thr
            420                 425                 430

Gly Lys Ile Thr Lys Ser Ala Lys Glu Lys Val Gln Arg Ser Leu Lys
            435                 440                 445

His Glu Asp Ile Asn Leu Gln Glu Ile Ile Ser Ala Ala Gly Lys Glu
            450                 455                 460

Leu Ser Glu Ala Phe Lys Gln Lys Thr Ser Glu Ile Leu Ser His Ala
465                 470                 475                 480

His Ala Ala Leu Asp Gln Pro Leu Pro Thr Thr Leu Lys Lys Gln Glu
                485                 490                 495

Glu Lys Glu Ile Leu Lys Ser Gln Leu Asp Ser Leu Leu Gly Leu Tyr
            500                 505                 510

His Leu Leu Asp Trp Phe Ala Val Asp Glu Ser Asn Glu Val Asp Pro
            515                 520                 525

Glu Phe Ser Ala Arg Leu Thr Gly Ile Lys Leu Glu Met Glu Pro Ser
530                 535                 540

Leu Ser Phe Tyr Asn Lys Ala Arg Asn Tyr Ala Thr Lys Lys Pro Tyr
545                 550                 555                 560

Ser Val Glu Lys Phe Lys Leu Asn Phe Gln Met Pro Thr Leu Ala Ser
                565                 570                 575

Gly Trp Asp Val Asn Lys Glu Lys Asn Asn Gly Ala Ile Leu Phe Val
            580                 585                 590

Lys Asn Gly Leu Tyr Tyr Leu Gly Ile Met Pro Lys Gln Lys Gly Arg
            595                 600                 605

Tyr Lys Ala Leu Ser Phe Glu Pro Thr Glu Lys Thr Ser Glu Gly Phe
            610                 615                 620

Asp Lys Met Tyr Tyr Asp Tyr Phe Pro Asp Ala Ala Lys Met Ile Pro
625                 630                 635                 640

Lys Cys Ser Thr Gln Leu Lys Ala Val Thr Ala His Phe Gln Thr His
```

-continued

```
                645                 650                 655
Thr Thr Pro Ile Leu Ser Asn Asn Phe Ile Glu Pro Leu Glu Ile
            660                 665                 670
Thr Lys Glu Ile Tyr Asp Leu Asn Asn Pro Glu Lys Glu Pro Lys Lys
        675                 680                 685
Phe Gln Thr Ala Tyr Ala Lys Lys Thr Gly Asp Gln Lys Gly Tyr Arg
    690                 695                 700
Glu Ala Leu Cys Lys Trp Ile Asp Phe Thr Arg Asp Phe Leu Ser Lys
705                 710                 715                 720
Tyr Thr Lys Thr Thr Ser Ile Asp Leu Ser Ser Leu Arg Pro Ser Ser
                725                 730                 735
Gln Tyr Lys Asp Leu Gly Glu Tyr Tyr Ala Glu Leu Asn Pro Leu Leu
            740                 745                 750
Tyr His Ile Ser Phe Gln Arg Ile Ala Glu Lys Glu Ile Met Asp Ala
        755                 760                 765
Val Glu Thr Gly Lys Leu Tyr Leu Phe Gln Ile Tyr Asn Lys Asp Phe
    770                 775                 780
Ala Lys Gly His His Gly Lys Pro Asn Leu His Thr Leu Tyr Trp Thr
785                 790                 795                 800
Gly Leu Phe Ser Pro Glu Asn Leu Ala Lys Thr Ser Ile Lys Leu Asn
                805                 810                 815
Gly Gln Ala Glu Leu Phe Tyr Arg Pro Lys Ser Arg Met Lys Arg Met
            820                 825                 830
Ala His Arg Leu Gly Glu Lys Met Leu Asn Lys Lys Leu Lys Asp Gln
        835                 840                 845
Lys Thr Pro Ile Pro Asp Thr Leu Tyr Gln Glu Leu Tyr Asp Tyr Val
    850                 855                 860
Asn His Arg Leu Ser His Asp Leu Ser Asp Glu Ala Arg Ala Leu Leu
865                 870                 875                 880
Pro Asn Val Ile Thr Lys Glu Val Ser His Glu Ile Ile Lys Asp Arg
                885                 890                 895
Arg Phe Thr Ser Asp Lys Phe Phe His Val Pro Ile Thr Leu Asn
            900                 905                 910
Tyr Gln Ala Ala Asn Ser Pro Ser Lys Phe Asn Gln Arg Val Asn Ala
        915                 920                 925
Tyr Leu Lys Glu His Pro Glu Thr Pro Ile Ile Gly Ile Asp Arg Gly
    930                 935                 940
Glu Arg Asn Leu Ile Tyr Ile Thr Val Ile Asp Ser Thr Gly Lys Ile
945                 950                 955                 960
Leu Glu Gln Arg Ser Leu Asn Thr Ile Gln Gln Phe Asp Tyr Gln Lys
                965                 970                 975
Lys Leu Asp Asn Arg Glu Lys Glu Arg Val Ala Ala Arg Gln Ala Trp
            980                 985                 990
Ser Val Val Gly Thr Ile Lys Asp Leu Lys Gln Gly Tyr Leu Ser Gln
        995                 1000                1005
Val Ile His Glu Ile Val Asp Leu Met Ile His Tyr Gln Ala Val
    1010                1015                1020
Val Val Leu Glu Asn Leu Asn Phe Gly Phe Lys Ser Lys Arg Thr
    1025                1030                1035
Gly Ile Ala Glu Lys Ala Val Tyr Gln Gln Phe Glu Lys Met Leu
    1040                1045                1050
Ile Asp Lys Leu Asn Cys Leu Val Leu Lys Asp Tyr Pro Ala Glu
    1055                1060                1065
```

| | | | | | | | | | | |
|---|---|---|---|---|---|---|---|---|---|---|
|Lys|Val|Gly|Gly|Val|Leu|Asn|Pro|Tyr|Gln|Leu|Thr|Asp|Gln|Phe|
| |1070| | | |1075| | | |1080| |

Lys Val Gly Gly Val Leu Asn Pro Tyr Gln Leu Thr Asp Gln Phe
       1070              1075              1080

Thr Ser Phe Ala Lys Met Gly Thr Gln Ser Gly Phe Leu Phe Tyr
       1085              1090              1095

Val Pro Ala Pro Tyr Thr Ser Lys Ile Asp Pro Leu Thr Gly Phe
       1100              1105              1110

Val Asp Pro Phe Val Trp Lys Thr Ile Lys Asn His Glu Ser Arg
       1115              1120              1125

Lys His Phe Leu Glu Gly Phe Asp Phe Leu His Tyr Asp Val Lys
       1130              1135              1140

Thr Gly Asp Phe Ile Leu His Phe Lys Met Asn Arg Asn Leu Ser
       1145              1150              1155

Phe Gln Arg Gly Leu Pro Gly Phe Met Pro Ala Trp Asp Ile Val
       1160              1165              1170

Phe Glu Lys Asn Glu Thr Gln Phe Asp Ala Lys Gly Thr Pro Phe
       1175              1180              1185

Ile Ala Gly Lys Arg Ile Val Pro Val Ile Glu Asn His Arg Phe
       1190              1195              1200

Thr Gly Arg Tyr Arg Asp Leu Tyr Pro Ala Asn Glu Leu Ile Ala
       1205              1210              1215

Leu Leu Glu Glu Lys Gly Ile Val Phe Arg Asp Gly Ser Asn Ile
       1220              1225              1230

Leu Pro Lys Leu Leu Glu Asn Asp Asp Ser His Ala Ile Asp Thr
       1235              1240              1245

Met Val Ala Leu Ile Arg Ser Val Leu Gln Met Arg Asn Ser Asn
       1250              1255              1260

Ala Ala Thr Gly Glu Asp Tyr Ile Asn Ser Pro Val Arg Asp Leu
       1265              1270              1275

Asn Gly Val Cys Phe Asp Ser Arg Phe Gln Asn Pro Glu Trp Pro
       1280              1285              1290

Met Asp Ala Asp Ala Asn Gly Ala Tyr His Ile Ala Leu Lys Gly
       1295              1300              1305

Gln Leu Leu Leu Asn His Leu Lys Glu Ser Lys Asp Leu Lys Leu
       1310              1315              1320

Gln Asn Gly Ile Ser Asn Gln Asp Trp Leu Ala Tyr Ile Gln Glu
       1325              1330              1335

Leu Arg Asn Pro Lys Lys Lys Arg Lys Val Lys Leu Ala Ala Ala
       1340              1345              1350

Leu Glu His His His His His His
       1355              1360

<210> SEQ ID NO 13
<211> LENGTH: 3876
<212> TYPE: DNA
<213> ORGANISM: Artificial Sequence
<220> FEATURE:
<223> OTHER INFORMATION: Synthetic DNA

<400> SEQUENCE: 13
atgggtaaac cgattccgaa tccgctgctg gtctggata gcaccgcacc gaaaaaaaaa      60
cgtaaagttg gtattcatgg tgttccggca gcactgaaaa acgtgggtat tgatcgtctg     120
gatgttgaaa aggtcgcaa aaatatgagc aaactgaaa agttcaccaa ctgttatagc      180
ctgagcaaaa ccctgcgttt taaagcaatt ccggttggta aaacccaaga gaacattgat    240

```
aataaacgcc tgctggtcga agatgaaaaa cgcgctgaag attataaagg cgtgaaaaaa    300
ctgctggatc gctattatct gagcttcatt aacgatgtgc tgcacagcat taaactgaag    360
aacctgaaca actatatcag cctgtttcgt aaaaaaaccc gcaccgaaaa agaaaacaaa    420
gagctggaaa acctggaaat caatctgcgt aagaaatcg ccaaagcgtt taaaggtaac    480
gagggttata aaagcctgtt caagaaagac atcatcgaaa ccattctgcc ggaatttctg    540
gatgataaag atgaaattgc cctggtgaat agctttaatg gctttaccac cgcatttacc    600
ggcttttttg ataatcgcga aacatgttc agcgaagaag caaaaagcac cagcattgca    660
tttcgctgca ttaatgaaaa tctgacccgc tacattagca acatggatat ctttgaaaaa    720
gtggacgcga tcttcgataa acacgaagtg caagagatca agagaaaat cctgaacagc    780
gattatgacg tcgaagattt ttttgaaggc gagttcttta acttcgttct gacccaagaa    840
ggtatcgacg tttataacgc aattattggt ggttttgtta ccgaaagcgg tgagaaaatc    900
aaaggcctga tgaatatat caacctgtat aaccagaaaa ccaaacagaa actgccgaaa    960
ttcaaaccgc tgtataaaca ggttctgagc gatcgtgaaa gcctgagctt ttatggtgaa   1020
ggttatacca gtgatgaaga ggttctggaa gttttttcgta acaccctgaa taaaaacagc   1080
gagatcttta gcagcatcaa aaagcttgag aaactgttca aaaactttga tgagtatagc   1140
agcgcaggca tctttgttaa aaatggtccg gcaattagca ccatcagcaa agatattttt   1200
ggcgaatgga atgtgatccg cgataaatgg aatgccgaat atgatgatat ccacctgaaa   1260
aaaaaggccg tggtgaccga gaaatatgaa gatgatcgtc gtaaaagctt caagaaaatt   1320
ggtagcttta gcctggaaca gctgcaagaa tatgcagatg cagatctgag cgttgtggaa   1380
aaactgaaag aaatcatcat tcagaaggtg gacgagatct ataaagttta tggtagcagc   1440
gaaaaactgt tcgatgcaga ttttgttctg gaaaaaagcc tgaaaagaa tgatgccgtt   1500
gtggccatta tgaaagatct gctggatagc gttaagagct tcgagaatta catcaaagcc   1560
tttttttggtg agggcaaaga aaccaatcgt gatgaaagtt tctatggcga ttttgtgctg   1620
gcctatgata ttctgctgaa agtggaccat atttatgatg ccattcgcaa ttatgttacc   1680
cagaaaccgt atagcaaaga caagttcaaa ctgtactttc agaacccgca gtttatgggt   1740
ggttgggata agataaaga aaccgattat cgtgccacca tcctgcgtta tggtagtaaa   1800
tactatctgg ccatcatgga caaaaaatac gcaaaatgcc tgcagaaaat cgacaaagat   1860
gatgtgaatg gcaactatga aaaatcaac tacaaactgc tgcctggtcc gaataaaatg   1920
ctgccgaaag tgttctttag caagaaatgg atggcctatt ataacccgag cgaggatatt   1980
caaaagatct acaaaaatgg caccttaaa aagggcgaca tgttcaatct gaacgattgc   2040
cacaaactga tcgatttctt caagattca atttcgcgtt atccgaaatg gtccaatgcc   2100
tatgatttta actttagcga aaccgaaaaa tacaaagaca ttgccggttt ttatcgcgaa   2160
gtggaagaac agggctataa agtgagcttt gaaagcgcaa gcaaaaaaga ggttgataag   2220
ctggttgaag agggcaaact gtatatgttc agatttaca acaaagattt tagcgacaaa   2280
agccatggca ccccgaatct gcataccatg tactttaaac tgctgttcga cgaaaataac   2340
catggtcaga ttcgtctgag cggtggtgcc gaactgttta tgcgtcgtgc aagtctgaaa   2400
aagaagaac tggttgttca tccggcaaat agcccgattg caaacaaaaa tccggacaat   2460
ccgaaaaaaa ccacgacact gagctatgat gtgtataaag acaacgtttt tagcgaggat   2520
cagtatgaac tgcatatccc gattgccatc aataaatgcc cgaaaacat ctttaagatc   2580
aacaccgaag ttcgcgtgct gctgaaacat gatgataatc cgtatgtgat tggcattgat   2640
```

```
cgtggtgaac gtaacctgct gtatattgtt gttgttgatg gtaaaggcaa catcgtggaa   2700
cagtatagtc tgaacgaaat tatcaacaac tttaacggca tccgcatcaa aaccgactat   2760
catagcctgc tggacaagaa agaaaaagaa cgttttgaag cacgtcagaa ctggaccagt   2820
attgaaaaca tcaaagaact gaaagccggt tatattagcc aggtggttca taaaatctgt   2880
gagctggtag aaaaatacga tgcagttatt gcactggaag atctgaatag cggtttcaaa   2940
aatagccgtg tgaaagtcga aaaacaggtg tatcagaaat tcgagaaaat gctgatcgac   3000

aaactgaact acatggtcga caaaaaaagc aatccgtgtg caaccggtgg tgcactgaaa   3060
ggttatcaga ttaccaacaa atttgaaagc tttaaaagca tgagcaccca gaacggcttt   3120
atcttctata ttccggcatg gctgaccagc aaaattgatc cgagcaccgg ttttgtgaac   3180
ctgctgaaaa caaaatatac ctccattgcc gacagcaaga agtttattag cagctttgat   3240
cgcattatgt atgttccgga agaggacctg tttgaattcg cactggatta caaaaatttc   3300
agccgtaccg atgccgacta catcaaaaaa tggaaactgt acagctatgg taaccgcatt   3360
cgcatttttc gcaacccgaa gaaaaacaat gtgttcgatt gggaagaagt ttgtctgacc   3420
agcgcatata aagaactttt caacaaatac ggcatcaact atcagcaggg tgatattcgt   3480
gcactgctgt gtgaacagag cgataaagcg ttttatagca gttttatggc actgatgagc   3540
ctgatgctgc agatgcgtaa tagcattacc ggtcgcaccg atgtggattt tctgattagt   3600
ccggtgaaaa attccgatgg catcttttat gatagccgca attacgaagc acaagaaaat   3660
gcaattctgc cgaaaaacgc agatgcaaat ggtgcatata acattgcacg taaagttctg   3720
tgggcaattg gccagtttaa gaaagcagaa gatgagaagc tggacaaagt gaaaattgcg   3780
atcagcaata aagagtggct ggaatacgca cagaccagcg ttaaacatcc gaaaaaaaaa   3840
cgcaaagtgc tcgagcacca ccaccaccac cactga                              3876
```

```

<210> SEQ ID NO 14
<211> LENGTH: 1291
<212> TYPE: PRT
<213> ORGANISM: Artificial Sequence
<220> FEATURE:
<223> OTHER INFORMATION: Synthetic Amino Acid Sequence

<400> SEQUENCE: 14

Met Gly Lys Pro Ile Pro Asn Pro Leu Leu Gly Leu Asp Ser Thr Ala
1               5                   10                  15

Pro Lys Lys Lys Arg Lys Val Gly Ile His Gly Val Pro Ala Ala Leu
            20                  25                  30

Lys Asn Val Gly Ile Asp Arg Leu Asp Val Glu Lys Gly Arg Lys Asn
        35                  40                  45

Met Ser Lys Leu Glu Lys Phe Thr Asn Cys Tyr Ser Leu Ser Lys Thr
    50                  55                  60

Leu Arg Phe Lys Ala Ile Pro Val Gly Lys Thr Gln Glu Asn Ile Asp
65                  70                  75                  80

Asn Lys Arg Leu Leu Val Glu Asp Glu Lys Arg Ala Glu Asp Tyr Lys
                85                  90                  95

Gly Val Lys Lys Leu Leu Asp Arg Tyr Tyr Leu Ser Phe Ile Asn Asp
            100                 105                 110

Val Leu His Ser Ile Lys Leu Lys Asn Leu Asn Asn Tyr Ile Ser Leu
        115                 120                 125

Phe Arg Lys Lys Thr Arg Thr Glu Lys Glu Asn Lys Glu Leu Glu Asn
    130                 135                 140
```

```
Leu Glu Ile Asn Leu Arg Lys Glu Ile Ala Lys Ala Phe Lys Gly Asn
145                 150                 155                 160

Glu Gly Tyr Lys Ser Leu Phe Lys Lys Asp Ile Ile Glu Thr Ile Leu
                165                 170                 175

Pro Glu Phe Leu Asp Asp Lys Asp Glu Ile Ala Leu Val Asn Ser Phe
            180                 185                 190

Asn Gly Phe Thr Thr Ala Phe Thr Gly Phe Phe Asp Asn Arg Glu Asn
                195                 200                 205

Met Phe Ser Glu Glu Ala Lys Ser Thr Ser Ile Ala Phe Arg Cys Ile
        210                 215                 220

Asn Glu Asn Leu Thr Arg Tyr Ile Ser Asn Met Asp Ile Phe Glu Lys
225                 230                 235                 240

Val Asp Ala Ile Phe Asp Lys His Glu Val Gln Glu Ile Lys Glu Lys
                245                 250                 255

Ile Leu Asn Ser Asp Tyr Asp Val Glu Asp Phe Phe Glu Gly Glu Phe
            260                 265                 270

Phe Asn Phe Val Leu Thr Gln Glu Gly Ile Asp Val Tyr Asn Ala Ile
        275                 280                 285

Ile Gly Gly Phe Val Thr Glu Ser Gly Glu Lys Ile Lys Gly Leu Asn
        290                 295                 300

Glu Tyr Ile Asn Leu Tyr Asn Gln Lys Thr Lys Gln Lys Leu Pro Lys
305                 310                 315                 320

Phe Lys Pro Leu Tyr Lys Gln Val Leu Ser Asp Arg Glu Ser Leu Ser
                325                 330                 335

Phe Tyr Gly Glu Gly Tyr Thr Ser Asp Glu Glu Val Leu Glu Val Phe
            340                 345                 350

Arg Asn Thr Leu Asn Lys Asn Ser Glu Ile Phe Ser Ser Ile Lys Lys
        355                 360                 365

Leu Glu Lys Leu Phe Lys Asn Phe Asp Glu Tyr Ser Ser Ala Gly Ile
        370                 375                 380

Phe Val Lys Asn Gly Pro Ala Ile Ser Thr Ile Ser Lys Asp Ile Phe
385                 390                 395                 400

Gly Glu Trp Asn Val Ile Arg Asp Lys Trp Asn Ala Glu Tyr Asp Asp
                405                 410                 415

Ile His Leu Lys Lys Lys Ala Val Val Thr Glu Lys Tyr Glu Asp Asp
            420                 425                 430

Arg Arg Lys Ser Phe Lys Lys Ile Gly Ser Phe Ser Leu Glu Gln Leu
        435                 440                 445

Gln Glu Tyr Ala Asp Ala Asp Leu Ser Val Val Glu Lys Leu Lys Glu
        450                 455                 460

Ile Ile Ile Gln Lys Val Asp Glu Ile Tyr Lys Val Tyr Gly Ser Ser
465                 470                 475                 480

Glu Lys Leu Phe Asp Ala Asp Phe Val Leu Glu Lys Ser Leu Lys Lys
                485                 490                 495

Asn Asp Ala Val Val Ala Ile Met Lys Asp Leu Leu Asp Ser Val Lys
            500                 505                 510

Ser Phe Glu Asn Tyr Ile Lys Ala Phe Phe Gly Glu Gly Lys Glu Thr
        515                 520                 525

Asn Arg Asp Glu Ser Phe Tyr Gly Asp Phe Val Leu Ala Tyr Asp Ile
        530                 535                 540

Leu Leu Lys Val Asp His Ile Tyr Asp Ala Ile Arg Asn Tyr Val Thr
545                 550                 555                 560
```

```
Gln Lys Pro Tyr Ser Lys Asp Lys Phe Lys Leu Tyr Phe Gln Asn Pro
                565                 570                 575

Gln Phe Met Gly Gly Trp Asp Lys Asp Lys Glu Thr Asp Tyr Arg Ala
            580                 585                 590

Thr Ile Leu Arg Tyr Gly Ser Lys Tyr Leu Ala Ile Met Asp Lys
        595                 600                 605

Lys Tyr Ala Lys Cys Leu Gln Lys Ile Asp Lys Asp Val Asn Gly
        610                 615                 620

Asn Tyr Glu Lys Ile Asn Tyr Lys Leu Leu Pro Gly Pro Asn Lys Met
625                 630                 635                 640

Leu Pro Lys Val Phe Phe Ser Lys Lys Trp Met Ala Tyr Tyr Asn Pro
                645                 650                 655

Ser Glu Asp Ile Gln Lys Ile Tyr Lys Asn Gly Thr Phe Lys Lys Gly
                660                 665                 670

Asp Met Phe Asn Leu Asn Asp Cys His Lys Leu Ile Asp Phe Phe Lys
            675                 680                 685

Asp Ser Ile Ser Arg Tyr Pro Lys Trp Ser Asn Ala Tyr Asp Phe Asn
        690                 695                 700

Phe Ser Glu Thr Glu Lys Tyr Lys Asp Ile Ala Gly Phe Tyr Arg Glu
705                 710                 715                 720

Val Glu Glu Gln Gly Tyr Lys Val Ser Phe Glu Ser Ala Ser Lys Lys
                725                 730                 735

Glu Val Asp Lys Leu Val Glu Gly Lys Leu Tyr Met Phe Gln Ile
            740                 745                 750

Tyr Asn Lys Asp Phe Ser Asp Lys Ser His Gly Thr Pro Asn Leu His
        755                 760                 765

Thr Met Tyr Phe Lys Leu Leu Phe Asp Glu Asn Asn His Gly Gln Ile
    770                 775                 780

Arg Leu Ser Gly Gly Ala Glu Leu Phe Met Arg Arg Ala Ser Leu Lys
785                 790                 795                 800

Lys Glu Glu Leu Val Val His Pro Ala Asn Ser Pro Ile Ala Asn Lys
                805                 810                 815

Asn Pro Asp Asn Pro Lys Lys Thr Thr Thr Leu Ser Tyr Asp Val Tyr
            820                 825                 830

Lys Asp Lys Arg Phe Ser Glu Asp Gln Tyr Glu Leu His Ile Pro Ile
        835                 840                 845

Ala Ile Asn Lys Cys Pro Lys Asn Ile Phe Lys Ile Asn Thr Glu Val
        850                 855                 860

Arg Val Leu Leu Lys His Asp Asp Asn Pro Tyr Val Ile Gly Ile Asp
865                 870                 875                 880

Arg Gly Glu Arg Asn Leu Leu Tyr Ile Val Val Val Asp Gly Lys Gly
                885                 890                 895

Asn Ile Val Glu Gln Tyr Ser Leu Asn Glu Ile Ile Asn Asn Phe Asn
            900                 905                 910

Gly Ile Arg Ile Lys Thr Asp Tyr His Ser Leu Leu Asp Lys Lys Glu
        915                 920                 925

Lys Glu Arg Phe Glu Ala Arg Gln Asn Trp Thr Ser Ile Glu Asn Ile
        930                 935                 940

Lys Glu Leu Lys Ala Gly Tyr Ile Ser Gln Val Val His Lys Ile Cys
945                 950                 955                 960

Glu Leu Val Glu Lys Tyr Asp Ala Val Ile Ala Leu Glu Asp Leu Asn
                965                 970                 975

Ser Gly Phe Lys Asn Ser Arg Val Lys Val Glu Lys Gln Val Tyr Gln
```

```
                 980             985             990
Lys Phe Glu Lys Met Leu Ile Asp Lys Leu Asn Tyr Met Val Asp Lys
            995             1000            1005

Lys Ser Asn Pro Cys Ala Thr Gly Gly Ala Leu Lys Gly Tyr Gln
    1010            1015            1020

Ile Thr Asn Lys Phe Glu Ser Phe Lys Ser Met Ser Thr Gln Asn
    1025            1030            1035

Gly Phe Ile Phe Tyr Ile Pro Ala Trp Leu Thr Ser Lys Ile Asp
    1040            1045            1050

Pro Ser Thr Gly Phe Val Asn Leu Leu Lys Thr Lys Tyr Thr Ser
    1055            1060            1065

Ile Ala Asp Ser Lys Lys Phe Ile Ser Ser Phe Asp Arg Ile Met
    1070            1075            1080

Tyr Val Pro Glu Glu Asp Leu Phe Glu Phe Ala Leu Asp Tyr Lys
    1085            1090            1095

Asn Phe Ser Arg Thr Asp Ala Asp Tyr Ile Lys Lys Trp Lys Leu
    1100            1105            1110

Tyr Ser Tyr Gly Asn Arg Ile Arg Ile Phe Arg Asn Pro Lys Lys
    1115            1120            1125

Asn Asn Val Phe Asp Trp Glu Glu Val Cys Leu Thr Ser Ala Tyr
    1130            1135            1140

Lys Glu Leu Phe Asn Lys Tyr Gly Ile Asn Tyr Gln Gln Gly Asp
    1145            1150            1155

Ile Arg Ala Leu Leu Cys Glu Gln Ser Asp Lys Ala Phe Tyr Ser
    1160            1165            1170

Ser Phe Met Ala Leu Met Ser Leu Met Leu Gln Met Arg Asn Ser
    1175            1180            1185

Ile Thr Gly Arg Thr Asp Val Asp Phe Leu Ile Ser Pro Val Lys
    1190            1195            1200

Asn Ser Asp Gly Ile Phe Tyr Asp Ser Arg Asn Tyr Glu Ala Gln
    1205            1210            1215

Glu Asn Ala Ile Leu Pro Lys Asn Ala Asp Ala Asn Gly Ala Tyr
    1220            1225            1230

Asn Ile Ala Arg Lys Val Leu Trp Ala Ile Gly Gln Phe Lys Lys
    1235            1240            1245

Ala Glu Asp Glu Lys Leu Asp Lys Val Lys Ile Ala Ile Ser Asn
    1250            1255            1260

Lys Glu Trp Leu Glu Tyr Ala Gln Thr Ser Val Lys His Pro Lys
    1265            1270            1275

Lys Lys Arg Lys Val Leu Glu His His His His His
    1280            1285            1290

<210> SEQ ID NO 15
<211> LENGTH: 4071
<212> TYPE: DNA
<213> ORGANISM: Artificial Sequence
<220> FEATURE:
<223> OTHER INFORMATION: Synthetic DNA

<400> SEQUENCE: 15
atgggcaagc ccattcctaa tcctctgctg ggcctcgaca gcacagcccc taagaaaaag     60
cggaaagtgg gcatccatgg cgtgccagcc gccacacagt ttgagggctt caccaacctg    120
taccaggtgt ccaagacact gcgcttcgag ctgatccctc agggcaagac cctgaagcac    180
atccaagagc agggcttcat cgaagaggac aaggcccgga cgaccactac aaagagctg    240
```

```
aagcccatca tcgaccggat ctacaagacc tacgccgacc agtgtctgca gctggtgcag    300
ctcgattggg agaatctgag cgccgccatc gacagctacc ggaaagagaa aaccgaggaa    360
acccggaacg ccctgatcga ggaacaggcc acctacagaa cgccatcca cgactacttc     420
atcggccgga ccgacaacct gaccgacgcc atcaacaaga gacacgccga gatctataag    480
ggcctgttca aggccgagct gttcaacggc aaggtgctga agcagctggg caccgtgaca    540
accaccgagc acgaaaatgc cctgctgcgg agcttcgaca gttcaccac ctacttcagc     600
ggcttctacg agaaccggaa gaacgtgttc agcgccgagg acatcagcac cgccattcct    660
cacagaatct gcaggacaa cttccccaag ttcaaagaga actgccacat cttcacccgg     720
ctgatcacag ccgtgcctag cctgagagaa cacttcgaga cgtgaagaa ggccatcggc     780
atcttcgtgt ccaccagcat cgaggaagtg ttcagcttcc cattctacaa ccagctgctg    840
acccagacac agatcgacct gtataatcag ctgctcggcg gcatcagcag agaggccgga    900
acagagaaga tcaagggcct gaacgaagtg ctgaacctgg ccatccagaa gaacgacgag    960
acagcccaca tcattgccag cctgcctcac cggttcatcc ctctgttcaa gcagatcctg   1020
agcgacagaa acaccctgag cttcatcctg gaagagttca gtccgatga ggaagtgatc    1080
cagagcttct gcaagtataa gaccctgctg aggaacgaga atgtgctgga aaccgccgag   1140
gctctgttta cgagctgaa cagcatcgat ctgacccaca tctttatcag ccacaagaag    1200
ctcgagacaa tcagcagcgc cctgtgcgac cactgggata ccctgagaaa cgccctgtac   1260
gagcggagaa tcagcgagct gaccggcaag atcaccaaga cgccaaaga aaaggtgcag    1320
cggagcctga acacgagga tatcaacctg caagagatca tcagcgccgc tggcaaagaa   1380
ctgagcgagg cctttaagca gaaaaccagc gagatcctgt ctcacgccca cgctgctctt   1440
gatcagcctc tgcctaccac actgaagaag caagaggaaa aagagatcct gaagtcccag   1500
ctggacagcc tgctgggact gtaccatctg ctggattggt cgccgtgga cgagagcaat    1560
gaggtggacc ctgagttctc cgccagactg acaggcatca gctggaaat ggaacccagc    1620
ctgtccttct acaacaaggc cagaaactac gccaccaaga agccctacag cgtcgagaag   1680
ttcaagctca acttccagat gcctacactg gccagcggct gggacgtgaa caaagagaag   1740
aacaacggcg ccatcctgtt cgtgaagaac ggactgtact acctgggcat catgccaaag   1800
cagaagggca gatacaaggc cctgtccttt gagcccaccg aaaagaccag cgagggcttc   1860
gataagatgt actacgatta cttccccgac gccgccaaga tgatcccca gtgtagcaca   1920
cagctgaagg ccgtgaccgc tcactttcag acccacacca cctatcct gctgagcaac     1980
aacttcatcg agcccctgga aatcaccaaa gagatctacg acctgaacaa ccccgagaaa   2040
gagcccaaga agttccagac cgcctacgcc aagaaaaccg cgaccagaa gggctacaga   2100
gaagccctgt gcaagtggat cgactttacc cgggacttcc tgagcaagta caccaagacc   2160
acctccatcg acctgagcag cctgaggcct agcagccagt ataaggacct gggcgagtac   2220
tacgccgagc tgaatccact gctgtaccac atcagcttcc agcggatcgc cgaaaagaa    2280
atcatggacg ccgtggaaac cggcaagctg tacctgttcc agatatacaa caaagacttc   2340
gccaagggcc accacggcaa gcctaatctg cacaccctgt actggaccgg cctgtttagc   2400
cctgagaatc tggccaagac ctctatcaag ctgaacggcc aggccgaact gttttacaga   2460
cccaagagcc ggatgaagcg gatggcccac agactgggag agaagatgct gaacaagaaa   2520
ctgaaggacc agaaaacgcc cattccggac acactgtacc aagagctgta cgactacgtg   2580
```

```
aaccaccggc tgagccacga tctgagcgac gaagctagag cactgctgcc caacgtgatc    2640
acaaaagagg tgtcccacga gatcattaag gaccggcggt ttacctccga taagttcttc    2700
ttccacgtgc cgatcacact gaactaccag gccgccaact ctcccagcaa gttcaaccag    2760
agagtgaacg cctacctgaa agagcacccc gagacaccca tcattggcat cgacagaggc    2820
gagcggaacc tgatctacat caccgtgatc gactccacag gcaagatcct ggaacagcgg    2880
tccctgaaca ccatccagca gttcgactac agaagaagc tggacaaccg agagaaagaa    2940
agagtggccg ccagacaggc ttggagcgtt gtgggcacaa tcaaggatct gaagcagggc    3000
tacctgagcc aagtgattca cgagatcgtg gacctgatga tccactatca ggctgtggtg    3060
gtgctcgaga acctgaactt cggcttcaag agcaagcgga ccggaatcgc cgagaaagcc    3120
gtgtaccagc agtttgagaa aatgctgatc gacaagctga attgcctggt cctgaaggac    3180
taccccgctg agaaagttgg cggagtgctg aatccctacc agctgaccga tcagttcacc    3240
agctttgcca agatgggaac ccagagcggc ttcctgttct acgtgccagc tccttacacc    3300
tccaagatcg accctctgac cggcttcgtg gaccccttcg tgtggaaaac catcaagaac    3360
cacgagtccc ggaagcactt cctggaaggc tttgacttcc tgcactacga cgtgaaaaca    3420
ggcgatttca tcctgcactt caagatgaat cggaatctgt ccttccagag gggcctgcct    3480
ggcttcatgc ctgcttggga tatcgtgttc gagaagaatg agactcagtt cgacgccaag    3540 gggaccccctt ttatcgccgg caagagaatt gtgcctgtga tcgagaacca caggttcacc    3600
ggcagatacc gggatctgta ccccgccaat gagctgatcg ccctgctgga gagaagggc    3660 atcgtgttta gagatggcag caacatcctg cctaagctgc tggaaaacga cgacagccac    3720
gccatcgata ccatggtggc actgatcaga tccgtgctgc agatgcggaa cagcaatgcc    3780
gctaccggcg aggactacat caatagcccc gtgcgggatc tgaacggcgt gtgcttcgac    3840
agcagatttc agaaccccga gtggcctatg gatgccgacg ccaatggcgc ctatcacatt    3900
gccctgaaag acagctgct gctgaaccat ctgaaagaga gcaaggacct gaaactgcag    3960
aacggcatct ccaaccagga ctggctggcc tacattcaag agctgcggaa tcccaaaaag    4020
aaacggaaag tgaagctggc cgctgctctg gaacaccacc accatcacca t             4071
```

<210> SEQ ID NO 16
<211> LENGTH: 1357
<212> TYPE: PRT
<213> ORGANISM: Artificial Sequence
<220> FEATURE:
<223> OTHER INFORMATION: Synthetic Amino Acid Sequence

<400> SEQUENCE: 16

```
Met Gly Lys Pro Ile Pro Asn Pro Leu Leu Gly Leu Asp Ser Thr Ala
1               5                   10                  15

Pro Lys Lys Lys Arg Lys Val Gly Ile His Gly Val Pro Ala Ala Thr
            20                  25                  30

Gln Phe Glu Gly Phe Thr Asn Leu Tyr Gln Val Ser Lys Thr Leu Arg
        35                  40                  45

Phe Glu Leu Ile Pro Gln Gly Lys Thr Leu Lys His Ile Gln Glu Gln
    50                  55                  60

Gly Phe Ile Glu Glu Asp Lys Ala Arg Asn Asp His Tyr Lys Glu Leu
65                  70                  75                  80

Lys Pro Ile Ile Asp Arg Ile Tyr Lys Thr Tyr Ala Asp Gln Cys Leu
                85                  90                  95

Gln Leu Val Gln Leu Asp Trp Glu Asn Leu Ser Ala Ala Ile Asp Ser
```

```
                100              105              110
Tyr Arg Lys Glu Lys Thr Glu Glu Thr Arg Asn Ala Leu Ile Glu Glu
            115                  120                  125
Gln Ala Thr Tyr Arg Asn Ala Ile His Asp Tyr Phe Ile Gly Arg Thr
        130                  135                  140
Asp Asn Leu Thr Asp Ala Ile Asn Lys Arg His Ala Glu Ile Tyr Lys
145                  150                  155                  160
Gly Leu Phe Lys Ala Glu Leu Phe Asn Gly Lys Val Leu Lys Gln Leu
                165                  170                  175
Gly Thr Val Thr Thr Thr Glu His Glu Asn Ala Leu Leu Arg Ser Phe
            180                  185                  190
Asp Lys Phe Thr Thr Tyr Phe Ser Gly Phe Tyr Glu Asn Arg Lys Asn
        195                  200                  205
Val Phe Ser Ala Glu Asp Ile Ser Thr Ala Ile Pro His Arg Ile Val
        210                  215                  220
Gln Asp Asn Phe Pro Lys Phe Lys Glu Asn Cys His Ile Phe Thr Arg
225                  230                  235                  240
Leu Ile Thr Ala Val Pro Ser Leu Arg Glu His Phe Glu Asn Val Lys
                245                  250                  255
Lys Ala Ile Gly Ile Phe Val Ser Thr Ser Ile Glu Glu Val Phe Ser
                260                  265                  270
Phe Pro Phe Tyr Asn Gln Leu Leu Thr Gln Thr Gln Ile Asp Leu Tyr
            275                  280                  285
Asn Gln Leu Leu Gly Gly Ile Ser Arg Glu Ala Gly Thr Glu Lys Ile
        290                  295                  300
Lys Gly Leu Asn Glu Val Leu Asn Leu Ala Ile Gln Lys Asn Asp Glu
305                  310                  315                  320
Thr Ala His Ile Ile Ala Ser Leu Pro His Arg Phe Ile Pro Leu Phe
                325                  330                  335
Lys Gln Ile Leu Ser Asp Arg Asn Thr Leu Ser Phe Ile Leu Glu Glu
            340                  345                  350
Phe Lys Ser Asp Glu Glu Val Ile Gln Ser Phe Cys Lys Tyr Lys Thr
        355                  360                  365
Leu Leu Arg Asn Glu Asn Val Leu Glu Thr Ala Glu Ala Leu Phe Asn
        370                  375                  380
Glu Leu Asn Ser Ile Asp Leu Thr His Ile Phe Ile Ser His Lys Lys
385                  390                  395                  400
Leu Glu Thr Ile Ser Ser Ala Leu Cys Asp His Trp Asp Thr Leu Arg
                405                  410                  415
Asn Ala Leu Tyr Glu Arg Arg Ile Ser Glu Leu Thr Gly Lys Ile Thr
            420                  425                  430
Lys Ser Ala Lys Glu Lys Val Gln Arg Ser Leu Lys His Glu Asp Ile
            435                  440                  445
Asn Leu Gln Glu Ile Ile Ser Ala Ala Gly Lys Glu Leu Ser Glu Ala
        450                  455                  460
Phe Lys Gln Lys Thr Ser Glu Ile Leu Ser His Ala His Ala Ala Leu
465                  470                  475                  480
Asp Gln Pro Leu Pro Thr Thr Leu Lys Lys Gln Glu Glu Lys Glu Ile
            485                  490                  495
Leu Lys Ser Gln Leu Asp Ser Leu Leu Gly Leu Tyr His Leu Leu Asp
            500                  505                  510
Trp Phe Ala Val Asp Glu Ser Asn Glu Val Asp Pro Glu Phe Ser Ala
            515                  520                  525
```

```
Arg Leu Thr Gly Ile Lys Leu Glu Met Glu Pro Ser Leu Ser Phe Tyr
    530                 535                 540

Asn Lys Ala Arg Asn Tyr Ala Thr Lys Lys Pro Tyr Ser Val Glu Lys
545                 550                 555                 560

Phe Lys Leu Asn Phe Gln Met Pro Thr Leu Ala Ser Gly Trp Asp Val
                565                 570                 575

Asn Lys Glu Lys Asn Asn Gly Ala Ile Leu Phe Val Lys Asn Gly Leu
                580                 585                 590

Tyr Tyr Leu Gly Ile Met Pro Lys Gln Lys Gly Arg Tyr Lys Ala Leu
            595                 600                 605

Ser Phe Glu Pro Thr Glu Lys Thr Ser Glu Gly Phe Asp Lys Met Tyr
    610                 615                 620

Tyr Asp Tyr Phe Pro Asp Ala Ala Lys Met Ile Pro Lys Cys Ser Thr
625                 630                 635                 640

Gln Leu Lys Ala Val Thr Ala His Phe Gln Thr His Thr Thr Pro Ile
                645                 650                 655

Leu Leu Ser Asn Asn Phe Ile Glu Pro Leu Glu Ile Thr Lys Glu Ile
                660                 665                 670

Tyr Asp Leu Asn Asn Pro Glu Lys Glu Pro Lys Lys Phe Gln Thr Ala
            675                 680                 685

Tyr Ala Lys Lys Thr Gly Asp Gln Lys Gly Tyr Arg Glu Ala Leu Cys
690                 695                 700

Lys Trp Ile Asp Phe Thr Arg Asp Phe Leu Ser Lys Tyr Thr Lys Thr
705                 710                 715                 720

Thr Ser Ile Asp Leu Ser Ser Leu Arg Pro Ser Ser Gln Tyr Lys Asp
                725                 730                 735

Leu Gly Glu Tyr Tyr Ala Glu Leu Asn Pro Leu Leu Tyr His Ile Ser
            740                 745                 750

Phe Gln Arg Ile Ala Glu Lys Glu Ile Met Asp Ala Val Glu Thr Gly
    755                 760                 765

Lys Leu Tyr Leu Phe Gln Ile Tyr Asn Lys Asp Phe Ala Lys Gly His
    770                 775                 780

His Gly Lys Pro Asn Leu His Thr Leu Tyr Trp Thr Gly Leu Phe Ser
785                 790                 795                 800

Pro Glu Asn Leu Ala Lys Thr Ser Ile Lys Leu Asn Gly Gln Ala Glu
                805                 810                 815

Leu Phe Tyr Arg Pro Lys Ser Arg Met Lys Arg Met Ala His Arg Leu
                820                 825                 830

Gly Glu Lys Met Leu Asn Lys Lys Leu Lys Asp Gln Lys Thr Pro Ile
    835                 840                 845

Pro Asp Thr Leu Tyr Gln Glu Leu Tyr Asp Tyr Val Asn His Arg Leu
    850                 855                 860

Ser His Asp Leu Ser Asp Glu Ala Arg Ala Leu Leu Pro Asn Val Ile
865                 870                 875                 880

Thr Lys Glu Val Ser His Glu Ile Ile Lys Asp Arg Arg Phe Thr Ser
                885                 890                 895

Asp Lys Phe Phe Phe His Val Pro Ile Thr Leu Asn Tyr Gln Ala Ala
                900                 905                 910

Asn Ser Pro Ser Lys Phe Asn Gln Arg Val Asn Ala Tyr Leu Lys Glu
            915                 920                 925

His Pro Glu Thr Pro Ile Ile Gly Ile Asp Arg Gly Glu Arg Asn Leu
    930                 935                 940
```

-continued

Ile Tyr Ile Thr Val Ile Asp Ser Thr Gly Lys Ile Leu Glu Gln Arg
945                 950                 955                 960

Ser Leu Asn Thr Ile Gln Gln Phe Asp Tyr Gln Lys Lys Leu Asp Asn
            965                 970                 975

Arg Glu Lys Glu Arg Val Ala Ala Arg Gln Ala Trp Ser Val Val Gly
            980                 985                 990

Thr Ile Lys Asp Leu Lys Gln Gly Tyr Leu Ser Gln Val Ile His Glu
        995                 1000                1005

Ile Val Asp Leu Met Ile His Tyr Gln Ala Val Val Val Leu Glu
    1010                1015                1020

Asn Leu Asn Phe Gly Phe Lys Ser Lys Arg Thr Gly Ile Ala Glu
    1025                1030                1035

Lys Ala Val Tyr Gln Gln Phe Glu Lys Met Leu Ile Asp Lys Leu
    1040                1045                1050

Asn Cys Leu Val Leu Lys Asp Tyr Pro Ala Glu Lys Val Gly Gly
    1055                1060                1065

Val Leu Asn Pro Tyr Gln Leu Thr Asp Gln Phe Thr Ser Phe Ala
    1070                1075                1080

Lys Met Gly Thr Gln Ser Gly Phe Leu Phe Tyr Val Pro Ala Pro
    1085                1090                1095

Tyr Thr Ser Lys Ile Asp Pro Leu Thr Gly Phe Val Asp Pro Phe
    1100                1105                1110

Val Trp Lys Thr Ile Lys Asn His Glu Ser Arg Lys His Phe Leu
    1115                1120                1125

Glu Gly Phe Asp Phe Leu His Tyr Asp Val Lys Thr Gly Asp Phe
    1130                1135                1140

Ile Leu His Phe Lys Met Asn Arg Asn Leu Ser Phe Gln Arg Gly
    1145                1150                1155

Leu Pro Gly Phe Met Pro Ala Trp Asp Ile Val Phe Glu Lys Asn
    1160                1165                1170

Glu Thr Gln Phe Asp Ala Lys Gly Thr Pro Phe Ile Ala Gly Lys
    1175                1180                1185

Arg Ile Val Pro Val Ile Glu Asn His Arg Phe Thr Gly Arg Tyr
    1190                1195                1200

Arg Asp Leu Tyr Pro Ala Asn Glu Leu Ile Ala Leu Leu Glu Glu
    1205                1210                1215

Lys Gly Ile Val Phe Arg Asp Gly Ser Asn Ile Leu Pro Lys Leu
    1220                1225                1230

Leu Glu Asn Asp Asp Ser His Ala Ile Asp Thr Met Val Ala Leu
    1235                1240                1245

Ile Arg Ser Val Leu Gln Met Arg Asn Ser Asn Ala Ala Thr Gly
    1250                1255                1260

Glu Asp Tyr Ile Asn Ser Pro Val Arg Asp Leu Asn Gly Val Cys
    1265                1270                1275

Phe Asp Ser Arg Phe Gln Asn Pro Glu Trp Pro Met Asp Ala Asp
    1280                1285                1290

Ala Asn Gly Ala Tyr His Ile Ala Leu Lys Gly Gln Leu Leu Leu
    1295                1300                1305

Asn His Leu Lys Glu Ser Lys Asp Leu Lys Leu Gln Asn Gly Ile
    1310                1315                1320

Ser Asn Gln Asp Trp Leu Ala Tyr Ile Gln Glu Leu Arg Asn Pro
    1325                1330                1335

Lys Lys Lys Arg Lys Val Lys Leu Ala Ala Ala Leu Glu His His

His His  His His
     1355

<210> SEQ ID NO 17
<211> LENGTH: 3873
<212> TYPE: DNA
<213> ORGANISM: Artificial Sequence
<220> FEATURE:
<223> OTHER INFORMATION: Synthetic DNA

<400> SEQUENCE: 17

| | | | | | |
|---|---|---|---|---|---|
| atgggcaagc | ccattcctaa | tcctctgctg | ggcctcgaca | gcacagcccc | taagaaaaag | 60 |
| cggaaagtgg | gcatccatgg | cgtgccagcc | gctctgaaga | atgtgggcat | cgacagactg | 120 |
| gacgtggaaa | agggcagaaa | gaacatgagc | aagctcgaga | agttcaccaa | ctgctacagc | 180 |
| ctgagcaaga | ccctgcggtt | caaggccatt | cctgtgggca | agacccaaga | gaacatcgac | 240 |
| aacaagcggc | tgctggtgga | agatgagaag | agagccgagg | actacaaggg | cgtgaagaag | 300 |
| ctgctggacc | ggtactacct | gagcttcatc | aacgacgtgc | tgcacagcat | caagctgaag | 360 |
| aacctgaaca | actacatcag | cctgttccgg | aagaaaaccc | ggaccgagaa | agagaacaaa | 420 |
| gagctggaaa | acctcgagat | caacctgcgg | aaagagatcg | ccaaggcctt | caagggcaac | 480 |
| gagggctaca | gagcctgtt | caagaaggac | atcatcgaga | caatcctgcc | tgagttcctg | 540 |
| gacgacaagg | acgagatcgc | cctggtcaac | agcttcaacg | gcttcacaac | cgccttcacc | 600 |
| ggcttttttcg | acaaccgcga | gaatatgttc | agcgaggaag | ccaagagcac | tctctatcgcc | 660 |
| ttccggtgca | tcaacgagaa | tctgacccgg | tacatcagca | acatggatat | cttcgagaag | 720 |
| gtggacgcca | tcttcgacaa | gcacgaggtg | caagagatca | agaaaaagat | cctgaacagc | 780 |
| gactacgacg | tcgaggactt | cttcgagggc | gagttcttca | acttcgtgct | gacacaagag | 840 |
| ggcatcgatg | tgtacaacgc | catcatcggc | ggcttcgtga | cagagagcgg | cgagaagatc | 900 |
| aagggcctga | cgagtacat | caacctctac | aaccagaaaa | cgaagcagaa | gctgcccaag | 960 |
| ttcaagcccc | tgtacaaaca | ggtgctgagc | gacagagaga | gcctgtcctt | ttacggcgag | 1020 |
| ggctatacca | gcgacgaaga | ggtgctggaa | gtgttcagaa | acaccctgaa | caagaacagc | 1080 |
| gagatcttca | gctccatcaa | gaagctcgaa | aagctgttta | gaacttcga | cgagtacagc | 1140 |
| agcgccggca | tcttcgtgaa | aatggccct | gccatcagca | ccatctccaa | ggacatcttc | 1200 |
| ggcgagtgga | acgtgatccg | ggacaagtgg | aacgccgagt | acgacgacat | ccacctgaag | 1260 |
| aaaaaggccg | tggtcaccga | gaagtacgag | gacgacagaa | gaaagagctt | caagaagatc | 1320 |
| ggcagcttca | gcctggaaca | gctgcaagag | tacgccgacg | ccgatctgag | cgtggtggaa | 1380 |
| aagctgaaag | agattatcat | ccagaaggtc | gacgagatct | acaaggtgta | cggcagcagc | 1440 |
| gagaagctgt | tcgacgccga | ctttgtgctg | gaaaagagcc | tcaaaaagaa | cgacgccgtg | 1500 |
| gtggccatca | tgaaggacct | gctggatagc | gtgaagtcct | tcgagaacta | tattaaggcc | 1560 |
| ttctttggcg | agggcaaaga | gacaaaccgg | gacgagagct | tctacggcga | tttcgtgctg | 1620 |
| gcctacgaca | tcctgctgaa | agtggaccac | atctacgacg | ccatccggaa | ctacgtgacc | 1680 |
| cagaagcctt | tacagcaagga | caagtttaag | ctgtacttcc | agaatccgca | gttcatgggc | 1740 |
| ggctgggaca | agacaaaga | aaccgactac | cgggccacca | tcctgagata | cggctccaag | 1800 |
| tactatctgg | ccattatgga | caagaaatac | gccaagtgcc | tgcagaagat | cgataaggac | 1860 |
| gacgtgaacg | gcaactacga | gaagattaac | tacaagctgc | tgcccggacc | taacaagatg | 1920 |

| | |
|---|---|
| ctgcctaagg tgttctttag caagaaatgg atggcctact acaaccccag cgaggatatc | 1980 |
| cagaaaatct acaagaacgg caccttcaag aaaggcgaca tgttcaacct gaacgactgc | 2040 |
| cacaagctga tcgatttctt caaggacagc atcagcagat accccaagtg gtccaacgcc | 2100 |
| tacgacttca atttcagcga cacagagaag tataaggata tcgccgggtt ctaccgcgag | 2160 |
| gtggaagaac agggctataa ggtgtccttt gagagcgcca gcaagaaaga ggtggacaag | 2220 |
| ctggtcgaag agggcaagct gtacatgttc cagatctata acaaggactt ctccgacaag | 2280 |
| agccacggca cccctaacct gcacaccatg tactttaagc tgctgttcga tgagaacaac | 2340 |
| cacggccaga tcagactgtc tggcggagcc gagctgtttta tgagaagggc cagcctgaaa | 2400 |
| aaagaggaac tggtcgttca ccccgccaac tctccaatcg ccaacaagaa ccccgacaat | 2460 |
| cccaagaaaa ccaccacact gagctacgac gtgtacaagg ataagcggtt ctccgaggac | 2520 |
| cagtacgagc tgcacatccc tatcgccatc aacaagtgcc ccaagaatat cttcaagatc | 2580 |
| aacaccgaag tgcgggtgct gctgaagcac gacgacaacc cttacgtgat cggcatcgat | 2640 |
| cggggcgaga gaaacctgct gtatatcgtg gtggtggacg gcaagggcaa tatcgtggaa | 2700 |
| cagtactccc tgaatgagat catcaacaac ttcaatggca tccggatcaa gacggactac | 2760 |
| cacagcctgc tggacaaaaa agagaaagaa cgcttcgagg ccaggcagaa ctggaccagc | 2820 |
| atcgagaaca tcaaagaact gaaggccggc tacatctccc aggtggtgca agatctgc | 2880 |
| gagctggttg agaagtatga cgccgtgatt gccctggaag atctgaatag cggctttaag | 2940 |
| aacagccgcg tgaaggtcga gaaacaggtg taccagaaat tcgagaagat gctgatcgac | 3000 |
| aagctgaact acatggtcga caagaagtct aaccccgcg ccacaggcgg agccctgaag | 3060 |
| ggatatcaga tcaccaacaa gttcgagtcc ttcaagagca tgagcaccca gaatggcttc | 3120 |
| atcttctaca tccccgcctg gctgaccagc aagatcgatc ctagcaccgg attcgtgaac | 3180 |
| ctgctcaaga ccaagtacac cagcattgcc gacagcaaga gttcatctc cagcttcgac | 3240 |
| cggattatgt acgtgcccga agaggacctg ttcgaattcg ccctggatta caagaacttc | 3300 |
| agccggaccg atgccgacta tatcaagaag tggaagctgt atagctacgg caaccgcatc | 3360 |
| cgcatcttca gaaacccgaa gaaaacaac gtgttcgact gggaagaagt gtgcctgacc | 3420 |
| agcgcctaca aagaactctt caacaaatac ggcatcaact accagcaggg cgacatcaga | 3480 |
| gccctgctgt gcgagcagag cgacaaggcc ttttacagct ccttcatggc cctgatgagc | 3540 |
| ctgatgctgc agatgcggaa tagcatcacc ggcagaaccg acgtggactt cctgatcagc | 3600 |
| cccgtgaaaa actccgacgg catcttttac gacagccgga attcgaggc tcaagagaac | 3660 |
| gccatcctgc ctaagaacgc cgatgccaac ggcgcctata atatcgccag aaaggtgctg | 3720 |
| tgggccatcg ccagtttaa gaaggccgag gacgagaaac tggacaaagt gaagatcgcc | 3780 |
| atctctaaca aagagtggct ggaatacgcc cagaccagcg tgaagcaccc caaaaagaaa | 3840 |
| cggaaagtgc tggaacacca ccaccatcac cac | 3873 |

```
<210> SEQ ID NO 18
<211> LENGTH: 4092
<212> TYPE: DNA
<213> ORGANISM: Artificial Sequence
<220> FEATURE:
<223> OTHER INFORMATION: Synthetic DNA

<400> SEQUENCE: 18
```

| | |
|---|---|
| atgacccagt tgaaggtttt caccaatctg tatcaggtta gcaaaccct gcgttttgaa | 60 |
| ctgattccgc agggtaaaac cctgaaacat attcaagaac agggcttcat cgaagaggat | 120 |

```
aaagcacgta acgatcacta caaagaactg aaaccgatta tcgaccgcat ctataaaacc    180
tatgcagatc agtgtctgca gctggttcag ctggattggg aaaatctgag cgcagcaatt    240
gatagttatc gcaaagaaaa aaccgaagaa acccgtaatg cactgattga agaacaggca    300
acctatcgta atgccatcca tgattatttc attggtcgta ccgataatct gaccgatgca    360
attaacaaac gtcacgccga atctataaa ggcctgttta agccgaact gtttaatggc    420 aaagttctga acagctggg caccgttacc accaccgaac atgaaaatgc actgctgcgt    480
agctttgata aattcaccac ctatttcagc ggcttttatg agaatcgcaa aaacgtgttt    540
agcgcagaag atattagcac cgcaattccg catcgtattg tgcaggataa tttcccgaaa    600
ttcaaagaga actgccacat ttttacccgt ctgattaccg cagttccgag cctgcgtgaa    660
cattttgaaa acgttaaaaa agccatcggc atctttgtta gcaccagcat tgaagaagtt    720
tttagcttcc cgttttacaa tcagctgctg acccagaccc agattgatct gtataaccaa    780
ctgctgggtg gtattagccg tgaagcaggc accgaaaaaa tcaaaggtct gaatgaagtg    840
ctgaatctgg ccattcagaa aaatgatgaa accgcacata ttattgcaag cctgccgcat    900
cgttttattc cgctgttcaa acaaattctg agcgatcgta ataccctgag ctttattctg    960
gaagaattca atccgatga agaggtgatt cagagctttt gcaaatacaa aacgctgctg   1020
cgcaatgaaa atgttctgga aactgccgaa gcactgttta cgaactgaa tagcattgat   1080 ctgacccaca tctttatcag ccacaaaaaa ctggaaacca tttcaagcgc actgtgtgat   1140
cattgggata ccctgcgtaa tgccctgtat gaacgtcgta ttagcgaact gaccggtaaa   1200
attaccaaaa gcgcgaaaga aaagttcag cgcagtctga acatgagga tattaatctg   1260 caagagatta ttagcgcagc cggtaaagaa ctgtcagaag catttaaaca gaaaaccagc   1320
gaaattctgt cacatgcaca tgcagcactg gatcagccgc tgccgaccac cctgaaaaaa   1380
caagaagaaa aagaaatcct gaaaagccag ctggatagcc tgctgggtct gtatcatctg   1440
ctggactggt ttgcagttga tgaaagcaat gaagttgatc cggaatttag cgcacgtctg   1500
accggcatta aactggaaat ggaaccgagc ctgagctttt ataacaaagc ccgtaattat   1560
gccaccaaaa aaccgtatag cgtcgaaaaa ttcaaactga actttcagat gccgaccctg   1620
gcaagcggtt gggatgttaa taagaaaaa aacaacggtg ccatcctgtt cgtgaaaaat   1680
ggcctgtatt atctgggtat tatgccgaaa cagaaaggtc gttataaagc gctgagcttt   1740
gaaccgacgg aaaaaaccag tgaaggtttt gataaaatgt actacgacta ttttccggat   1800
gcagccaaaa tgattccgaa atgtagcacc cagctgaaag cagttaccgc acattttcag   1860
acccatacca ccccgattct gctgagcaat aactttattg aaccgctgga atcaccaaa   1920 gagatctacg atctgaataa cccggaaaaa gagccgaaaa aattccagac cgcatatgca   1980
aaaaaaaccg gtgatcagaa aggttatcgt gaagcgctgt gtaaatggat tgatttcacc   2040
cgtgattttc tgagcaaata caccaaaaacc accagtatcg atctgagcag cctgcgtccg   2100
agcagccagt ataaagatct gggcgaatat tatgcagaaac tgaatccgct gctgtatcat   2160
attagctttc agcgtattgc cgagaaagaa atcatggacg cagttgaaac cggtaaactg   2220
tacctgttcc agatctacaa taagattttt gccaaaggcc atcatggcaa accgaatctg   2280
cataccctgt attggaccgg tctgtttagc cctgaaaatc tggcaaaaac ctcgattaaa   2340
ctgaatggtc aggcggaact gttttatcgt ccgaaaagcc gtatgaaacg tatggcacat   2400
cgtctgggtg aaaaaatgct gaacaaaaaa ctgaaagacc agaaaacccc gatcccggat   2460
```

```
acactgtatc aagaactgta tgattatgtg aaccatcgtc tgagccatga tctgagtgat    2520
gaagcacgtg ccctgctgcc gaatgttatt accaaagaag ttagccacga gatcattaaa    2580
gatcgtcgtt ttaccagcga caaattcttt tttcatgtgc cgattaccct gaattatcag    2640
gcagcaaata gcccgagcaa atttaaccag cgtgttaatg catatctgaa agaacatcca    2700
gaaacgccga ttattggtat tgatcgtggt gaacgtaacc tgatttatat caccgttatt    2760
gatagcaccg gcaaaatcct ggaacagcgt agcctgaata ccattcagca gtttgattac    2820
cagaaaaaac tggataatcg cgagaaagaa cgtgttgcag cacgtcaggc atggtcagtt    2880
gttggtacaa ttaaagacct gaaacagggt tatctgagcc aggttattca tgaaattgtg    2940
gatctgatga ttcactatca ggccgttgtt gtgctggaaa acctgaattt tggctttaaa    3000
agcaaacgta ccggcattgc agaaaaagca gtttatcagc agttcgagaa aatgctgatt    3060
gacaaactga attgcctggt gctgaaagat tatccggctg aaaaagttgg tggtgttctg    3120
aatccgtatc agctgaccga tcagtttacc agctttgcaa aaatgggcac ccagagcgga    3180
tttctgtttt atgttccggc accgtatacg agcaaaattg atccgctgac cggttttgtt    3240
gatccgtttg tttggaaaac catcaaaaac catgaaagcc gcaaacattt tctggaaggt    3300
ttcgattttc tgcattacga cgttaaaacg ggtgatttca tcctgcactt taaaatgaat    3360
cgcaatctga gttttcagcg tggcctgcct ggttttatgc ctgcatggga tattgtgttt    3420
gagaaaaacg aaacacagtt cgatgcaaaa ggcaccccgt ttattgcagg taaacgtatt    3480
gttccggtga ttgaaaatca tcgtttcacc ggtcgttatc gcgatctgta tccggcaaat    3540
gaactgatcg cactgctgga agagaaaggt attgtttttc gtgatggctc aaacattctg    3600
ccgaaactgc tggaaaatga tgatagccat gcaattgata ccatggttgc actgattcgt    3660
agcgttctgc agatgcgtaa tagcaatgca gcaaccggtg aagattacat taatagtccg    3720
gttcgtgatc tgaatggtgt ttgttttgat agccgttttc agaatccgga atggccgatg    3780
gatgcagatg caaatggtgc atatcatatt gcactgaaag acagctgct gctgaaccac    3840
ctgaaagaaa gcaaagatct gaaactgcaa aacggcatta gcaatcagga ttggctggca    3900
tatatccaag aactgcgtaa cggtcgtagc agtgatgatg aagcaaccgc agatagccag    3960
catgcagcac cgcctaaaaa gaaacgtaaa gttggtggta gcggtggttc aggtggtagt    4020
ggcggtagtg gtggctcagg gggttctggt ggctctggtg gtagcctcga gcaccaccac    4080
caccaccact ga                                                         4092
```

<210> SEQ ID NO 19
<211> LENGTH: 1363
<212> TYPE: PRT
<213> ORGANISM: Artificial Sequence
<220> FEATURE:
<223> OTHER INFORMATION: Synthetic Amino Acid Sequence

<400> SEQUENCE: 19

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile

```
            65                  70                  75                  80
Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
            115                 120                 125

Tyr Lys Gly Leu Phe Lys Ala Glu Leu Phe Asn Gly Lys Val Leu Lys
            130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
            210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
            370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
            450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495
```

```
Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
            530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
            565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
            645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
            770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
            835                 840                 845

Val Ile Thr Lys Glu Val Ser His Glu Ile Ile Lys Asp Arg Arg Phe
            850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
            900                 905                 910
```

```
Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
        930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
            995                1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn Gly
    1295                1300                1305

Arg Ser Ser Asp Asp Glu Ala Thr Ala Asp Ser Gln His Ala Ala
```

```
            1310                1315                1320

Pro Pro Lys Lys Lys Arg Lys Val Gly Gly Ser Gly Gly Ser Gly
        1325                1330                1335

Gly Ser Gly Gly Ser Gly Gly Ser Gly Ser Gly Gly Ser Gly
    1340                1345                1350

Gly Ser Leu Glu His His His His His His
    1355                1360

<210> SEQ ID NO 20
<211> LENGTH: 1281
<212> TYPE: PRT
<213> ORGANISM: Artificial Sequence
<220> FEATURE:
<223> OTHER INFORMATION: Synthetic Amino Acid Sequence

<400> SEQUENCE: 20

Met Gly Asp Pro Leu Lys Asn Val Gly Ile Asp Arg Leu Asp Val Glu
1               5                   10                  15

Lys Gly Arg Lys Asn Met Ser Lys Leu Glu Lys Phe Thr Asn Cys Tyr
            20                  25                  30

Ser Leu Ser Lys Thr Leu Arg Phe Lys Ala Ile Pro Val Gly Lys Thr
        35                  40                  45

Gln Glu Asn Ile Asp Asn Lys Arg Leu Leu Val Glu Asp Glu Lys Arg
    50                  55                  60

Ala Glu Asp Tyr Lys Gly Val Lys Lys Leu Leu Asp Arg Tyr Tyr Leu
65                  70                  75                  80

Ser Phe Ile Asn Asp Val Leu His Ser Ile Lys Leu Lys Asn Leu Asn
                85                  90                  95

Asn Tyr Ile Ser Leu Phe Arg Lys Lys Thr Arg Thr Glu Lys Glu Asn
            100                 105                 110

Lys Glu Leu Glu Asn Leu Glu Ile Asn Leu Arg Lys Glu Ile Ala Lys
        115                 120                 125

Ala Phe Lys Gly Asn Glu Gly Tyr Lys Ser Leu Phe Lys Lys Asp Ile
    130                 135                 140

Ile Glu Thr Ile Leu Pro Glu Phe Leu Asp Asp Lys Asp Glu Ile Ala
145                 150                 155                 160

Leu Val Asn Ser Phe Asn Gly Phe Thr Thr Ala Phe Thr Gly Phe Phe
                165                 170                 175

Asp Asn Arg Glu Asn Met Phe Ser Glu Glu Ala Lys Ser Thr Ser Ile
            180                 185                 190

Ala Phe Arg Cys Ile Asn Glu Asn Leu Thr Arg Tyr Ile Ser Asn Met
        195                 200                 205

Asp Ile Phe Glu Lys Val Asp Ala Ile Phe Asp Lys His Glu Val Gln
    210                 215                 220

Glu Ile Lys Glu Lys Ile Leu Asn Ser Asp Tyr Asp Val Glu Asp Phe
225                 230                 235                 240

Phe Glu Gly Glu Phe Phe Asn Phe Val Leu Thr Gln Glu Gly Ile Asp
                245                 250                 255

Val Tyr Asn Ala Ile Ile Gly Gly Phe Val Thr Glu Ser Gly Glu Lys
            260                 265                 270

Ile Lys Gly Leu Asn Glu Tyr Ile Asn Leu Tyr Asn Gln Lys Thr Lys
        275                 280                 285

Gln Lys Leu Pro Lys Phe Lys Pro Leu Tyr Lys Gln Val Leu Ser Asp
    290                 295                 300

Arg Glu Ser Leu Ser Phe Tyr Gly Glu Gly Tyr Thr Ser Asp Glu Glu
```

```
            305                 310                 315                 320
        Val Leu Glu Val Phe Arg Asn Thr Leu Asn Lys Asn Ser Glu Ile Phe
                        325                 330                 335

Ser Ser Ile Lys Lys Leu Glu Lys Leu Phe Lys Asn Phe Asp Glu Tyr
                        340                 345                 350

Ser Ser Ala Gly Ile Phe Val Lys Asn Gly Pro Ala Ile Ser Thr Ile
                        355                 360                 365

Ser Lys Asp Ile Phe Gly Glu Trp Asn Val Ile Arg Asp Lys Trp Asn
                        370                 375                 380

Ala Glu Tyr Asp Asp Ile His Leu Lys Lys Ala Val Val Thr Glu
        385                 390                 395                 400

Lys Tyr Glu Asp Asp Arg Arg Lys Ser Phe Lys Lys Ile Gly Ser Phe
                        405                 410                 415

Ser Leu Glu Gln Leu Gln Glu Tyr Ala Asp Ala Asp Leu Ser Val Val
                        420                 425                 430

Glu Lys Leu Lys Glu Ile Ile Ile Gln Lys Val Asp Glu Ile Tyr Lys
                        435                 440                 445

Val Tyr Gly Ser Ser Glu Lys Leu Phe Asp Ala Asp Phe Val Leu Glu
                        450                 455                 460

Lys Ser Leu Lys Lys Asn Asp Ala Val Val Ala Ile Met Lys Asp Leu
        465                 470                 475                 480

Leu Asp Ser Val Lys Ser Phe Glu Asn Tyr Ile Lys Ala Phe Phe Gly
                        485                 490                 495

Glu Gly Lys Glu Thr Asn Arg Asp Glu Ser Phe Tyr Gly Asp Phe Val
                        500                 505                 510

Leu Ala Tyr Asp Ile Leu Leu Lys Val Asp His Ile Tyr Asp Ala Ile
                        515                 520                 525

Arg Asn Tyr Val Thr Gln Lys Pro Tyr Ser Lys Asp Lys Phe Lys Leu
                        530                 535                 540

Tyr Phe Gln Asn Pro Gln Phe Met Gly Gly Trp Asp Lys Asp Lys Glu
        545                 550                 555                 560

Thr Asp Tyr Arg Ala Thr Ile Leu Arg Tyr Gly Ser Lys Tyr Tyr Leu
                        565                 570                 575

Ala Ile Met Asp Lys Lys Tyr Ala Lys Cys Leu Gln Lys Ile Asp Lys
                        580                 585                 590

Asp Asp Val Asn Gly Asn Tyr Glu Lys Ile Asn Tyr Lys Leu Leu Pro
                        595                 600                 605

Gly Pro Asn Lys Met Leu Pro Lys Val Phe Phe Ser Lys Lys Trp Met
        610                 615                 620

Ala Tyr Tyr Asn Pro Ser Glu Asp Ile Gln Lys Ile Tyr Lys Asn Gly
        625                 630                 635                 640

Thr Phe Lys Lys Gly Asp Met Phe Asn Leu Asn Asp Cys His Lys Leu
                        645                 650                 655

Ile Asp Phe Phe Lys Asp Ser Ile Ser Arg Tyr Pro Lys Trp Ser Asn
                        660                 665                 670

Ala Tyr Asp Phe Asn Phe Ser Glu Thr Glu Lys Tyr Lys Asp Ile Ala
                        675                 680                 685

Gly Phe Tyr Arg Glu Val Glu Glu Gln Gly Tyr Lys Val Ser Phe Glu
                        690                 695                 700

Ser Ala Ser Lys Lys Glu Val Asp Lys Leu Val Glu Glu Gly Lys Leu
        705                 710                 715                 720

Tyr Met Phe Gln Ile Tyr Asn Lys Asp Phe Ser Asp Lys Ser His Gly
                        725                 730                 735
```

```
Thr Pro Asn Leu His Thr Met Tyr Phe Lys Leu Leu Phe Asp Glu Asn
            740                 745                 750

Asn His Gly Gln Ile Arg Leu Ser Gly Gly Ala Glu Leu Phe Met Arg
            755                 760                 765

Arg Ala Ser Leu Lys Lys Glu Glu Leu Val Val His Pro Ala Asn Ser
            770                 775             780

Pro Ile Ala Asn Lys Asn Pro Asp Asn Pro Lys Lys Thr Thr Thr Leu
785                 790                 795                 800

Ser Tyr Asp Val Tyr Lys Asp Lys Arg Phe Ser Glu Asp Gln Tyr Glu
                805                 810                 815

Leu His Ile Pro Ile Ala Ile Asn Lys Cys Pro Lys Asn Ile Phe Lys
            820                 825                 830

Ile Asn Thr Glu Val Arg Val Leu Leu Lys His Asp Asp Asn Pro Tyr
            835                 840                 845

Val Ile Gly Ile Asp Arg Gly Glu Arg Asn Leu Leu Tyr Ile Val Val
            850                 855                 860

Val Asp Gly Lys Gly Asn Ile Val Glu Gln Tyr Ser Leu Asn Glu Ile
865                 870                 875                 880

Ile Asn Asn Phe Asn Gly Ile Arg Ile Lys Thr Asp Tyr His Ser Leu
            885                 890                 895

Leu Asp Lys Lys Glu Lys Glu Arg Phe Glu Ala Arg Gln Asn Trp Thr
            900                 905                 910

Ser Ile Glu Asn Ile Lys Glu Leu Lys Ala Gly Tyr Ile Ser Gln Val
            915                 920                 925

Val His Lys Ile Cys Glu Leu Val Glu Lys Tyr Asp Ala Val Ile Ala
            930                 935                 940

Leu Glu Asp Leu Asn Ser Gly Phe Lys Asn Ser Arg Val Lys Val Glu
945                 950                 955                 960

Lys Gln Val Tyr Gln Lys Phe Glu Lys Met Leu Ile Asp Lys Leu Asn
                965                 970                 975

Tyr Met Val Asp Lys Lys Ser Asn Pro Cys Ala Thr Gly Gly Ala Leu
            980                 985                 990

Lys Gly Tyr Gln Ile Thr Asn Lys Phe Glu Ser Phe Lys Ser Met Ser
            995                 1000                1005

Thr Gln Asn Gly Phe Ile Phe Tyr Ile Pro Ala Trp Leu Thr Ser
     1010                1015                1020

Lys Ile Asp Pro Ser Thr Gly Phe Val Asn Leu Leu Lys Thr Lys
     1025                1030                1035

Tyr Thr Ser Ile Ala Asp Ser Lys Lys Phe Ile Ser Ser Phe Asp
     1040                1045                1050

Arg Ile Met Tyr Val Pro Glu Glu Asp Leu Phe Glu Phe Ala Leu
     1055                1060                1065

Asp Tyr Lys Asn Phe Ser Arg Thr Asp Ala Asp Tyr Ile Lys Lys
     1070                1075                1080

Trp Lys Leu Tyr Ser Tyr Gly Asn Arg Ile Arg Ile Phe Arg Asn
     1085                1090                1095

Pro Lys Lys Asn Asn Val Phe Asp Trp Glu Glu Val Cys Leu Thr
     1100                1105                1110

Ser Ala Tyr Lys Glu Leu Phe Asn Lys Tyr Gly Ile Asn Tyr Gln
     1115                1120                1125

Gln Gly Asp Ile Arg Ala Leu Leu Cys Glu Gln Ser Asp Lys Ala
     1130                1135                1140
```

| | | | | | | | | | | | |
|---|---|---|---|---|---|---|---|---|---|---|---|
|Phe|Tyr|Ser|Ser|Phe|Met|Ala|Leu|Met|Ser|Leu|Met|Leu|Gln|Met|
| |1145| | | |1150| | | |1155| | |

Arg Asn Ser Ile Thr Gly Arg Thr Asp Val Asp Phe Leu Ile Ser
    1160                1165                1170

Pro Val Lys Asn Ser Asp Gly Ile Phe Tyr Asp Ser Arg Asn Tyr
    1175                1180                1185

Glu Ala Gln Glu Asn Ala Ile Leu Pro Lys Asn Ala Asp Ala Asn
    1190                1195                1200

Gly Ala Tyr Asn Ile Ala Arg Lys Val Leu Trp Ala Ile Gly Gln
    1205                1210                1215

Phe Lys Lys Ala Glu Asp Glu Lys Leu Asp Lys Val Lys Ile Ala
    1220                1225                1230

Ile Ser Asn Lys Glu Trp Leu Glu Tyr Ala Gln Thr Ser Val Lys
    1235                1240                1245

His Gly Arg Ser Ser Asp Asp Glu Ala Thr Ala Asp Ser Gln His
    1250                1255                1260

Ala Ala Pro Pro Lys Lys Lys Arg Lys Val Leu Glu His His His
    1265                1270                1275

His His His
    1280

<210> SEQ ID NO 21
<211> LENGTH: 3843
<212> TYPE: DNA
<213> ORGANISM: Artificial Sequence
<220> FEATURE:
<223> OTHER INFORMATION: Synthetic DNA

<400> SEQUENCE: 21

```
atgggcgacc ctctgaagaa cgtgggcatc gacagactgg acgtggaaaa gggcagaaag      60
aacatgagca agctcgagaa gttcaccaac tgctacagcc tgagcaagac cctgcggttc     120
aaggccattc tgtgggcaa gacccaagag aacatcgaca caagcggct gctggtggaa      180
gatgagaaga gagccgagga ctacaagggc gtgaagaagc tgctggaccg gtactacctg     240
agcttcatca cgacgtgct gcacagcatc aagctgaaga acctgaacaa ctacatcagc     300
ctgttccgga gaaaaacccg gaccgagaaa gagaacaaag agctggaaaa cctcgagatc     360
aacctgcgga agagatcgc caaggccttc aagggcaacg agggctacaa gagcctgttc     420
aagaaggaca tcatcgagac aatcctgcct gagttcctgg acgacaagga cgagatcgcc     480
ctggtcaaca gcttcaacgg cttcacaacc gccttcaccg ctttttcga caaccgcgag     540
aatatgttca gcgaggaagc caagagcacc tctatcgcct tccggtgcat caacgagaat     600
ctgaccccggt acatcagcaa catggatatc ttcgagaagg tggacgccat cttcgacaag     660
cacgaggtgc aagagatcaa agaaaagatc ctgaacagcg actacgacgt cgaggacttc     720
ttcgagggcg agttcttcaa cttcgtgctg acacaagagg gcatcgatgt gtacaacgcc     780
atcatcggcg gcttcgtgac agagagcggc gagaagatca gggcctgaa cgagtacatc     840
aacctctaca accagaaaac gaagcagaag ctgcccaagt caagccccct gtacaaacag     900
gtgctgagcg acagagagag cctgtccttt tacggcgagg ctataccag cgacgaagag     960
gtgctggaag tgttcagaaa caccctgaac aagaacagcg atcttcag ctccatcaag    1020
aagctcgaaa agctgtttaa gaacttcgac gagtacagca gcgccggcat cttcgtgaag    1080
aatggccctg ccatcagcac catctccaag gacatcttcg gcgagtggaa cgtgatccgg    1140
gacaagtgga acgccgagta cgacgacatc caccctgaaga aaaaggccgt ggtcaccgag    1200
```

```
aagtacgagg acgacagaag aaagagcttc aagaagatcg gcagcttcag cctggaacag    1260
ctgcaagagt acgccgacgc cgatctgagc gtggtggaaa agctgaaaga gattatcatc    1320
cagaaggtcg acgagatcta caaggtgtac ggcagcagcg agaagctgtt cgacgccgac    1380
tttgtgctgg aaaagagcct caaaaagaac gacgccgtgg tggccatcat gaaggacctg    1440
ctggatagcg tgaagtcctt cgagaactat attaaggcct tctttggcga gggcaaagag    1500
acaaaccggg acgagagctt ctacggcgat ttcgtgctgg cctacgacat cctgctgaaa    1560
gtggaccaca tctacgacgc catccggaac tacgtgaccc agaagcctta cagcaaggac    1620
aagtttaagc tgtacttcca gaatccgcag ttcatgggcg gctgggacaa agacaaagaa    1680
accgactacc gggccaccat cctgagatac ggctccaagt actatctggc cattatggac    1740
aagaaatacg ccaagtgcct gcagaagatc gataaggacg acgtgaacgg caactacgag    1800
aagattaact acaagctgct gcccggacct aacaagatgc tgcctaaggt gttctttagc    1860
aagaaatgga tggcctacta caaccccagc gaggatatcc agaaaatcta caagaacggc    1920
accttcaaga aggcgacat gttcaacctg aacgactgcc acaagctgat cgatttcttc    1980
aaggacagca tcagcagata ccccaagtgg tccaacgcct acgacttcaa tttcagcgag    2040
acagagaagt ataaggatat cgccgggttc taccgcgagg tggaagaaca gggctataag    2100
gtgtcctttg agagcgccag caagaaagag gtggacaagc tggtcgaaga gggcaagctg    2160
tacatgttcc agatctataa caaggacttc tccgacaaga gccacggcac ccctaacctg    2220
cacaccatgt actttaagct gctgttcgat gagaacaacc acggccagat cagactgtct    2280
ggcggagccg agctgttat gagaagggcc agcctgaaaa agaggaact ggtcgttcac    2340 cccgccaact ctccaatcgc caacaagaac cccgacaatc caagaaaac caccacactg    2400 agctacgacg tgtacaagga taagcggttc tccgaggacc agtacgagct gcacatccct    2460
atcgccatca acaagtgccc caagaatatc ttcaagatca caccgaagt gcgggtgctg    2520 ctgaagcacg acgacaaccc ttacgtgatc ggcatcgatc ggggcgagag aaacctgctg    2580
tatatcgtgg tggtgacgg caagggcaat atcgtggaac agtactccct gaatgagatc    2640
atcaacaact tcaatggcat ccggatcaag acggactacc acagcctgct ggacaaaaaa    2700
gagaaagaac gcttcgaggc ccggcagaac tggaccagca tcgagaacat caagaactg    2760 aaggccggct acatctccca ggtggtgcac aagatctgcg agctggttga agtatgac    2820 gccgtgattg ccctggaaga tctgaatagc ggctttaaga cagccgcgt gaaggtcgag    2880 aaacaggtgt accagaaatt cgagaagatg ctgatcgaca gctgaacta catggtcgac    2940 aagaagtcta accctgcgc cacaggcgga gccctgaagg gatatcagat caccaacaag    3000
ttcgagtcct tcaagagcat gagcaccag aatggcttca tcttctacat ccccgcctgg    3060
ctgaccagca gatcgatcc tagcaccgga ttcgtgaacc tgctcaagac caagtacacc    3120
agcattgccg acagcaagaa gttcatctcc agcttcgacc ggattatgta cgtgcccgaa    3180
gaggacctgt tcgaattcgc cctggattac aagaacttca gccggaccga tgccgactat    3240
atcaagaagt ggaagctgta tagctacggc aaccgcatcc gcatcttcag aaacccgaag    3300
aaaaacaacg tgttcgactg ggaagaagtg tgcctgacca gcgcctacaa gaactcttc    3360 aacaaatacg gcatcaacta ccagcagggc gacatcagag ccctgctgtg cgagcagagc    3420
gacaaggcct tttacagctc cttcatggcc ctgatgagcc tgatgctgca gatgcggaat    3480
agcatcaccg gcaggaccga cgtggacttc ctgatcagcc ctgtgaagaa ttccgacggg    3540
```

-continued

```
atcttctacg acagcagaaa ctacgaggct caagagaacg ccatcctgcc taagaacgcc    3600
gatgccaacg gcgcctataa tatcgccaga aaggtgctgt gggccatcgg ccagtttaag    3660
aaggccgagg acgagaaact ggacaaagtg aagatcgcca tctctaacaa agagtggctg    3720
gaatacgccc agaccagcgt gaagcacggc agatctagtg acgatgaggc caccgccgat    3780
agccagcatg cagcccctcc aaagaaaaag cggaaagtgc tggaacacca ccaccatcac    3840
cac                                                                  3843
```

<210> SEQ ID NO 22
<211> LENGTH: 1363
<212> TYPE: PRT
<213> ORGANISM: Artificial Sequence
<220> FEATURE:
<223> OTHER INFORMATION: Synthetic Amino Acid Sequence

<400> SEQUENCE: 22

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300
```

-continued

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
            325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu

```
                    725                 730                 735
Thr Gly Lys Leu Tyr Leu Phe Gln Ile Tyr Asn Lys Asp Phe Ala Lys
                740                 745                 750
Gly His His Gly Lys Pro Asn Leu His Thr Leu Tyr Trp Thr Gly Leu
                755                 760                 765
Phe Ser Pro Glu Asn Leu Ala Lys Thr Ser Ile Lys Leu Asn Gly Gln
                770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Leu Lys Asp Gln Lys Thr
                805                 810                 815
Pro Ile Pro Asp Thr Leu Tyr Gln Glu Leu Tyr Asp Tyr Val Asn His
                820                 825                 830
Arg Leu Ser His Asp Leu Ser Asp Glu Ala Arg Ala Leu Leu Pro Asn
                835                 840                 845
Val Ile Thr Lys Glu Val Ser His Glu Ile Ile Lys Asp Arg Arg Phe
850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
                900                 905                 910
Asn Leu Ile Tyr Ile Thr Val Ile Asp Ser Thr Gly Lys Ile Leu Glu
                915                 920                 925
Gln Arg Ser Leu Asn Thr Ile Gln Gln Phe Asp Tyr Gln Lys Lys Leu
                930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
His Glu Ile Val Asp Leu Met Ile His Tyr Gln Ala Val Val Val Leu
                980                 985                 990
Glu Asn Leu Asn Phe Gly Phe Lys  Ser Lys Arg Thr Gly Ile Ala Glu
                995                1000                1005
Lys Ala Val Tyr Gln Gln Phe Glu Lys Met Leu Ile Asp Lys Leu
                1010                1015                1020
Asn Cys Leu Val Leu Lys Asp Tyr Pro Ala Glu Lys Val Gly Gly
                1025                1030                1035
Val Leu Asn Pro Tyr Gln Leu Thr Asp Gln Phe Thr Ser Phe Ala
                1040                1045                1050
Lys Met Gly Thr Gln Ser Gly Phe Leu Phe Tyr Val Pro Ala Pro
                1055                1060                1065
Tyr Thr Ser Lys Ile Asp Pro Leu Thr Gly Phe Val Asp Pro Phe
                1070                1075                1080
Val Trp Lys Thr Ile Lys Asn His Glu Ser Arg Lys His Phe Leu
                1085                1090                1095
Glu Gly Phe Asp Phe Leu His Tyr Asp Val Lys Thr Gly Asp Phe
                1100                1105                1110
Ile Leu His Phe Lys Met Asn Arg Asn Leu Ser Phe Gln Arg Gly
                1115                1120                1125
Leu Pro Gly Phe Met Pro Ala Trp Asp Ile Val Phe Glu Lys Asn
                1130                1135                1140
```

| | | | | | | | | | | | | | | |
|---|---|---|---|---|---|---|---|---|---|---|---|---|---|---|
| Glu | Thr | Gln | Phe | Asp | Ala | Lys | Gly | Thr | Pro | Phe | Ile | Ala | Gly | Lys |
| | 1145 | | | | 1150 | | | | | 1155 | | | | |
| Arg | Ile | Val | Pro | Val | Ile | Glu | Asn | His | Arg | Phe | Thr | Gly | Arg | Tyr |
| | 1160 | | | | 1165 | | | | | 1170 | | | | |
| Arg | Asp | Leu | Tyr | Pro | Ala | Asn | Glu | Leu | Ile | Ala | Leu | Leu | Glu | Glu |
| | 1175 | | | | 1180 | | | | | 1185 | | | | |
| Lys | Gly | Ile | Val | Phe | Arg | Asp | Gly | Ser | Asn | Ile | Leu | Pro | Lys | Leu |
| | 1190 | | | | 1195 | | | | | 1200 | | | | |
| Leu | Glu | Asn | Asp | Asp | Ser | His | Ala | Ile | Asp | Thr | Met | Val | Ala | Leu |
| | 1205 | | | | 1210 | | | | | 1215 | | | | |
| Ile | Arg | Ser | Val | Leu | Gln | Met | Arg | Asn | Ser | Asn | Ala | Ala | Thr | Gly |
| | 1220 | | | | 1225 | | | | | 1230 | | | | |
| Glu | Asp | Tyr | Ile | Asn | Ser | Pro | Val | Arg | Asp | Leu | Asn | Gly | Val | Cys |
| | 1235 | | | | 1240 | | | | | 1245 | | | | |
| Phe | Asp | Ser | Arg | Phe | Gln | Asn | Pro | Glu | Trp | Pro | Met | Asp | Ala | Asp |
| | 1250 | | | | 1255 | | | | | 1260 | | | | |
| Ala | Asn | Gly | Ala | Tyr | His | Ile | Ala | Leu | Lys | Gly | Gln | Leu | Leu | Leu |
| | 1265 | | | | 1270 | | | | | 1275 | | | | |
| Asn | His | Leu | Lys | Glu | Ser | Lys | Asp | Leu | Lys | Leu | Gln | Asn | Gly | Ile |
| | 1280 | | | | 1285 | | | | | 1290 | | | | |
| Ser | Asn | Gln | Asp | Trp | Leu | Ala | Tyr | Ile | Gln | Glu | Leu | Arg | Asn | Gly |
| | 1295 | | | | 1300 | | | | | 1305 | | | | |
| Arg | Ser | Ser | Asp | Asp | Glu | Ala | Thr | Ala | Asp | Ser | Gln | His | Ala | Ala |
| | 1310 | | | | 1315 | | | | | 1320 | | | | |
| Pro | Pro | Lys | Lys | Lys | Arg | Lys | Val | Gly | Gly | Ser | Gly | Gly | Ser | Gly |
| | 1325 | | | | 1330 | | | | | 1335 | | | | |
| Gly | Ser | Gly | Gly | Ser | Gly | Gly | Ser | Gly | Gly | Ser | Gly | Gly | Ser | Gly |
| | 1340 | | | | 1345 | | | | | 1350 | | | | |
| Gly | Ser | Leu | Glu | His | His | His | His | His | His | | | | | |
| | 1355 | | | | 1360 | | | | | | | | | |

<210> SEQ ID NO 23
<211> LENGTH: 3846
<212> TYPE: DNA
<213> ORGANISM: Artificial Sequence
<220> FEATURE:
<223> OTHER INFORMATION: Synthetic DNA

<400> SEQUENCE: 23

```
atgggggatc cactgaaaaa cgtgggtatt gatcgtctgg atgttgaaaa aggtcgcaaa      60
aatatgagca aactggaaaa gttcaccaac tgttatagcc tgagcaaaac cctgcgtttt     120
aaagcaattc cggttggtaa aacccaagag aacattgata taaacgcct gctggtcgaa      180
gatgaaaaac gcgctgaaga ttataaaggc gtgaaaaaac tgctggatcg ctattatctg     240
agcttcatta cgatgtgct gcacagcatt aaactgaaga acctgaacaa ctatatcagc      300
ctgtttcgta aaaaacccg caccgaaaaa gaaaacaaag agctggaaaa cctggaaatc      360
aatctgcgta agaaatcgc caaagcgttt aaaggtaacg agggttataa agcctgttc       420
aagaaagaca tcatcgaaac cattctgccg gaatttctgg atgataaaga tgaaattgcc     480
ctggtgaata gctttaatgg ctttaccacc gcatttaccg gcttttttga taatcgcgaa     540
aacatgttca gcgaagaagc aaaaagcacc agcattgcat tcgctgcat taatgaaaat     600
ctgacccgct acattagcaa catggatatc tttgaaaaag tggacgcgat cttcgataaa     660
cacgaagtgc aagagatcaa agagaaaatc ctgaacagcg attatgacgt cgaagatttt     720
```

-continued

```
tttgaaggcg agttctttaa cttcgttctg acccaagaag gtatcgacgt ttataacgca    780
attattggtg gttttgttac cgaaagcggt gagaaaatca aaggcctgaa tgaatatatc    840
aacctgtata accagaaaac caaacagaaa ctgccgaaat tcaaaccgct gtataaacag    900
gttctgagcg atcgtgaaag cctgagcttt tatggtgaag gttataccag tgatgaagag    960
gttctggaag ttttttcgtaa caccctgaat aaaaacagcg agatctttag cagcatcaaa   1020
aagcttgaga aactgttcaa aaactttgat gagtatagca gcgcaggcat ctttgttaaa   1080
aatggtccgg caattagcac catcagcaaa gatattttg gcgaatggaa tgtgatccgc    1140
gataaatgga atgccgaata tgatgatatc cacctgaaaa aaaaggccgt ggtgaccgag    1200
aaatatgaag atgatcgtcg taaaagcttc aagaaaattg gtagctttag cctggaacag   1260
ctgcaagaat atgcagatgc agatctgagc gttgtggaaa aactgaaaga aatcatcatt   1320
cagaaggtgg acgagatcta taaagtttat ggtagcagcg aaaaactgtt cgatgcagat   1380
tttgttctgg aaaaaagcct gaaaagaat gatgccgttg tggccattat gaaagatctg   1440
ctggatagcg ttaagagctt cgagaattac atcaaagcct tttttggtga gggcaaagaa   1500
accaatcgtg atgaaagttt ctatggcgat tttgtgctgg cctatgatat tctgctgaaa   1560
gtggaccata tttatgatgc cattcgcaat tatgttaccc agaaaccgta tagcaaagac   1620
aagttcaaac tgtactttca gaacccgcag tttatgggtg gttgggataa agataaagaa   1680
accgattatc gtgccaccat cctgcgttat ggtagtaaat actatctggc catcatggac   1740
aaaaaatacg caaaatgcct gcagaaaatc gacaaagatg atgtgaatgg caactatgaa   1800
aaaatcaact acaaactgct gcctggtccg aataaaatgc tgccgaaagt gttctttagc   1860
aagaaatgga tggcctatta taacccgagc gaggatattc aaaagatcta caaaaatggc   1920
acctttaaaa agggcgacat gttcaatctg aacgattgcc acaaactgat cgatttcttc   1980
aaagattcaa tttcgcgtta tccgaaatgg tccaatgcct atgatttaa ctttagcgaa   2040 accgaaaaat acaaagacat tgccggtttt tatcgcgaag tggaagaaca gggctataaa   2100
gtgagctttg aaagcgcaag caaaaaagag gttgataagc tggttgaaga gggcaaactg   2160
tatatgttcc agatttacaa caaagatttt agcgacaaaa gccatggcac cccgaatctg   2220
cataccatgt actttaaact gctgttcgac gaaataacc atggtcagat tcgtctgagc   2280
ggtggtgccg aactgtttat gcgtcgtgca agtctgaaaa agaagaact ggttgttcat   2340 ccggcaaata gcccgattgc aaacaaaaat ccggacaatc cgaaaaaaac cacgacactg   2400
agctatgatg tgtataaaga caacgttttt agcgaggatc agtatgaact gcatatcccg   2460
attgccatca ataaatgccc gaaaaacatc tttaagatca caccgaagt tcgcgtgctg   2520 ctgaaacatg atgataatcc gtatgtgatt ggcattgatc gtggtgaacg taacctgctg   2580
tatattgttg ttgttgatgg taaaggcaac atcgtggaac agtatagtct gaacgaaatt   2640
atcaacaact ttaacggcat ccgcatcaaa accgactatc atagcctgct ggacaagaaa   2700
gaaaaagaac gttttgaagc acgtcagaac tggaccagta ttgaaaacat caagaactg   2760 aaagccggtt atattagcca ggtggttcat aaaatctgtg agctggtaga aaaatacgat   2820
gcagttattg cactggaaga tctgaatagc ggtttcaaa atagccgtgt gaaagtcgaa   2880 aacaggtgt atcagaaatt cgagaaaatg ctgatcgaca aactgaacta catggtcgac   2940
aaaaaaagca atccgtgtgc aaccggtggt gcactgaaag gttatcagat taccaacaaa   3000
tttgaaagct ttaaaagcat gagcacccag aacggcttta tcttctatat tccggcatgg   3060
```

```
ctgaccagca aaattgatcc gagcaccggt tttgtgaacc tgctgaaaac aaaatatacc   3120
tccattgccg acagcaagaa gtttattagc agctttgatc gcattatgta tgttccggaa   3180
gaggacctgt ttgaattcgc actggattac aaaaatttca gccgtaccga tgccgactac   3240
atcaaaaaat ggaaactgta cagctatggt aaccgcattc gcattttttcg caacccgaag   3300 aaaaacaatg tgttcgattg ggaagaagtt tgtctgacca gcgcatataa agaactttc    3360 aacaaatacg gcatcaacta tcagcagggt gatattcgtg cactgctgtg tgaacagagc   3420
gataaagcgt tttatagcag ttttatggca ctgatgagcc tgatgctgca gatgcgtaat   3480
agcattaccg gtcgcaccga tgtggatttt ctgattagtc cggtgaaaaa ttccgatggc   3540
atcttttatg atagccgcaa ttcgaagca caagaaaatg caattctgcc gaaaaacgca    3600
gatgcaaatg gtgcatataa cattgcacgt aaagttctgt gggcaattgg ccagtttaag   3660
aaagcagaag atgagaagct ggacaaagtg aaaattgcga tcagcaataa agagtggctg   3720
gaatacgcac agaccagcgt taaacatggt cgtagcagtg atgatgaagc aaccgcagat   3780
agccagcatg cagcaccgcc gaaaaaaaaa cgcaaagtgc tcgagcacca ccaccaccac   3840
cactga                                                              3846
```

<210> SEQ ID NO 24
<211> LENGTH: 1278
<212> TYPE: PRT
<213> ORGANISM: Artificial Sequence
<220> FEATURE:
<223> OTHER INFORMATION: Synthetic Amino Acid Sequence

<400> SEQUENCE: 24

```
Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220
```

```
Glu Lys Ile Leu Asn Ser Asp Tyr Asp Val Glu Asp Phe Glu Gly
225                 230                 235                 240

Glu Phe Phe Asn Phe Val Leu Thr Gln Glu Gly Ile Asp Val Tyr Asn
            245                 250                 255

Ala Ile Ile Gly Gly Phe Val Thr Glu Ser Gly Glu Lys Ile Lys Gly
                260                 265                 270

Leu Asn Glu Tyr Ile Asn Leu Tyr Asn Gln Lys Thr Lys Gln Lys Leu
            275                 280                 285

Pro Lys Phe Lys Pro Leu Tyr Lys Gln Val Leu Ser Asp Arg Glu Ser
            290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
                340                 345                 350

Gly Ile Phe Val Lys Asn Gly Pro Ala Ile Ser Thr Ile Ser Lys Asp
                355                 360                 365

Ile Phe Gly Glu Trp Asn Val Ile Arg Asp Lys Trp Asn Ala Glu Tyr
370                 375                 380

Asp Asp Ile His Leu Lys Lys Lys Ala Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
                420                 425                 430

Lys Glu Ile Ile Ile Gln Lys Val Asp Glu Ile Tyr Lys Val Tyr Gly
                435                 440                 445

Ser Ser Glu Lys Leu Phe Asp Ala Asp Phe Val Leu Glu Lys Ser Leu
                450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
                500                 505                 510

Asp Ile Leu Leu Lys Val Asp His Ile Tyr Asp Ala Ile Arg Asn Tyr
                515                 520                 525

Val Thr Gln Lys Pro Tyr Ser Lys Asp Lys Phe Lys Leu Tyr Phe Gln
                530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
                580                 585                 590

Asn Gly Asn Tyr Glu Lys Ile Asn Tyr Lys Leu Leu Pro Gly Pro Asn
                595                 600                 605

Lys Met Leu Pro Lys Val Phe Phe Ser Lys Lys Trp Met Ala Tyr Tyr
                610                 615                 620

Asn Pro Ser Glu Asp Ile Gln Lys Ile Tyr Lys Asn Gly Thr Phe Lys
625                 630                 635                 640
```

-continued

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
        660                 665                 670

Phe Asn Phe Ser Glu Thr Glu Lys Tyr Lys Asp Ile Ala Gly Phe Tyr
            675                 680                 685

Arg Glu Val Glu Glu Gln Gly Tyr Lys Val Ser Phe Glu Ser Ala Ser
690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
                755                 760                 765

Leu Lys Lys Glu Glu Leu Val Val His Pro Ala Asn Ser Pro Ile Ala
770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
            835                 840                 845

Ile Asp Arg Gly Glu Arg Asn Leu Leu Tyr Ile Val Val Val Asp Gly
850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
            915                 920                 925

Ile Cys Glu Leu Val Glu Lys Tyr Asp Ala Val Ile Ala Leu Glu Asp
930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser Phe Lys Ser Met Ser Thr Gln Asn
                995                 1000                1005

Gly Phe Ile Phe Tyr Ile Pro Ala Trp Leu Thr Ser Lys Ile Asp
    1010                1015                1020

Pro Ser Thr Gly Phe Val Asn Leu Leu Lys Thr Lys Tyr Thr Ser
    1025                1030                1035

Ile Ala Asp Ser Lys Lys Phe Ile Ser Ser Phe Asp Arg Ile Met
    1040                1045                1050

Tyr Val Pro Glu Glu Asp Leu Phe Glu Phe Ala Leu Asp Tyr Lys

```
                1055                1060                1065

Asn  Phe  Ser  Arg  Thr  Asp  Ala  Asp  Tyr  Ile  Lys  Lys  Trp  Lys  Leu
          1070                1075                1080

Tyr  Ser  Tyr  Gly  Asn  Arg  Ile  Arg  Ile  Phe  Arg  Asn  Pro  Lys  Lys
          1085                1090                1095

Asn  Asn  Val  Phe  Asp  Trp  Glu  Glu  Val  Cys  Leu  Thr  Ser  Ala  Tyr
     1100                1105                1110

Lys  Glu  Leu  Phe  Asn  Lys  Tyr  Gly  Ile  Asn  Tyr  Gln  Gln  Gly  Asp
     1115                1120                1125

Ile  Arg  Ala  Leu  Leu  Cys  Glu  Gln  Ser  Asp  Lys  Ala  Phe  Tyr  Ser
     1130                1135                1140

Ser  Phe  Met  Ala  Leu  Met  Ser  Leu  Met  Leu  Gln  Met  Arg  Asn  Ser
     1145                1150                1155

Ile  Thr  Gly  Arg  Thr  Asp  Val  Asp  Phe  Leu  Ile  Ser  Pro  Val  Lys
     1160                1165                1170

Asn  Ser  Asp  Gly  Ile  Phe  Tyr  Asp  Ser  Arg  Asn  Tyr  Glu  Ala  Gln
     1175                1180                1185

Glu  Asn  Ala  Ile  Leu  Pro  Lys  Asn  Ala  Asp  Ala  Asn  Gly  Ala  Tyr
     1190                1195                1200

Asn  Ile  Ala  Arg  Lys  Val  Leu  Trp  Ala  Ile  Gly  Gln  Phe  Lys  Lys
     1205                1210                1215

Ala  Glu  Asp  Glu  Lys  Leu  Asp  Lys  Val  Lys  Ile  Ala  Ile  Ser  Asn
     1220                1225                1230

Lys  Glu  Trp  Leu  Glu  Tyr  Ala  Gln  Thr  Ser  Val  Lys  His  Gly  Arg
     1235                1240                1245

Ser  Ser  Asp  Asp  Glu  Ala  Thr  Ala  Asp  Ser  Gln  His  Ala  Ala  Pro
     1250                1255                1260

Pro  Lys  Lys  Lys  Arg  Lys  Val  Leu  Glu  His  His  His  His  His  His
     1265                1270                1275

<210> SEQ ID NO 25
<211> LENGTH: 21
<212> TYPE: DNA
<213> ORGANISM: Artificial Sequence
<220> FEATURE:
<223> OTHER INFORMATION: Synthetic DNA

<400> SEQUENCE: 25
gtgtccaaga ccctgagatt c                                              21

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
gggcttcagc tctttgtagt                                                20

<210> SEQ ID NO 27
<211> LENGTH: 24
<212> TYPE: DNA
<213> ORGANISM: Artificial Sequence
<220> FEATURE:
<223> OTHER INFORMATION: Synthetic DNA

<400> SEQUENCE: 27
agggcaagac actgaagcac atcc                                           24
```

<210> SEQ ID NO 28
<211> LENGTH: 20
<212> TYPE: DNA
<213> ORGANISM: Artificial Sequence
<220> FEATURE:
<223> OTHER INFORMATION: Synthetic DNA

<400> SEQUENCE: 28
cagaaactac gccaccaaga                                              20

<210> SEQ ID NO 29
<211> LENGTH: 22
<212> TYPE: DNA
<213> ORGANISM: Artificial Sequence
<220> FEATURE:
<223> OTHER INFORMATION: Synthetic DNA

<400> SEQUENCE: 29
gccgttgttc ttctctttgt tc                                           22

<210> SEQ ID NO 30
<211> LENGTH: 25
<212> TYPE: DNA
<213> ORGANISM: Artificial Sequence
<220> FEATURE:
<223> OTHER INFORMATION: Synthetic DNA

<400> SEQUENCE: 30
taagctgaac ttccagatgc ccacc                                        25

<210> SEQ ID NO 31
<211> LENGTH: 22
<212> TYPE: DNA
<213> ORGANISM: Artificial Sequence
<220> FEATURE:
<223> OTHER INFORMATION: Synthetic DNA

<400> SEQUENCE: 31
gtggacctga tgatccacta tc                                           22

<210> SEQ ID NO 32
<211> LENGTH: 18
<212> TYPE: DNA
<213> ORGANISM: Artificial Sequence
<220> FEATURE:
<223> OTHER INFORMATION: Synthetic DNA

<400> SEQUENCE: 32
gctggtacac ggctttct                                                18

<210> SEQ ID NO 33
<211> LENGTH: 24
<212> TYPE: DNA
<213> ORGANISM: Artificial Sequence
<220> FEATURE:
<223> OTHER INFORMATION: Synthetic DNA

<400> SEQUENCE: 33
acctgaactt cggcttcaag agca                                         24

<210> SEQ ID NO 34
<211> LENGTH: 22
<212> TYPE: DNA
<213> ORGANISM: Artificial Sequence
<220> FEATURE:

```
<223> OTHER INFORMATION: Synthetic DNA

<400> SEQUENCE: 34
tgctgaacca tctgaaagag ag                                              22

<210> SEQ ID NO 35
<211> LENGTH: 22
<212> TYPE: DNA
<213> ORGANISM: Artificial Sequence
<220> FEATURE:
<223> OTHER INFORMATION: Synthetic DNA

<400> SEQUENCE: 35
gttccgcagt tcctggatat ag                                              22

<210> SEQ ID NO 36
<211> LENGTH: 23
<212> TYPE: DNA
<213> ORGANISM: Artificial Sequence
<220> FEATURE:
<223> OTHER INFORMATION: Synthetic DNA

<400> SEQUENCE: 36
agtcctggtt ggagatgccg ttc                                             23

<210> SEQ ID NO 37
<211> LENGTH: 44
<212> TYPE: RNA
<213> ORGANISM: Artificial Sequence
<220> FEATURE:
<223> OTHER INFORMATION: Synthetic RNA

<400> SEQUENCE: 37
uaauuucuac ucuuguagau uaaacacugu uucauuucau ccgu                      44

<210> SEQ ID NO 38
<211> LENGTH: 44
<212> TYPE: RNA
<213> ORGANISM: Artificial Sequence
<220> FEATURE:
<223> OTHER INFORMATION: Synthetic RNA

<400> SEQUENCE: 38
uaauuucuac ucuuguagau accagcaagc uguuaauuac aaaa                      44

<210> SEQ ID NO 39
<211> LENGTH: 44
<212> TYPE: RNA
<213> ORGANISM: Artificial Sequence
<220> FEATURE:
<223> OTHER INFORMATION: Synthetic RNA

<400> SEQUENCE: 39
uaauuucuac ucuuguagau accaucuuua accuaaaaga guuu                      44

<210> SEQ ID NO 40
<211> LENGTH: 44
<212> TYPE: RNA
<213> ORGANISM: Artificial Sequence
<220> FEATURE:
<223> OTHER INFORMATION: Synthetic RNA

<400> SEQUENCE: 40
uaauuucuac ucuuguagau gguuaaagau gguuaaauga uuga                      44
```

```
<210> SEQ ID NO 41
<211> LENGTH: 44
<212> TYPE: RNA
<213> ORGANISM: Artificial Sequence
<220> FEATURE:
<223> OTHER INFORMATION: Synthetic RNA

<400> SEQUENCE: 41
uaauuucuac ucuuguagau ugugaaaugg cuuauaauug cuua                    44

<210> SEQ ID NO 42
<211> LENGTH: 44
<212> TYPE: RNA
<213> ORGANISM: Artificial Sequence
<220> FEATURE:
<223> OTHER INFORMATION: Synthetic RNA

<400> SEQUENCE: 42
uaauuucuac ucuuguagau aauguaagua auugcuucuu uuuc                    44

<210> SEQ ID NO 43
<211> LENGTH: 43
<212> TYPE: RNA
<213> ORGANISM: Artificial Sequence
<220> FEATURE:
<223> OTHER INFORMATION: Synthetic RNA

<400> SEQUENCE: 43
aauuucuacu cuuguagauu aaacacuguu ucauuucauc cgu                     43

<210> SEQ ID NO 44
<211> LENGTH: 42
<212> TYPE: RNA
<213> ORGANISM: Artificial Sequence
<220> FEATURE:
<223> OTHER INFORMATION: Synthetic RNA

<400> SEQUENCE: 44
auuucuacuc uuguagauua aacacuguuu cauuucaucc gu                      42

<210> SEQ ID NO 45
<211> LENGTH: 41
<212> TYPE: RNA
<213> ORGANISM: Artificial Sequence
<220> FEATURE:
<223> OTHER INFORMATION: Synthetic RNA

<400> SEQUENCE: 45
uuucuacucu uguagauuaa acacuguuuc auuucauccg u                       41

<210> SEQ ID NO 46
<211> LENGTH: 43
<212> TYPE: RNA
<213> ORGANISM: Artificial Sequence
<220> FEATURE:
<223> OTHER INFORMATION: Synthetic RNA

<400> SEQUENCE: 46
aauuucuacu cuuguagaua ccagcaagcu guuaauuaca aaa                     43

<210> SEQ ID NO 47
<211> LENGTH: 42
<212> TYPE: RNA
<213> ORGANISM: Artificial Sequence
<220> FEATURE:
<223> OTHER INFORMATION: Synthetic RNA
```

-continued

<400> SEQUENCE: 47
auuucuacuc uuguagauac cagcaagcug uuaauuacaa aa  42

<210> SEQ ID NO 48
<211> LENGTH: 41
<212> TYPE: RNA
<213> ORGANISM: Artificial Sequence
<220> FEATURE:
<223> OTHER INFORMATION: Synthetic RNA

<400> SEQUENCE: 48
uuucuacucu uguagauacc agcaagcugu uaauuacaaa a  41

<210> SEQ ID NO 49
<211> LENGTH: 43
<212> TYPE: RNA
<213> ORGANISM: Artificial Sequence
<220> FEATURE:
<223> OTHER INFORMATION: Synthetic RNA

<400> SEQUENCE: 49
aauuucuacu cuuguagaua ccaucuuuaa ccuaaaagag uuu  43

<210> SEQ ID NO 50
<211> LENGTH: 42
<212> TYPE: RNA
<213> ORGANISM: Artificial Sequence
<220> FEATURE:
<223> OTHER INFORMATION: Synthetic RNA

<400> SEQUENCE: 50
auuucuacuc uuguagauac caucuuuaac cuaaaagagu uu  42

<210> SEQ ID NO 51
<211> LENGTH: 41
<212> TYPE: RNA
<213> ORGANISM: Artificial Sequence
<220> FEATURE:
<223> OTHER INFORMATION: Synthetic RNA

<400> SEQUENCE: 51
uuucuacucu uguagauacc aucuuuaacc uaaaagaguu u  41

<210> SEQ ID NO 52
<211> LENGTH: 43
<212> TYPE: RNA
<213> ORGANISM: Artificial Sequence
<220> FEATURE:
<223> OTHER INFORMATION: Synthetic RNA

<400> SEQUENCE: 52
aauuucuacu cuuguagaug guuaaagaug guuaaaugau uga  43

<210> SEQ ID NO 53
<211> LENGTH: 42
<212> TYPE: RNA
<213> ORGANISM: Artificial Sequence
<220> FEATURE:
<223> OTHER INFORMATION: Synthetic RNA

<400> SEQUENCE: 53
auuucuacuc uuguagaugg uuaaagaugg uuaaaugauu ga  42

<210> SEQ ID NO 54
<211> LENGTH: 41

```
<212> TYPE: RNA
<213> ORGANISM: Artificial Sequence
<220> FEATURE:
<223> OTHER INFORMATION: Synthetic RNA

<400> SEQUENCE: 54
uuucuacucu uguagauggu uaaagauggu uaaaugauug a                    41

<210> SEQ ID NO 55
<211> LENGTH: 43
<212> TYPE: RNA
<213> ORGANISM: Artificial Sequence
<220> FEATURE:
<223> OTHER INFORMATION: Synthetic RNA

<400> SEQUENCE: 55
aauuucuacu cuuguagauu gugaaauggc uuauaauugc uua                  43

<210> SEQ ID NO 56
<211> LENGTH: 42
<212> TYPE: RNA
<213> ORGANISM: Artificial Sequence
<220> FEATURE:
<223> OTHER INFORMATION: Synthetic RNA

<400> SEQUENCE: 56
auuucuacuc uuguagauug ugaaauggcu uauaauugcu ua                   42

<210> SEQ ID NO 57
<211> LENGTH: 41
<212> TYPE: RNA
<213> ORGANISM: Artificial Sequence
<220> FEATURE:
<223> OTHER INFORMATION: Synthetic RNA

<400> SEQUENCE: 57
uuucuacucu uguagauugu gaaauggcuu auaauugcuu a                    41

<210> SEQ ID NO 58
<211> LENGTH: 43
<212> TYPE: RNA
<213> ORGANISM: Artificial Sequence
<220> FEATURE:
<223> OTHER INFORMATION: Synthetic RNA

<400> SEQUENCE: 58
aauuucuacu cuuguagaua auguaaguaa uugcuucuuu uuc                  43

<210> SEQ ID NO 59
<211> LENGTH: 42
<212> TYPE: RNA
<213> ORGANISM: Artificial Sequence
<220> FEATURE:
<223> OTHER INFORMATION: Synthetic RNA

<400> SEQUENCE: 59
auuucuacuc uuguagauaa uguaaguaau ugcuucuuuu uc                   42

<210> SEQ ID NO 60
<211> LENGTH: 41
<212> TYPE: RNA
<213> ORGANISM: Artificial Sequence
<220> FEATURE:
<223> OTHER INFORMATION: Synthetic RNA

<400> SEQUENCE: 60
``` uucuacucu uguagauaau guaaguaauu gcuucuuuuu c          41

<210> SEQ ID NO 61
<211> LENGTH: 41
<212> TYPE: RNA
<213> ORGANISM: Artificial Sequence
<220> FEATURE:
<223> OTHER INFORMATION: Synthetic RNA

<400> SEQUENCE: 61
uaauuucuac ucuuguagau uaaacacugu uucauuucau c          41

<210> SEQ ID NO 62
<211> LENGTH: 40
<212> TYPE: RNA
<213> ORGANISM: Artificial Sequence
<220> FEATURE:
<223> OTHER INFORMATION: Synthetic RNA

<400> SEQUENCE: 62
aauuucuacu cuuguagauu aaacacuguu ucauuucauc          40

<210> SEQ ID NO 63
<211> LENGTH: 39
<212> TYPE: RNA
<213> ORGANISM: Artificial Sequence
<220> FEATURE:
<223> OTHER INFORMATION: Synthetic RNA

<400> SEQUENCE: 63
auuucuacuc uuguagauua aacacuguuu cauuucauc          39

<210> SEQ ID NO 64
<211> LENGTH: 38
<212> TYPE: RNA
<213> ORGANISM: Artificial Sequence
<220> FEATURE:
<223> OTHER INFORMATION: Synthetic RNA

<400> SEQUENCE: 64
uuucuacucu uguagauuaa acacuguuuc auuucauc          38

<210> SEQ ID NO 65
<211> LENGTH: 41
<212> TYPE: RNA
<213> ORGANISM: Artificial Sequence
<220> FEATURE:
<223> OTHER INFORMATION: Synthetic RNA

<400> SEQUENCE: 65
uaauuucuac ucuuguagau accagcaagc uguuaauuac a          41

<210> SEQ ID NO 66
<211> LENGTH: 40
<212> TYPE: RNA
<213> ORGANISM: Artificial Sequence
<220> FEATURE:
<223> OTHER INFORMATION: Synthetic RNA

<400> SEQUENCE: 66
aauuucuacu cuuguagaua ccagcaagcu guuaauuaca          40

<210> SEQ ID NO 67
<211> LENGTH: 39
<212> TYPE: RNA
<213> ORGANISM: Artificial Sequence

```
<220> FEATURE:
<223> OTHER INFORMATION: Synthetic RNA

<400> SEQUENCE: 67
auuucuacuc uuguagauac cagcaagcug uuaauuaca                                    39

<210> SEQ ID NO 68
<211> LENGTH: 38
<212> TYPE: RNA
<213> ORGANISM: Artificial Sequence
<220> FEATURE:
<223> OTHER INFORMATION: Synthetic RNA

<400> SEQUENCE: 68
uuucuacucu uguagauacc agcaagcugu uaauuaca                                     38

<210> SEQ ID NO 69
<211> LENGTH: 41
<212> TYPE: RNA
<213> ORGANISM: Artificial Sequence
<220> FEATURE:
<223> OTHER INFORMATION: Synthetic RNA

<400> SEQUENCE: 69
uaauuucuac ucuuguagau accaucuuua accuaaaaga g                                 41

<210> SEQ ID NO 70
<211> LENGTH: 40
<212> TYPE: RNA
<213> ORGANISM: Artificial Sequence
<220> FEATURE:
<223> OTHER INFORMATION: Synthetic RNA

<400> SEQUENCE: 70
aauuucuacu cuuguagaua ccaucuuuaa ccuaaaagag                                   40

<210> SEQ ID NO 71
<211> LENGTH: 39
<212> TYPE: RNA
<213> ORGANISM: Artificial Sequence
<220> FEATURE:
<223> OTHER INFORMATION: Synthetic RNA

<400> SEQUENCE: 71
auuucuacuc uuguagauac caucuuuaac cuaaaagag                                    39

<210> SEQ ID NO 72
<211> LENGTH: 38
<212> TYPE: RNA
<213> ORGANISM: Artificial Sequence
<220> FEATURE:
<223> OTHER INFORMATION: Synthetic RNA

<400> SEQUENCE: 72
uuucuacucu uguagauacc aucuuuaacc uaaaagag                                     38

<210> SEQ ID NO 73
<211> LENGTH: 41
<212> TYPE: RNA
<213> ORGANISM: Artificial Sequence
<220> FEATURE:
<223> OTHER INFORMATION: Synthetic RNA

<400> SEQUENCE: 73
uaauuucuac ucuuguagau gguuaaagau gguuaaauga u                                 41
```

```
<210> SEQ ID NO 74
<211> LENGTH: 40
<212> TYPE: RNA
<213> ORGANISM: Artificial Sequence
<220> FEATURE:
<223> OTHER INFORMATION: Synthetic RNA

<400> SEQUENCE: 74
aauuucuacu cuuguagaug guuaaagaug guuaaaugau                          40

<210> SEQ ID NO 75
<211> LENGTH: 39
<212> TYPE: RNA
<213> ORGANISM: Artificial Sequence
<220> FEATURE:
<223> OTHER INFORMATION: Synthetic RNA

<400> SEQUENCE: 75
auuucuacuc uuguagaugg uuaaagaugg uuaaaugau                           39

<210> SEQ ID NO 76
<211> LENGTH: 38
<212> TYPE: RNA
<213> ORGANISM: Artificial Sequence
<220> FEATURE:
<223> OTHER INFORMATION: Synthetic RNA

<400> SEQUENCE: 76
uuucuacucu uguagauggu uaaagauggu uaaaugau                            38

<210> SEQ ID NO 77
<211> LENGTH: 41
<212> TYPE: RNA
<213> ORGANISM: Artificial Sequence
<220> FEATURE:
<223> OTHER INFORMATION: Synthetic RNA

<400> SEQUENCE: 77
uaauuucuac ucuuguagau gugaaaugg cuuauaauug c                         41

<210> SEQ ID NO 78
<211> LENGTH: 40
<212> TYPE: RNA
<213> ORGANISM: Artificial Sequence
<220> FEATURE:
<223> OTHER INFORMATION: Synthetic RNA

<400> SEQUENCE: 78
aauuucuacu cuuguagauu gugaaauggc uuauaauugc                          40

<210> SEQ ID NO 79
<211> LENGTH: 39
<212> TYPE: RNA
<213> ORGANISM: Artificial Sequence
<220> FEATURE:
<223> OTHER INFORMATION: Synthetic RNA

<400> SEQUENCE: 79
auuucuacuc uuguagauug ugaaauggcu uauaauugc                           39

<210> SEQ ID NO 80
<211> LENGTH: 38
<212> TYPE: RNA
<213> ORGANISM: Artificial Sequence
<220> FEATURE:
<223> OTHER INFORMATION: Synthetic RNA
```

```
<400> SEQUENCE: 80
uuucuacucu uguagauugu gaaauggcuu auaauugc                           38

<210> SEQ ID NO 81
<211> LENGTH: 41
<212> TYPE: RNA
<213> ORGANISM: Artificial Sequence
<220> FEATURE:
<223> OTHER INFORMATION: Synthetic RNA

<400> SEQUENCE: 81
uaauuucuac ucuuguagau aauguaagua auugcuucuu u                      41

<210> SEQ ID NO 82
<211> LENGTH: 40
<212> TYPE: RNA
<213> ORGANISM: Artificial Sequence
<220> FEATURE:
<223> OTHER INFORMATION: Synthetic RNA

<400> SEQUENCE: 82
aauuucuacu cuuguagaua auguaaguaa uugcuucuuu                         40

<210> SEQ ID NO 83
<211> LENGTH: 39
<212> TYPE: RNA
<213> ORGANISM: Artificial Sequence
<220> FEATURE:
<223> OTHER INFORMATION: Synthetic RNA

<400> SEQUENCE: 83
auuucuacuc uuguagauaa uguaaguaau ugcuucuuu                          39

<210> SEQ ID NO 84
<211> LENGTH: 38
<212> TYPE: RNA
<213> ORGANISM: Artificial Sequence
<220> FEATURE:
<223> OTHER INFORMATION: Synthetic RNA

<400> SEQUENCE: 84
uuucuacucu uguagauaau guaaguaauu gcuucuuu                           38

<210> SEQ ID NO 85
<211> LENGTH: 39
<212> TYPE: RNA
<213> ORGANISM: Artificial Sequence
<220> FEATURE:
<223> OTHER INFORMATION: Synthetic RNA

<400> SEQUENCE: 85
uaauuucuac ucuuguagau uaaacacugu uucauuuca                          39

<210> SEQ ID NO 86
<211> LENGTH: 38
<212> TYPE: RNA
<213> ORGANISM: Artificial Sequence
<220> FEATURE:
<223> OTHER INFORMATION: Synthetic RNA

<400> SEQUENCE: 86
uaauuucuac ucuuguagau uaaacacugu uucauuuc                           38

<210> SEQ ID NO 87
```

```
<211> LENGTH: 37
<212> TYPE: RNA
<213> ORGANISM: Artificial Sequence
<220> FEATURE:
<223> OTHER INFORMATION: Synthetic RNA

<400> SEQUENCE: 87
uaauuucuac ucuuguagau uaaacacugu uucauuu                              37

<210> SEQ ID NO 88
<211> LENGTH: 39
<212> TYPE: RNA
<213> ORGANISM: Artificial Sequence
<220> FEATURE:
<223> OTHER INFORMATION: Synthetic RNA

<400> SEQUENCE: 88
uaauuucuac ucuuguagau accagcaagc uguuaauua                            39

<210> SEQ ID NO 89
<211> LENGTH: 38
<212> TYPE: RNA
<213> ORGANISM: Artificial Sequence
<220> FEATURE:
<223> OTHER INFORMATION: Synthetic RNA

<400> SEQUENCE: 89
uaauuucuac ucuuguagau accagcaagc uguuaauu                             38

<210> SEQ ID NO 90
<211> LENGTH: 37
<212> TYPE: RNA
<213> ORGANISM: Artificial Sequence
<220> FEATURE:
<223> OTHER INFORMATION: Synthetic RNA

<400> SEQUENCE: 90
uaauuucuac ucuuguagau accagcaagc uguuaau                              37

<210> SEQ ID NO 91
<211> LENGTH: 39
<212> TYPE: RNA
<213> ORGANISM: Artificial Sequence
<220> FEATURE:
<223> OTHER INFORMATION: Synthetic RNA

<400> SEQUENCE: 91
uaauuucuac ucuuguagau accaucuuua accuaaaag                            39

<210> SEQ ID NO 92
<211> LENGTH: 38
<212> TYPE: RNA
<213> ORGANISM: Artificial Sequence
<220> FEATURE:
<223> OTHER INFORMATION: Synthetic RNA

<400> SEQUENCE: 92
uaauuucuac ucuuguagau accaucuuua accuaaaa                             38

<210> SEQ ID NO 93
<211> LENGTH: 37
<212> TYPE: RNA
<213> ORGANISM: Artificial Sequence
<220> FEATURE:
<223> OTHER INFORMATION: Synthetic RNA

<400> SEQUENCE: 93
```
uaauuucuac ucuuguagau accaucuuua accuaaa           37

<210> SEQ ID NO 94
<211> LENGTH: 39
<212> TYPE: RNA
<213> ORGANISM: Artificial Sequence
<220> FEATURE:
<223> OTHER INFORMATION: Synthetic RNA

<400> SEQUENCE: 94
uaauuucuac ucuuguagau gguaaagau gguuaaaug           39

<210> SEQ ID NO 95
<211> LENGTH: 38
<212> TYPE: RNA
<213> ORGANISM: Artificial Sequence
<220> FEATURE:
<223> OTHER INFORMATION: Synthetic RNA

<400> SEQUENCE: 95
uaauuucuac ucuuguagau gguaaagau gguaaau            38

<210> SEQ ID NO 96
<211> LENGTH: 37
<212> TYPE: RNA
<213> ORGANISM: Artificial Sequence
<220> FEATURE:
<223> OTHER INFORMATION: Synthetic RNA

<400> SEQUENCE: 96
uaauuucuac ucuuguagau gguaaagau gguaaa             37

<210> SEQ ID NO 97
<211> LENGTH: 39
<212> TYPE: RNA
<213> ORGANISM: Artificial Sequence
<220> FEATURE:
<223> OTHER INFORMATION: Synthetic RNA

<400> SEQUENCE: 97
uaauuucuac ucuuguagau ugugaaaugg cuuauaauu         39

<210> SEQ ID NO 98
<211> LENGTH: 38
<212> TYPE: RNA
<213> ORGANISM: Artificial Sequence
<220> FEATURE:
<223> OTHER INFORMATION: Synthetic RNA

<400> SEQUENCE: 98
uaauuucuac ucuuguagau ugugaaaugg cuuauaau          38

<210> SEQ ID NO 99
<211> LENGTH: 37
<212> TYPE: RNA
<213> ORGANISM: Artificial Sequence
<220> FEATURE:
<223> OTHER INFORMATION: Synthetic RNA

<400> SEQUENCE: 99
uaauuucuac ucuuguagau ugugaaaugg cuuauaa           37

<210> SEQ ID NO 100
<211> LENGTH: 39
<212> TYPE: RNA

```
<213> ORGANISM: Artificial Sequence
<220> FEATURE:
<223> OTHER INFORMATION: Synthetic RNA

<400> SEQUENCE: 100
uaauuucuac ucuuguagau aauguaagua auugcuucu                    39

<210> SEQ ID NO 101
<211> LENGTH: 38
<212> TYPE: RNA
<213> ORGANISM: Artificial Sequence
<220> FEATURE:
<223> OTHER INFORMATION: Synthetic RNA

<400> SEQUENCE: 101
uaauuucuac ucuuguagau aauguaagua auugcuuc                     38

<210> SEQ ID NO 102
<211> LENGTH: 37
<212> TYPE: RNA
<213> ORGANISM: Artificial Sequence
<220> FEATURE:
<223> OTHER INFORMATION: Synthetic RNA

<400> SEQUENCE: 102
uaauuucuac ucuuguagau aauguaagua auugcuu                      37

<210> SEQ ID NO 103
<211> LENGTH: 44
<212> TYPE: RNA
<213> ORGANISM: Artificial Sequence
<220> FEATURE:
<223> OTHER INFORMATION: Synthetic RNA

<400> SEQUENCE: 103
uaauuucuac ucuuguagau ugugaaaugg cuuauaauug cuua              44

<210> SEQ ID NO 104
<211> LENGTH: 44
<212> TYPE: RNA
<213> ORGANISM: Artificial Sequence
<220> FEATURE:
<223> OTHER INFORMATION: Synthetic RNA

<400> SEQUENCE: 104
uaauuucuac ucuuguagau ugugaaaugg cuuauaauug cuua              44

<210> SEQ ID NO 105
<211> LENGTH: 44
<212> TYPE: RNA
<213> ORGANISM: Artificial Sequence
<220> FEATURE:
<223> OTHER INFORMATION: Synthetic RNA

<400> SEQUENCE: 105
uaauuucuac ucuuguagau ugugaaaugg cuuauaauug cuua              44

<210> SEQ ID NO 106
<211> LENGTH: 44
<212> TYPE: RNA
<213> ORGANISM: Artificial Sequence
<220> FEATURE:
<223> OTHER INFORMATION: Synthetic RNA

<400> SEQUENCE: 106
uaauuucuac ucuuguagau ugugaaaugg cuuauaauug cuua              44
```

<210> SEQ ID NO 107
<211> LENGTH: 44
<212> TYPE: RNA
<213> ORGANISM: Artificial Sequence
<220> FEATURE:
<223> OTHER INFORMATION: Synthetic RNA

<400> SEQUENCE: 107
uaauuucuac ucuguagau ugugaaaugg cuuauaauug cuua            44

<210> SEQ ID NO 108
<211> LENGTH: 44
<212> TYPE: RNA
<213> ORGANISM: Artificial Sequence
<220> FEATURE:
<223> OTHER INFORMATION: Synthetic RNA

<400> SEQUENCE: 108
uaauuucuac ucuguagau ugugaaaugg cuuauaauug cuua            44

<210> SEQ ID NO 109
<211> LENGTH: 44
<212> TYPE: RNA
<213> ORGANISM: Artificial Sequence
<220> FEATURE:
<223> OTHER INFORMATION: Synthetic RNA

<400> SEQUENCE: 109
uaauuucuac ucuguagau ugugaaaugg cuuauaauug cuua            44

<210> SEQ ID NO 110
<211> LENGTH: 44
<212> TYPE: RNA
<213> ORGANISM: Artificial Sequence
<220> FEATURE:
<223> OTHER INFORMATION: Synthetic RNA

<400> SEQUENCE: 110
uaauuucuac ucuguagau ugugaaaugg cuuauaauug cuua            44

<210> SEQ ID NO 111
<211> LENGTH: 44
<212> TYPE: RNA
<213> ORGANISM: Artificial Sequence
<220> FEATURE:
<223> OTHER INFORMATION: Synthetic RNA

<400> SEQUENCE: 111
uaauuucuac ucuguagau ugugaaaugg cuuauaauug cuua            44

<210> SEQ ID NO 112
<211> LENGTH: 44
<212> TYPE: RNA
<213> ORGANISM: Artificial Sequence
<220> FEATURE:
<223> OTHER INFORMATION: Synthetic RNA

<400> SEQUENCE: 112
uaauuucuac ucuguagau ugugaaaugg cuuauaauug cuua            44

<210> SEQ ID NO 113
<211> LENGTH: 44
<212> TYPE: RNA
<213> ORGANISM: Artificial Sequence
<220> FEATURE:

<223> OTHER INFORMATION: Synthetic RNA

<400> SEQUENCE: 113
uaauuucuac ucuuguagau ugugaaaugg cuuauaauug cuua                    44

<210> SEQ ID NO 114
<211> LENGTH: 44
<212> TYPE: RNA
<213> ORGANISM: Artificial Sequence
<220> FEATURE:
<223> OTHER INFORMATION: Synthetic RNA

<400> SEQUENCE: 114
uaauuucuac ucuuguagau ugugaaaugg cuuauaauug cuua                    44

<210> SEQ ID NO 115
<211> LENGTH: 44
<212> TYPE: RNA
<213> ORGANISM: Artificial Sequence
<220> FEATURE:
<223> OTHER INFORMATION: Synthetic RNA

<400> SEQUENCE: 115
uaauuucuac ucuuguagau ugugaaaugg cuuauaauug cuua                    44

<210> SEQ ID NO 116
<211> LENGTH: 44
<212> TYPE: RNA
<213> ORGANISM: Artificial Sequence
<220> FEATURE:
<223> OTHER INFORMATION: Synthetic RNA

<400> SEQUENCE: 116
uaauuucuac ucuuguagau ugugaaaugg cuuauaauug cuua                    44

<210> SEQ ID NO 117
<211> LENGTH: 44
<212> TYPE: RNA
<213> ORGANISM: Artificial Sequence
<220> FEATURE:
<223> OTHER INFORMATION: Synthetic RNA

<400> SEQUENCE: 117
uaauuucuac ucuuguagau ugugaaaugg cuuauaauug cuua                    44

<210> SEQ ID NO 118
<211> LENGTH: 44
<212> TYPE: RNA
<213> ORGANISM: Artificial Sequence
<220> FEATURE:
<223> OTHER INFORMATION: Synthetic RNA

<400> SEQUENCE: 118
uaauuucuac ucuuguagau ugugaaaugg cuuauaauug cuua                    44

<210> SEQ ID NO 119
<211> LENGTH: 44
<212> TYPE: RNA
<213> ORGANISM: Artificial Sequence
<220> FEATURE:
<223> OTHER INFORMATION: Synthetic RNA

<400> SEQUENCE: 119
uaauuucuac ucuuguagau ugugaaaugg cuuauaauug cuua                    44

```
<210> SEQ ID NO 120
<211> LENGTH: 44
<212> TYPE: RNA
<213> ORGANISM: Artificial Sequence
<220> FEATURE:
<223> OTHER INFORMATION: Synthetic RNA

<400> SEQUENCE: 120
uaauuucuac ucuuguagau ugugaaaugg cuuauaauug cuua                    44

<210> SEQ ID NO 121
<211> LENGTH: 44
<212> TYPE: RNA
<213> ORGANISM: Artificial Sequence
<220> FEATURE:
<223> OTHER INFORMATION: Synthetic RNA

<400> SEQUENCE: 121
uaauuucuac ucuuguagau ugugaaaugg cuuauaauug cuua                    44

<210> SEQ ID NO 122
<211> LENGTH: 44
<212> TYPE: RNA
<213> ORGANISM: Artificial Sequence
<220> FEATURE:
<223> OTHER INFORMATION: Synthetic RNA

<400> SEQUENCE: 122
uaauuucuac ucuuguagau ugugaaaugg cuuauaauug cuua                    44

<210> SEQ ID NO 123
<211> LENGTH: 44
<212> TYPE: RNA
<213> ORGANISM: Artificial Sequence
<220> FEATURE:
<223> OTHER INFORMATION: Synthetic RNA

<400> SEQUENCE: 123
uaauuucuac ucuuguagau ugugaaaugg cuuauaauug cuua                    44

<210> SEQ ID NO 124
<211> LENGTH: 44
<212> TYPE: RNA
<213> ORGANISM: Artificial Sequence
<220> FEATURE:
<223> OTHER INFORMATION: Synthetic RNA

<400> SEQUENCE: 124
uaauuucuac ucuuguagau ugugaaaugg cuuauaauug cuua                    44

<210> SEQ ID NO 125
<211> LENGTH: 44
<212> TYPE: RNA
<213> ORGANISM: Artificial Sequence
<220> FEATURE:
<223> OTHER INFORMATION: Synthetic RNA

<400> SEQUENCE: 125
uaauuucuac ucuuguagau ugugaaaugg cuuauaauug cuua                    44

<210> SEQ ID NO 126
<211> LENGTH: 44
<212> TYPE: RNA
<213> ORGANISM: Artificial Sequence
<220> FEATURE:
<223> OTHER INFORMATION: Synthetic RNA
```

```
<400> SEQUENCE: 126
uaauuucuac ucuuguagau ugugaaaugg cuuauaauug cuua          44

<210> SEQ ID NO 127
<211> LENGTH: 44
<212> TYPE: RNA
<213> ORGANISM: Artificial Sequence
<220> FEATURE:
<223> OTHER INFORMATION: Synthetic RNA

<400> SEQUENCE: 127
uaauuucuac ucuuguagau ugugaaaugg cuuauaauug cuua          44

<210> SEQ ID NO 128
<211> LENGTH: 44
<212> TYPE: RNA
<213> ORGANISM: Artificial Sequence
<220> FEATURE:
<223> OTHER INFORMATION: Synthetic RNA

<400> SEQUENCE: 128
uaauuucuac ucuuguagau ugugaaaugg cuuauaauug cuua          44

<210> SEQ ID NO 129
<211> LENGTH: 44
<212> TYPE: RNA
<213> ORGANISM: Artificial Sequence
<220> FEATURE:
<223> OTHER INFORMATION: Synthetic RNA

<400> SEQUENCE: 129
uaauuucuac ucuuguagau ugugaaaugg cuuauaauug cuua          44

<210> SEQ ID NO 130
<211> LENGTH: 44
<212> TYPE: RNA
<213> ORGANISM: Artificial Sequence
<220> FEATURE:
<223> OTHER INFORMATION: Synthetic RNA

<400> SEQUENCE: 130
uaauuucuac ucuuguagau ugugaaaugg cuuauaauug cuua          44

<210> SEQ ID NO 131
<211> LENGTH: 44
<212> TYPE: RNA
<213> ORGANISM: Artificial Sequence
<220> FEATURE:
<223> OTHER INFORMATION: Synthetic RNA

<400> SEQUENCE: 131
uaauuucuac ucuuguagau ugugaaaugg cuuauaauug cuua          44

<210> SEQ ID NO 132
<211> LENGTH: 44
<212> TYPE: RNA
<213> ORGANISM: Artificial Sequence
<220> FEATURE:
<223> OTHER INFORMATION: Synthetic RNA

<400> SEQUENCE: 132
uaauuucuac ucuuguagau ugugaaaugg cuuauaauug cuua          44

<210> SEQ ID NO 133
<211> LENGTH: 44
```

```
-continued

<212> TYPE: RNA
<213> ORGANISM: Artificial Sequence
<220> FEATURE:
<223> OTHER INFORMATION: Synthetic RNA

<400> SEQUENCE: 133
uaauuucuac ucuuguagau ugugaaaugg cuuauaauug cuua            44

<210> SEQ ID NO 134
<211> LENGTH: 44
<212> TYPE: RNA
<213> ORGANISM: Artificial Sequence
<220> FEATURE:
<223> OTHER INFORMATION: Synthetic RNA

<400> SEQUENCE: 134
uaauuucuac ucuuguagau ugugaaaugg cuuauaauug cuua            44

<210> SEQ ID NO 135
<211> LENGTH: 44
<212> TYPE: RNA
<213> ORGANISM: Artificial Sequence
<220> FEATURE:
<223> OTHER INFORMATION: Synthetic RNA

<400> SEQUENCE: 135
uaauuucuac ucuuguagau ugugaaaugg cuuauaauug cuua            44

<210> SEQ ID NO 136
<211> LENGTH: 44
<212> TYPE: RNA
<213> ORGANISM: Artificial Sequence
<220> FEATURE:
<223> OTHER INFORMATION: Synthetic RNA

<400> SEQUENCE: 136
uaauuucuac ucuuguagau ugugaaaugg cuuauaauug cuua            44

<210> SEQ ID NO 137
<211> LENGTH: 44
<212> TYPE: RNA
<213> ORGANISM: Artificial Sequence
<220> FEATURE:
<223> OTHER INFORMATION: Synthetic RNA

<400> SEQUENCE: 137
uaauuucuac ucuuguagau ugugaaaugg cuuauaauug cuua            44

<210> SEQ ID NO 138
<211> LENGTH: 44
<212> TYPE: RNA
<213> ORGANISM: Artificial Sequence
<220> FEATURE:
<223> OTHER INFORMATION: Synthetic RNA

<400> SEQUENCE: 138
uaauuucuac ucuuguagau ugugaaaugg cuuauaauug cuua            44

<210> SEQ ID NO 139
<211> LENGTH: 44
<212> TYPE: RNA
<213> ORGANISM: Artificial Sequence
<220> FEATURE:
<223> OTHER INFORMATION: Synthetic RNA

<400> SEQUENCE: 139
```
uaauuucuac ucuuguagau ugugaaaugg cuuauaauug cuua        44

<210> SEQ ID NO 140
<211> LENGTH: 44
<212> TYPE: RNA
<213> ORGANISM: Artificial Sequence
<220> FEATURE:
<223> OTHER INFORMATION: Synthetic RNA

<400> SEQUENCE: 140
uaauuucuac ucuuguagau ugugaaaugg cuuauaauug cuua        44

<210> SEQ ID NO 141
<211> LENGTH: 44
<212> TYPE: RNA
<213> ORGANISM: Artificial Sequence
<220> FEATURE:
<223> OTHER INFORMATION: Synthetic RNA

<400> SEQUENCE: 141
uaauuucuac ucuuguagau ugugaaaugg cuuauaauug cuua        44

<210> SEQ ID NO 142
<211> LENGTH: 44
<212> TYPE: RNA
<213> ORGANISM: Artificial Sequence
<220> FEATURE:
<223> OTHER INFORMATION: Synthetic RNA

<400> SEQUENCE: 142
uaauuucuac ucuuguagau ugugaaaugg cuuauaauug cuua        44

<210> SEQ ID NO 143
<211> LENGTH: 44
<212> TYPE: RNA
<213> ORGANISM: Artificial Sequence
<220> FEATURE:
<223> OTHER INFORMATION: Synthetic RNA

<400> SEQUENCE: 143
uaauuucuac ucuuguagau ugugaaaugg cuuauaauug cuua        44

<210> SEQ ID NO 144
<211> LENGTH: 44
<212> TYPE: RNA
<213> ORGANISM: Artificial Sequence
<220> FEATURE:
<223> OTHER INFORMATION: Synthetic RNA

<400> SEQUENCE: 144
uaauuucuac ucuuguagau ugugaaaugg cuuauaauug cuua        44

<210> SEQ ID NO 145
<211> LENGTH: 44
<212> TYPE: RNA
<213> ORGANISM: Artificial Sequence
<220> FEATURE:
<223> OTHER INFORMATION: Synthetic RNA

<400> SEQUENCE: 145
uaauuucuac ucuuguagau ugugaaaugg cuuauaauug cuua        44

<210> SEQ ID NO 146
<211> LENGTH: 44
<212> TYPE: RNA
<213> ORGANISM: Artificial Sequence

```
<220> FEATURE:
<223> OTHER INFORMATION: Synthetic RNA

<400> SEQUENCE: 146
uaauuucuac ucuuguagau ugugaaaugg cuuauaauug cuua          44

<210> SEQ ID NO 147
<211> LENGTH: 44
<212> TYPE: RNA
<213> ORGANISM: Artificial Sequence
<220> FEATURE:
<223> OTHER INFORMATION: Synthetic RNA

<400> SEQUENCE: 147
uaauuucuac ucuuguagau ugugaaaugg cuuauaauug cuua          44

<210> SEQ ID NO 148
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 148
uaauuucuac ucuuguagau ugugaaaugg cuuauaauug c             41

<210> SEQ ID NO 149
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 149
uaauuucuac ucuuguagau ugugaaaugg cuuauaauug c             41

<210> SEQ ID NO 150
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 150
uaauuucuac ucuuguagau ugugaaaugg cuuauaauug c             41

<210> SEQ ID NO 151
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 151
uaauuucuac ucuuguagau ugugaaaugg cuuauaauug c             41

<210> SEQ ID NO 152
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 152
uaauuucuac ucuuguagau ugugaaaugg cuuauaauug c             41
```

<210> SEQ ID NO 153
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 153
uaauuucuac ucuuguagau ugugaaaugg cuuauaauug c         41

<210> SEQ ID NO 154
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 154
uaauuucuac ucuuguagau ugugaaaugg cuuauaauug c         41

<210> SEQ ID NO 155
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 155
uaauuucuac ucuuguagau ugugaaaugg cuuauaauug c         41

<210> SEQ ID NO 156
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 156
uaauuucuac ucuuguagau ugugaaaugg cuuauaauug c         41

<210> SEQ ID NO 157
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 157
uaauuucuac ucuuguagau ugugaaaugg cuuauaauug c         41

<210> SEQ ID NO 158
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 158
uaauuucuac ucuuguagau ugugaaaugg cuuauaauug c         41

<210> SEQ ID NO 159
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 159
uaauuucuac ucuuguagau ugugaaaugg cuuauaauug c             41

<210> SEQ ID NO 160
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 160
uaauuucuac ucuuguagau ugugaaaugg cuuauaauug c             41

<210> SEQ ID NO 161
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 161
uaauuucuac ucuuguagau ugugaaaugg cuuauaauug c             41

<210> SEQ ID NO 162
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 162
uaauuucuac ucuuguagau ugugaaaugg cuuauaauug c             41

<210> SEQ ID NO 163
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 163
uaauuucuac ucuuguagau ugugaaaugg cuuauaauug c             41

<210> SEQ ID NO 164
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 164
uaauuucuac ucuuguagau ugugaaaugg cuuauaauug c             41

<210> SEQ ID NO 165
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 165
uaauuucuac ucuuguagau ugugaaaugg cuuauaauug c             41

<210> SEQ ID NO 166

-continued

<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 166
uaauuucuac ucuuguagau ugugaaaugg cuuauaauug c                          41

<210> SEQ ID NO 167
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 167
uaauuucuac ucuuguagau ugugaaaugg cuuauaauug c                          41

<210> SEQ ID NO 168
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 168
uaauuucuac ucuuguagau ugugaaaugg cuuauaauug c                          41

<210> SEQ ID NO 169
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 169
uaauuucuac ucuuguagau ugugaaaugg cuuauaauug c                          41

<210> SEQ ID NO 170
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 170
uaauuucuac ucuuguagau ugugaaaugg cuuauaauug c                          41

<210> SEQ ID NO 171
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 171
uaauuucuac ucuuguagau ugugaaaugg cuuauaauug c                          41

<210> SEQ ID NO 172
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 172
uaauuucuac ucuuguagau ugugaaaugg cuuauaauug c        41

<210> SEQ ID NO 173
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 173
uaauuucuac ucuuguagau ugugaaaugg cuuauaauug c        41

<210> SEQ ID NO 174
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 174
uaauuucuac ucuuguagau ugugaaaugg cuuauaauug c        41

<210> SEQ ID NO 175
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 175
uaauuucuac ucuuguagau ugugaaaugg cuuauaauug c        41

<210> SEQ ID NO 176
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 176
uaauuucuac ucuuguagau ugugaaaugg cuuauaauug c        41

<210> SEQ ID NO 177
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 177
uaauuucuac ucuuguagau ugugaaaugg cuuauaauug c        41

<210> SEQ ID NO 178
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 178
uaauuucuac ucuuguagau ugugaaaugg cuuauaauug c        41

<210> SEQ ID NO 179
<211> LENGTH: 41
<212> TYPE: RNA

<213> ORGANISM: Artificial Sequence
<220> FEATURE:
<223> OTHER INFORMATION: SYNTHETIC RNA

<400> SEQUENCE: 179
uaauuucuac ucuuguagau ugugaaaugg cuuauaauug c    41

<210> SEQ ID NO 180
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 180
uaauuucuac ucuuguagau ugugaaaugg cuuauaauug c    41

<210> SEQ ID NO 181
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 181
uaauuucuac ucuuguagau ugugaaaugg cuuauaauug c    41

<210> SEQ ID NO 182
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 182
uaauuucuac ucuuguagau ugugaaaugg cuuauaauug c    41

<210> SEQ ID NO 183
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 183
uaauuucuac ucuuguagau ugugaaaugg cuuauaauug c    41

<210> SEQ ID NO 184
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 184
uaauuucuac ucuuguagau ugugaaaugg cuuauaauug c    41

<210> SEQ ID NO 185
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 185
uaauuucuac ucuuguagau ugugaaaugg cuuauaauug c    41

```
<210> SEQ ID NO 186
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 186
uaauuucuac ucuuguagau ugugaaaugg cuuauaauug c                           41

<210> SEQ ID NO 187
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 187
uaauuucuac ucuuguagau ugugaaaugg cuuauaauug c                           41

<210> SEQ ID NO 188
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 188
uaauuucuac ucuuguagau ugugaaaugg cuuauaauug c                           41

<210> SEQ ID NO 189
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 189
uaauuucuac ucuuguagau ggaaagagaa uuguuuucuc cuuc                        44

<210> SEQ ID NO 190
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 190
uaauuucuac ucuuguagau ggaaagagaa uuguuuucuc cuuc                        44

<210> SEQ ID NO 191
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 191
uaauuucuac ucuuguagau ggaaagagaa uuguuuucuc cuuc                        44

<210> SEQ ID NO 192
<211> LENGTH: 44
<212> TYPE: RNA
<213> ORGANISM: Artificial Sequence
<220> FEATURE:
```

<223> OTHER INFORMATION: SYNTHETIC RNA

<400> SEQUENCE: 192
uaauuucuac ucuuguagau ggaaagagaa uuguuucuc cuuc                44

<210> SEQ ID NO 193
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 193
uaauuucuac ucuuguagau ggaaagagaa uuguuucuc cuuc                44

<210> SEQ ID NO 194
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 194
uaauuucuac ucuuguagau ggaaagagaa uuguuucuc cuuc                44

<210> SEQ ID NO 195
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 195
uaauuucuac ucuuguagau ggaaagagaa uuguuucuc cuuc                44

<210> SEQ ID NO 196
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 196
uaauuucuac ucuuguagau ggaaagagaa uuguuucuc cuuc                44

<210> SEQ ID NO 197
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 197
uaauuucuac ucuuguagau ggaaagagaa uuguuucuc cuuc                44

<210> SEQ ID NO 198
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 198
uaauuucuac ucuuguagau ggaaagagaa uuguuucuc cuuc                44

-continued

```
<210> SEQ ID NO 199
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 199
uaauuucuac ucuuguagau ggaaagagaa uuguuuucuc cuuc          44

<210> SEQ ID NO 200
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 200
uaauuucuac ucuuguagau ggaaagagaa uuguuuucuc cuuc          44

<210> SEQ ID NO 201
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 201
uaauuucuac ucuuguagau ggaaagagaa uuguuuucuc cuuc          44

<210> SEQ ID NO 202
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 202
uaauuucuac ucuuguagau ggaaagagaa uuguuuucuc cuuc          44

<210> SEQ ID NO 203
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 203
uaauuucuac ucuuguagau ggaaagagaa uuguuuucuc cuuc          44

<210> SEQ ID NO 204
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 204
uaauuucuac ucuuguagau ggaaagagaa uuguuuucuc cuuc          44

<210> SEQ ID NO 205
<211> LENGTH: 44
<212> TYPE: RNA
<213> ORGANISM: Artificial Sequence
<220> FEATURE:
<223> OTHER INFORMATION: SYNTHETIC RNA
```

```
<400> SEQUENCE: 205
uaauuucuac ucuguagau ggaaagagaa uuguuucuc cuuc                44

<210> SEQ ID NO 206
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 206
uaauuucuac ucuguagau ggaaagagaa uuguuucuc cuuc                44

<210> SEQ ID NO 207
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 207
uaauuucuac ucuguagau ggaaagagaa uuguuucuc cuuc                44

<210> SEQ ID NO 208
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 208
uaauuucuac ucuguagau ggaaagagaa uuguuucuc cuuc                44

<210> SEQ ID NO 209
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 209
uaauuucuac ucuguagau ggaaagagaa uuguuucuc cuuc                44

<210> SEQ ID NO 210
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 210
uaauuucuac ucuguagau ggaaagagaa uuguuucuc cuuc                44

<210> SEQ ID NO 211
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 211
uaauuucuac ucuguagau ggaaagagaa uuguuucuc cuuc                44

<210> SEQ ID NO 212
<211> LENGTH: 44
```

```
<212> TYPE: RNA
<213> ORGANISM: Artificial Sequence
<220> FEATURE:
<223> OTHER INFORMATION: SYNTHETIC RNA

<400> SEQUENCE: 212
uaauuucuac ucuuguagau ggaaagagaa uuguuuucuc cuuc                    44

<210> SEQ ID NO 213
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 213
uaauuucuac ucuuguagau ggaaagagaa uuguuuucuc cuuc                    44

<210> SEQ ID NO 214
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 214
uaauuucuac ucuuguagau ggaaagagaa uuguuuucuc cuuc                    44

<210> SEQ ID NO 215
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 215
uaauuucuac ucuuguagau ggaaagagaa uuguuuucuc cuuc                    44

<210> SEQ ID NO 216
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 216
uaauuucuac ucuuguagau ggaaagagaa uuguuuucuc cuuc                    44

<210> SEQ ID NO 217
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 217
uaauuucuac ucuuguagau ggaaagagaa uuguuuucuc cuuc                    44

<210> SEQ ID NO 218
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 218
```
uaauuucuac ucuuguagau ggaaagagaa uuguuucuc cuuc                44

<210> SEQ ID NO 219
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 219
uaauuucuac ucuuguagau ggaaagagaa uuguuucuc cuuc                44

<210> SEQ ID NO 220
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 220
uaauuucuac ucuuguagau ggaaagagaa uuguuucuc cuuc                44

<210> SEQ ID NO 221
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 221
uaauuucuac ucuuguagau ggaaagagaa uuguuucuc cuuc                44

<210> SEQ ID NO 222
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 222
uaauuucuac ucuuguagau ggaaagagaa uuguuucuc cuuc                44

<210> SEQ ID NO 223
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 223
uaauuucuac ucuuguagau ggaaagagaa uuguuucuc cuuc                44

<210> SEQ ID NO 224
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 224
uaauuucuac ucuuguagau ggaaagagaa uuguuucuc cuuc                44

<210> SEQ ID NO 225
<211> LENGTH: 44
<212> TYPE: RNA
<213> ORGANISM: Artificial Sequence

```
<220> FEATURE:
<223> OTHER INFORMATION: SYNTHETIC RNA

<400> SEQUENCE: 225
uaauuucuac ucuuguagau ggaaagagaa uuguuuucuc cuuc                        44

<210> SEQ ID NO 226
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 226
uaauuucuac ucuuguagau ggaaagagaa uuguuuucuc cuuc                        44

<210> SEQ ID NO 227
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 227
uaauuucuac ucuuguagau ggaaagagaa uuguuuucuc cuuc                        44

<210> SEQ ID NO 228
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 228
uaauuucuac ucuuguagau ggaaagagaa uuguuuucuc cuuc                        44

<210> SEQ ID NO 229
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 229
uaauuucuac ucuuguagau ggaaagagaa uuguuuucuc cuuc                        44

<210> SEQ ID NO 230
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 230
uaauuucuac ucuuguagau ggaaagagaa uuguuuucuc cuuc                        44

<210> SEQ ID NO 231
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 231
uaauuucuac ucuuguagau ggaaagagaa uuguuuucuc cuuc                        44
```

```
<210> SEQ ID NO 232
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 232
uaauuucuac ucuuguagau ggaaagagaa uuguuuucuc cuuc            44

<210> SEQ ID NO 233
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 233
uaauuucuac ucuuguagau ggaaagagaa uuguuuucuc cuuc            44

<210> SEQ ID NO 234
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 234
uaauuucuac ucuuguagau ggaaagagaa uuguuuucuc c               41

<210> SEQ ID NO 235
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 235
uaauuucuac ucuuguagau ggaaagagaa uuguuuucuc c               41

<210> SEQ ID NO 236
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 236
uaauuucuac ucuuguagau ggaaagagaa uuguuuucuc c               41

<210> SEQ ID NO 237
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 237
uaauuucuac ucuuguagau ggaaagagaa uuguuuucuc c               41

<210> SEQ ID NO 238
<211> LENGTH: 41
<212> TYPE: RNA
<213> ORGANISM: Artificial Sequence
<220> FEATURE:
<223> OTHER INFORMATION: SYNTHETIC RNA
```

-continued

```
<400> SEQUENCE: 238
uaauuucuac ucuuguagau ggaaagagaa uuguuucuc c                              41

<210> SEQ ID NO 239
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 239
uaauuucuac ucuuguagau ggaaagagaa uuguuucuc c                              41

<210> SEQ ID NO 240
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 240
uaauuucuac ucuuguagau ggaaagagaa uuguuucuc c                              41

<210> SEQ ID NO 241
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 241
uaauuucuac ucuuguagau ggaaagagaa uuguuucuc c                              41

<210> SEQ ID NO 242
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 242
uaauuucuac ucuuguagau ggaaagagaa uuguuucuc c                              41

<210> SEQ ID NO 243
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 243
uaauuucuac ucuuguagau ggaaagagaa uuguuucuc c                              41

<210> SEQ ID NO 244
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 244
uaauuucuac ucuuguagau ggaaagagaa uuguuucuc c                              41

<210> SEQ ID NO 245
```

<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 245
uaauuucuac ucuuguagau ggaaagagaa uuguuuucuc c          41

<210> SEQ ID NO 246
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 246
uaauuucuac ucuuguagau ggaaagagaa uuguuuucuc c          41

<210> SEQ ID NO 247
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 247
uaauuucuac ucuuguagau ggaaagagaa uuguuuucuc c          41

<210> SEQ ID NO 248
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 248
uaauuucuac ucuuguagau ggaaagagaa uuguuuucuc c          41

<210> SEQ ID NO 249
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 249
uaauuucuac ucuuguagau ggaaagagaa uuguuuucuc c          41

<210> SEQ ID NO 250
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 250
uaauuucuac ucuuguagau ggaaagagaa uuguuuucuc c          41

<210> SEQ ID NO 251
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 251
uaauuucuac ucuuguagau ggaaagagaa uuguuuucuc c        41

<210> SEQ ID NO 252
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 252
uaauuucuac ucuuguagau ggaaagagaa uuguuuucuc c        41

<210> SEQ ID NO 253
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 253
uaauuucuac ucuuguagau ggaaagagaa uuguuuucuc c        41

<210> SEQ ID NO 254
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 254
uaauuucuac ucuuguagau ggaaagagaa uuguuuucuc c        41

<210> SEQ ID NO 255
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 255
uaauuucuac ucuuguagau ggaaagagaa uuguuuucuc c        41

<210> SEQ ID NO 256
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 256
uaauuucuac ucuuguagau ggaaagagaa uuguuuucuc c        41

<210> SEQ ID NO 257
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 257
uaauuucuac ucuuguagau ggaaagagaa uuguuuucuc c        41

<210> SEQ ID NO 258
<211> LENGTH: 41
<212> TYPE: RNA

```
<213> ORGANISM: Artificial Sequence
<220> FEATURE:
<223> OTHER INFORMATION: SYNTHETIC RNA

<400> SEQUENCE: 258
uaauuucuac ucuuguagau ggaaagagaa uuguuuucuc c                    41

<210> SEQ ID NO 259
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 259
uaauuucuac ucuuguagau ggaaagagaa uuguuuucuc c                    41

<210> SEQ ID NO 260
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 260
uaauuucuac ucuuguagau ggaaagagaa uuguuuucuc c                    41

<210> SEQ ID NO 261
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 261
uaauuucuac ucuuguagau ggaaagagaa uuguuuucuc c                    41

<210> SEQ ID NO 262
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 262
uaauuucuac ucuuguagau ggaaagagaa uuguuuucuc c                    41

<210> SEQ ID NO 263
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 263
uaauuucuac ucuuguagau ggaaagagaa uuguuuucuc c                    41

<210> SEQ ID NO 264
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 264
uaauuucuac ucuuguagau ggaaagagaa uuguuuucuc c                    41
```

<210> SEQ ID NO 265
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 265
uaauuucuac ucuuguagau ggaaagagaa uuguuuucuc c        41

<210> SEQ ID NO 266
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 266
uaauuucuac ucuuguagau ggaaagagaa uuguuuucuc c        41

<210> SEQ ID NO 267
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 267
uaauuucuac ucuuguagau ggaaagagaa uuguuuucuc c        41

<210> SEQ ID NO 268
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 268
uaauuucuac ucuuguagau ggaaagagaa uuguuuucuc c        41

<210> SEQ ID NO 269
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 269
uaauuucuac ucuuguagau ggaaagagaa uuguuuucuc c        41

<210> SEQ ID NO 270
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 270
uaauuucuac ucuuguagau ggaaagagaa uuguuuucuc c        41

<210> SEQ ID NO 271
<211> LENGTH: 41
<212> TYPE: RNA
<213> ORGANISM: Artificial Sequence
<220> FEATURE:

<223> OTHER INFORMATION: SYNTHETIC RNA

<400> SEQUENCE: 271
uaauuucuac ucuuguagau ggaaagagaa uuguuuucuc c     41

<210> SEQ ID NO 272
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 272
uaauuucuac ucuuguagau ggaaagagaa uuguuuucuc c     41

<210> SEQ ID NO 273
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 273
uaauuucuac ucuuguagau ggaaagagaa uuguuuucuc c     41

<210> SEQ ID NO 274
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 274
uaauuucuac ucuuguagau ggaaagagaa uuguuuucuc c     41

<210> SEQ ID NO 275
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 275
uaauuucuac ucuuguagau ggaaagagaa uuguuuucuc c     41

<210> SEQ ID NO 276
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 276
uaauuucuac ucuuguagau ugugaaaugg cuuauaauug cuua     44

<210> SEQ ID NO 277
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 277
uaauuucuac ucuuguagau ugugaaaugg cuuauaauug cuua     44

-continued

```
<210> SEQ ID NO 278
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 278
uaauuucuac ucuuguagau ugugaaaugg cuuauaauug cuua                    44

<210> SEQ ID NO 279
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 279
uaauuucuac ucuuguagau ugugaaaugg cuuauaauug c                       41

<210> SEQ ID NO 280
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 280
uaauuucuac ucuuguagau ugugaaaugg cuuauaauug c                       41

<210> SEQ ID NO 281
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 281
uaauuucuac ucuuguagau ugugaaaugg cuuauaauug c                       41

<210> SEQ ID NO 282
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 282
uaauuucuac ucuuguagau ggaaagagaa uuguuucuc cuuc                     44

<210> SEQ ID NO 283
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 283
uaauuucuac ucuuguagau ggaaagagaa uuguuucuc cuuc                     44

<210> SEQ ID NO 284
<211> LENGTH: 44
<212> TYPE: RNA
<213> ORGANISM: Artificial Sequence
<220> FEATURE:
<223> OTHER INFORMATION: SYNTHETIC RNA
```

```
<400> SEQUENCE: 284
uaauuucuac ucuuguagau ggaaagagaa uuguuuucuc cuuc            44

<210> SEQ ID NO 285
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 285
uaauuucuac ucuuguagau ggaaagagaa uuguuuucuc c               41

<210> SEQ ID NO 286
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 286
uaauuucuac ucuuguagau ggaaagagaa uuguuuucuc c               41

<210> SEQ ID NO 287
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 287
uaauuucuac ucuuguagau ggaaagagaa uuguuuucuc c               41

<210> SEQ ID NO 288
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 288
uaauuucuac ucuuguagau ggaaagagaa uuguuuucuc c               41

<210> SEQ ID NO 289
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 289
uaauuucuac ucuuguagau ggaaagagaa uuguuuucuc c               41

<210> SEQ ID NO 290
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 290
uaauuucuac ucuuguagau ggaaagagaa uuguuuucuc c               41

<210> SEQ ID NO 291
<211> LENGTH: 41
```

```
<212> TYPE: RNA
<213> ORGANISM: Artificial Sequence
<220> FEATURE:
<223> OTHER INFORMATION: SYNTHETIC RNA

<400> SEQUENCE: 291
uaauuucuac ucuuguagau ggaaagagaa uuguuucuc c                                41

<210> SEQ ID NO 292
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 292
uaauuucuac ucuuguagau ggaaagagaa uuguuucuc c                                41

<210> SEQ ID NO 293
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 293
uaauuucuac ucuuguagau ggaaagagaa uuguuucuc c                                41

<210> SEQ ID NO 294
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 294
uaauuucuac ucuuguagau ggaaagagaa uuguuucuc c                                41

<210> SEQ ID NO 295
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 295
uaauuucuac ucuuguagau ggaaagagaa uuguuucuc c                                41

<210> SEQ ID NO 296
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 296
uaauuucuac ucuuguagau ggaaagagaa uuguuucuc c                                41

<210> SEQ ID NO 297
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 297
```
uaauuucuac ucuuguagau ggaaagagaa uuguuucuc c          41

<210> SEQ ID NO 298
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 298
uaauuucuac ucuuguagau ggaaagagaa uuguuucuc c          41

<210> SEQ ID NO 299
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 299
uaauuucuac ucuuguagau ggaaagagaa uuguuucuc c          41

<210> SEQ ID NO 300
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 300
uaauuucuac ucuuguagau ggaaagagaa uuguuucuc c          41

<210> SEQ ID NO 301
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 301
uaauuucuac ucuuguagau ggaaagagaa uuguuucuc c          41

<210> SEQ ID NO 302
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 302
uaauuucuac ucuuguagau ggaaagagaa uuguuucuc c          41

<210> SEQ ID NO 303
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 303
uaauuucuac ucuuguagau ggaaagagaa uuguuucuc c          41

<210> SEQ ID NO 304
<211> LENGTH: 41
<212> TYPE: RNA
<213> ORGANISM: Artificial Sequence

```
<220> FEATURE:
<223> OTHER INFORMATION: SYNTHETIC RNA

<400> SEQUENCE: 304
uaauuucuac ucuuguagau ggaaagagaa uuguuuucuc c                      41

<210> SEQ ID NO 305
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 305
uaauuucuac ucuuguagau ggaaagagaa uuguuuucuc c                      41

<210> SEQ ID NO 306
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 306
uaauuucuac ucuuguagau ggaaagagaa uuguuuucuc c                      41

<210> SEQ ID NO 307
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 307
uaauuucuac ucuuguagau ggaaagagaa uuguuuucuc c                      41

<210> SEQ ID NO 308
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 308
uaauuucuac ucuuguagau ggaaagagaa uuguuuucuc c                      41

<210> SEQ ID NO 309
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 309
uaauuucuac ucuuguagau ggaaagagaa uuguuuucuc c                      41

<210> SEQ ID NO 310
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 310
uaauuucuac ucuuguagau ggaaagagaa uuguuuucuc c                      41
```

<210> SEQ ID NO 311
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 311
uaauuucuac ucuuguagau ggaaagagaa uuguuuucuc c          41

<210> SEQ ID NO 312
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 312
uaauuucuac ucuuguagau ggaaagagaa uuguuuucuc c          41

<210> SEQ ID NO 313
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 313
uaauuucuac ucuuguagau ggaaagagaa uuguuuucuc c          41

<210> SEQ ID NO 314
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 314
uaauuucuac ucuuguagau ggaaagagaa uuguuuucuc c          41

<210> SEQ ID NO 315
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 315
uaauuucuac ucuuguagau ggaaagagaa uuguuuucuc c          41

<210> SEQ ID NO 316
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 316
uaauuucuac ucuuguagau ggaaagagaa uuguuuucuc c          41

<210> SEQ ID NO 317
<211> LENGTH: 41
<212> TYPE: RNA
<213> ORGANISM: Artificial Sequence
<220> FEATURE:
<223> OTHER INFORMATION: SYNTHETIC RNA

```
<400> SEQUENCE: 317
uaauuucuac ucuuguagau ggaaagagaa uuguuucuc c                    41

<210> SEQ ID NO 318
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 318
uaauuucuac ucuuguagau ggaaagagaa uuguuucuc c                    41

<210> SEQ ID NO 319
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 319
uaauuucuac ucuuguagau ggaaagagaa uuguuucuc c                    41

<210> SEQ ID NO 320
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 320
uaauuucuac ucuuguagau ggaaagagaa uuguuucuc c                    41

<210> SEQ ID NO 321
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 321
uaauuucuac ucuuguagau ggaaagagaa uuguuucuc c                    41

<210> SEQ ID NO 322
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 322
uaauuucuac ucuuguagau ggaaagagaa uuguuucuc c                    41

<210> SEQ ID NO 323
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 323
uaauuucuac ucuuguagau ggaaagagaa uuguuucuc c                    41

<210> SEQ ID NO 324
```

```
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 324
uaauuucuac ucuuguagau ggaaagagaa uuguuuucuc c          41

<210> SEQ ID NO 325
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 325
uaauuucuac ucuuguagau ggaaagagaa uuguuuucuc c          41

<210> SEQ ID NO 326
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 326
uaauuucuac ucuuguagau ggaaagagaa uuguuuucuc c          41

<210> SEQ ID NO 327
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 327
uaauuucuac ucuuguagau ggaaagagaa uuguuuucuc c          41

<210> SEQ ID NO 328
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 328
uaauuucuac ucuuguagau ggaaagagaa uuguuuucuc c          41

<210> SEQ ID NO 329
<211> LENGTH: 41
<212> TYPE: DNA
<213> ORGANISM: Artificial Sequence
<220> FEATURE:
<223> OTHER INFORMATION: SYNTHETIC RNA-DNA

<400> SEQUENCE: 329
taauuucuac ucuuguagau ggaaagagaa uuguuuucuc c          41

<210> SEQ ID NO 330
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 330
```
uaauuucuac ucuuguagau ggaaagagaa uuguuucuc c                41

<210> SEQ ID NO 331
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 331
uaauuucuac ucuuguagau ggaaagagaa uuguuucuc c                41

<210> SEQ ID NO 332
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 332
uaauuucuac ucuuguagau ggaaagagaa uuguuucuc c                41

<210> SEQ ID NO 333
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 333
uaauuucuac ucuuguagau ggaaagagaa uuguuucuc c                41

<210> SEQ ID NO 334
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 334
uaauuucuac ucuuguagau ggaaagagaa uuguuucuc c                41

<210> SEQ ID NO 335
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 335
uaauuucuac ucuuguagau ggaaagagaa uuguuucuc c                41

<210> SEQ ID NO 336
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 336
uaauuucuac ucuuguagau ggaaagagaa uuguuucuc c                41

<210> SEQ ID NO 337
<211> LENGTH: 41
<212> TYPE: RNA

```
<213> ORGANISM: Artificial Sequence
<220> FEATURE:
<223> OTHER INFORMATION: SYNTHETIC RNA

<400> SEQUENCE: 337
uaauuucuac ucuuguagau ggaaagagaa uuguuuucuc c        41

<210> SEQ ID NO 338
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 338
uaauuucuac ucuuguagau cuugggugug uuaaaaguga c        41

<210> SEQ ID NO 339
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 339
uaauuucuac ucuuguagau cuugggugug uuaaaaguga c        41

<210> SEQ ID NO 340
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 340
uaauuucuac ucuuguagau cuugggugug uuaaaaguga c        41

<210> SEQ ID NO 341
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 341
uaauuucuac ucuuguagau cuugggugug uuaaaaguga c        41

<210> SEQ ID NO 342
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 342
uaauuucuac ucuuguagau cuugggugug uuaaaaguga c        41

<210> SEQ ID NO 343
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 343
uaauuucuac ucuuguagau acauaaaacu cuuuuagguu a        41
```

<210> SEQ ID NO 344
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 344
uaauuucuac ucuguagau acauaaaacu cuuuuagguu a        41

<210> SEQ ID NO 345
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 345
uaauuucuac ucuguagau acauaaaacu cuuuuagguu a        41

<210> SEQ ID NO 346
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 346
uaauuucuac ucuguagau acauaaaacu cuuuuagguu a        41

<210> SEQ ID NO 347
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 347
uaauuucuac ucuguagau acauaaaacu cuuuuagguu a        41

<210> SEQ ID NO 348
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 348
uaauuucuac ucuguagau acauaaaacu cuuuuagguu a        41

<210> SEQ ID NO 349
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 349
uaauuucuac ucuguagau acauaaaacu cuuuuagguu a        41

<210> SEQ ID NO 350
<211> LENGTH: 41
<212> TYPE: RNA
<213> ORGANISM: Artificial Sequence
<220> FEATURE:

<223> OTHER INFORMATION: SYNTHETIC RNA

<400> SEQUENCE: 350
uaauuucuac ucuguagau acauaaaacu cuuuuagguu a    41

<210> SEQ ID NO 351
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 351
uaauuucuac ucuguagau acauaaaacu cuuuuagguu a    41

<210> SEQ ID NO 352
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 352
uaauuucuac ucuguagau acauaaaacu cuuuuagguu a    41

<210> SEQ ID NO 353
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 353
uaauuucuac ucuguagau acauaaaacu cuuuuagguu a    41

<210> SEQ ID NO 354
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 354
uaauuucuac ucuguagau acauaaaacu cuuuuagguu a    41

<210> SEQ ID NO 355
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 355
uaauuucuac ucuguagau acauaaaacu cuuuuagguu a    41

<210> SEQ ID NO 356
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 356
uaauuucuac ucuguagau acauaaaacu cuuuuagguu a    41

```
<210> SEQ ID NO 357
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 357
uaauuucuac ucuuguagau auagucuuuc cuugggugug u                    41

<210> SEQ ID NO 358
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 358
uaauuucuac uaaguguaga uauagucuuu ccuugggugu gu                   42

<210> SEQ ID NO 359
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 359
uaauuucuac uaaguguaga uauagucuuu ccuugggugu guua                 44

<210> SEQ ID NO 360
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 360
uaauuucuac ucuuguagau cuugggugug uuaaaaguga c                    41

<210> SEQ ID NO 361
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 361
uaauuucuac uaaguguaga ucuugggugu guuaaaagug ac                   42

<210> SEQ ID NO 362
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 362
uaauuucuac uaaguguaga ucuugggugu guuaaaagug acca                 44

<210> SEQ ID NO 363
<211> LENGTH: 44
<212> TYPE: RNA
<213> ORGANISM: Artificial Sequence
<220> FEATURE:
<223> OTHER INFORMATION: SYNTHETIC RNA
```

```
<400> SEQUENCE: 363
uaauuucuac uaaguguaga ucuugggugu guuaaaagug acca        44

<210> SEQ ID NO 364
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 364
uaauuucuac uaaguguaga uacacaccca aggaaagacu au          42

<210> SEQ ID NO 365
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 365
uaauuucuac uaaguguaga uacacaccca aggaaagacu auga        44

<210> SEQ ID NO 366
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 366
uaauuucuac ucuuguagau auccgugcug aguguaccau g           41

<210> SEQ ID NO 367
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 367
uaauuucuac uaaguguaga uauccgugcu gaguguacca ug          42

<210> SEQ ID NO 368
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 368
uaauuucuac uaaguguaga uauccgugcu gaguguacca ugca        44

<210> SEQ ID NO 369
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 369
uaauuucuac ucuuguagau uaaacacugu uucauuucau c           41

<210> SEQ ID NO 370
<211> LENGTH: 42
```

```
<212> TYPE: RNA
<213> ORGANISM: Artificial Sequence
<220> FEATURE:
<223> OTHER INFORMATION: SYNTHETIC RNA

<400> SEQUENCE: 370
uaauuucuac uaaguguaga uuaaacacug uuucauuuca uc              42

<210> SEQ ID NO 371
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 371
uaauuucuac uaaguguaga uuaaacacug uuucauuuca uccg            44

<210> SEQ ID NO 372
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 372
uaauuucuac ucuuguagau gaaacgucag ucuucucuuu u               41

<210> SEQ ID NO 373
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 373
uaauuucuac uaaguguaga ugaaacguca gucuucucuu uu              42

<210> SEQ ID NO 374
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 374
uaauuucuac uaaguguaga ugaaacguca gucuucucuu uugu            44

<210> SEQ ID NO 375
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 375
uaauuucuac ucuuguagau uaaugcccug uagucucucu g               41

<210> SEQ ID NO 376
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 376
```

```
uaauuucuac uaaguguaga uuaaugcccu guagucucuc ug            42

<210> SEQ ID NO 377
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 377
uaauuucuac uaaguguaga uuaaugcccu guagucucuc ugua          44

<210> SEQ ID NO 378
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 378
uaauuucuac ucuuguagau uaauuaacag cuugcuggug a             41

<210> SEQ ID NO 379
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 379
uaauuucuac uaaguguaga uuaauuaaca gcuugcuggu ga            42

<210> SEQ ID NO 380
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 380
uaauuucuac uaaguguaga uuaauuaaca gcuugcuggu gaaa          44

<210> SEQ ID NO 381
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 381
uaauuucuac ucuuguagau gguuaaagau gguuaaauga u             41

<210> SEQ ID NO 382
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 382
uaauuucuac uaaguguaga ugguuaaaga ugguuaaaug au            42

<210> SEQ ID NO 383
<211> LENGTH: 44
<212> TYPE: RNA
<213> ORGANISM: Artificial Sequence
```

```
<220> FEATURE:
<223> OTHER INFORMATION: SYNTHETIC RNA

<400> SEQUENCE: 383
uaauuucuac uaaguguaga ugguuaaaga ugguuaaaug auug                    44

<210> SEQ ID NO 384
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 384
uaauuucuac ucuuguagau gugaaaugg cuuauaauug c                        41

<210> SEQ ID NO 385
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 385
uaauuucuac uaaguguaga uugugaaaug gcuuauaauu gc                      42

<210> SEQ ID NO 386
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 386
uaauuucuac uaaguguaga uugugaaaug gcuuauaauu gcuu                    44

<210> SEQ ID NO 387
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 387
uaauuucuac ucuuguagau guuguuggau uugaaauucc a                       41

<210> SEQ ID NO 388
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 388
uaauuucuac uaaguguaga uguuguugga uugaaauuc ca                       42

<210> SEQ ID NO 389
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 389
uaauuucuac uaaguguaga uguuguugga uugaaauuc caga                     44
```

<210> SEQ ID NO 390
<211> LENGTH: 41
<212> TYPE: RNA
<213> ORGANISM: Artificial Sequence
<220> FEATURE:
<223> OTHER INFORMATION: SYNTHETIC RNA

<400> SEQUENCE: 390
uaauuucuac ucuuguagau uuguaggaua ugcccuugac u                41

<210> SEQ ID NO 391
<211> LENGTH: 42
<212> TYPE: RNA
<213> ORGANISM: Artificial Sequence
<220> FEATURE:
<223> OTHER INFORMATION: SYNTHETIC RNA

<400> SEQUENCE: 391
uaauuucuac uaaguguaga uuuguaggau augcccuuga cu               42

<210> SEQ ID NO 392
<211> LENGTH: 44
<212> TYPE: RNA
<213> ORGANISM: Artificial Sequence
<220> FEATURE:
<223> OTHER INFORMATION: SYNTHETIC RNA

<400> SEQUENCE: 392
uaauuucuac uaaguguaga uuuguaggau augcccuuga cuau             44

<210> SEQ ID NO 393
<211> LENGTH: 27
<212> TYPE: DNA
<213> ORGANISM: Artificial Sequence
<220> FEATURE:
<223> OTHER INFORMATION: SYNTHETIC DNA

<400> SEQUENCE: 393
aagaatgttg tgataaaagg tgatgct                                27

<210> SEQ ID NO 394
<211> LENGTH: 24
<212> TYPE: DNA
<213> ORGANISM: Artificial Sequence
<220> FEATURE:
<223> OTHER INFORMATION: SYNTHETIC DNA

<400> SEQUENCE: 394
acacatccat gggacttctg cctc                                   24

<210> SEQ ID NO 395
<211> LENGTH: 3834
<212> TYPE: DNA
<213> ORGANISM: Artificial Sequence
<220> FEATURE:
<223> OTHER INFORMATION: SYNTHETIC DNA

<400> SEQUENCE: 395
atgctgaaga acgtgggcat cgaccggctg gacgtggaaa agggcagaaa gaacatgagc    60
aagctcgaga agttcaccaa ctgctacagc ctgagcaaga ccctgcggtt caaggccatt   120
cctgtgggca agacccaaga gaacatcgac aacaagcggc tgctggtgga agatgagaag   180
agagccgagg actacaaggg cgtgaagaag ctgctggacc ggtactacct gagcttcatc   240
aacgacgtgc tgcacagcat caagctcaag aacctgaaca actacatcag cctgttccgg   300

```
aagaaaaccc ggaccgagaa agagaacaaa gagctggaaa acctcgagat caacctgcgg      360
aaagagatcg ccaaggcctt caagggcaac gagggctaca agagcctgtt caagaaggac      420
atcatcgaga caatcctgcc tgagttcctg gacgacaagg acgagatcgc cctggtcaac      480
agcttcaacg gcttcacaac cgccttcacc ggcttttttcg acaaccgcga gaatatgttc     540
agcgaggaag ccaagagcac ctctatcgcc ttccggtgca tcaacgagaa tctgacccgg      600
tacatcagca acatggatat cttcgagaag gtggacgcca tcttcgacaa gcacgaggtg      660
caagagatca agaaaagat cctgaacagc gactacgacg tcgaggactt cttcgagggc       720
gagttcttca acttcgtgct gacacaagag ggcatcgatg tgtacaacgc catcatcggc      780
ggcttcgtga cagagagcgg cgagaagatc aagggcctga cgagtacat caacctctac       840 aaccagaaaa cgaagcagaa gctgcccaag ttcaagcccc tgtacaaaca ggtgctgagc      900
gacagagaga gcctgtcctt ttacggcgag ggctatacca gcgacgaaga ggtgctggaa      960
gtgttcagaa acaccctgaa caagaacagc gagatcttca gctccatcaa gaagctcgaa     1020 aagctgtttta agaacttcga cgagtacagc agcgccggca tcttcgtgaa gaatggccct    1080
gccatcagca ccatctccaa ggacatcttc ggcgagtgga acgtgatccg ggacaagtgg     1140
aacgccgagt acgacgacat ccacctgaag aaaaaggccg tggtcaccga agtacgag       1200 gacgacagaa gaaagagctt caagaagatc ggcagcttca gcctggaaca gctgcaagag    1260
tacgccgacg ccgatctgag cgtggtggaa aagctgaaag agattatcat ccagaaggtc    1320
gacgagatct acaaggtgta cggcagcagc gagaagctgt tcgacgccga ctttgtgctg    1380
gaaaagagcc tcaaaagaa cgacgccgtg gtggccatca tgaaggacct gctggatagc     1440
gtgaagtcct tcgagaacta tattaaggcc ttctttggcg agggcaaaga gacaaaccgg    1500
gacgagagct tctacggcga tttcgtgctg gcctacgaca tcctgctgaa agtggaccac    1560
atctacgacg ccatccggaa ctacgtgacc cagaagccttt acagcaagga caagtttaag   1620
ctgtacttcc agaatccgca gttcatgggc ggctgggaca agacaaaga aaccgactac     1680 cgggccacca tcctgagata cggctccaag tactatctgg ccattatgga caagaaatac   1740
gccaagtgcc tgcagaagat cgataaggac gacgtgaacg gcaactacga agagattaac   1800
tacaagctgc tgcccggacc taacaagatg ctgcctaagg tgttcttag caagaaatgg    1860 atggcctact acaaccccag cgaggatatc cagaaaatct acaagaacgg cacccttcaag  1920 aaaggcgaca tgttcaacct gaacgactgc cacaagctga tcgatttctt caaggacagc   1980
atcagcagat acccaagtg gtccaacgcc tacgacttca atttcagcga gacagagaag    2040
tataaggata tcgccgggtt ctaccgcgag gtggaagaac agggctataa ggtgtccttt    2100
gagagcgcca gcaagaaaga ggtggacaag ctggtcgaag agggcaagct gtacatgttc    2160
cagatctata acaaggactt ctccgacaag agccacggca ccctaacct gcacaccatg    2220 tactttaagc tgctgttcga tgagaacaac cacggccaga tcagactgtc tggcggagcc    2280
gagctgttta tgagaagggc cagcctgaaa aagaggaac tggtcgttca ccccgccaac     2340
tctccaatcg ccaacaagaa ccccgacaat cccaagaaaa ccaccacact gagctacgac   2400
gtgtacaagg ataagcggtt ctccgaggac cagtacgagc tgcacatccc tatcgccatc   2460
aacaagtgcc ccaagaatat cttcaagatc aacaccgaag tgcgggtgct gctgaagcac   2520
gacgacaacc cttacgtgat cggcatcgac agaggcgagc ggaacctgct gtatatcgtg   2580
gtggtggacg gcaagggcaa tatcgtggaa cagtactccc tgaatgagat catcaacaac   2640
```

```
ttcaatggca tccggatcaa gacggactac cacagcctgc tggacaaaaa agagaaagaa    2700
cgcttcgagg cccggcagaa ctggaccagc atcgagaaca tcaaagaact gaaggccggc    2760
tacatctccc aggtggtgca caagatctgc gagctggttg agaagtatga cgccgtgatt    2820
gccctggaag atctgaatag cggctttaag aacagccgcg tgaaggtcga gaaacaggtg    2880
taccagaaat tcgagaagat gctgatcgac aagctgaact acatggtcga caagaagtct    2940
aacccctgcg ccacaggcgg agccctgaag ggatatcaga tcaccaacaa gttcgagtcc    3000
ttcaagagca tgagcaccca gaatggcttc atcttctaca tccccgcctg gctgaccagc    3060
aagatcgatc ctagcaccgg attcgtgaac ctgctcaaga ccaagtacac cagcattgcc    3120
gacagcaaga agttcatctc cagcttcgac cggattatgt acgtgcccga agaggacctg    3180
ttcgaattcg ccctggatta caagaacttc agccggaccg atgccgacta tatcaagaag    3240
tggaagctgt atagctacgg caaccgcatc cgcatcttca gaaacccgaa gaaaaacaac    3300
gtgttcgact gggaagaagt gtgcctgacc agcgcctaca aagaactctt caacaaatac    3360
ggcatcaact accagcaggg cgacatcaga gccctgctgt gcgagcagag cgacaaggcc    3420
ttttacagct ccttcatggc cctgatgtcc ctgatgctgc agatgcggaa tagcatcacc    3480
ggcaggaccg acgtggactt cctgatcagc cctgtgaaga attccgacgg gatcttctac    3540
gacagcagaa actacgaggc tcaagagaac gccatcctgc ctaagaacgc cgatgccaac    3600
ggcgcctata atatcgccag aaaggtgctg tgggccatcg gccagtttaa gaaggccgag    3660
gacgagaaac tggacaaagt gaagatcgcc atctctaaca aagagtggct ggaatacgcc    3720
cagaccagcg tgaagcacgg cagatctagt gacgatgagg ccaccgccga tagccagcat    3780
gcagcccctc caaagaaaaa gcggaaagtg ctggaacacc accaccatca ccac          3834
```

CRISPR/CPF1 SYSTEMS AND METHODS

CROSS-REFERENCE TO RELATED APPLICATIONS

This application claims benefit of priority under 35 U.S.C. 119 to U.S. Provisional Patent Application Ser. No. 62/425,307, filed Nov. 22, 2016 and entitled "CPF1 CRISPR SYSTEMS AND METHODS," and U.S. Provisional Patent Application Ser. No. 62/482,896, filed Apr. 7, 2017 and entitled "HEK293 CELL LINE WITH STABLE EXPRESSION OF *ACIDAMINOCOCCUS* SP. BV3L6 CPF1," the contents of which are herein incorporated by reference in their entirety.

SEQUENCE LISTING

The instant application contains a Sequence Listing that has been submitted in ASCII format via EFS-Web and is hereby incorporated by reference in its entirety. The ASCII copy, created on Jan. 4, 2018, is named IDT01-010-US ST25.txt, and is 263,473 bytes in size.

FIELD OF THE INVENTION

This invention pertains to Cpf1-based CRISPR genes, polypeptides encoded by the same, mammalian cell lines that stably express Cpf1, crRNAs and the use of these materials in compositions of CRISPR-Cpf1 systems and methods.

BACKGROUND OF THE INVENTION

The use of clustered regularly interspaced short palindromic repeats (CRISPR) and associated Cas proteins (CRISPR-Cas system) for site-specific DNA cleavage has shown great potential for a number of biological applications. CRISPR is used for genome editing; the genome-scale-specific targeting of transcriptional repressors (CRISPRi) and activators (CRISPRa) to endogenous genes; and other applications of RNA-directed DNA targeting with Cas enzymes.

CRISPR-Cas systems are native to bacteria and Archaea and provide adaptive immunity against viruses and plasmids. Three classes of CRISPR-Cas systems could potentially be adapted for research and therapeutic reagents. Type-II CRISPR systems have a desirable characteristic in utilizing a single CRISPR associated (Cas) nuclease (specifically Cas9) in a complex with the appropriate guide RNAs (gRNAs). In bacteria or Archaea, Cas9 guide RNAs comprise 2 separate RNA species. A target-specific CRISPR-activating RNA (crRNA) directs the Cas9/gRNA complex to bind and target a specific DNA sequence. The crRNA has 2 functional domains, a 5'-domain that is target specific and a 3'-domain that directs binding of the crRNA to the transactivating crRNA (tracrRNA). The tracrRNA is a longer, universal RNA that binds the crRNA and mediates binding of the gRNA complex to Cas9. Binding of the tracrRNA induces an alteration of Cas9 structure, shifting from an inactive to an active conformation. The gRNA function can also be provided as an artificial single guide RNA (sgRNA), where the crRNA and tracrRNA are fused into a single species (see Jinek, M., et al., Science 337 p 816-21, 2012). The sgRNA format permits transcription of a functional gRNA from a single transcription unit that can be provided by a double-stranded DNA (dsDNA) cassette containing a transcription promoter and the sgRNA sequence. In mammalian systems, these RNAs have been introduced by transfection of DNA cassettes containing RNA Pol III promoters (such as U6 or H1) driving RNA transcription, viral vectors, and single-stranded RNA following in vitro transcription (see Xu, T., et al., Appl Environ Microbiol, 2014. 80(5): p. 1544-52). In bacterial systems, these RNAs are expressed as part of a primitive immune system, or can be artificially expressed from a plasmid that is introduced by transformation (see Fonfara, I., et al., Nature, 2016. 532(7600): p. 517-21).

In the CRISPR-Cas system, using the system present in *Streptococcus pyogenes* as an example (S.py. or Spy), native crRNAs are about 42 bases long and contain a 5'-region of about 20 bases in length that is complementary to a target sequence (also referred to as a protospacer sequence or protospacer domain of the crRNA) and a 3' region typically of about 22 bases in length that is complementary to a region of the tracrRNA sequence and mediates binding of the crRNA to the tracrRNA. A crRNA:tracrRNA complex comprises a functional gRNA capable of directing Cas9 cleavage of a complementary target DNA. The native tracrRNAs are about 85-90 bases long and have a 5'-region containing the region complementary to the crRNA. The remaining 3' region of the tracrRNA includes secondary structure motifs (herein referred to as the "tracrRNA 3'-tail") that mediate binding of the crRNA:tracrRNA complex to Cas9.

Jinek et al. extensively investigated the physical domains of the crRNA and tracrRNA that are required for proper functioning of the CRISPR-Cas system (Science, 2012. 337(6096): p. 816-21). They devised a truncated crRNA: tracrRNA fragment that could still function in CRISPR-Cas wherein the crRNA was the wild type 42 nucleotides and the tracrRNA was truncated to 75 nucleotides. They also developed an embodiment wherein the crRNA and tracrRNA are attached with a linker loop, forming a single guide RNA (sgRNA), which varies between 99-123 nucleotides in different embodiments.

At least three groups have elucidated the crystal structure of *Streptococcus pyogenes* Cas9 (SpyCas9). In Jinek, M., et al., the structure did not show the nuclease in complex with either a guide RNA or target DNA. They carried out molecular modeling experiments to reveal predictive interactions between the protein in complex with RNA and DNA (Science, 2014. 343, p. 1215, DOI: 10.1126/science/1247997).

In Nishimasu, H., et al., the crystal structure of Spy Cas9 is shown in complex with sgRNA and its target DNA at 2.5 angstrom resolution (Cell, 2014. 156(5): p. 935-49, incorporated herein in its entirety). The crystal structure identified two lobes to the Cas9 enzyme: a recognition lobe (REC) and a nuclease lobe (NUC). The sgRNA:target DNA heteroduplex (negatively charged) sits in the positively charged groove between the two lobes. The REC lobe, which shows no structural similarity with known proteins and therefore likely a Cas9-specific functional domain, interacts with the portions of the crRNA and tracrRNA that are complementary to each other.

Another group, Briner et al. (Mol Cell, 2014. 56(2): p. 333-9, incorporated herein in its entirety), identified and characterized the six conserved modules within native crRNA:tracrRNA duplexes and sgRNA. Anders et al. (Nature, 2014, 513(7519) p. 569-73) elucidated the structural basis for DNA sequence recognition of protospacer associate motif (PAM) sequences by Cas9 in association with an sgRNA guide.

The CRISPR-Cas endonuclease system is utilized in genomic engineering as follows: the gRNA complex (either a crRNA:tracrRNA complex or an sgRNA) binds to Cas9, inducing a conformational change that activates Cas9 and opens the DNA binding cleft, the protospacer domain of the crRNA (or sgRNA) aligns with the complementary target DNA and Cas9 binds the PAM sequence, initiating unwinding of the target DNA followed by annealing of the protospacer domain to the target, after which cleavage of the target DNA occurs. The Cas9 contains two domains, homologous to endonucleases HNH and RuvC respectively, wherein the HNH domain cleaves the DNA strand complementary to the crRNA and the RuvC-like domain cleaves the non-complementary strand. This results in a double-stranded break in the genomic DNA. When repaired by non-homologous end joining (NHEJ) the break is typically repaired in an imprecise fashion, resulting in the DNA sequence being shifted by 1 or more bases, leading to disruption of the natural DNA sequence and, in many cases, leading to a frameshift mutation if the event occurs in a coding exon of a protein-encoding gene. The break may also be repaired by homology directed recombination (HDR), which permits insertion of new genetic material based upon exogenous DNA introduced into the cell with the Cas9/gRNA complex, which is introduced into the cut site created by Cas9 cleavage.

While SpyCas9 is the protein being most widely used, it does hold some barriers to its effectiveness. SpyCas9 recognizes targeted sequences in the genome that are immediately followed by a GG dinucleotide sequence, and this system is therefore limited to GC-rich regions of the genome. AT-rich species or genomic regions are therefore often not targetable with the SpyCas9 system. Furthermore, the fact that the Cas9 system includes a gRNA having both a crRNA and a tracrRNA moiety that comprise over 100 bases means that more RNA must be optimized and synthesized for sequence-specific targeting. As such, a shorter simpler gRNA would be desirable.

A second class 2 CRISPR system, assigned to type V, has been identified. This type V CRISPR-associated system contains Cpf1, which is a ~1300 amino acid protein—slightly smaller than Cas9 from *S. pyogenes*. The PAM recognition sequence of Cpf1 from *Acidaminococcus* sp. BV3L6 or *Lachnospiraceae bacterium* ND2006 is TTTN, in contrast to the NGG PAM recognition domain of *S. pyogenes* Cas9 (FIG. 1). Having the ability to target AT-rich areas of the genome will be greatly beneficial to manipulate and study gene targets in regions that are lacking GG dinucleotide motifs. The Cpf1 system is also remarkably simple in that it does not utilize a separate tracrRNA, and only requires a single short crRNA of 40-45 base length that both specifies target DNA sequence and directs binding of the RNA to the Cpf1 nuclease.

In contrast to Cas9 which produces blunt-ended cleavage products, Cpf1 facilitates double stranded breaks with 4-5 nucleotide overhangs. The advantage of this is that it may ensure proper orientation as well as providing microhomology during non-homologous end joining (NHEJ). This could also be advantageous in non-dividing cell types that tend to be resistant to homology-directed repair (HDR). Furthermore, when Cpf1 cleaves, it does so further away from PAM than Cas9, which is also further away from the target site. As a result, the protospacer, and especially the seed sequence of the protospacer, are less likely to be edited, thereby leaving open the potential for a second round of cleavage if the desired repair event doesn't happen the first time.

The Cpf1 protein forms a complex with a single stranded RNA oligonucleotide to mediate targeted DNA cleavage. The single strand guide RNA oligonucleotide consists of a constant region of 20 nt and a target region of 21-24 nt for an overall length of 41-44 nt. There are many known orthologs of Cpf1 from a variety of different bacterial and Archaea sources that differ with respect to activity and target preference and may be candidates for use in genome editing applications. For the purposes of this invention, we primarily studied, as representative examples, the Cpf1 nucleases from A.s. (*Acidaminococcus* sp. BV3L6) Cpf1 and L.b. (*Lachnospiraceae bacterium* ND2006), both of which have already been shown to be active in mammalian cells as a tool for genome editing. Of note, the PAM recognition sequence is TTTN. The structure of the Cpf1 crRNA and relationship of RNA binding to the PAM site in genomic DNA is shown in FIG. 1.

Since the discovery of Cpf1 as another CRISPR pathway with potential utility for genome editing in mammalian cells, several publications have confirmed that the system works in mammals, can be used for embryo engineering, and the crystal structure and mechanism of PAM site recognition have been described. This system has also shown utility for screening purposes in genetically-tractable bacterial species such as *E. coli*. The system therefore has proven utility and developing optimized reagents to perform genome editing using Cpf1 would be beneficial.

Previous work done on the SpyCas9 crRNA and tracrRNA demonstrated that significant shortening of the naturally occurring crRNA and tracrRNA species could be done for RNAs made by chemical synthesis and that such shortened RNAs were 1) higher quality, 2) less costly to manufacture, and 3) showed improved performance in mammalian genome editing compared with the wild-type (WT) RNAs. See Collingwood, M. A., Jacobi, A. M., Rettig, G. R., Schubert, M. S., and Behlke, M. A., "CRISPR-BASED COMPOSITIONS AND METHOD OF USE," U.S. patent application Ser. No. 14/975,709, filed Dec. 18, 2015, published now as U.S. Patent Application Publication No. US2016/0177304A1 on Jun. 23, 2016 and issued as U.S. Pat. No. 9,840,702 on Dec. 12, 2017.

Prior work demonstrated that reducing the length of the FnCpf1 crRNA from 22 to 18 base length with deletions from the 3'-end supported cleavage of target DNA but that lengths of 17 or shorter showed reduced activity. Deletions or mutations that disrupted base-pairing in the universal loop domain disrupted activity. See Zetsche, B., Gootenberg, J. S., Abudayyeh, O. O., Slaymaker, I. M., Makarova, K. S., Essletzbichler, P., Volz, S. E., Joung, J., van der Oost, J., Regev, A., Koonin, E. V., and Zhang, F. (2015) Cpf1 is a single RNA-guided endonuclease of a class 2 CRISPR-Cas system. Cell 163:1-13. The FnCpf1 nuclease, however, does not work in mammalian cells to perform genome editing. It is unknown if the same length rules apply to the AsCpf1 crRNA as were observed for the FnCpf1 crRNA. We establish herein the shortest version of AsCpf1 crRNAs having full activity in mammalian genome editing applications. We also establish chemical modification patterns that maintain or improve functioning of synthetic Cpf1 crRNAs when used in mammalian or prokaryotic cells.

BRIEF SUMMARY OF THE INVENTION

This invention pertains to Cpf1-based CRISPR genes, polypeptides encoded by the same, mammalian cell lines that stably express Cpf1, and chemically synthesized Cpf1 crRNAs and their use in compositions of CRISPR-Cpf1 systems and methods. Examples are shown employing the Cpf1 systems from *Acidaminococcus* sp. BV3L6 and *Lachnospiraceae bacterium* ND2006, however this is not intended to limit scope, which extends to Cpf1 homologs or orthologs isolated from other species.

In a first aspect, an isolated nucleic acid is provided. The isolated nucleic acid encodes an As Cpf1 polypeptide codon optimized for expression in *H. sapiens* as seen in SEQ ID NO:8, SEQ ID NO:15 and SEQ ID NO:22 which includes the use of nuclear localization signals as well as an epitope tag. The isolated nucleic acid also encodes as As Cpf1 polypeptide codon optimized for expression in *E. coli* which comprises SEQ ID NO:5 and may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:12 and SEQ ID NO:19.

In a second aspect, an isolated polypeptide encoding a wild-type As Cpf1 protein is provided. In a first respect, the isolated polypeptide comprises SEQ ID NO:2. The protein may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:12, SEQ ID NO:16 and SEQ ID NO:19.

In a third aspect, an isolated nucleic acid is provided. The isolated nucleic acid encodes an Lb Cpf1 polypeptide codon optimized for expression in *H. sapiens* as seen in SEQ ID NO:9 and SEQ ID NO:17, which includes the use of nuclear localization signals as well as an epitope tag. The isolated nucleic acid also encodes as Lb Cpf1 polypeptide codon optimized for expression in *E. coli* which comprises SEQ ID NO:6 and may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:13.

In a fourth aspect, an isolated polypeptide encoding a wild-type Lb Cpf1 protein is provided. In a first respect, the isolated polypeptide comprises SEQ ID NO:7 and SEQ ID NO:10. The protein may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:14.

In a fifth aspect, an isolated expression vector encoding SEQ ID NO:11, SEQ ID NO:13, SEQ ID NO:15 and SEQ ID NO:17 is provided. The isolated expression vectors include a transcriptional initiator element, such as a promoter and enhancer, operably-linked to SEQ ID NO:11, SEQ ID NO:13, SEQ ID NO:15 or SEQ ID NO:17 to permit expression of the polypeptide encoded by SEQ ID NO:12, SEQ ID NO:14 or SEQ ID NO:16.

In a sixth aspect, a host cell including an isolated expression vector encoding SEQ ID NO:11, SEQ ID NO:13, SEQ ID NO:15 and SEQ ID NO:17 is provided. The isolated expression vector encoding SEQ ID NO:11, SEQ ID NO:13, SEQ ID NO:15 or SEQ ID NO:17 is operably linked to a suitable promoter and other genetic elements (as necessary) to permit expression of a polypeptide comprising SEQ ID NO:12, SEQ ID NO:14 or SEQ ID NO:16.

In a seventh aspect, an isolated CRISPR/Cpf1 endonuclease system is provided. The system includes an AsCpf1 polypeptide and a suitable AsCpf1 crRNA.

In an eighth aspect, an isolated CRISPR/Cpf1 endonuclease system is provided. The system includes a human cell line expressing a AsCpf1 polypeptide and a suitable AsCpf1 crRNA.

In a ninth aspect, an isolated AsCpf1 crRNA is provided. The isolated AsCpf1 crRNA is active in a Clustered Regularly Interspaced Short Palindromic Repeats (CRISPR)/CRISPR-associated protein endonuclease system. Different variants of the crRNA are provided including species optimized for performance in mammalian cells and species optimized for performance in bacteria.

In a tenth aspect, a method of performing gene editing is provided. The method includes the step of contacting a candidate editing target site locus with an active CRISPR/Cpf1 endonuclease system having a wild-type AsCpf1 polypeptide and a suitable AsCpf1 crRNA.

BRIEF DESCRIPTION OF THE DRAWINGS

FIG. 8 depicts exemplary modified variants AsCpf1 crRNAs that are active in genome editing applications in mammalian cells at multiple target sites and therefore are not site-specific. The sequence of the universal 5'-loop domain is shown (5'-3' orientation) and indicated with underline. The sequence of the variable 3'-target specific protospacer domain is indicated as "N" bases, as this sequence varies for every target. 2'OMe RNA modifications are indicated in uppercase and RNA residues are indicated in lowercase. "X" indicates a terminal non-base modifier, such as a C3 spacer (propanediol) or ZEN (napthyl-azo) group. "*" indicates a phosphorothioate (PS) internucleotide linkage.

DETAILED DESCRIPTION OF THE INVENTION

Figure 1:
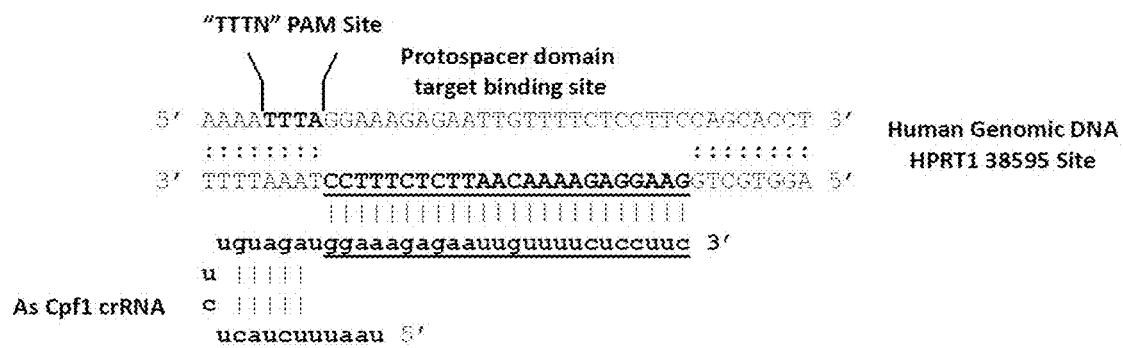
FIG. 1 is a graphical representation of Cpf1 PAM recognition sites and alignment of guide crRNA to target DNA. Genomic DNA sequence of the human HPRT1 gene is shown at site '38595'. The "TTTN" PAM site that identifies As Cpf1 sites is highlighted and the sequence of the guide-binding site is underlined. DNA is shown in uppercase and RNA is shown in lowercase. In the Cpf1 crRNA, the protospacer target-specific domain s underlined and comprises the 3'-domain. The universal hairpin RNA sequence that mediates binding to Cpf1 protein comprises the 5'-domain.

The methods and compositions of the invention described herein provide wild-type AsCpf1 nucleic acids and polypeptides for use in a CRISPR/Cpf1 system. The present invention describes an HEK293 cell line that has stable, low levels of expression of AsCpf1 in HEK293 and can be used as a platform for investigation and optimization of the nucleic acid components of the system. AsCpf1 provides a useful complement to SpyCas9 by expanding the range of PAM sequences that can be targeted from GC-rich areas (Cas9) to AT-rich areas of the genome (Cpf1), thereby expanding the range of sequences that can be modified using CRISPR genome engineering methods. In addition to having a T-rich PAM site, another advantage of the AsCpf1 system compared with Cas9 is the use of a single, short RNA molecule. However, unlike Cas9 that shows activity at most sites in the human genome, AsCpf1 shows little to no activity at half of TTTN PAM sites. Thus, exploiting the full potential of the AsCpf1 CRISPR system will be enhanced by the availability of suitable predictive software that enriches for high activity sites based on sequence context. The use of a stable constitutive Cpf1-expressing cell line makes the development of an algorithm easier to develop with reduced effort and cost as compared to using alternative methods, such as electroporation of ribonucleoprotein protein (RNP) complexes. HEK293 cells are an immortalized cell line that are easily cultured, passaged and cryogenically preserved. We established clonal cell lines that constitutively express SpyCas9 and AsCpf1 as suitable test vehicles for algorithm development or rapid testing/optimization of the chemical structure of guide RNAs. The present invention describes length and chemical modification of length-optimized variants of the AsCpf1 and LbCpf1 crRNAs that improve function in genome editing.

AsCpf1-Encoded Genes, Polypeptides, Expression Vectors and Host Cells

The term "wild-type AsCpf1 protein" ("WT-AsCpf1" or "WT-AsCpf1 protein") encompasses a protein having the identical amino acid sequence of the naturally-occurring *Acidaminococcus* sp. BV3L6 Cpf1 (e.g., SEQ ID NO:2) and that has biochemical and biological activity when combined with a suitable crRNA to form an active CRISPR/Cpf1 endonuclease system.

The term "wild-type LbCpf1 protein" ("WT-LbCpf1" or "WT-LbCpf1 protein") encompasses a protein having the identical amino acid sequence of the naturally-occurring *Lachnospiraceae bacterium* ND2006 Cpf1 (e.g., SEQ ID NO:4) and that has biochemical and biological activity when combined with a suitable crRNA to form an active CRISPR/Cpf1 endonuclease system.

The term "wild-type CRISPR/Cpf1 endonuclease system" refers to a CRISPR/Cpf1 endonuclease system that includes wild-type AsCpf1 protein and a suitable AsCpf1 crRNA as a guide RNA.

The term "polypeptide" refers to any linear or branched peptide comprising more than one amino acid. Polypeptide includes protein or fragment thereof or fusion thereof, provided such protein, fragment or fusion retains a useful biochemical or biological activity.

Fusion proteins typically include extra amino acid information that is not native to the protein to which the extra amino acid information is covalently attached. Such extra amino acid information may include tags that enable purification or identification of the fusion protein. Such extra amino acid information may include peptides that enable the fusion proteins to be transported into cells and/or transported to specific locations within cells. Examples of tags for these purposes include the following: AviTag, which is a peptide allowing biotinylation by the enzyme BirA so the protein can be isolated by streptavidin (GLNDIFEAQKIEWHE); Calmodulin-tag, which is a peptide bound by the protein calmodulin (KRRWKKNFIAVSAANRFKKISSSGAL); polyglutamate tag, which is a peptide binding efficiently to anion-exchange resin such as Mono-Q (EEEEEE); E-tag, which is a peptide recognized by an antibody (GAPVPYPDPLEPR); FLAG-tag, which is a peptide recognized by an antibody (DYKDDDDK); HA-tag, which is a peptide from hemagglutinin recognized by an antibody (YPYDVPDYA); His-tag, which is typically 5-10 histidines and can direct binding to a nickel or cobalt chelate (HHHHHH); Myc-tag, which is a peptide derived from c-myc recognized by an antibody (EQKLISEEDL); NE-tag, which is a novel 18-amino-acid synthetic peptide (TKENPRSNQEESYDDNES) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, which is a peptide derived from Ribonuclease A (KETAAAKFERQHMDS); SBP-tag, which is a peptide which binds to streptavidin; (MDEKTTGWRGGHVVEGLAGELEQLRAR-LEHHPQGQREP); Softag 1, which is intended for mammalian expression (SLAELLNAGLGGS); Softag 3, which is intended for prokaryotic expression (TQDPSRVG); Strep-tag, which is a peptide which binds to streptavidin or the modified streptavidin called streptactin (Strep-tag II: WSHPQFEK); TC tag, which is a tetracysteine tag that is recognized by FlAsH and ReAsH biarsenical compounds (CCPGCC)V5 tag, which is a peptide recognized by an antibody (GKPIPNPLLGLDST); VSV-tag, a peptide recognized by an antibody (YTDIEMNRLGK); Xpress tag (DLYDDDDK); Isopeptag, which is a peptide which binds covalently to pilin-C protein (TDKDMTITFTNKKDAE); SpyTag, which is a peptide which binds covalently to SpyCatcher protein (AHIVMVDAYKPTK); SnoopTag, a peptide which binds covalently to SnoopCatcher protein (KLGDIEFIKVNK); BCCP (Biotin Carboxyl Carrier Protein), which is a protein domain biotinylated by BirA to enable recognition by streptavidin; Glutathione-S-transferase-tag, which is a protein that binds to immobilized glutathione; Green fluorescent protein-tag, which is a protein which is spontaneously fluorescent and can be bound by antibodies; HaloTag, which is a mutated bacterial haloalkane dehalogenase that covalently attaches to a reactive haloalkane substrate to allow attachment to a wide variety of substrates; Maltose binding protein-tag, a protein which binds to amylose agarose; Nus-tag; Thioredoxin-tag; and Fc-tag, derived from immunoglobulin Fc domain, which allows dimerization and solubilization and can be used for purification on Protein-A Sepharose.

Nuclear localization signals (NLS), such as those obtained from SV40, allow for proteins to be transported to the nucleus immediately upon entering the cell. Given that the native AsCpf1 protein is bacterial in origin and therefore does not naturally comprise a NLS motif, addition of one or more NLS motifs to the recombinant AsCpf1 protein is expected to show improved genome editing activity when used in eukaryotic cells where the target genomic DNA substrate resides in the nucleus. Functional testing in HEK293 cells revealed that using a bipartite NLS (nucleoplasmin) increased editing in comparison to the current commercial design (3 SV40 NLS) and the use of single or dual OpT NLS that showed promise in the Cpf1 protein. Additional combinations of NLS elements including the bipartite are envisioned. Of note, the nucleoplasmin functions best in mammalian cells while the SV40 NLS appears to function in almost any nucleated cell. The bipartite SV40 NLS is functional in both Cas9 and Cpf1. Having two different NLS domains may expand effectiveness across a broad spectrum of species.

One skilled in the art would appreciate these various fusion tag technologies, as well as how to make and use fusion proteins that include them.

The term "isolated nucleic acid" include DNA, RNA, cDNA, and vectors encoding the same, where the DNA, RNA, cDNA and vectors are free of other biological materials from which they may be derived or associated, such as cellular components. Typically, an isolated nucleic acid will be purified from other biological materials from which they may be derived or associated, such as cellular components.

The term "isolated wild-type AsCpf1 nucleic acid" is an isolated nucleic acid that encodes a wild-type AsCpf1 protein. Examples of an isolated wild-type AsCpf1 nucleic acid include SEQ ID NO:1.

The term "isolated wild-type LbCpf1 nucleic acid" is an isolated nucleic acid that encodes a wild-type LbCpf1 protein. Examples of an isolated wild-type LbCpf1 nucleic acid include SEQ ID NO:3.

In a first aspect, an isolated nucleic acid is provided. The isolated nucleic acid encodes an As Cpf1 polypeptide codon optimized for expression in *H. sapiens*. In a first respect, the isolated nucleic acid comprises SEQ ID NO:8, SEQ ID NO:15 and SEQ ID NO:22 which includes the use of nuclear localization signals as well as an epitope tag. The isolated nucleic acid also encodes as As Cpf1 polypeptide codon optimized for expression in *E. coli* which comprises SEQ ID NO:5 and may be fused or linked to a nuclear localization signal, multiple nuclear localization signals, or sequences encoding an epitope tag enabling detection by antibodies or other methods, and/or an affinity tag that enables simple purification of recombinants proteins expressed from the nucleic acid, such as a His-Tag as seen in SEQ ID NO:12 and SEQ ID NO:19.

In a second aspect, an isolated polypeptide encoding a wild-type As Cpf1 protein is provided. In a first respect, the isolated polypeptide comprises SEQ ID NO:2, SEQ ID NO:12, SEQ ID NO:16 or SEQ ID NO:19.

In a third aspect, an isolated expression vector encoding SEQ ID NO:15 is provided. The isolated expression vector includes transcriptional initiator elements, such as a promoter and enhancer, operably-linked to SEQ ID NO:15 to permit expression of the polypeptide encoded by SEQ ID NO:16. The isolated expression vector may additionally include transcriptional termination elements, posttranscriptional processing elements (for example, splicing donor and acceptor sequences and/or polyadenylation signaling sequences), mRNA stability elements and mRNA translational enhancer elements. Such genetic elements are understood and used by those having ordinary skill in the art.

In a fourth aspect, a host cell comprising an isolated expression vector encoding SEQ ID NO:15 is provided. The isolated expression vector encoding SEQ ID NO:15 is operably linked to a suitable promoter and other genetic elements (as necessary) to permit expression of a polypeptide comprising SEQ ID NO:16. In a first respect, the host cell includes a human cell. In a second respect, the human cell comprises an immortalized cell line. In a third respect, the immortalized cell line is a HEK293 cell line. As a further elaboration of this third respect, the immortalized cell line comprises an isolated AsCpf1 crRNA capable of forming a ribonucleoprotein complex with the polypeptide comprising SEQ ID NO:2 to form a wild-type CRISPR/Cpf1 endonuclease.

Length- and Chemical Structure-Optimized AsCpf1 crRNAs

The term "length-modified," as that term modifies RNA, refers to a shortened or truncated form of a reference RNA lacking nucleotide sequences or an elongated form of a reference RNA including additional nucleotide sequences.

The term "chemically-modified," as that term modifies RNA, refers to a form of a reference RNA containing a chemically-modified nucleotide or a non-nucleotide chemical group covalently linked to the RNA. Chemically-modified RNA, as described herein, generally refers to synthetic RNA prepared using oligonucleotide synthesis procedures wherein modified nucleotides are incorporated during synthesis of an RNA oligonucleotide. However, chemically-modified RNA also includes synthetic RNA oligonucleotides modified with suitable modifying agents post-synthesis.

A competent CRISPR/Cpf1 endonuclease system includes a ribonucleoprotein (RNP) complex formed with isolated AsCpf1 protein and a guide RNA consisting of an isolated AsCpf1 crRNA. In some embodiments, an isolated length-modified and/or chemically-modified form of AsCpf1 crRNA is combined with purified AsCpf1 protein, an isolated mRNA encoding AsCpf1 protein or a gene encoding AsCpf1 protein in an expression vector. In certain assays, an isolated length-modified and/or chemically-modified form of AsCpf1 crRNA can be introduced into cell lines that stably express AsCpf1 protein from an endogenous expression cassette encoding the AsCpf1 gene.

It is desirable for synthesis of synthetic RNAs that sequences are shortened of unnecessary bases but not so shortened that loss of function results. The 5'-constant regions that mediates binding of the crRNA to the Cpf1 nuclease shows loss of activity if truncated below 20 residues. The 3'-variable domain that comprises the protospacer guide region which confers target sequence specificity to the crRNA naturally occurs as long as 25 bases. This domain can be shortened to around 20-21 bases with no loss of functional activity. The optimized length of the Cpf1 crRNA is therefore 40-41 bases, comprising a 20 base 5'-constant domain and a 20-21 base 3'-variable domain.

The present invention provides suitable guide RNAs for triggering DNA nuclease activity of the AsCpf1 nuclease. These optimized reagents, both in terms of length-modified and/or chemically-modified forms of crRNA's, provide for improved genome editing in any application with AsCpf1. The applications of CRISPR-based tools include, but are not limited to: plant gene editing, yeast gene editing, rapid generation of knockout/knockin animal lines, generating an animal model of disease state, correcting a disease state, inserting reporter genes, and whole genome functional screening. The "tool-kit" could be further expanded by including nickase versions and a dead mutant of AsCpf1 as a fusion protein with transcriptional activators (CRISPRa) and repressors (CRISPRi).

RNA-guided DNA cleavage by AsCpf1 is primarily useful for its ability to target AT-rich gene regions (as compared with the GC-rich targeting by SpyCas9). The newly-discovered AsCpf1 crRNA truncation and modification variants will be suitable to promote AsCpf1-mediated staggered cutting and beneficial in gene silencing, homology directed repair or exon excision. The present invention defines the shortest AsCpf1 guide RNA that has full potency to direct gene editing by the CRISPR/Cpf1 endonuclease. This is useful for manufacturing to synthesize the shortest compound that fully functions, leading to higher quality, lower cost, while maximizing functionality.

Unlike S.py. Cas9 which requires a complex of 2 RNAs to recognize and cleave a target DNA sequence (comprising a hybridized crRNA:tracrRNA pair) or a long synthetic single-guide sgRNA, the Cpf1 nuclease only requires a short, single crRNA species to direct target recognition. This RNA comprises 2 domains, a 5'-domain of 20 RNA residues that is universal and mediates binding of the RNA species to the Cpf1 protein and a 3'domain of 21-24 RNA residues which is target specific and mediates binding of the RNP complex to a precise DNA sequence. A functional nuclease complex comprises a single crRNA (41-44 bases in length) and isolated Cpf1 protein, which combine in a 1:1 molar ratio to form an active complex. The guide crRNA species can be expressed in mammalian cells from expression plasmids or viral vectors. The crRNA can also be made as an in vitro transcript (IVT) and isolated as a pure enzymatic RNA species. More preferably, the crRNAs can be manufactured as a synthetic chemical RNA oligonucleotide. Chemical manufacturing enables use of modified residues, which have many advantages as will be outlined below.

Synthetic nucleic acids are attacked by cellular nucleases and rapidly degrade in mammalian cells or in serum. Chemical modification can confer relative nuclease resistance to the synthetic nucleic acids and prolong their half-lives, thereby dramatically improving functional performance and potency. As a further complication, synthetic nucleic acids are often recognized by the antiviral surveillance machinery in mammalian cells that are part of the innate immune system and lead to interferon response pathway activation, which can lead to cell death. Chemical modification can reduce or eliminate unwanted immune responses to synthetic RNAs. It is therefore useful to establish methods to chemically modify synthetic RNA oligonucleotides intended for use in live cells. Nucleic acid species that have specific interactions with protein factors, however, cannot be blindly modified as chemical modification will change tertiary structure of the nucleic acid and can block critical contact points between the nucleic acid and amino-acid residues. For example, the 2'-O-methyl RNA modification (2'OMe) will block the 2'-oxygen of RNA from interaction with amino-acid residues that in turn can disrupt functional interaction between a modified RNA and a protein. Likewise, a phosphorothioate modification can disrupt protein binding along the phosphate backbone of a nucleic acid through substitution of a non-bridging oxygen at the phosphate.

The 2'OMe modification is particularly useful in this setting as it has previously been shown to increase nuclease stability of antisense oligonucleotides (ASOs) and siRNAs and at the same kind can also reduce the risk that a chemically-synthesized RNA will trigger an innate immune response when introduced into mammalian cells. Specific modification patterns have been established that permit incorporation of this modified residue into an ASO or siRNA and retain function. Likewise, we have recently developed chemical modification patterns that improved the stability of the crRNA and tracrRNA that serve as guide RNA in the SpyCas9 system. Use of 2'OMe-modified residues in a CRISPR guide RNA improves RNA stability to nucleases and boosts the overall efficiency of editing in nuclease-rich environments while at the same time reduces cell death and toxicity associated with immunogenic triggers (such as is seen with long, unmodified RNAs).

The present invention relates to defining chemical modification patterns for the AsCpf1 crRNA that retain function in forming an active RNP complex capable of use in genome editing in mammalian cells. Modification 'walks' were performed where a single 2'OMe residue was place sequentially at every position with the Cpf1 crRNA. Sites that reduced or killed function of the RNP complex in genome editing were identified. Chemical modification patterns were defined that were compatible with high efficiency genome editing. The utility of 2'-fluoro (2'F) and locked nucleic acid (LNA) modifications at 'modification competent' position in the crRNA were also demonstrated. The use of phosphorothioate internucleotide linkages to modify select sites to reduce nuclease susceptibility was shown, as well as successful use of non-base modifiers as end blocks to reduce exonuclease attack on the synthetic RNAs. Taken together, these studies provide a 'map' of sites in the Cpf1 crRNA amenable to chemical modification along with a suite of modification chemistries demonstrated to function in the intended application in mammalian cells.

Specific examples of modification patterns are shown in the examples below. The 20-base 5'-constant domain could be heavily modified and retain function. In particular, using a 20-base 5'-constant region and counting from the 5'-end, RNA residues at position 1, 5, 6, 7, 8, 9, 10, 12, 13, 14, 16, 17, 18, and 19 can all be substituted with 2'OMe RNA residues with no loss of activity. Such substitutions can be made single, multiply, or all 14 residues modified, such that 14/20 residues have been changed in this domain from RNA to 2'OMe RNA. Maximum modification patterns that are tolerated in the 21-base 3'-variable domain vary with sequence of the domain. Within this domain, residues 21, 22, 23, 28, 29, 30, 32, 34, 35, 39, 40, and 41 (counting from the first base of the 5'-constant region) can be substituted with 2'OMe residues with no loss of activity.

Figure 7:
FIG. 7 depicts a modification tolerance map of AsCpf1 crRNAs at 2 sequence target sites, HPRT1-38351 (panel (i)) and HPRT1-38595 (panel (ii)), wherein the sequence of the universal 5'-loop domain is shown (5'-3' orientation) for both the 24-nt protospacer domains (panels (i.a) and (ii.a)) and the 21-nt protospacer domains (panels (i.b) and (ii.b)). The sequence of the variable 3'-target specific protospacer domain is indicated as "N" bases, as this sequence varies for every target. Positions that did not suffer loss of activity when modified as a 2'OMe RNA residue in the single base walk are indicated in upper case whereas positions that showed loss of activity with modification are indicated in lower case. Above the lower case residues an arrow is shown that indicates the relative magnitude of the loss of activity, wherein a large arrow represents a large loss of activity, a mid-sized arrow represents a medium loss of activity, and a small arrow represents a minor loss of activity when the respective RNA residues are changed to 2'OMe RNA.

Only select positions within the 21-24-base 3'-target specific domain can be modified without compromising activity. Based on the crystal structure of Cpf1, there are many protein contact points within the constant region as well as the target region. For constant region modification, there is no obvious correlation that emerges when comparing the Cpf1 crystal structure contact points with the identified functional positions that can be modified—meaning that a good modification pattern cannot be predicted from the crystal structure. Likewise, empirical testing was needed to determine target region modification patterns. Based on the early 2'OMe modification testing, selected areas within the Cpf1 crRNA were modified using 2'OMe as an attempt to narrow down an area that will tolerate modification. The position of single residues within the Cpf1 crRNA that are sensitive to 2'OMe modification are shown in FIG. 7. Higher-level modification patterns that are potent triggers of Cpf1-mediated genome editing are shown in FIG. 8. 2'F modifications can be positioned at any residue that is tolerant to 2'OMe modification. Further, the 3'-variable domain is more tolerate of large blocks of 2'F modification than large blocks of 2'OMe modification. Hence a highly modified version of the Cpf1 crRNA comprises 2'OMe modification in the 3'-domain and 2'F modification in the 5'-domain. For medium or light modification patterns, either 2'OMe or 2'F (or both) modifications can be used in both domains. Also, LNA residues can be incorporated into the crRNA without compromising function, as defined in the examples below.

As an alternative to extensive use of 2'OMe or other modified sugar approaches, blocking exonuclease attack with non-base modifiers at the 3'-end and 5'-end are compatible with crRNA function and improve function in cells. Small C3 spacer (propanediol) or large ZEN groups work equally well for this approach. Further, phosphorothioate internucleotide linkages can be placed at select sites, such as between the terminal 2-3 bases on each end of the crRNA, but complete PS modification of the crRNA or complete modification of either the loop domain or the protospacer domain show reduced activity.

Guide RNAs are required in RNA-directed dsDNA cleavage by AsCpf1, which initiate the subsequent repair events that are involved in most CRISPR applications in mammalian cells. The use of modified synthetic AsCpf1 crRNAs as guides for AsCpf1 genome editing is provided. The utility of 2'OMe-modified AsCpf1 crRNAs, 2'F-modified AsCpf1 crRNAs, LNA modified AsCpf1 crRNAs, and end-blocked AsCpf1 crRNAs for CRISPR/Cpf1 applications in mammalian cells is demonstrated. Those with skill in the art will recognize and appreciate additional chemical modifications are possible based upon this disclosure. It is expected that many of these base modifying groups will likewise function according to the patterns taught in the present invention. Heretofore, all crRNAs used with Cpf1 for genome editing were unmodified RNA. In the present invention, functional modification patterns that improve properties of the AsCpf1 crRNA and lower risk of toxicity are provided.

AsCpf1 crRNAs can be made in cells from RNA transcription vectors, as in vitro transcripts (IVTs), or by chemical synthesis. Synthetic RNA oligonucleotides offer a distinct advantage because they alone allow for precise insertion of modified bases at specific sites in the molecule. The present invention provides a map of positions amenable to chemical modification that can be used to improve AsCpf1 crRNA performance in cells. For some applications, "minimal modification" approaches will be sufficient. In higher nuclease environments or for use in cells with particularly high innate immune reactivity, "high modification" approaches may work better. The present invention provides methods for low, medium, or high modification needs.

The applications of AsCpf1-based tools are many and varied. They include, but are not limited to: bacterial gene editing, plant gene editing, yeast gene editing, mammalian gene editing, editing of cells in the organs of live animals, editing of embryos, rapid generation of knockout/knock-in animal lines, generating an animal model of disease state, correcting a disease state, inserting a reporter gene, and whole genome functional screening.

In a fifth aspect, an isolated CRISPR/Cpf1 endonuclease system is provided. The system includes an AsCpf1 polypeptide and a suitable AsCpf1 crRNA. In a first respect, the AsCpf1 polypeptide comprises SEQ ID NO:2. In a second respect, the suitable AsCpf1 crRNA is selected from a length-truncated AsCpf1 crRNA or a chemically-modified AsCpf1 crRNA, or an AsCpf1 crRNA containing both length truncations and chemical modifications.

In a sixth aspect, an isolated CRISPR/Cpf1 endonuclease system is provided. The system includes a human cell line expressing an AsCpf1 polypeptide and a suitable AsCpf1 crRNA. In a first respect, the AsCpf1 polypeptide comprises at least one member selected from the group consisting of SEQ ID NO:2, SEQ ID NO:12, SEQ ID NO:16 and SEQ ID NO:19. In a second respect, the suitable AsCpf1 crRNA is selected from a length-truncated AsCpf1 crRNA or a chemically-modified AsCpf1 crRNA, or an AsCpf1 crRNA containing both length truncations and chemical modifications.

In a seventh aspect, an isolated AsCpf1 crRNA is provided. The isolated AsCpf1 crRNA is active in a Clustered Regularly Interspaced Short Palindromic Repeats (CRISPR)/CRISPR-associated protein endonuclease system. In a first respect, the isolated AsCpf1 crRNA is selected from length-truncated AsCpf1 crRNA, a chemically-modified AsCpf1 crRNA, or an AsCpf1 crRNA containing both length truncations and chemical modifications.

In an eighth aspect, a method of performing gene editing is provided. The method includes the step of contacting a candidate editing target site locus with an active CRISPR/Cpf1 endonuclease system having a wild-type AsCpf1 polypeptide and a suitable AsCpf1 crRNA. In a first respect, the wild-type AsCpf1 polypeptide comprises at least one member selected from the group consisting of SEQ ID NO:2, SEQ ID NO:12, SEQ ID NO:16 and SEQ ID NO:19. In a second respect, the suitable AsCpf1 crRNA is selected from a length-truncated AsCpf1 crRNA, a chemically-modified AsCpf1 crRNA, or an AsCpf1 crRNA containing both length truncations and chemical modifications.

In another aspect, an isolated nucleic acid encoding an Lb Cpf1 polypeptide codon optimized for expression in *H. sapiens* is provided. In a first respect the isolated nucleic acid comprises SEQ ID NO:17 or SEQ ID NO:396.

In another aspect, an isolated polypeptide encoding a wild-type Lp Cpf1 protein is provided. In a first respect, the isolated polypeptide comprises SEQ ID NO:14 or SEQ ID NO:24.

In another aspect, an isolated expression vector encoding SEQ ID NO:17 or SEQ ID NO:396 is provided.

In another aspect, a host cell including an isolated expression vector encoding SEQ ID NO:17 or SEQ ID NO:396 is provided. The isolated expression vector encoding SEQ ID NO:17 or SEQ ID NO:396 is operably linked to a suitable promoter to permit expression of a polypeptide comprising SEQ ID NO:14 or SEQ ID NO:24, respectively. In a first respect, the host cell comprises a human cell. In a second respect, the human cell comprises an immortalized cell line. In a third respect, the immortalized cell line is a HEK293 cell line. In a further elaboration of this respect, the host cell includes an isolated Lb Cpf1 crRNA capable of forming a ribonucleoprotein complex with the polypeptide selected from the group consisting of SEQ ID NO:4, SEQ ID NO:14, SEQ ID NO:20 and SEQ ID NO:24 to form a wild-type CRISPR/Cpf1 endonuclease.

In another aspect, an isolated CRISPR/Cpf1 endonuclease system having an Lb Cpf1 polypeptide and a suitable Cpf1 crRNA is provided. In a first respect, the CRISPR/Cpf1 endonuclease system includes a Lb Cpf1 polypeptide in the form of SEQ ID NO:14. In a second respect, the isolated CRISPR/Cpf1 endonuclease system includes a suitable Cpf1 crRNA selected from a length-truncated Cpf1 crRNA or a chemically-modified Cpf1 crRNA, or a Cpf1 crRNA comprising both length truncations and chemical modifications.

In another aspect, an isolated CRISPR/Cpf1 endonuclease system having a human cell line expressing an Lb Cpf1 polypeptide and a suitable Cpf1 crRNA is provided. In a first respect, the Lb Cpf1 polypeptide is SEQ ID NO:14 or SEQ ID NO:24. In a second respect, the suitable Cpf1 crRNA is selected from a length-truncated Cpf1 crRNA or a chemically-modified Cpf1 crRNA, or a Cpf1 crRNA comprising both length truncations and chemical modifications.

In another respect, a method of performing gene editing is provided. The method includes the steps of contacting a candidate editing target site locus with an active CRISPR/Cpf1 endonuclease system having a wild-type Lb Cpf1 polypeptide and a suitable Cpf1 crRNA. In a first respect, the method includes a wild-type Lb Cpf1 polypeptide selected from the group consisting of SEQ ID NO:4, SEQ ID NO:14, SEQ ID NO:20 and SEQ ID NO:24. In a second respect, the suitable Cpf1 crRNA is selected from a length-truncated Cpf1 crRNA, a chemically-modified Cpf1 crRNA, or a Cpf1 crRNA comprising both length truncations and chemical modifications.

In another respect, a CRISPR endonuclease system having a recombinant Cpf1 fusion protein and a suitable crRNA is provided. In a first respect, the recombinant Cpf1 fusion protein is an isolated, purified protein. In a second respect, the recombinant Cpf1 fusion protein includes an N-terminal NLS, a C-terminal NLS and a plurality of affinity tags located at either the N-terminal or C-terminal ends. In one preferred embodiment, the recombinant Cpf1 fusion protein includes an N-terminal NLS, a C-terminal NLS and 3 N-terminal FLAG tags and a C-terminal 6×His tag. In a third respect, the recombinant Cpf1 fusion protein and a suitable crRNA is provided in a 1:1 stoichiometric ratio (that is, in equimolar amounts).

Example 1

DNA and Amino Acid Sequences of Wild Type as Cpf1 Polypeptide, as Encoded in Isolated Nucleic Acid Vectors The list below shows wild type (WT) As Cpf1 nucleases expressed as a polypeptide fusion protein described in the present invention. It will be appreciated by one with skill in the art that many different DNA sequences can encode/express the same amino acid (AA) sequence since in many cases more than one codon can encode for the same amino acid. The DNA sequences shown below only serve as example and other DNA sequences that encode the same protein (e.g., same amino acid sequence) are contemplated. It is further appreciated that additional features, elements or tags may be added to said sequences, such as NLS domains and the like. Examples are shown for WT AsCpf1 showing amino acid and DNA sequences for those proteins as Cpf1 alone and Cpf1 fused to both C-terminal and N-terminal SV40 NLS domains and a HIS-tag. Amino acid sequences that represent NLS sequences, domain linkers, or purification tags are indicated in bold font.

```
AsCpf1 Native Nucleotide Sequence
                                                                SEQ ID NO: 1
ATGACCCAATTTGAAGGTTTTACCAATTTATACCAAGTTTCGAAGACCCTTCGTTTTGAACTGATTC

CCCAAGGAAAAACACTCAAACATATCCAGGAGCAAGGGTTCATTGAGGAGGATAAAGCTCGCAATGA

CCATTACAAAGAGTTAAAACCAATCATTGACCGCATCTATAAGACTTATGCTGATCAATGTCTCCAA

CTGGTACAGCTTGACTGGGAGAATCTATCTGCAGCCATAGACTCCTATCGTAAGGAAAAAACCGAAG

AAACACGAAATGCGCTGATTGAGGAGCAAGCAACATATAGAAATGCGATTCATGACTACTTTATAGG

TCGGACGGATAATCTGACAGATGCCATAAATAAGCGCCATGCTGAAATCTATAAAGGACTTTTTAAA

GCTGAACTTTTCAATGGAAAAGTTTTAAAGCAATTAGGGACCGTAACCACGACAGAACATGAAAATG

CTCTACTCCGTTCGTTTGACAAATTTACGACCTATTTTTCCGGCTTTTATGAAAACCGAAAAAATGT

CTTTAGCGCTGAAGATATCAGCACGGCAATTCCCCATCGAATCGTCCAGGACAATTTCCCTAAATTT

AAGGAAAACTGCCATATTTTTACAAGATTGATAACCGCAGTTCCTTCTTTGCGGGAGCATTTTGAAA

ATGTCAAAAAGGCCATTGGAATCTTTGTTAGTACGTCTATTGAAGAAGTCTTTTCCTTTCCCTTTTA

TAATCAACTTCTAACCCAAACGCAAATTGATCTTTATAATCAACTTCTCGGCGGCATATCTAGGGAA

GCAGGCACAGAAAAAATCAAGGGACTTAATGAAGTTCTCAATCTGGCTATCCAAAAAAATGATGAAA

CAGCCCATATAATCGCGTCCCTGCCGCATCGTTTTATTCCTCTTTTTAAACAAATTCTTTCCGATCG

AAATACGTTATCCTTTATTTTGGAAGAATTCAAAAGCGATGAGGAAGTCATCCAATCCTTCTGCAAA

TATAAAACCCTCTTGAGAAACGAAAATGTACTGGAGACTGCAGAAGCCCTTTTCAATGAATTAAATT

CCATTGATTTGACTCATATCTTTATTTCCCATAAAAAGTTAGAAACCATCTCTTCAGCGCTTTGTGA

CCATTGGGATACCTTGCGCAATGCACTTTACGAAAGACGGATTTCTGAACTCACTGGCAAAATAACA
```

-continued

```
AAAAGTGCCAAAGAAAAAGTTCAAAGGTCATTAAAACATGAGGATATAAATCTCCAAGAAATTATTT
CTGCTGCAGGAAAAGAACTATCAGAAGCATTCAAACAAAAAACAAGTGAAATTCTTTCCCATGCCCA
TGCTGCACTTGACCAGCCTCTTCCCACAACATTAAAAAAACAGGAAGAAAAAGAAATCCTCAAATCA
CAGCTCGATTCGCTTTTAGGCCTTTATCATCTTCTTGATTGGTTTGCTGTCGATGAAAGCAATGAAG
TCGACCCAGAATTCTCAGCACGGCTGACAGGCATTAAACTAGAAATGGAACCAAGCCTTTCGTTTTA
TAATAAAGCAAGAAATTATGCGACAAAAAAGCCCTATTCGGTGGAAAAATTTAAATTGAATTTTCAA
ATGCCAACCCTTGCCTCTGGTTGGGATGTCAATAAAGAAAAAAATAATGGAGCTATTTTATTCGTAA
AAAATGGTCTCTATTACCTTGGTATCATGCCTAAACAGAAGGGGCGCTATAAAGCCCTGTCTTTTGA
GCCGACAGAAAAAACATCAGAAGGATTCGATAAGATGTACTATGACTACTTCCCAGATGCCGCAAAA
ATGATTCCTAAGTGTTCCACTCAGCTAAAGGCTGTAACCGCTCATTTTCAAACTCATACCACCCCCA
TTCTTCTCTCAAATAATTTCATTGAACCTCTTGAAATCACAAAAGAAATTTATGACCTGAACAATCC
TGAAAAGGAGCCTAAAAAGTTTCAAACGGCTTATGCAAAGAAGACAGGCGATCAAAAAGGCTATAGA
GAAGCGCTTTGCAAATGGATTGACTTTACGCGGGATTTTCTCTAAATATACGAAAACAACTTCAA
TCGATTTATCTTCACTCCGCCCTTCTTCGCAATATAAAGATTTAGGGGAATATTACGCCGAACTGAA
TCCGCTTCTCTATCATATCTCCTTCCAACGAATTGCTGAAAAGGAAATCATGGATGCTGTAGAAACG
GGAAAATTGTATCTGTTCCAAATCTACAATAAGGATTTTGCGAAGGGCCATCACGGGAAACCAAATC
TCCACACCCTGTATTGGACAGGTCTCTTCAGTCCTGAAAACCTTGCGAAAACCAGCATCAAACTTAA
TGGTCAAGCAGAATTGTTCTATCGACCTAAAAGCCGCATGAAGCGGATGGCCCATCGTCTTGGGGAA
AAAATGCTGAACAAAAAACTAAAGGACCAGAAGACACCGATTCCAGATACCCTCTACCAAGAACTGT
ACGATTATGTCAACCACCGGCTAAGCCATGATCTTTCCGATGAAGCAAGGGCCCTGCTTCCAAATGT
TATCACCAAAGAAGTCTCCCATGAAATTATAAAGGATCGGCGGTTTACTTCCGATAAATTTTTCTTC
CATGTTCCCATTACACTGAATTATCAAGCAGCCAATAGTCCCAGTAAATTCAACCAGCGTGTCAATG
CCTACCTTAAGGAGCATCCGGAAACGCCCATCATTGGTATCGATCGTGGAGAACGCAATCTAATCTA
TATTACCGTCATTGACAGTACTGGGAAAATTTTGGAGCAGCGTTCCCTGAATACCATCCAGCAATTT
GACTACCAAAAAAAATTGGACAACAGGGAAAAAGAGCGTGTTGCCGCCCGTCAAGCCTGGTCCGTCG
TCGGAACGATCAAAGACCTTAAACAAGGCTACTTGTCACAGGTCATCCATGAAATTGTAGACCTGAT
GATTCATTACCAAGCTGTTGTCGTCCTTGAAAACCTCAACTTCGGATTTAAATCAAAACGGACAGGC
ATTGCCGAAAAGCAGTCTACCAACAATTTGAAAAGATGCTAATAGATAAACTCAACTGTTTGGTTC
TCAAAGATTATCCTGCTGAGAAAGTGGGAGGCGTCTTAAACCCGTATCAACTTACAGATCAGTTCAC
GAGCTTTGCAAAAATGGGCACGCAAAGCGGCTTCCTTTTCTATGTACCGGCCCCTTATACCTCAAAG
ATTGATCCCCTGACTGGTTTTGTCGATCCCTTTGTATGGAAGACCATTAAAAATCATGAAAGTCGGA
AGCATTTCCTAGAAGGATTTGATTTCCTGCATTATGATGTCAAAACAGGTGATTTTATCCTCCATTT
TAAAATGAATCGGAATCTCTCTTTCCAGAGAGGGCTTCCTGGCTTCATGCCAGCTTGGGATATTGTT
TTCGAAAAGAATGAAACCCAATTTGATGCAAAAGGGACGCCCTTCATTGCAGGAAAACGAATTGTTC
CTGTAATCGAAAATCATCGTTTTACGGGTCGTTACAGAGACCTCTATCCCGCTAATGAACTCATTGC
CCTTCTGGAAGAAAAGGCATTGTCTTTAGAGACGGAAGTAATATATTACCCAAACTTTTAGAAAAT
GATGATTCTCATGCAATTGATACGATGGTCGCCTTGATTCGCAGTGTACTCCAAATGAGAAACAGCA
ATGCCGCAACGGGGAAGACTACATCAACTCTCCCGTTAGGGATCTGAACGGGGTGTGTTTCGACAG
TCGATTCCAAAATCCAGAATGGCCAATGGATGCGGATGCCAACGGAGCTTATCATATTGCCTTAAAA
GGGCAGCTTCTTCTGAACCACCTCAAAGAAAGCAAAGATCTGAAATTACAAAACGGCATCAGCAACC
AAGATTGGCTGGCCTACATTCAGGAACTGAGAAACTGA
```

AsCpf1 Native Protein Sequence

SEQ ID NO: 2

MTQFEGFTNLYQVSKTLRFELIPQGKTLKHIQEQGFIEEDKARNDHYKELKPIIDRIYKTYADQCLQ

LVQLDWENLSAAIDSYRKEKTEETRNALIEEQATYRNAIHDYFIGRTDNLTDAINKRHAEIYKGLFK

AELFNGKVLKQLGTVTTTEHENALLRSFDKFTTYFSGFYENRKNVFSAEDISTAIPHRIVQDNFPKF

KENCHIFTRLITAVPSLREHFENVKKAIGIFVSTSIEEVFSFPFYNQLLTQTQIDLYNQLLGGISRE

AGTEKIKGLNEVLNLAIQKNDETAHIIASLPHRFIPLFKQILSDRNTLSFILEEFKSDEEVIQSFCK

YKTLLRNENVLETAEALFNELNSIDLTHIFISHKKLETISSALCDHWDTLRNALYERRISELTGKIT

KSAKEKVQRSLKHEDINLQEIISAAGKELSEAFKQKTSEILSHAHAALDQPLPTTLKKQEEKEILKS

QLDSLLGLYHLLDWFAVDESNEVDPEFSARLTGIKLEMEPSLSFYNKARNYATKKPYSVEKFKLNFQ

MPTLASGWDVNKEKNNGAILFVKNGLYYLGIMPKQKGRYKALSFEPTEKTSEGFDKMYYDYFPDAAK

MIPKCSTQLKAVTAHFQTHTTPILLSNNFIEPLEITKEIYDLNNPEKEPKKFQTAYAKKTGDQKGYR

EALCKWIDFTRDFLSKYTKTTSIDLSSLRPSSQYKDLGEYYAELNPLLYHISFQRIAEKEIMDAVET

GKLYLFQIYNKDFAKGHHGKPNLHTLYWTGLFSPENLAKTSIKLNGQAELFYRPKSRMKRMAHRLGE

KMLNKKLKDQKTPIPDTLYQELYDYVNHRLSHDLSDEARALLPNVITKEVSHEIIKDRRFTSDKFFF

HVPITLNYQAANSPSKFNQRVNAYLKEHPETPIIGIDRGERNLIYITVIDSTGKILEQRSLNTIQQF

DYQKKLDNREKERVAARQAWSVVGTIKDLKQGYLSQVIHEIVDLMIHYQAVVVLENLNFGFKSKRTG

IAEKAVYQQFEKMLIDKLNCLVLKDYPAEKVGGVLNPYQLTDQFTSFAKMGTQSGFLFYVPAPYTSK

IDPLTGFVDPFVWKTIKNHESRKHFLEGFDFLHYDVKTGDFILHFKMNRNLSFQRGLPGFMPAWDIV

FEKNETQFDAKGTPFIAGKRIVPVIENHRFTGRYRDLYPANELIALLEEKGIVFRDGSNILPKLLEN

DDSHAIDTMVALIRSVLQMRNSNAATGEDYINSPVRDLNGVCFDSRFQNPEWPMDADANGAYHIALK

GQLLLNHLKESKDLKLQNGISNQDWLAYIQELRN

*E. coli* optimized AsCpf1 DNA

SEQ ID NO: 5

ATGACCCAGTTTGAAGGTTTCACCAATCTGTATCAGGTTAGCAAAACCCTGCGTTTTGAACTGATTC

CGCAGGGTAAAACCCTGAAACATATTCAAGAACAGGGCTTCATCGAAGAGGATAAAGCACGTAACGA

TCACTACAAAGAACTGAAACCGATTATCGACCGCATCTATAAAACCTATGCAGATCAGTGTCTGCAG

CTGGTTCAGCTGGATTGGGAAAATCTGAGCGCAGCAATTGATAGTTATCGCAAAGAAAAAACCGAAG

AAACCCGTAATGCACTGATTGAAGAACAGGCAACCTATCGTAATGCCATCCATGATTATTTCATTGG

TCGTACCGATAATCTGACCGATGCAATTAACAAACGTCACGCCGAAATCTATAAAGGCCTGTTTAAA

GCCGAACTGTTTAATGGCAAAGTTCTGAAACAGCTGGGCACCGTTACCACCACCGAACATGAAAATG

CACTGCTGCGTAGCTTTGATAAATTCACCACCTATTTCAGCGGCTTTTATGAGAATCGCAAAAACGT

GTTTAGCGCAGAAGATATTAGCACCGCAATTCCGCATCGTATTGTGCAGGATAATTTCCCGAAATTC

AAAGAGAACTGCCACATTTTTACCCGTCTGATTACCGCAGTTCCGAGCCTGCGTGAACATTTTGAAA

ACGTTAAAAAAGCCATCGGCATCTTTGTTAGCACCAGCATTGAAGAAGTTTTTAGCTTCCCGTTTTA

CAATCAGCTGCTGACCCAGACCCAGATTGATCTGTATAACCAACTGCTGGGTGGTATTAGCCGTGAA

GCAGGCACCGAAAAAATCAAAGGTCTGAATGAAGTGCTGAATCTGGCCATTCAGAAAAATGATGAAA

CCGCACATATTATTGCAAGCCTGCCGCATCGTTTTATTCCGCTGTTCAAACAAATTCTGAGCGATCG

TAATACCCTGAGCTTTATTCTGGAAGAATTCAAATCCGATGAAGAGGTGATTCAGAGCTTTTGCAAA

TACAAAACGCTGCTGCGCAATGAAAATGTTCTGGAAACTGCCGAAGCACTGTTTAACGAACTGAATA

GCATTGATCTGACCCACATCTTTATCAGCCACAAAAAACTGGAAACCATTTCAAGCGCACTGTGTGA

TCATTGGGATACCCTGCGTAATGCCCTGTATGAACGTCGTATTAGCGAACTGACCGGTAAAATTACC

-continued

```
AAAAGCGCGAAAGAAAAAGTTCAGCGCAGTCTGAAACATGAGGATATTAATCTGCAAGAGATTATTA
GCGCAGCCGGTAAAGAACTGTCAGAAGCATTTAAACAGAAAACCAGCGAAATTCTGTCACATGCACA
TGCAGCACTGGATCAGCCGCTGCCGACCACCCTGAAAAAACAAGAAGAAAAAGAAATCCTGAAAAGC
CAGCTGGATAGCCTGCTGGGTCTGTATCATCTGCTGGACTGGTTTGCAGTTGATGAAAGCAATGAAG
TTGATCCGGAATTTAGCGCACGTCTGACCGGCATTAAACTGGAAATGGAACCGAGCCTGAGCTTTTA
TAACAAAGCCCGTAATTATGCCACCAAAAAACCGTATAGCGTCGAAAAATTCAAACTGAACTTTCAG
ATGCCGACCCTGGCAAGCGGTTGGGATGTTAATAAAGAAAAAAACAACGGTGCCATCCTGTTCGTGA
AAAATGGCCTGTATTATCTGGGTATTATGCCGAAACAGAAAGGTCGTTATAAAGCGCTGAGCTTTGA
ACCGACGGAAAAAACCAGTGAAGGTTTTGATAAAATGTACTACGACTATTTTCCGGATGCAGCCAAA
ATGATTCCGAAATGTAGCACCCAGCTGAAAGCAGTTACCGCACATTTTCAGACCCATACCACCCCGA
TTCTGCTGAGCAATAACTTTATTGAACCGCTGGAAATCACCAAAGAGATCTACGATCTGAATAACCC
GGAAAAAGAGCCGAAAAAATTCCAGACCGCATATGCAAAAAAACCGGTGATCAGAAAGGTTATCGT
GAAGCGCTGTGTAAATGGATTGATTTCACCCGTGATTTTCTGAGCAAATACACCAAAACCACCAGTA
TCGATCTGAGCAGCCTGCGTCCGAGCAGCCAGTATAAAGATCTGGGCGAATATTATGCAGAACTGAA
TCCGCTGCTGTATCATATTAGCTTTCAGCGTATTGCCGAGAAAGAAATCATGGACGCAGTTGAAACC
GGTAAACTGTACCTGTTCCAGATCTACAATAAAGATTTTGCCAAAGGCCATCATGGCAAACCGAATC
TGCATACCCTGTATTGGACCGGTCTGTTTAGCCCTGAAAATCTGGCAAAAACCTCGATTAAACTGAA
TGGTCAGGCGGAACTGTTTTATCGTCCGAAAAGCCGTATGAAACGTATGGCACATCGTCTGGGTGAA
AAAATGCTGAACAAAAACTGAAAGACCAGAAAACCCCGATCCCGGATACACTGTATCAAGAACTGT
ATGATTATGTGAACCATCGTCTGAGCCATGATCTGAGTGATGAAGCACGTGCCCTGCTGCCGAATGT
TATTACCAAAGAAGTTAGCCACGAGATCATTAAAGATCGTCGTTTTACCAGCGACAAATTCTTTTTT
CATGTGCCGATTACCCTGAATTATCAGGCAGCAAATAGCCCGAGCAAATTTAACCAGCGTGTTAATG
CATATCTGAAAGAACATCCAGAAACGCCGATTATTGGTATTGATCGTGGTGAACGTAACCTGATTTA
TATCACCGTTATTGATAGCACCGGCAAAATCCTGGAACAGCGTAGCCTGAATACCATTCAGCAGTTT
GATTACCAGAAAAAACTGGATAATCGCGAGAAAGAACGTGTTGCAGCACGTCAGGCATGGTCAGTTG
TTGGTACAATTAAAGACCTGAAACAGGGTTATCTGAGCCAGGTTATTCATGAAATTGTGGATCTGAT
GATTCACTATCAGGCCGTTGTTGTGCTGGAAAACCTGAATTTTGGCTTTAAAAGCAAACGTACCGGC
ATTGCAGAAAAAGCAGTTTATCAGCAGTTCGAGAAAATGCTGATTGACAAACTGAATTGCCTGGTGC
TGAAAGATTATCCGGCTGAAAAAGTTGGTGGTGTTCTGAATCCGTATCAGCTGACCGATCAGTTTAC
CAGCTTTGCAAAAATGGGCACCCAGAGCGGATTTCTGTTTTATGTTCCGGCACCGTATACGAGCAAA
ATTGATCCGCTGACCGGTTTTGTTGATCCGTTTGTTTGGAAAACCATCAAAAACCATGAAAGCCGCA
AACATTTTCTGGAAGGTTTCGATTTTCTGCATTACGACGTTAAAACGGGTGATTTCATCCTGCACTT
TAAAATGAATCGCAATCTGAGTTTTCAGCGTGGCCTGCCTGGTTTTATGCCTGCATGGGATATTGTG
TTTGAGAAAAACGAAACACAGTTCGATGCAAAAGGCACCCCGTTTATTGCAGGTAAACGTATTGTTC
CGGTGATTGAAAATCATCGTTTCACCGGTCGTTATCGCGATCTGTATCCGGCAAATGAACTGATCGC
ACTGCTGGAAGAGAAAGGTATTGTTTTCGTGATGGCTCAAACATTCTGCCGAAACTGCTGGAAAAT
GATGATAGCCATGCAATTGATACCATGGTTGCACTGATTCGTAGCGTTCTGCAGATGCGTAATAGCA
ATGCAGCAACCGGTGAAGATTACATTAATAGTCCGGTTCGTGATCTGAATGGTGTTTGTTTTGATAG
CCGTTTTCAGAATCCGGAATGGCCGATGGATGCAGATGCAAATGGTGCATATCATATTGCACTGAAA
GGACAGCTGCTGCTGAACCACCTGAAAGAAAGCAAAGATCTGAAACTGCAAAACGGCATTAGCAATC
AGGATTGGCTGGCATATATCCAAGAACTGCGTAACTGA
```

AsCpf1 Human Codon Optimized Nucleotide Sequence

SEQ ID NO: 8

ATGACCCAGTTCGAGGGCTTCACCAACCTGTACCAGGTGTCCAAGACCCTGAGATTCGAGCTGATCC

CCCAGGGCAAGACACTGAAGCACATCCAGGAACAGGGCTTCATCGAAGAGGACAAGGCCCGGAACGA

CCACTACAAAGAGCTGAAGCCCATCATCGACCGGATCTACAAGACCTACGCCGACCAGTGCCTGCAG

CTGGTGCAGCTGGACTGGGAGAATCTGAGCGCCGCCATCGACAGCTACCGGAAAGAGAAAACCGAGG

AAAACCCGGAACGCCCTGATCGAGGAACAGGCCACCTACAGAAACGCCATCCACGACTACTTCATCGG

CCGGACCGACAACCTGACCGACGCCATCAACAAGCGGCACGCCGAGATCTATAAGGGCCTGTTCAAG

GCCGAGCTGTTCAACGGCAAGGTGCTGAAGCAGCTGGGCACCGTGACCACCACCGAGCACGAAAACG

CCCTGCTGCGGAGCTTCGACAAGTTCACCACCTACTTCAGCGGCTTCTACGAGAACCGGAAGAACGT

GTTCAGCGCCGAGGACATCAGCACCGCCATCCCCCACAGAATCGTGCAGGACAACTTCCCCAAGTTC

AAAGAGAACTGCCACATCTTCACCCGGCTGATCACCGCCGTGCCCAGCCTGAGAGAACACTTCGAGA

ACGTGAAGAAGGCCATCGGCATCTTCGTGTCCACCAGCATCGAGGAAGTGTTCAGCTTCCCATTCTA

CAACCAGCTGCTGACCCAGACCCAGATCGACCTGTATAATCAGCTGCTGGGCGGCATCAGCAGAGAG

GCCGGCACCGAGAAGATCAAGGGCCTGAACGAAGTGCTGAACCTGGCCATCCAGAAGAACGACGAGA

CAGCCCACATCATTGCCAGCCTGCCCCACCGGTTCATCCCTCTGTTCAAGCAGATCCTGAGCGACAG

AAACACCCTGAGCTTCATCCTGGAAGAGTTCAAGTCCGATGAGGAAGTGATCCAGAGCTTCTGCAAG

TATAAGACCCTGCTGAGGAACGAGAATGTGCTGGAAACCGCCGAGGCCCTGTTCAATGAGCTGAACA

GCATCGACCTGACCCACATCTTTATCAGCCACAAGAAGCTGGAAACAATCAGCAGCGCCCTGTGCGA

CCACTGGGACACACTGCGGAATGCCCTGTACGAGCGGCGGATCTCTGAGCTGACCGGCAAGATCACC

AAGAGCGCCAAAGAAAAGGTGCAGCGGAGCCTGAAGCACGAGGATATCAACCTGCAGGAAATCATCA

GCGCCGCTGGCAAAGAACTGAGCGAGGCCTTTAAGCAGAAAACCAGCGAGATCCTGTCCCACGCCCA

CGCCGCACTGGATCAGCCTCTGCCTACCACCCTGAAGAAGCAGGAAGAGAAAGAGATCCTGAAGTCC

CAGCTGGACAGCCTGCTGGGCCTGTACCATCTGCTGGATTGGTTCGCCGTGGACGAGAGCAACGAGG

TGGACCCCGAGTTCTCCGCCAGACTGACAGGCATCAAACTGGAAATGGAACCCAGCCTGTCCTTCTA

CAACAAGGCCAGAAACTACGCCACCAAGAAACCCTACAGCGTGGAAAAGTTTAAGCTGAACTTCCAG

ATGCCCACCCTGGCCAGCGGCTGGGACGTGAACAAAGAGAAGAACAACGGCGCCATCCTGTTCGTGA

AGAACGGACTGTACTACCTGGGCATCATGCCTAAGCAGAAGGGCAGATACAAGGCCCTGTCCTTTGA

GCCCACCGAAAAGACCAGCGAGGGCTTTGACAAGATGTACTACGATTACTTCCCCGACGCCGCCAAG

ATGATCCCCAAGTGCAGCACCCAGCTGAAGGCCGTGACCGCCCACTTTCAGACCCACACCACCCCCA

TCCTGCTGAGCAACAACTTCATCGAGCCCCTGGAAATCACCAAAGAGATCTACGACCTGAACAACCC

CGAGAAAGAGCCCAAGAAGTTCCAGACCGCCTACGCCAAGAAAACCGGCGACCAGAAGGGCTACCGC

GAGGCTCTGTGCAAGTGGATCGACTTTACCCGGGACTTCCTGAGCAAGTACACCAAGACCACCTCCA

TCGATCTGAGCAGCCTGCGGCCCAGCTCCCAGTACAAGGATCTGGGCGAGTACTACGCCGAGCTGAA

CCCTCTGCTGTACCACATCAGCTTCCAGCGGATCGCCGAAAAAGAAATCATGGACGCCGTGGAAACC

GGCAAGCTGTACCTGTTCCAGATCTATAACAAGGACTTCGCCAAGGGCCACCACGGCAAGCCCAATC

TGCACACCCTGTACTGGACCGGCCTGTTTAGCCCCGAGAATCTGGCCAAGACCAGCATCAAGCTGAA

CGGCCAGGCCGAACTGTTTTACCGGCCCAAGAGCCGGATGAAGCGGATGGCCCATAGACTGGGCGAG

AAGATGCTGAACAAGAAACTGAAGGACCAGAAAACCCCTATCCCCGACACACTGTATCAGGAACTGT

ACGACTACGTGAACCACCGGCTGAGCCACGACCTGTCCGACGAAGCTAGAGCACTGCTGCCCAACGT

GATCACAAAAGAGGTGTCCCACGAGATCATCAAGGACCGGCGGTTTACCTCCGATAAGTTCTTCTTC

-continued

CACGTGCCCATCACCCTGAACTACCAGGCCGCCAACAGCCCCAGCAAGTTCAACCAGAGAGTGAACG

CCTACCTGAAAGAGCACCCCGAGACACCCATCATTGGCATCGACAGAGGCGAGCGGAACCTGATCTA

CATCACCGTGATCGACAGCACAGGCAAAATCCTGGAACAGAGAAGCCTGAACACCATCCAGCAGTTC

GACTACCAGAAGAAACTGGACAACCGGGAAAAAGAACGGGTGGCCGCCAGACAGGCTTGGAGCGTCG

TGGGCACCATTAAGGACCTGAAGCAGGGCTACCTGAGCCAAGTGATTCACGAGATCGTGGACCTGAT

GATCCACTATCAGGCTGTGGTGGTGCTGGAAAACCTGAACTTCGGCTTCAAGAGCAAGCGGACCGGA

ATCGCCGAGAAAGCCGTGTACCAGCAGTTTGAGAAAATGCTGATCGACAAGCTGAATTGCCTGGTGC

TGAAAGACTACCCCGCTGAGAAAGTGGGAGGCGTGCTGAATCCCTACCAGCTGACCGACCAGTTCAC

CTCCTTTGCCAAGATGGGAACCCAGAGCGGCTTCCTGTTCTACGTGCCAGCCCCCTACACCAGCAAG

ATCGACCCTCTGACCGGCTTCGTGGACCCCTTCGTGTGGAAAACCATCAAGAACCACGAGTCCCGGA

AGCACTTCCTGGAAGGCTTTGACTTCCTGCACTACGACGTGAAAACAGGCGATTTCATCCTGCACTT

CAAGATGAATCGGAATCTGTCCTTCCAGAGGGGCCTGCCCGGCTTCATGCCTGCCTGGGATATCGTG

TTCGAGAAGAATGAGACACAGTTCGACGCCAAGGGAACCCCCTTTATCGCCGGCAAGAGGATCGTGC

CTGTGATCGAGAACCACAGATTCACCGGCAGATACCGGGACCTGTACCCCGCCAACGAGCTGATTGC

CCTGCTGGAAGAGAAGGGCATCGTGTTCCGGGACGGCAGCAACATCCTGCCCAAGCTGCTGGAAAAT

GACGACAGCCACGCCATCGATACCATGGTGGCACTGATCCGCAGCGTGCTGCAGATGCGGAACAGCA

ATGCCGCCACCGGCGAGGACTACATCAATAGCCCAGTGCGGGACCTGAACGGCGTGTGCTTCGACAG

CAGATTCCAGAACCCCGAGTGGCCCATGGATGCCGACGCCAATGGCGCCTACCACATTGCCCTGAAG

GGACAGCTGCTGCTGAACCATCTGAAAGAGAGCAAAGACCTGAAACTGCAGAACGGCATCTCCAACC

AGGACTGGCTGGCCTATATCCAGGAACTGCGGAACTGA

E. coli optimized As Cpf1 with flanking NLS's, V5 tag and 6x His-DNA    SEQ ID NO: 11

ATGGGTCGGGATCCAGGTAAACCGATTCCGAATCCGCTGCTGGGTCTGGATAGCACCGCACCGAAAA

AAAAACGTAAAGTTGGTATTCATGGTGTTCCGGCAGCAACCCAGTTTGAAGGTTTCACCAATCTGTA

TCAGGTTAGCAAAACCCTGCGTTTTGAACTGATTCCGCAGGGTAAAACCCTGAAACATATTCAAGAA

CAGGGCTTCATCGAAGAGGATAAAGCACGTAACGATCACTACAAAGAACTGAAACCGATTATCGACC

GCATCTATAAAACCTATGCAGATCAGTGTCTGCAGCTGGTTCAGCTGGATTGGGAAAATCTGAGCGC

AGCAATTGATAGTTATCGCAAAGAAAAAACCGAAGAAACCCGTAATGCACTGATTGAAGAACAGGCA

ACCTATCGTAATGCCATCCATGATTATTTCATTGGTCGTACCGATAATCTGACCGATGCAATTAACA

AACGTCACGCCGAAATCTATAAAGGCCTGTTTAAAGCCGAACTGTTTAATGGCAAAGTTCTGAAACA

GCTGGGCACCGTTACCACCACCGAACATGAAAATGCACTGCTGCGTAGCTTTGATAAATTCACCACC

TATTTCAGCGGCTTTTATGAGAATCGCAAAAACGTGTTTAGCGCAGAAGATATTAGCACCGCAATTC

CGCATCGTATTGTGCAGGATAATTTCCCGAAATTCAAAGAGAACTGCCACATTTTTACCCGTCTGAT

TACCGCAGTTCCGAGCCTGCGTGAACATTTTGAAAACGTTAAAAAAGCCATCGGCATCTTTGTTAGC

ACCAGCATTGAAGAAGTTTTTAGCTTCCCGTTTTACAATCAGCTGCTGACCCAGACCCAGATTGATC

TGTATAACCAACTGCTGGGTGGTATTAGCCGTGAAGCAGGCACCGAAAAAATCAAAGGTCTGAATGA

AGTGCTGAATCTGGCCATTCAGAAAAATGATGAAACCGCACATATTATTGCAAGCCTGCCGCATCGT

TTTATTCCGCTGTTCAAACAAATTCTGAGCGATCGTAATACCCTGAGCTTTATTCTGGAAGAATTCA

AATCCGATGAAGAGGTGATTCAGAGCTTTTGCAAATACAAAACGCTGCTGCGCAATGAAAATGTTCT

GGAAACTGCCGAAGCACTGTTTAACGAACTGAATAGCATTGATCTGACCCACATCTTTATCAGCCAC

AAAAAACTGGAAACCATTTCAAGCGCACTGTGTGATCATTGGGATACCCTGCGTAATGCCCTGTATG

AACGTCGTATTAGCGAACTGACCGGTAAAATTACCAAAAGCGCGAAAGAAAAAGTTCAGCGCAGTCT

-continued

```
GAAACATGAGGATATTAATCTGCAAGAGATTATTAGCGCAGCCGGTAAAGAACTGTCAGAAGCATTT

AAACAGAAAACCAGCGAAATTCTGTCACATGCACATGCAGCACTGGATCAGCCGCTGCCGACCACCC

TGAAAAAACAAGAAGAAAAAGAAATCCTGAAAAGCCAGCTGGATAGCCTGCTGGGTCTGTATCATCT

GCTGGACTGGTTTGCAGTTGATGAAAGCAATGAAGTTGATCCGGAATTTAGCGCACGTCTGACCGGC

ATTAAACTGGAAATGGAACCGAGCCTGAGCTTTTATAACAAAGCCCGTAATTATGCCACCAAAAAAC

CGTATAGCGTCGAAAAATTCAAACTGAACTTTCAGATGCCGACCCTGGCAAGCGGTTGGGATGTTAA

TAAAGAAAAAAACAACGGTGCCATCCTGTTCGTGAAAAATGGCCTGTATTATCTGGGTATTATGCCG

AAACAGAAAGGTCGTTATAAAGCGCTGAGCTTTGAACCGACGGAAAAAACCAGTGAAGGTTTTGATA

AAATGTACTACGACTATTTTCCGGATGCAGCCAAAATGATTCCGAAATGTAGCACCCAGCTGAAAGC

AGTTACCGCACATTTTCAGACCCATACCACCCCGATTCTGCTGAGCAATAACTTTATTGAACCGCTG

GAAATCACCAAAGAGATCTACGATCTGAATAACCCGGAAAAAGAGCCGAAAAAATTCCAGACCGCAT

ATGCAAAAAAACCGGTGATCAGAAAGGTTATCGTGAAGCGCTGTGTAAATGGATTGATTTCACCCG

TGATTTTCTGAGCAAATACACCAAAACCACCAGTATCGATCTGAGCAGCCTGCGTCCGAGCAGCCAG

TATAAAGATCTGGGCGAATATTATGCAGAACTGAATCCGCTGCTGTATCATATTAGCTTTCAGCGTA

TTGCCGAGAAAGAAATCATGGACGCAGTTGAAACCGGTAAACTGTACCTGTTCCAGATCTACAATAA

AGATTTTGCCAAAGGCCATCATGGCAAACCGAATCTGCATACCCTGTATTGGACCGGTCTGTTTAGC

CCTGAAAATCTGGCAAAAACCTCGATTAAACTGAATGGTCAGGCGGAACTGTTTTATCGTCCGAAAA

GCCGTATGAAACGTATGGCACATCGTCTGGGTGAAAAAATGCTGAACAAAAAACTGAAAGACCAGAA

AACCCCGATCCCGGATACACTGTATCAAGAACTGTATGATTATGTGAACCATCGTCTGAGCCATGAT

CTGAGTGATGAAGCACGTGCCCTGCTGCCGAATGTTATTACCAAAGAAGTTAGCCACGAGATCATTA

AGATCGTCGTTTTACCAGCGACAAATTCTTTTTTCATGTGCCGATTACCCTGAATTATCAGGCAGC

AAATAGCCCGAGCAAATTTAACCAGCGTGTTAATGCATATCTGAAAGAACATCCAGAAACGCCGATT

ATTGGTATTGATCGTGGTGAACGTAACCTGATTTATATCACCGTTATTGATAGCACCGGCAAAATCC

TGGAACAGCGTAGCCTGAATACCATTCAGCAGTTTGATTACCAGAAAAAACTGGATAATCGCGAGAA

AGAACGTGTTGCAGCACGTCAGGCATGGTCAGTTGTTGGTACAATTAAAGACCTGAAACAGGGTTAT

CTGAGCCAGGTTATTCATGAAATTGTGGATCTGATGATTCACTATCAGGCCGTTGTTGTGCTGGAAA

ACCTGAATTTTGGCTTTAAAAGCAAACGTACCGGCATTGCAGAAAAAGCAGTTTATCAGCAGTTCGA

GAAAATGCTGATTGACAAACTGAATTGCCTGGTGCTGAAAGATTATCCGGCTGAAAAAGTTGGTGGT

GTTCTGAATCCGTATCAGCTGACCGATCAGTTTACCAGCTTTGCAAAAATGGGCACCCAGAGCGGAT

TTCTGTTTTATGTTCCGGCACCGTATACGAGCAAAATTGATCCGCTGACCGGTTTTGTTGATCCGTT

TGTTTGGAAAACCATCAAAAACCATGAAAGCCGCAAACATTTTCTGGAAGGTTTCGATTTTCTGCAT

TACGACGTTAAAACGGGTGATTTCATCCTGCACTTTAAAATGAATCGCAATCTGAGTTTTCAGCGTG

GCCTGCCTGGTTTTATGCCTGCATGGGATATTGTGTTTGAGAAAAACGAAACACAGTTCGATGCAAA

AGGCACCCCGTTTATTGCAGGTAAACGTATTGTTCCGGTGATTGAAAATCATCGTTTCACCGGTCGT

TATCGCGATCTGTATCCGGCAAATGAACTGATCGCACTGCTGGAAGAGAAAGGTATTGTTTTTCGTG

ATGGCTCAAACATTCTGCCGAAACTGCTGGAAAATGATGATAGCCATGCAATTGATACCATGGTTGC

ACTGATTCGTAGCGTTCTGCAGATGCGTAATAGCAATGCAGCAACCGGTGAAGATTACATTAATAGT

CCGGTTCGTGATCTGAATGGTGTTTGTTTTGATAGCCGTTTTCAGAATCCGGAATGGCCGATGGATG
```

-continued

```
CAGATGCAAATGGTGCATATCATATTGCACTGAAAGGACAGCTGCTGCTGAACCACCTGAAAGAAAG
CAAAGATCTGAAACTGCAAAACGGCATTAGCAATCAGGATTGGCTGGCATATATCCAAGAACTGCGT
AACCCTAAAAAAAAACGCAAAGTGAAGCTTGCGGCCGCACTCGAGCACCACCACCACCACCACTGA
```

E. coli optimized As Cpf1 with 5'- and 3'-flanking NLS's, 5'-V5 tag and 3'-6x His

SEQ ID NO: 12

MGRDPGKPIPNPLLGLDSTAPKKKRKVGIHGVPAATQFEGFTNLYQVSKTLRFELIPQGKTLKHIQE
QGFIEEDKARNDHYKELKPIIDRIYKTYADQCLQLVQLDWENLSAAIDSYRKEKTEETRNALIEEQA
TYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVS
TSIEEVFSFPFYNQLLTQTQIDLYNQLLGGISREAGTEKIKGLNEVLNLAIQKNDETAHIIASLPHR
FIPLFKQILSDRNTLSFILEEFKSDEEVIQSFCKYKTLLRNENVLETAEALFNELNSIDLTHIFISH
KKLETISSALCDHWDTLRNALYERRISELTGKITKSAKEKVQRSLKHEDINLQEIISAAGKELSEAF
KQKTSEILSHAHAALDQPLPTTLKKQEEKEILKSQLDSLLGLYHLLDWFAVDESNEVDPEFSARLTG
IKLEMEPSLSFYNKARNYATKKPYSVEKFKLNFQMPTLASGWDVNKEKNNGAILFVKNGLYYLGIMP
KQKGRYKALSFEPTEKTSEGFDKMYYDYFPDAAKMIPKCSTQLKAVTAHFQTHTTPILLSNNFIEPL
EITKEIYDLNNPEKEPKKFQTAYAKKTGDQKGYREALCKWIDFTRDFLSKYTKTTSIDLSSLRPSSQ
YKDLGEYYAELNPLLYHISFQRIAEKEIMDAVETGKLYLFQIYNKDFAKGHHGKPNLHTLYWTGLFS
PENLAKTSIKLNGQAELFYRPKSRMKRMAHRLGEKMLNKKLKDQKTPIPDTLYQELYDYVNHRLSHD
LSDEARALLPNVITKEVSHEIIKDRRFTSDKFFFHVPITLNYQAANSPSKFNQRVNAYLKEHPETPI
IGIDRGERNLIYITVIDSTGKILEQRSLNTIQQFDYQKKLDNREKERVAARQAWSVVGTIKDLKQGY
LSQVIHEIVDLMIHYQAVVVLENLNFGFKSKRTGIAEKAVYQQFEKMLIDKLNCLVLKDYPAEKVGG
VLNPYQLTDQFTSFAKMGTQSGFLFYVPAPYTSKIDPLTGFVDPFVWKTIKNHESRKHFLEGFDFLH
YDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMRNSAATGEDYINS
PVRDLNGVCFDSRFQNPEWPMDADANGAYHIALKGQLLLNHLKESKDLKLQNGISNQDWLAYIQELR
NPKKKRKVKLAAALEHHHHHH

Hs optimized As Cpf1 with flanking NLS's, V5 tag and 6x His-DNA

SEQ ID NO: 15

```
ATGGGCAAGCCCATTCCTAATCCTCTGCTGGGCCTCGACAGCACAGCCCCTAAGAAAAAGCGGAAAG
TGGGCATCCATGGCGTGCCAGCCGCCACACAGTTTGAGGGCTTCACCAACCTGTACCAGGTGTCCAA
GACACTGCGCTTCGAGCTGATCCCTCAGGGCAAGACCCTGAAGCACATCCAAGAGCAGGGCTTCATC
GAAGAGGACAAGGCCCGGAACGACCACTACAAAGAGCTGAAGCCCATCATCGACCGGATCTACAAGA
CCTACGCCGACCAGTGTCTGCAGCTGGTGCAGCTCGATTGGGAGAATCTGAGCGCCGCCATCGACAG
CTACCGGAAAGAGAAACCGAGGAAACCCGGAACGCCCTGATCGAGGAACAGGCCACCTACAGAAAC
GCCATCCACGACTACTTCATCGGCCGGACCGACAACCTGACCGACGCCATCAACAAGAGACACGCCG
AGATCTATAAGGGCCTGTTCAAGGCCGAGCTGTTCAACGGCAAGGTGCTGAAGCAGCTGGGCACCGT
GACAACCACCGAGCACGAAAATGCCCTGCTGCGGAGCTTCGACAAGTTCACCACCTACTTCAGCGGC
TTCTACGAGAACCGGAAGAACGTGTTCAGCGCCGAGGACATCAGCACCGCCATTCCTCACAGAATCG
TGCAGGACAACTTCCCCAAGTTCAAAGAGAACTGCCACATCTTCACCCGGCTGATCACAGCCGTGCC
TAGCCTGAGAGAACACTTCGAGAACGTGAAGAAGGCCATCGGCATCTTCGTGTCCACCAGCATCGAG
GAAGTGTTCAGCTTCCCATTCTACAACCAGCTGCTGACCCAGACACAGATCGACCTGTATAATCAGC
TGCTCGGCGGCATCAGCAGAGAGGCCGGAACAGAGAAGATCAAGGGCCTGAACGAAGTGCTGAACCT
```

-continued

```
GGCCATCCAGAAGAACGACGAGACAGCCCACATCATTGCCAGCCTGCCTCACCGGTTCATCCCTCTG

TTCAAGCAGATCCTGAGCGACAGAAACACCCTGAGCTTCATCCTGGAAGAGTTCAAGTCCGATGAGG

AAGTGATCCAGAGCTTCTGCAAGTATAAGACCCTGCTGAGGAACGAGAATGTGCTGGAAACCGCCGA

GGCTCTGTTTAACGAGCTGAACAGCATCGATCTGACCCACATCTTTATCAGCCACAAGAAGCTCGAG

ACAATCAGCAGCGCCCTGTGCGACCACTGGGATACCCTGAGAAACGCCCTGTACGAGCGGAGAATCA

GCGAGCTGACCGGCAAGATCACCAAGAGCGCCAAAGAAAAGGTGCAGCGGAGCCTGAAACACGAGGA

TATCAACCTGCAAGAGATCATCAGCGCCGCTGGCAAAGAACTGAGCGAGGCCTTTAAGCAGAAAACC

AGCGAGATCCTGTCTCACGCCCACGCTGCTCTTGATCAGCCTCTGCCTACCACACTGAAGAAGCAAG

AGGAAAAAGAGATCCTGAAGTCCCAGCTGGACAGCCTGCTGGGACTGTACCATCTGCTGGATTGGTT

CGCCGTGGACGAGAGCAATGAGGTGGACCCTGAGTTCTCCGCCAGACTGACAGGCATCAAGCTGGAA

ATGGAACCCAGCCTGTCCTTCTACAACAAGGCCAGAAACTACGCCACCAAGAAGCCCTACAGCGTCG

AGAAGTTCAAGCTCAACTTCCAGATGCCTACACTGGCCAGCGGCTGGGACGTGAACAAAGAGAAGAA

CAACGGCGCCATCCTGTTCGTGAAGAACGGACTGTACTACCTGGGCATCATGCCAAAGCAGAAGGGC

AGATACAAGGCCCTGTCCTTTGAGCCCACCGAAAAGACCAGCGAGGGCTTCGATAAGATGTACTACG

ATTACTTCCCCGACGCCGCCAAGATGATCCCCAAGTGTAGCACACAGCTGAAGGCCGTGACCGCTCA

CTTTCAGACCCACACCACACCTATCCTGCTGAGCAACAACTTCATCGAGCCCCTGGAAATCACCAAA

GAGATCTACGACCTGAACAACCCCGAGAAAGAGCCCAAGAAGTTCCAGACCGCCTACGCCAAGAAAA

CCGGCGACCAGAAGGGCTACAGAGAAGCCCTGTGCAAGTGGATCGACTTTACCCGGGACTTCCTGAG

CAAGTACACCAAGACCACCTCCATCGACCTGAGCAGCCTGAGGCCTAGCAGCCAGTATAAGGACCTG

GGCGAGTACTACGCCGAGCTGAATCCACTGCTGTACCACATCAGCTTCCAGCGGATCGCCGAAAAAG

AAATCATGGACGCCGTGGAAACCGGCAAGCTGTACCTGTTCCAGATATACAACAAAGACTTCGCCAA

GGGCCACCACGGCAAGCCTAATCTGCACACCCTGTACTGGACCGGCCTGTTTAGCCCTGAGAATCTG

GCCAAGACCTCTATCAAGCTGAACGGCCAGGCCGAACTGTTTTACAGACCCAAGAGCCGGATGAAGC

GGATGGCCCACAGACTGGGAGAGAAGATGCTGAACAAGAAACTGAAGGACCAGAAAACGCCCATTCC

GGACACACTGTACCAAGAGCTGTACGACTACGTGAACCACCGGCTGAGCCACGATCTGAGCGACGAA

GCTAGAGCACTGCTGCCCAACGTGATCACAAAAGAGGTGTCCCACGAGATCATTAAGGACCGGCGGT

TTACCTCCGATAAGTTCTTCTTCCACGTGCCGATCACACTGAACTACCAGGCCGCCAACTCTCCCAG

CAAGTTCAACCAGAGAGTGAACGCCTACCTGAAAGAGCACCCCGAGACACCCATCATTGGCATCGAC

AGAGGCGAGCGGAACCTGATCTACATCACCGTGATCGACTCCACAGGCAAGATCCTGGAACAGCGGT

CCCTGAACACCATCCAGCAGTTCGACTACCAGAAGAAGCTGGACAACCGAGAGAAAGAAAGAGTGGC

CGCCAGACAGGCTTGGAGCGTTGTGGGCACAATCAAGGATCTGAAGCAGGGCTACCTGAGCCAAGTG

ATTCACGAGATCGTGGACCTGATGATCCACTATCAGGCTGTGGTGGTGCTCGAGAACCTGAACTTCG

GCTTCAAGAGCAAGCGGACCGGAATCGCCGAGAAAGCCGTGTACCAGCAGTTTGAGAAAATGCTGAT

CGACAAGCTGAATTGCCTGGTCCTGAAGGACTACCCCGCTGAGAAAGTTGGCGGAGTGCTGAATCCC

TACCAGCTGACCGATCAGTTCACCAGCTTTGCCAAGATGGGAACCCAGAGCGGCTTCCTGTTCTACG

TGCCAGCTCCTTACACCTCCAAGATCGACCCTCTGACCGGCTTCGTGGACCCCTTCGTGTGGAAAAC

CATCAAGAACCACGAGTCCCGGAAGCACTTCCTGGAAGGCTTTGACTTCCTGCACTACGACGTGAAA

ACAGGCGATTTCATCCTGCACTTCAAGATGAATCGGAATCTGTCCTTCCAGAGGGGCCTGCCTGGCT

TCATGCCTGCTTGGGATATCGTGTTCGAGAAGAATGAGACTCAGTTCGACGCCAAGGGGACCCCTTT

TATCGCCGGCAAGAGAATTGTGCCTGTGATCGAGAACCACAGGTTCACCGGCAGATACCGGGATCTG

TACCCCGCCAATGAGCTGATCGCCCTGCTGGAAGAGAAGGGCATCGTGTTTAGAGATGGCAGCAACA
```

-continued

TCCTGCCTAAGCTGCTGGAAAACGACGACAGCCACGCCATCGATACCATGGTGGCACTGATCAGATC

CGTGCTGCAGATGCGGAACAGCAATGCCGCTACCGGCGAGGACTACATCAATAGCCCCGTGCGGGAT

CTGAACGGCGTGTGCTTCGACAGCAGATTTCAGAACCCCGAGTGGCCTATGGATGCCGACGCCAATG

GCGCCTATCACATTGCCCTGAAAGGACAGCTGCTGCTGAACCATCTGAAAGAGAGCAAGGACCTGAA

ACTGCAGAACGGCATCTCCAACCAGGACTGGCTGGCCTACATTCAAGAGCTGCGGAATCCCAAAAAG

AAACGGAAAGTGAAGCTGGCCGCTGCTCTGGAACACCACCACCATCACCAT

Hs optimized As Cpf1 with 5'- and 3'-flanking NLS's, 5'-V5 tag and 3'-6x His-AA
SEQ ID NO: 16

MGKPIPNPLLGLDSTAPKKKRKVGIHGVPAATQFEGFTNLYQVSKTLRFELIPQGKTLKHIQEQGFI

EEDKARNDHYKELKPIIDRIYKTYADQCLQLVQLDWENLSAAIDSYRKEKTEETRNALIEEQATYRN

AIHDYFIGRTDNLTDAINKRHAEIYKGLFKAELFNGKVLKQLGTVTTTEHENALLRSFDKFTTYFSG

FYENRKNVFSAEDISTAIPHRIVQDNFPKFKENCHIFTRLITAVPSLREHFENVKKAIGIFVSTSIE

EVFSFPFYNQLLTQTQIDLYNQLLGGISREAGTEKIKGLNEVLNLAIQKNDETAHIIASLPHRFIPL

FKQILSDRNTLSFILEEFKSDEEVIQSFCKYKTLLRNENVLETAEALFNELNSIDLTHIFISHKKLE

TISSALCDHWDTLRNALYERRISELTGKITKSAKEKVQRSLKHEDINLQEIISAAGKELSEAFKQKT

SEILSHAHAALDQPLPTTLKKQEEKEILKSQLDSLLGLYHLLDWFAVDESNEVDPEFSARLTGIKLE

MEPSLSFYNKARNYATKKPYSVEKFKLNFQMPTLASGWDVNKEKNNGAILFVKNGLYYLGIMPKQKG

RYKALSFEPTEKTSEGFDKMYYDYFPDAAKMIPKCSTQLKAVTAHFQTHTTPILLSNNFIEPLEITK

EIYDLNNPEKEPKKFQTAYAKKTGDQKGYREALCKWIDFTRDFLSKYTKTTSIDLSSLRPSSQYKDL

GEYYAELNPLLYHISFQRIAEKEIMDAVETGKLYLFQIYNKDFAKGHHGKPNLHTLYWTGLFSPENL

AKTSIKLNGQAELFYRPKSRMKRMAHRLGEKMLNKKLKDQKTPIPDTLYQELYDYVNHRLSHDLSDE

ARALLPNVITKEVSHEIIKDRRFTSDKFFFHVPITLNYQAANSPSKFNQRVNAYLKEHPETPIIGID

RGERNLIYITVIDSTGKILEQRSLNTIQQFDYQKKLDNREKERVAARQAWSVVGTIKDLKQGYLSQV

IHEIVDLMIHYQAVVVLENLNFGFKSKRTGIAEKAVYQQFEKMLIDKLNCLVLKDYPAEKVGGVLNP

YQLTDQFTSFAKMGTQSGFLFYVPAPYTSKIDPLTGFVDPFVWKTIKNHESRKHFLEGFDFLHYDVK

TGDFILHFKMNRNLSFQRGLPGFMPAWDIVFEKNETQFDAKGTPFIAGKRIVPVIENHRFTGRYRDL

YPANELIALLEEKGIVFRDGSNILPKLLENDDSHAIDTMVALIRSVLQMRNSNAATGEDYINSPVRD

LNGVCFDSRFQNPEWPMDADANGAYHIALKGQLLLNHLKESKDLKLQNGISNQDWLAYIQELRNPKK

KRKVKLAAALEHHHHHH

*E. coli* optimized As Cpf1 with OpT NLS and 6x His-DNA
SEQ ID NO: 18

ATGACCCAGTTTGAAGGTTTCACCAATCTGTATCAGGTTAGCAAAACCCTGCGTTTTGAACTGATTC

CGCAGGGTAAAACCCTGAAACATATTCAAGAACAGGGCTTCATCGAAGAGGATAAAGCACGTAACGA

TCACTACAAAGAACTGAAACCGATTATCGACCGCATCTATAAAACCTATGCAGATCAGTGTCTGCAG

CTGGTTCAGCTGGATTGGGAAAATCTGAGCGCAGCAATTGATAGTTATCGCAAAGAAAAAACCGAAG

AAACCCGTAATGCACTGATTGAAGAACAGGCAACCTATCGTAATGCCATCCATGATTATTTCATTGG

TCGTACCGATAATCTGACCGATGCAATTAACAAAGTCACGCCGAAATCTATAAAGGCCTGTTTAAA

GCCGAACTGTTTAATGGCAAAGTTCTGAAACAGCTGGGCACCGTTACCACCACCGAACATGAAAATG

CACTGCTGCGTAGCTTTGATAAAATTCACCACCTATTTCAGCGGCTTTTATGAGAATCGCAAAAACGT

GTTTAGCGCAGAAGATATTAGCACCGCAATTCCGCATCGTATTGTGCAGGATAATTTCCCGAAATTC

AAAGAGAACTGCCACATTTTTACCCGTCTGATTACCGCAGTTCCGAGCCTGCGTGAACATTTTGAAA

ACGTTAAAAAAGCCATCGGCATCTTTGTTAGCACCAGCATTGAAGAAGTTTTTAGCTTCCCGTTTTA

-continued

CAATCAGCTGCTGACCCAGACCCAGATTGATCTGTATAACCAACTGCTGGGTGGTATTAGCCGTGAA
GCAGGCACCGAAAAAATCAAAGGTCTGAATGAAGTGCTGAATCTGGCCATTCAGAAAAATGATGAAA
CCGCACATATTATTGCAAGCCTGCCGCATCGTTTTATTCCGCTGTTCAAACAAATTCTGAGCGATCG
TAATACCCTGAGCTTTATTCTGGAAGAATTCAAATCCGATGAAGAGGTGATTCAGAGCTTTTGCAAA
TACAAAACGCTGCTGCGCAATGAAATGTTCTGGAAACTGCCGAAGCACTGTTTAACGAACTGAATA
GCATTGATCTGACCCACATCTTTATCAGCCACAAAAAACTGGAAACCATTTCAAGCGCACTGTGTGA
TCATTGGGATACCCTGCGTAATGCCCTGTATGAACGTCGTATTAGCGAACTGACCGGTAAAATTACC
AAAAGCGCGAAAGAAAAAGTTCAGCGCAGTCTGAAACATGAGGATATTAATCTGCAAGAGATTATTA
GCGCAGCCGGTAAAGAACTGTCAGAAGCATTTAAACAGAAAACCAGCGAAATTCTGTCACATGCACA
TGCAGCACTGGATCAGCCGCTGCCGACCACCCTGAAAAAACAAGAAGAAAAAGAAATCCTGAAAAGC
CAGCTGGATAGCCTGCTGGGTCTGTATCATCTGCTGGACTGGTTTGCAGTTGATGAAAGCAATGAAG
TTGATCCGGAATTTAGCGCACGTCTGACCGGCATTAAACTGGAAATGGAACCGAGCCTGAGCTTTTA
TAACAAAGCCCGTAATTATGCCACCAAAAAACCGTATAGCGTCGAAAAATTCAAACTGAACTTTCAG
ATGCCGACCCTGGCAAGCGGTTGGGATGTTAATAAAGAAAAAAACAACGGTGCCATCCTGTTCGTGA
AAAATGGCCTGTATTATCTGGGTATTATGCCGAAACAGAAAGGTCGTTATAAAGCGCTGAGCTTTGA
ACCGACGGAAAAAACCAGTGAAGGTTTTGATAAAATGTACTACGACTATTTTCCGGATGCAGCCAAA
ATGATTCCGAAATGTAGCACCCAGCTGAAAGCAGTTACCGCACATTTTCAGACCCATACCACCCCGA
TTCTGCTGAGCAATAACTTTATTGAACCGCTGGAAATCACCAAAGAGATCTACGATCTGAATAACCC
GGAAAAAGAGCCGAAAAAATTCCAGACCGCATATGCAAAAAAACCGGTGATCAGAAAGGTTATCGT
GAAGCGCTGTGTAAATGGATTGATTTCACCCGTGATTTTCTGAGCAAATACACCAAAACCACCAGTA
TCGATCTGAGCAGCCTGCGTCCGAGCAGCCAGTATAAAGATCTGGGCGAATATTATGCAGAACTGAA
TCCGCTGCTGTATCATATTAGCTTTCAGCGTATTGCCGAGAAAGAAATCATGGACGCAGTTGAAACC
GGTAAACTGTACCTGTTCCAGATCTACAATAAAGATTTTGCCAAAGGCCATCATGGCAAACCGAATC
TGCATACCCTGTATTGGACCGGTCTGTTTAGCCCTGAAAATCTGGCAAAAACCTCGATTAAACTGAA
TGGTCAGGCGGAACTGTTTTATCGTCCGAAAAGCCGTATGAAACGTATGGCACATCGTCTGGGTGAA
AAAATGCTGAACAAAAAACTGAAAGACCAGAAAACCCCGATCCCGGATACACTGTATCAAGAACTGT
ATGATTATGTGAACCATCGTCTGAGCCATGATCTGAGTGATGAAGCACGTGCCCTGCTGCCGAATGT
TATTACCAAAGAAGTTAGCCACGAGATCATTAAAGATCGTCGTTTTACCAGCGACAAATTCTTTTTT
CATGTGCCGATTACCCTGAATTATCAGGCAGCAAATAGCCCGAGCAAATTTAACCAGCGTGTTAATG
CATATCTGAAAGAACATCCAGAAACGCCGATTATTGGTATTGATCGTGGTGAACGTAACCTGATTTA
TATCACCGTTATTGATAGCACCGGCAAAATCCTGGAACAGCGTAGCCTGAATACCATTCAGCAGTTT
GATTACCAGAAAAAACTGGATAATCGCGAGAAAGAACGTGTTGCAGCACGTCAGGCATGGTCAGTTG
TTGGTACAATTAAAGACCTGAAACAGGGTTATCTGAGCCAGGTTATTCATGAAATTGTGGATCTGAT
GATTCACTATCAGGCCGTTGTTGTGCTGGAAAACCTGAATTTTGGCTTTAAAAGCAAACGTACCGGC
ATTGCAGAAAAGCAGTTTATCAGCAGTTCGAGAAAATGCTGATTGACAAACTGAATTGCCTGGTGC
TGAAAGATTATCCGGCTGAAAAAGTTGGTGGTGTTCTGAATCCGTATCAGCTGACCGATCAGTTTAC
CAGCTTTGCAAAAATGGGCACCCAGAGCGGATTTCTGTTTTATGTTCCGGCACCGTATACGAGCAAA
ATTGATCCGCTGACCGGTTTTGTTGATCCGTTTGTTTGGAAAACCATCAAAAACCATGAAAGCCGCA
AACATTTTCTGGAAGGTTTCGATTTTCTGCATTACGACGTTAAAACGGGTGATTTCATCCTGCACTT
TAAAATGAATCGCAATCTGAGTTTTCAGCGTGGCCTGCCTGGTTTTATGCCTGCATGGGATATTGTG
TTTGAGAAAAACGAAACACAGTTCGATGCAAAAGGCACCCCGTTTATTGCAGGTAAACGTATTGTTC

-continued

```
CGGTGATTGAAAATCATCGTTTCACCGGTCGTTATCGCGATCTGTATCCGGCAAATGAACTGATCGC

ACTGCTGGAAGAGAAAGGTATTGTTTTTCGTGATGGCTCAAACATTCTGCCGAAACTGCTGGAAAAT

GATGATAGCCATGCAATTGATACCATGGTTGCACTGATTCGTAGCGTTCTGCAGATGCGTAATAGCA

ATGCAGCAACCGGTGAAGATTACATTAATAGTCCGGTTCGTGATCTGAATGGTGTTTGTTTTGATAG

CCGTTTTCAGAATCCGGAATGGCCGATGGATGCAGATGCAAATGGTGCATATCATATTGCACTGAAA

GGACAGCTGCTGCTGAACCACCTGAAAGAAAGCAAAGATCTGAAACTGCAAAACGGCATTAGCAATC

AGGATTGGCTGGCATATATCCAAGAACTGCGTAACGGTCGTAGCAGTGATGATGAAGCAACCGCAGA

TAGCCAGCATGCAGCACCGCCTAAAAAGAAACGTAAAGTTGGTGGTAGCGGTGGTTCAGGTGGTAGT

GGCGGTAGTGGTGGCTCAGGGGGTTCTGGTGGCTCTGGTGGTAGCCTCGAGCACCACCACCACCACC

ACTGA
```

Amino acid sequence for AsCpf1 fusion with OpT NLS and 6x
His used for gene editing in both *E. coli* and human cells

SEQ ID NO: 19

```
MTQFEGFTNLYQVSKTLRFELIPQGKTLKHIQEQGFIEEDKARNDHYKELKPIIDRIYKTYADQCLQ

LVQLDWENLSAAIDSYRKEKTEETRNALIEEQATYRNAIHDYFIGRTDNLTDAINKRHAEIYKGLFK

AELFNGKVLKQLGTVTTTEHENALLRSFDKFTTYFSGFYENRKNVFSAEDISTAIPHRIVQDNFPKF

KENCHIFTRLITAVPSLREHFENVKKAIGIFVSTSIEEVFSFPFYNQLLTQTQIDLYNQLLGGISRE

AGTEKIKGLNEVLNLAIQKNDETAHIIASLPHRFIPLFKQILSDRNTLSFILEEFKSDEEVIQSFCK

YKTLLRNENVLETAEALFNELNSIDLTHIFISHKKLETISSALCDHWDTLRNALYERRISELTGKIT

KSAKEKVQRSLKHEDINLQEIISAAGKELSEAFKQKTSEILSHAHAALDQPLPTTLKKQEEKEILKS

QLDSLLGLYHLLDWFAVDESNEVDPEFSARLTGIKLEMEPSLSFYNKARNYATKKPYSVEKFKLNFQ

MPTLASGWDVNKEKNNGAILFVKNGLYYLGIMPKQKGRYKALSFEPTEKTSEGFDKMYYDYFPDAAK

MIPKCSTQLKAVTAHFQTHTTPILLSNNFIEPLEITKEIYDLNNPEKEPKKFQTAYAKKTGDQKGYR

EALCKWIDFTRDFLSKYTKTTSIDLSSLRPSSQYKDLGEYYAELNPLLYHISFQRIAEKEIMDAVET

GKLYLFQIYNKDFAKGHHGKPNLHTLYWTGLFSPENLAKTSIKLNGQAELFYRPKSRMKRMAHRLGE

KMLNKKLKDQKTPIPDTLYQELYDYVNHRLSHDLSDEARALLPNVITKEVSHEIIKDRRFTSDKFFF

HVPITLNYQAANSPSKFNQRVNAYLKEHPETPIIGIDRGERNLIYITVIDSTGKILEQRSLNTIQQF

DYQKKLDNREKERVAARQAWSVVGTIKDLKQGYLSQVIHEIVDLMIHYQAVVVLENLNFGFKSKRTG

IAEKAVYQQFEKMLIDKLNCLVLKDYPAEKVGGVLNPYQLTDQFTSFAKMGTQSGFLFYVPAPYTSK

IDPLTGFVDPFVWKTIKNHESRKHFLEGFDFLHYDVKTGDFILHFKMNRNLSFQRGLPGFMPAWDIV

FEKNETQFDAKGTPFIAGKRIVPVIENHRFTGRYRDLYPANELIALLEEKGIVFRDGSNILPKLLEN

DDSHAIDTMVALIRSVLQMRSNAATGEDYINSPVRDLNGVCFDSRFQNPEWPMDADANGAYHIALK

GQLLLNHLKESKDLKLQNGISNQDWLAYIQELRNGRSSDDEATADSQHAAPPKKKRKVGGSGGSGGS

GGSGGSGGSGGSGGSLEHHHHHH
```

Hs optimized As Cpf1 with OpT NLS and 6x His-DNA

SEQ ID NO: 21

```
ATGGGCGACCCTCTGAAGAACGTGGGCATCGACAGACTGGACGTGGAAAAGGGCAGAAAGAACATGA

GCAAGCTCGAGAAGTTCACCAACTGCTACAGCCTGAGCAAGACCCTGCGGTTCAAGGCCATTCCTGT

GGGCAAGACCCAAGAGAACATCGACAACAAGCGGCTGCTGGTGGAAGATGAGAAGAGAGCCGAGGAC

TACAAGGGCGTGAAGAAGCTGCTGGACCGGTACTACCTGAGCTTCATCAACGACGTGCTGCACAGCA

TCAAGCTGAAGAACCTGAACAACTACATCAGCCTGTTCCGGAAGAAACCCGGACCGAGAAAGAGAA

CAAAGAGCTGGAAACCTCGAGATCAACCTGCGGAAAGAGATCGCCAAGGCCTTCAAGGGCAACGAG

GGCTACAAGAGCCTGTTCAAGAAGGACATCATCGAGACAATCCTGCCTGAGTTCCTGGACGACAAGG
```

-continued

```
ACGAGATCGCCCTGGTCAACAGCTTCAACGGCTTCACAACCGCCTTCACCGGCTTTTTCGACAACCG

CGAGAATATGTTCAGCGAGGAAGCCAAGAGCACCTCTATCGCCTTCCGGTGCATCAACGAGAATCTG

ACCCGGTACATCAGCAACATGGATATCTTCGAGAAGGTGGACGCCATCTTCGACAAGCACGAGGTGC

AAGAGATCAAAGAAAAGATCCTGAACAGCGACTACGACGTCGAGGACTTCTTCGAGGGCGAGTTCTT

CAACTTCGTGCTGACACAAGAGGGCATCGATGTGTACAACGCCATCATCGGCGGCTTCGTGACAGAG

AGCGGCGAGAAGATCAAGGGCCTGAACGAGTACATCAACCTCTACAACCAGAAAACGAAGCAGAAGC

TGCCCAAGTTCAAGCCCCTGTACAAACAGGTGCTGAGCGACAGAGAGAGCCTGTCCTTTTACGGCGA

GGGCTATACCAGCGACGAAGAGGTGCTGGAAGTGTTCAGAAACACCCTGAACAAGAACAGCGAGATC

TTCAGCTCCATCAAGAAGCTCGAAAAGCTGTTTAAGAACTTCGACGAGTACAGCAGCGCCGGCATCT

TCGTGAAGAATGGCCCTGCCATCAGCACCATCTCCAAGGACATCTTCGGCGAGTGGAACGTGATCCG

GGACAAGTGGAACGCCGAGTACGACGACATCCACCTGAAGAAAAAGGCCGTGGTCACCGAGAAGTAC

GAGGACGACAGAAGAAAGAGCTTCAAGAAGATCGGCAGCTTCAGCCTGGAACAGCTGCAAGAGTACG

CCGACGCCGATCTGAGCGTGGTGGAAAAGCTGAAAGAGATTATCATCCAGAAGGTCGACGAGATCTA

CAAGGTGTACGGCAGCAGCGAGAAGCTGTTCGACGCCGACTTTGTGCTGGAAAAGAGCCTCAAAAAG

AACGACGCCGTGGTGGCCATCATGAAGGACCTGCTGGATAGCGTGAAGTCCTTCGAGAACTATATTA

AGGCCTTCTTTGGCGAGGGCAAAGAGACAAACCGGGACGAGAGCTTCTACGGCGATTTCGTGCTGGC

CTACGACATCCTGCTGAAAGTGGACCACATCTACGACGCCATCCGGAACTACGTGACCCAGAAGCCT

TACAGCAAGGACAAGTTTAAGCTGTACTTCCAGAATCCGCAGTTCATGGGCGGCTGGGACAAAGACA

AAGAAACCGACTACCGGGCCACCATCCTGAGATACGGCTCCAAGTACTATCTGGCCATTATGGACAA

GAAATACGCCAAGTGCCTGCAGAAGATCGATAAGGACGACGTGAACGGCAACTACGAGAAGATTAAC

TACAAGCTGCTGCCCGGACCTAACAAGATGCTGCCTAAGGTGTTCTTTAGCAAGAAATGGATGGCCT

ACTACAACCCCAGCGAGGATATCCAGAAAATCTACAAGAACGGCACCTTCAAGAAAGGCGACATGTT

CAACCTGAACGACTGCCACAAGCTGATCGATTTCTTCAAGGACAGCATCAGCAGATACCCCAAGTGG

TCCAACGCCTACGACTTCAATTTCAGCGAGACAGAGAAGTATAAGGATATCGCCGGGTTCTACCGCG

AGGTGGAAGAACAGGGCTATAAGGTGTCCTTTGAGAGCGCCAGCAAGAAAGAGGTGGACAAGCTGGT

CGAAGAGGGCAAGCTGTACATGTTCCAGATCTATAACAAGGACTTCTCCGACAAGAGCCACGGCACC

CCTAACCTGCACACCATGTACTTTAAGCTGCTGTTCGATGAGAACAACCACGGCCAGATCAGACTGT

CTGGCGGAGCCGAGCTGTTTATGAGAAGGGCCAGCCTGAAAAAAGAGGAACTGGTCGTTCACCCCGC

CAACTCTCCAATCGCCAACAAGAACCCCGACAATCCCAAGAAAACCACCACACTGAGCTACGACGTG

TACAAGGATAAGCGGTTCTCCGAGGACCAGTACGAGCTGCACATCCCTATCGCCATCAACAAGTGCC

CCAAGAATATCTTCAAGATCAACACCGAAGTGCGGGTGCTGCTGAAGCACGACGACAACCCTTACGT

GATCGGCATCGATCGGGGCGAGAGAAACCTGCTGTATATCGTGGTGGTGGACGGCAAGGGCAATATC

GTGGAACAGTACTCCCTGAATGAGATCATCAACAACTTCAATGGCATCCGGATCAAGACGGACTACC

ACAGCCTGCTGGACAAAAAGAGAAAGAACGCTTCGAGGCCCGGCAGAACTGGACCAGCATCGAGAA

CATCAAAGAACTGAAGGCCGGCTACATCTCCCAGGTGGTGCACAAGATCTGCGAGCTGGTTGAGAAG

TATGACGCCGTGATTGCCCTGGAAGATCTGAATAGCGGCTTTAAGAACAGCCGCGTGAAGGTCGAGA

AACAGGTGTACCAGAAATTCGAGAAGATGCTGATCGACAAGCTGAACTACATGGTCGACAAGAAGTC

TAACCCCTGCGCCACAGGCGGAGCCCTGAAGGGATATCAGATCACCAACAAGTTCGAGTCCTTCAAG

AGCATGAGCACCCAGAATGGCTTCATCTTCTACATCCCCGCCTGGCTGACCAGCAAGATCGATCCTA

GCACCGGATTCGTGAACCTGCTCAAGACCAAGTACACCAGCATTGCCGACAGCAAGAAGTTCATCTC
```

-continued
```
CAGCTTCGACCGGATTATGTACGTGCCCGAAGAGGACCTGTTCGAATTCGCCCTGGATTACAAGAAC

TTCAGCCGGACCGATGCCGACTATATCAAGAAGTGGAAGCTGTATAGCTACGGCAACCGCATCCGCA

TCTTCAGAAACCCGAAGAAAAACAACGTGTTCGACTGGGAAGAAGTGTGCCTGACCAGCGCCTACAA

AGAACTCTTCAACAAATACGGCATCAACTACCAGCAGGGCGACATCAGAGCCCTGCTGTGCGAGCAG

AGCGACAAGGCCTTTTACAGCTCCTTCATGGCCCTGATGAGCCTGATGCTGCAGATGCGGAATAGCA

TCACCGGCAGGACCGACGTGGACTTCCTGATCAGCCCTGTGAAGAATTCCGACGGGATCTTCTACGA

CAGCAGAAACTACGAGGCTCAAGAGAACGCCATCCTGCCTAAGAACGCCGATGCCAACGGCGCCTAT

AATATCGCCAGAAAGGTGCTGTGGGCCATCGGCCAGTTTAAGAAGGCCGAGGACGAGAAACTGGACA

AAGTGAAGATCGCCATCTCTAACAAAGAGTGGCTGGAATACGCCCAGACCAGCGTGAAGCACGGCAG

ATCTAGTGACGATGAGGCCACCGCCGATAGCCAGCATGCAGCCCCTCCAAAGAAAAAGCGGAAAGTG

CTGGAACACCACCACCATCACCAC
```

Hs optimized As Cpf1 with OpT NLS and 6x His-AA

SEQ ID NO: 22

```
MTQFEGFTNLYQVSKTLRFELIPQGKTLKHIQEQGFIEEDKARNDHYKELKPIIDRIYKTYADQCLQ

LVQLDWENLSAAIDSYRKEKTEETRNALIEEQATYRNAIHDYFIGRTDNLTDAINKRHAEIYKGLFK

AELFNGKVLKQLGTVTTTEHENALLRSFDKFTTYFSGFYENRKNVFSAEDISTAIPHRIVQDNFPKF

KENCHIFTRLITAVPSLREHFENVKKAIGIFVSTSIEEVFSFPFYNQLLTQTQIDLYNQLLGGISRE

AGTEKIKGLNEVLNLAIQKNDETAHIIASLPHRFIPLFKQILSDRNTLSFILEEFKSDEEVIQSFCK

YKTLLRNENVLETAEALFNELNSIDLTHIFISHKKLETISSALCDHWDTLRNALYERRISELTGKIT

KSAKEKVQRSLKHEDINLQEIISAAGKELSEAFKQKTSEILSHAHAALDQPLPTTLKKQEEKEILKS

QLDSLLGLYHLLDWFAVDESNEVDPEFSARLTGIKLEMEPSLSFYNKARNYATKKPYSVEKFKLNFQ

MPTLASGWDVNKEKNNGAILFVKNGLYYLGIMPKQKGRYKALSFEPTEKTSEGFDKMYYDYFPDAAK

MIPKCSTQLKAVTAHFQTHTTPILLSNNFIEPLEITKEIYDLNNPEKEPKKFQTAYAKKTGDQKGYR

EALCKWIDFTRDFLSKYTKTTSIDLSSLRPSSQYKDLGEYYAELNPLLYHISFQRIAEKEIMDAVET

GKLYLFQIYNKDFAKGHHGKPNLHTLYWTGLFSPENLAKTSIKLNGQAELFYRPKSRMKRMAHRLGE

KMLNKKLKDQKTPIPDTLYQELYDYVNHRLSHDLSDEARALLPNVITKEVSHEIIKDRRFTSDKFFF

HVPITLNYQAANSPSKFNQRVNAYLKEHPETPIIGIDRGERNLIYITVIDSTGKILEQRSLNTIQQF

DYQKKLDNREKERVAARQAWSVVGTIKDLKQGYLSQVIHEIVDLMIHYQAVVVLENLNFGFKSKRTG

IAEKAVYQQFEKMLIDKLNCLVLKDYPAEKVGGVLNPYQLTDQFTSFAKMGTQSGFLFYVPAPYTSK

IDPLTGFVDPFVWKTIKNHESRKHFLEGFDFLHYDVKTGDFILHFKMNRNLSFQRGLPGFMPAWDIV

FEKNETQFDAKGTPFIAGKRIVPVIENHRFTGRYRDLYPANELIALLEEKGIVFRDGSNILPKLLEN

DDSHAIDTMVALIRSVLQMRNSNAATGEDYINSPVRDLNGVCFDSRFQNPEWPMDADANGAYHIALK

GQLLLNHLKESKDLKLQNGISNQDWLAYIQELRNGRSSDDEATADSQHAAPPKKKRKVGGSGGSGGS

GGSGGSGGSGGSGGSLEHHHHHH
```

Example 2

Preparation of Isolated Vectors Expressing Nucleic Acid Encoding Human Codon-Optimized AsCpf1 Polypeptide Fusion Protein and Human Cell Lines Stably Expressing the as Cpf1 Polypeptide Fusion Protein.

Figure 2:
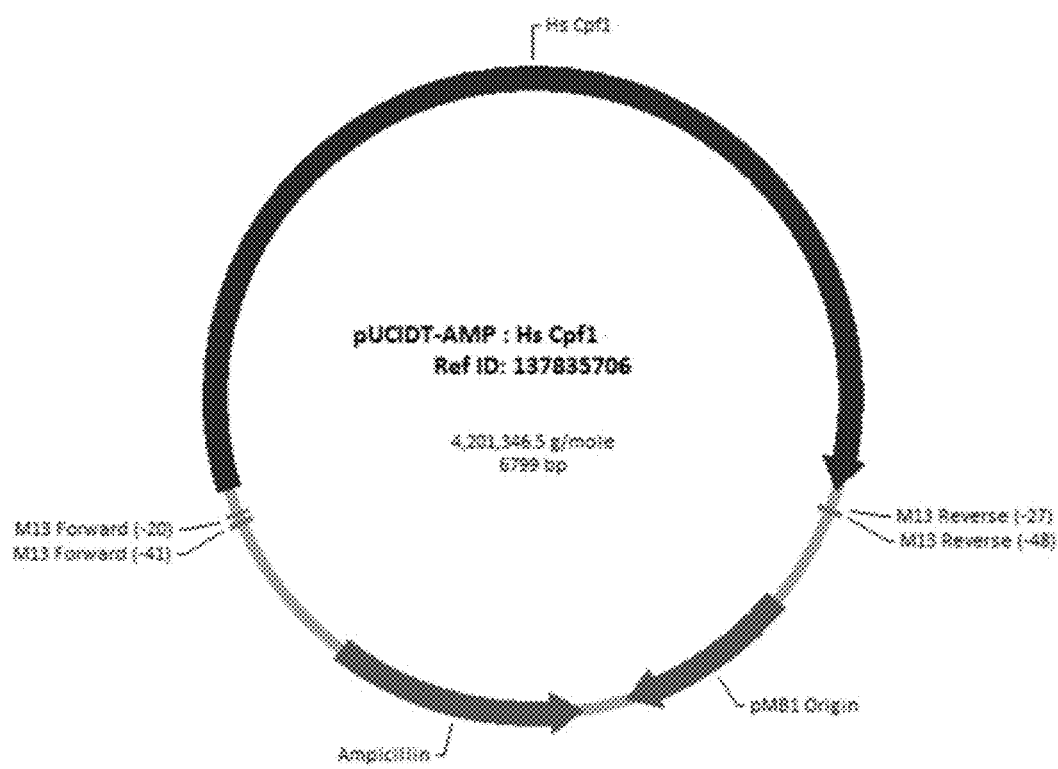
FIG. 2 depicts the map of a plasmid vector designed to express recombinant, synthetic, codon-optimized AsCpf1.
Figure 3:
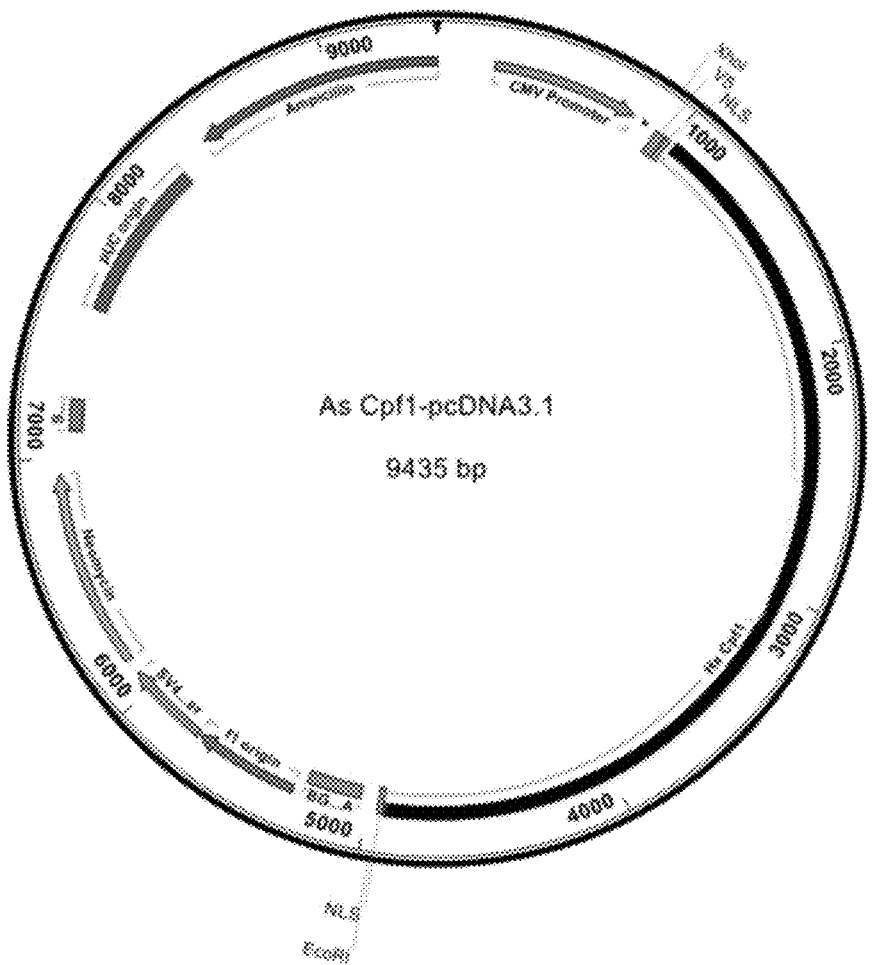
FIG. 3 depicts a schematic showing the final plasmid construct used to generate AsCpf1 stable cell lines.

The reference amino acid for AsCpf1 has been published. See Zetsche, B., Gootenberg, J. S., Abudayyeh, O. O., Slaymaker, I. M., Makarova, K. S., Essletzbichler, P., Volz, S. E., Joung, J., van der Oost, J., Regev, A., Koonin, E. V., and Zhang, F. (2015) Cpf1 is a single RNA-guided endonuclease of a class 2 CRISPR-Cas system. Cell 163:1-13. A plasmid encoding human codon optimized AsCpf1, flanking nuclear localization signals (NLS) and 5'-V5 epitope tag, was generated by the Synthetic Biology department at Integrated DNA Technologies. Flanking the expression cassette was a 5' XhoI and 3' EcoRI restriction enzyme sites (FIG. 2). The Cpf1 plasmid was digested with XhoI and EcoRI (NEB), gel purified using a column based purification system (Qiagen) and ligated using T4 DNA Ligase (NEB) into a predigested mammalian expression vector, pcDNA3.1-, from Life Technologies (FIG. 3). The resulting ligated construct was transformed into DH5a chemically competent E. coli cells. The resulting colonies were grown in LB media at 37° C. overnight and subjected to DNA isolation using a Promega miniprep plasmid DNA kit. Flanking primers (T7 forward and BGH reverse) as well as 10 internal Cpf1 specific primers were used for sequence verification of correct insertion using automated Sanger sequencing with BigDye Terminator reagents (ABI). The nucleic acid sequence of the Cpf1 clone employed herein is shown in SEQ ID NO:15. The amino acid sequence of the expressed recombinant protein is shown in SEQ ID NO:16.

The AsCpf1-pcDNA3.1 vector was linearized with PvuI (NEB), which is located within the ampicillin resistance gene, and transfected into HEK293 cells. Transfection employed 500,000 HEK293 cells plated in 100 mm dishes 24 hours prior to transfection. Using the transfection reagent TransIT-X2 (Minis), the linearized vector containing AsCpf1 and a neomycin-resistance gene was complexed and transfected into adherent cells. The transfection media was removed after 24 hrs and the cells were cultured in complete media for 48 hours. Using methods previously optimized for generation of stable transgenic HEK293 cells containing a stably integrated pcDNA3.1(-) vector neomycin resistance, we cultured transfected cells in the presence of the antibiotic Geneticin (G418; Gibco), which is a neomycin analog, in the complete media to select for cells that had been transfected with AsCpf1-pcDNA3.1(-) and would thus be resistant to this antibiotic. Initial G418 dosing was at 800 ug/ml with periodic media changes until the surviving cells began to recover and grow over a 10-day period. The parent HEK293 cell line was confirmed to be sensitive to the minimum dose of G418. The resulting polyclonal AsCpf1-pcDNA3.1(-) cell line, which showed G418 resistance, was split using limited dilutions. The cells were trypsinized, resuspended in complete media, counted to determine concentration and diluted in 96-well plates to a concentration of theoretically less than one cell per well.

Figure 4:
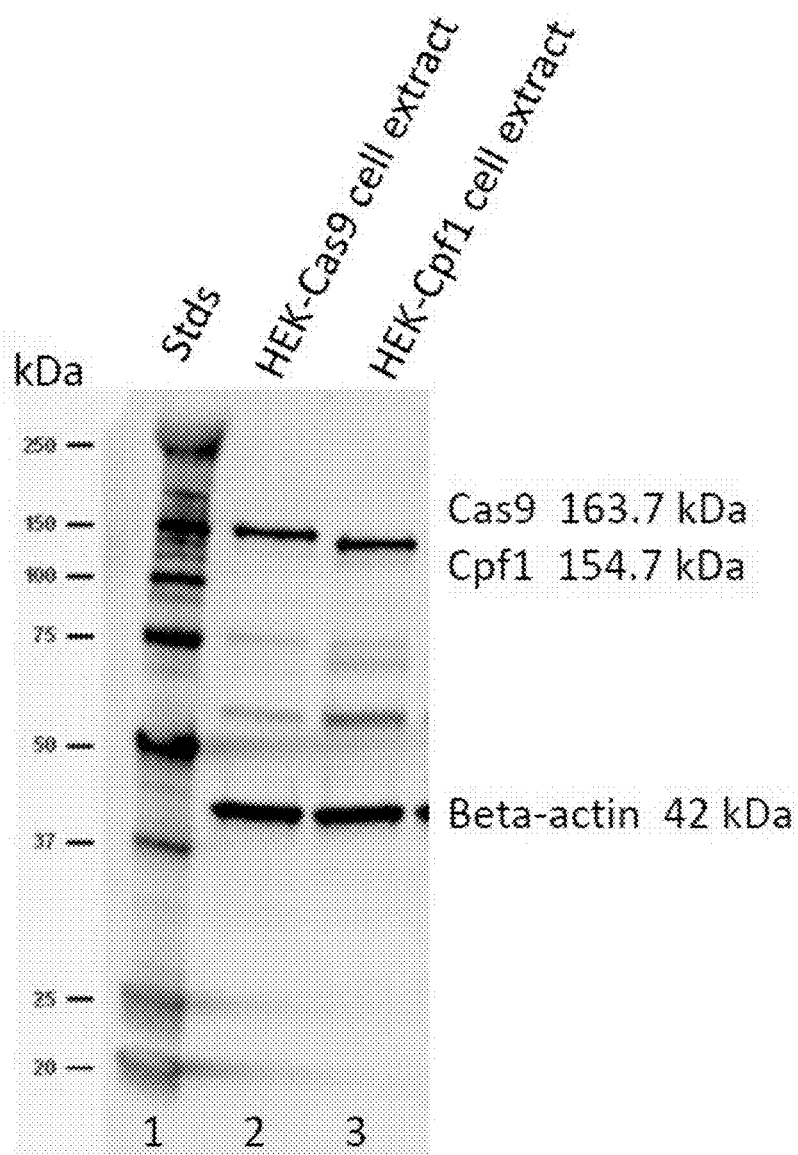
FIG. 4 depicts an exemplary Western blot showing expression of V5-tagged proteins. Cell extract from a monoclonal HEK cell line that stably expresses Cas9 with a V5 tag was run in Lane 2. Cell extract from the new polyclonal HEK cell culture that expresses a V5-tagged AsCpf1 was run in Lane 3. Beta-actin is indicated and represents a mass loading control. Lane 1 was run with mass standard markers.

At this time, aliquots of the cells were taken and lysed with a protein lysis buffer (RIPA) to determine, via western blot, if AsCpf1 was expressed. Cellular protein was quantitated using the Bio-Rad Protein Assay (Bio-Rad) and 15 ug total protein was loaded onto an SDS-PAGE Stainfree 4-20% gradient gel (Bio-Rad). As a positive control, protein from a previous cell line, SpyCas9-pcDNA3.1(-), was run in parallel for size and expression comparisons. The gel was run for 45 minutes at 180 volts and transferred to a PVDF membrane with the Bio-Rad TransBlot for 7 minutes. The blot was then blocked in SuperBlock T20 Blocking Buffer (Thermo), followed by a 1:1000 dilution of V5 primary antibody (Abcam) and 1:5000 β-actin primary antibody (Abcam) for 1 hour at room temperature. Next, the blot was washed 3 times for 15 minutes each in tris-buffered saline with Tween-20 (TBST). Goat anti-mouse HRP secondary antibody was used at a 1:3000 dilution along with the ladder specific StrepTactin secondary antibody and incubated at room temperature for 1 hour at room temperature. The blot was then washed 3 times for 15 minutes in TB ST. Luminescence detection was done using the Pierce West-Femto ECL (Thermo) substrate and results are shown in FIG. 4, which confirm expression of a recombinant protein of the expected size.

Cells were continuously grown under selection in G418-containing media, and individual cells (monoclonal colonies) were allowed to expand. Viable colonies were characterized for the presence of AsCpf1 by RT-qPCR, Western blotting and functional testing of crRNA guided dsDNA cleavage. Four RT-qPCR assays were designed to detect different locations within the large AsCpf1 mRNA. Sequences are shown in Table 1 below.

TABLE 1

RT-qPCR assays in AsCpf1

| Assay# | Location | Primers and Probe | SEQ ID NO |
|---|---|---|---|
| 1 | 34-153 | F34 GTGTCCAAGACCCTGAGATTC | 25 |
|  |  | R153 GGGCTTCAGCTCTTTGTAGT | 26 |
|  |  | P68 FAM-AGGGCAAG (ZEN) ACACTGAAGCACATCC-IBFQ | 27 |
| 2 | 1548-1656 | F1548 CAGAAACTACGCCACCAAGA | 28 |
|  |  | R1656 GCCGTTGTTCTTCTCTTTGTTC | 29 |
|  |  | P1590 HEX-TAAGCTGAA (ZEN) CTTCCAGATGCCCACC-IBFQ | 30 |
| 3 | 2935-3037 | F2935 GTGGACCTGATGATCCACTATC | 31 |
|  |  | R3037 GCTGGTACACGGCTTTCT | 32 |
|  |  | P2978 FAM-ACCTGAACT (ZEN) TCGGCTTCAAGAGCA-IBFQ | 33 |
| 4 | 3827-3918 | F3827 TGCTGAACCATCTGAAAGAGAG | 34 |
|  |  | R3918 GTTCCGCAGTTCCTGGATATAG | 35 |
|  |  | P3889 HEX-AGTCCTGGT (ZEN) TGGAGATGCCGTTC-IBFQ | 36 |

DNA bases are shown 5'-3' orientation.
Location is specified within the AsCpf1 gene construct employed herein.
FAM - 6 carboxyfluorescein,
HEX = hexachlorofluorescein,
IBFQ = Iowa Black dark quencher, and
ZEN = internal ZEN dark quencher.

Figure 5:
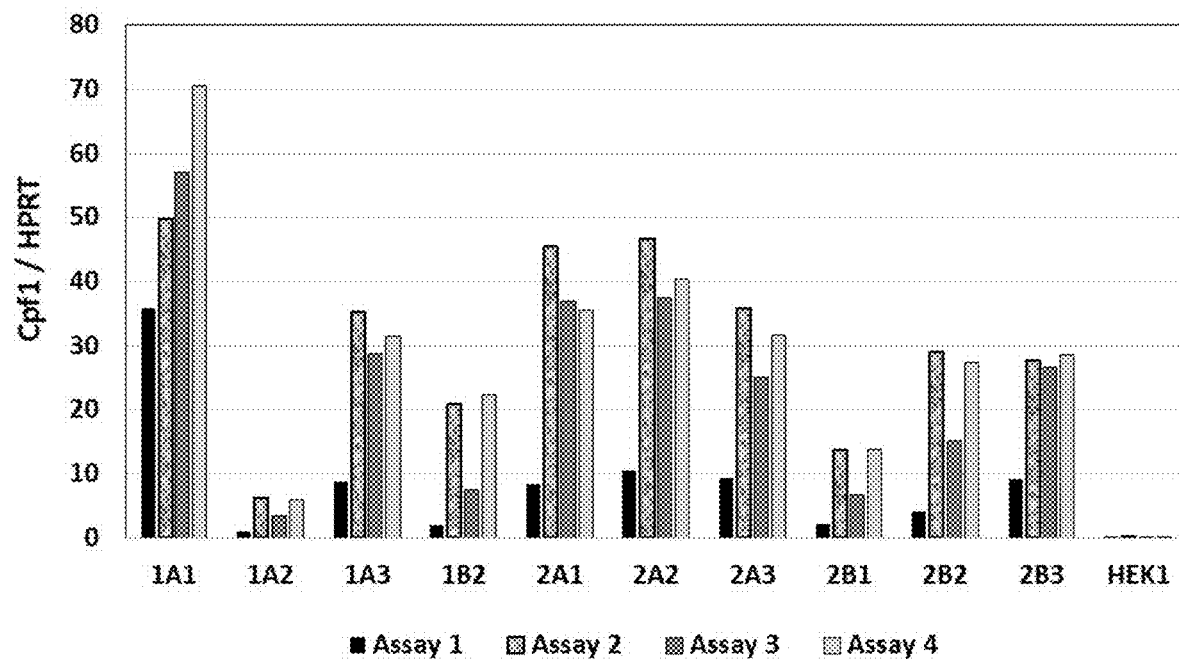
FIG. 5 depicts exemplary expression profiles of AsCpf1 mRNA normalized to internal control HPRT1 mRNA in 10 clonal transgenic cell lines. RT-qPCR assay locations vary in position along the AsCpf1 mRNA. Negative control non-transgenic HEK1 cells are shown on the far right.

Monoclonal cell lines resistant to G418 were plated in 6-well plates and cultured for 24 hrs. Cells were lysed with GITC-containing buffer and RNA was isolated using the Wizard 96-well RNA isolation binding plates (Promega) on a Corbett liquid handling robot. Liquid handling robotics (Perkin Elmer) were used to synthesize complementary DNA (cDNA) using SuperScriptII (Invitrogen) and set-up qPCR assays using Immolase (Bioline) along with 500 nmol primers and 250 nmol probes (IDT). qPCR plates were run on the AB7900-HT and analyzed using the associated software (Applied Biosystems). FIG. 5 shows the relative level of AsCpf1 mRNA expression normalized to HPRT1 expression for a series of clonal lines. Not surprisingly, different clones showed different levels of AsCpf1 mRNA expression.

Figure 6:
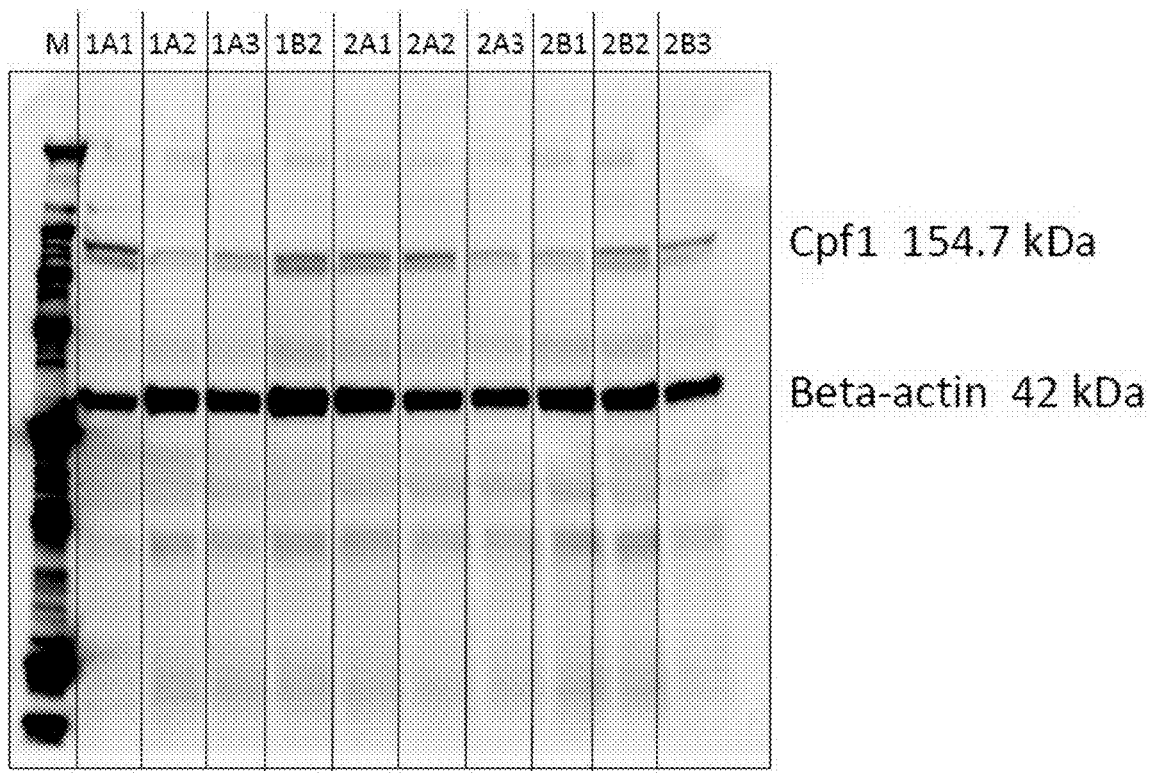
FIG. 6 depicts exemplary Western blot showing relative expression levels of AsCpf1 protein in 10 monoclonal transgenic cell lines based on detection of the V5 epitope. Beta-actin loading control is seen below the AsCpf1 bands.

Total protein was isolated from the same AsCpf1-expressing monoclonal cells lines in cultures grown in parallel. Cells were lysed in RIPA buffer in the presence of a proteinase inhibitor. Protein concentration in each lysate was determined by BCA assay (Pierce). Fifteen micrograms of total protein from each sample was loaded onto an SDS-PAGE stainfree 4-20% gradient gel (Bio-Rad) and run at 180V for 45 minutes in 1× Tris/Glycine running buffer alongside the broad-range molecular weight marker (Bio-Rad). Protein was transferred to a PDVF membrane using Bio-Rad TransBlot transfer unit for 7 minutes. The blot was blocked in SuperBlock T20 Blocking Buffer (Thermo), followed by incubation with a 1:1000 dilution of V5 primary antibody (Abcam) and 1:5000 (3-actin primary antibody (Abcam) for 1 hour at room temperature. The blot was washed 3 times for 15 minutes each in tris-buffered saline with Tween-20 (TBST). Goat anti-mouse HRP secondary antibody was used at a 1:3000 dilution along with the ladder specific StrepTactin secondary antibody and incubated at room temperature for 1 hour at room temperature. The blot was then washed 3 times for 15 minutes in TB ST. Luminescence detection was done using the Pierce West-Femto ECL (Thermo) substrate. FIG. 6 shows detection of V5-tagged AsCpf1 recombinant protein expression levels in 10 monoclonal cell lines. There is good concordance between observed protein levels seen in FIG. 6 and the corresponding mRNA levels from the same cell lines shown in FIG. 5.

Three monoclonal AsCpf1 stable cell lines (1A1, 2A2 and 2B1) were expanded and tested for the ability to support AsCpf1-directed genome editing. Based on AsCpf1 mRNA and protein levels previously determined, 1A1 is a "high" expressing line, 2A2 is a "medium" expressing line, and 2B1 is a "low" expressing line. The cell lines were transfected with 6 different crRNAs targeting different sites within an exon of the human HRPT1 gene, shown below in Table 2. The crRNAs comprise a universal 20 base Cpf1-binding domain at the 5'-end and a 24 base target-specific protospacer domain at the 3'-end.

TABLE 2

AsCpf1 crRNAs targeting human HPRT1

| Site | Sequence | SEQ ID NO: |
|---|---|---|
| 38171_AS | uaauuucuacucuuguagauuaaacacuguuucauuucauccgu | 37 |
| 38254_AS | uaauuucuacucuuguagauaccagcaagcuguuaauuacaaaa | 38 |
| 38325_S | uaauuucuacucuuguagauaccaucuuuaaccuaaaagaguuu | 39 |
| 38337_AS | uaauuucuacucuuguagaugguuaaagaugguuaaaugauuga | 40 |
| 38351_S | uaauuucuacucuuguagauugugaaauggcuuauaauugcuua | 41 |
| 38538_S | uaauuucuacucuuguagauaauguaaguaauugcuucuuuuuc | 42 |

RNA bases are shown 5'-3' orientation, RNA bases are shown in lower case.
Locations are specified within the human HPRT1 gene with orientation relative to the sense coding strand indicated (S = sense, AS = antisense).

(Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID NO:394); HPRT-low reverse primer: ACACATC-CATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. The cleavage efficiencies seen in the 3 cell lines are shown in Table 3 below.

TABLE 3

Gene targeting efficiency of 6 HPRT1 crRNAs in 3 HEK-Cpf1 cell lines

| | % Cleavage in T7EI assays | | |
|---|---|---|---|
| Site | 1A1 | 2A2 | 2B1 |
| 38171_AS | 19 | 19.1 | 8.3 |
| 38254_AS | 41 | 42.4 | 30.3 |
| 38325_S | 27.8 | 26.5 | 14.8 |
| 38337_AS | 65.3 | 73.7 | 71.6 |
| 38351_S | 73.3 | 78.6 | 73.4 |
| 38538_S | 44.6 | 47.9 | 32.8 |

Locations of the crRNAs are specified within the human HPRT1 gene with orientation relative to the sense coding strand indicated (S = sense, AS = antisense). % Cleavage demonstrates alteration in the sequence of the cell line after Cpf1-mediated genome editing at the HPRT1 locus relative to wild-type.

As expected, the different crRNAs targeting different sites in HPRT1 showed different levels of gene editing activity. In In a reverse transfection format, anti-HPRT1 crRNAs were individually mixed with Lipofectamine RNAiMAX (Life Technologies) and transfected into each of the 3 HEK-Cpf1 cell lines. Transfections were done with 40,000 cells per well in 96 well plate format. RNAs were introduced at a final concentration of 30 nM in 0.75 μl of the lipid reagent. Cells were incubated at 37° C. for 48 hours. Genomic DNA was isolated using QuickExtract solution cell line 1A1 this ranged from 18% to 73%. The "high" and "medium" Cpf1-expressing clones 1A1 and 2A2 showed nearly identical gene editing activity, indicating that both clones expressed Cpf1 at sufficient levels to reach maximal gene editing activity at each site. Clone 2B1, the "low" expressing clone, showed reduced editing activity. Clones 1A1 and 2A2 are therefore both suitable for Cpf1 crRNA optimization and site screening.

Example 3 crRNA Length Optimization: Testing Truncation of the 5'-20-Base Universal Loop Domain.

A set of 6 sites in the human HPRT1 gene were chosen to study length optimization of AsCpf1 crRNAs. A series of crRNAs were synthesized all having a 3'-24 base target-specific protospacer domain and having 5'-loop domains of 20, 19, 18, and 17 bases, representing a set of serial 1-base deletions from the 5'-end. A second set of crRNAs were synthesized at the same sites all having a 3'-21 base target-specific protospacer domain, likewise with 5'-loop domains of 20, 19, 18, and 17 bases.

An HEK cell line that stably expresses the AsCpf1 endonuclease was employed in these studies (Example 2). In a reverse transfection format, anti-HPRT1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 µl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGT-GATGCT (SEQ ID NO:394); HPRT-low reverse primer: ACACATCCATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)× 100. Results are shown in Table 4 below and demonstrate that 5'-universal loop domains of 20 and 19 base lengths work well but a significant loss of activity is seen when 18 or 17 base loops domains are employed. The observations are nearly identical whether a 24 base or 21 base protospacer domain is employed.

TABLE 4

Effect of truncation in the 5'-loop domain with 24 or 21 base 3'-protospacer domains

| Seq Name | Sequence 5'-3' | % Cleavage T7E1 Assay | SEQ ID NO: |
|---|---|---|---|
| 38171_AS 20-24 | uaauuucuacucuuguagauuaaacacuguuucauuucauccgu | 12% | 37 |
| 38171-AS 19-24 | aauuucuacucuuguagauuaaacacuguuucauuucauccgu | 15% | 43 |
| 38171-AS 18-24 | auuucuacucuuguagauuaaacacuguuucauuucauccgu | 4% | 44 |
| 38171-AS 17-24 | uuucuacucuuguagauuaaacacuguuucauuucauccgu | 1% | 45 |
| 38254_AS 20-24 | uaauuucuacucuuguagauaccagcaagcuguuaauuacaaaa | 15% | 38 |
| 38254-AS 19-24 | aauuucuacucuuguagauaccagcaagcuguuaauuacaaaa | 36% | 46 |
| 38254-AS 18-24 | auuucuacucuuguagauaccagcaagcuguuaauuacaaaa | 23% | 47 |
| 38254-AS 17-24 | uuucuacucuuguagauaccagcaagcuguuaauuacaaaa | 0% | 48 |
| 38325_S 20-24 | uaauuucuacucuuguagauaccaucuuuaaccuaaaagaguuu | 9% | 39 |
| 38325-S 19-24 | aauuucuacucuuguagauaccaucuuuaaccuaaaagaguuu | 37% | 49 |
| 38325-S 18-24 | auuucuacucuuguagauaccaucuuuaaccuaaaagaguuu | 27% | 50 |
| 38325-S 17-24 | uuucuacucuuguagauaccaucuuuaaccuaaaagaguuu | 0% | 51 |
| 38337_AS 20-24 | uaauuucuacucuuguagaugguuaaagaugguuaaaugauuga | 63% | 40 |
| 38337-AS 19-24 | aauuucuacucuuguagaugguuaaagaugguuaaaugauuga | 65% | 52 |
| 38337-AS 18-24 | auuucuacucuuguagaugguuaaagaugguuaaaugauuga | 46% | 53 |
| 38337-AS 17-24 | uuucuacucuuguagaugguuaaagaugguuaaaugauuga | 4% | 54 |
| 38351_S 20-24 | uaauuucuacucuuguagauugugaaauggcuuauaauugcuua | 57% | 41 |
| 38351-S 19-24 | aauuucuacucuuguagauugugaaauggcuuauaauugcuua | 76% | 55 |
| 38351-S 18-24 | auuucuacucuuguagauugugaaauggcuuauaauugcuua | 6% | 56 |
| 38351-S 17-24 | uuucuacucuuguagauugugaaauggcuuauaauugcuua | 0% | 57 |
| 38538_S 20-24 | uaauuucuacucuuguagauaauguaaguaauugcuucuuuuuc | 16% | 42 |
| 38538-S 19-24 | aauuucuacucuuguagauaauguaaguaauugcuucuuuuuc | 34% | 58 |
| 38538-S 18-24 | auuucuacucuuguagauaauguaaguaauugcuucuuuuuc | 2% | 59 |
| 38538-S 17-24 | uuucuacucuuguagauaauguaaguaauugcuucuuuuuc | 1% | 60 |
| 38171-AS 20-21 | uaauuucuacucuuguagauuaaacacuguuucauuucauc | 32% | 61 |
| 38171-AS 19-21 | aauuucuacucuuguagauuaaacacuguuucauuucauc | 44% | 62 |
| 38171-AS 18-21 | auuucuacucuuguagauuaaacacuguuucauuucauc | 16% | 63 |
| 38171-AS 17-21 | uuucuacucuuguagauuaaacacuguuucauuucauc | 1% | 64 |
| 38254-AS 20-21 | uaauuucuacucuuguagauaccagcaagcuguuaauuaca | 45% | 65 |
| 38254-AS 19-21 | aauuucuacucuuguagauaccagcaagcuguuaauuaca | 28% | 66 |
| 38254-AS 18-21 | auuucuacucuuguagauaccagcaagcuguuaauuaca | 50% | 67 |
| 38254-AS 17-21 | uuucuacucuuguagauaccagcaagcuguuaauuaca | 0% | 68 |
| 38325-S 20-21 | uaauuucuacucuuguagauaccaucuuuaaccuaaaagag | 50% | 69 |
| 38325-S 19-21 | aauuucuacucuuguagauaccaucuuuaaccuaaaagag | 49% | 70 |
| 38325-S 18-21 | auuucuacucuuguagauaccaucuuuaaccuaaaagag | 36% | 71 |
| 38325-S 17-21 | uuucuacucuuguagauaccaucuuuaaccuaaaagag | 0% | 72 |

TABLE 4-continued

Effect of truncation in the 5'-loop domain with 24 or 21 base 3'-protospacer domains

| Seq Name | Sequence 5'-3' | % Cleavage T7E1 Assay | SEQ ID NO: |
|---|---|---|---|
| 38337-AS 20-21 | uaauuucuacucuuguagaugguuaaagaugguuaaaugau | 72% | 73 |
| 38337-AS 19-21 | aauuucuacucuuguagaugguuaaagaugguuaaaugau | 73% | 74 |
| 38337-AS 18-21 | auuucuacucuuguagaugguuaaagaugguuaaaugau | 62% | 75 |
| 38337-AS 17-21 | uuucuacucuuguagaugguuaaagaugguuaaaugau | 12% | 76 |
| | | | |
| 38351-S 20-21 | uaauuucuacucuuguagauugugaaauggcuuauaauugc | 81% | 77 |
| 38351-S 19-21 | aauuucuacucuuguagauugugaaauggcuuauaauugc | 81% | 78 |
| 38351-S 18-21 | auuucuacucuuguagauugugaaauggcuuauaauugc | 20% | 79 |
| 38351-S 17-21 | uuucuacucuuguagauugugaaauggcuuauaauugc | 0% | 80 |
| | | | |
| 38538-S 20-21 | uaauuucuacucuuguagauaauguaaguaauugcuucuuu | 65% | 81 |
| 38538-S 19-21 | aauuucuacucuuguagauaauguaaguaauugcuucuuu | 41% | 82 |
| 38538-S 18-21 | auuucuacucuuguagauaauguaaguaauugcuucuuu | 11% | 83 |
| 38538-S 17-21 | uuucuacucuuguagauaauguaaguaauugcuucuuu | 1% | 84 |

RNA bases are shown in lower case. Locations are specified within the human HPRT1 gene with orientation relative to the sense coding strand indicated (S = sense, AS = antisense). Sequence names include length of the 5'-universal loop domain (17-20 bases) and the 3'-target specific protospacer domain (24 or 21 bases).

Example 4 crRNA Length Optimization: Testing Truncation of the 3'-24-Base Target Specific Protospacer Domain.

The same set of 6 sites in the human HPRT1 gene was used to study the effects of truncation in the 3'-protospacer (target specific) domain. A series of AsCpf1 crRNAs were synthesized all having the same 5'-20 base universal loop domain. These were paired with 3'-target specific protospacer domains of 21, 19, 18, or 17 bases, having serial deletions from the 3'-end.

An HEK cell line that stably expresses the AsCpf1 endonuclease was employed in these studies (Example 2). In a reverse transfection format, anti-HPRT1 AsCpf1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 µl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGA-TAAAAGGTGATGCT (SEQ ID NO:394); HPRT-low reverse primer: ACACATCCATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. Results are shown in Table 5 below and demonstrate that a 3'-protospacer (target specific) domain of 21 base lengths work well but loss of activity is observed in a sequence/site dependent fashion as this domain is shortened. Some highly active sites (such as 38351) maintain appreciate activity even when truncated to 17 bases, however to maintain the highest likelihood of functionality at all sites a protospacer of 21 bases is recommended. Therefore, a prudent minimal length AsCpf1 crRNA is 41 bases, comprising a 20-base 5'-universal loop domain and a 21-base 3'-protospacer target-specific domain.

TABLE 5

Effect of truncation in the 3'-protospacer domain with a 20 base 5'-loop domain

| Seq Name | Sequence 5'-3' | % Cleavage T7E1 Assay | SEQ ID NO: |
|---|---|---|---|
| 38171-AS 20-21 | uaauuucuacucuuguagauuaaacacuguuucauuucauc | 59% | 61 |
| 38171-AS 20-19 | uaauuucuacucuuguagauuaaacacuguuucauuuca | 13% | 85 |
| 38171-AS 20-18 | uaauuucuacucuuguagauuaaacacuguuucauuuc | 2% | 86 |
| 38171-AS 20-17 | uaauuucuacucuuguagauuaaacacuguuucauuu | 3% | 87 |
| | | | |
| 38254-AS 20-21 | uaauuucuacucuuguagauaccagcaagcuguuaauuaca | 61% | 65 |
| 38254-AS 20-19 | uaauuucuacucuuguagauaccagcaagcuguuaauua | 5% | 88 |
| 38254-AS 20-18 | uaauuucuacucuuguagauaccagcaagcuguuaauu | 0% | 89 |
| 38254-AS 20-17 | uaauuucuacucuuguagauaccagcaagcuguuaau | 0% | 90 |
| | | | |
| 38325-S 20-21 | uaauuucuacucuuguagauaccaucuuuaaccuaaaagag | 70% | 69 |
| 38325-S 20-19 | uaauuucuacucuuguagauaccaucuuuaaccuaaaag | 34% | 91 |
| 38325-S 20-18 | uaauuucuacucuuguagauaccaucuuuaaccuaaaa | 0% | 92 |
| 38325-S 20-17 | uaauuucuacucuuguagauaccaucuuuaaccuaaa | 0% | 93 |

TABLE 5-continued

Effect of truncation in the 3'-protospacer domain with a 20 base 5'-loop domain

| Seq Name | Sequence 5'-3' | % Cleavage T7E1 Assay | SEQ ID NO: |
|---|---|---|---|
| 38337-AS 20-21 | uaauuucuacucuuguagaugguuaaagaugguuaaaugau | 80% | 73 |
| 38337-AS 20-19 | uaauuucuacucuuguagaugguuaaagaugguuaaaug | 78% | 94 |
| 38337-AS 20-18 | uaauuucuacucuuguagaugguuaaagaugguuaaau | 3% | 95 |
| 38337-AS 20-17 | uaauuucuacucuuguagaugguuaaagaugguuaaa | 0% | 96 |
| 38351-S 20-21 | uaauuucuacucuuguagauugugaaauggcuuauaauugc | 85% | 77 |
| 38351-S 20-19 | uaauuucuacucuuguagauugugaaauggcuuauaauu | 87% | 97 |
| 38351-S 20-18 | uaauuucuacucuuguagauugugaaauggcuuauaau | 85% | 98 |
| 38351-S 20-17 | uaauuucuacucuuguagauugugaaauggcuuauaa | 67% | 99 |
| 38538-S 20-21 | uaauuucuacucuuguagauaauguaaguaauugcuucuuu | 75% | 81 |
| 38538-S 20-19 | uaauuucuacucuuguagauaauguaaguaauugcuucu | 55% | 100 |
| 38538-S 20-18 | uaauuucuacucuuguagauaauguaaguaauugcuuc | 11% | 101 |
| 38538-S 20-17 | uaauuucuacucuuguagauaauguaaguaauugcuu | 0% | 102 |

RNA bases are shown in lower case. Locations are specified within the human HPRT1 gene with orientation relative to the sense-coding strand indicated (S = sense, AS = antisense). Sequence names include length of the 5'-universal loop domain (20 bases) and the 3'-protospacer target-specific domain (21, 19, 18, or 17 bases).

Example 5

A Single-Base 2'OMe Modification Walk Through Two AsCpf1 crRNAs.

Two sites in the human HPRT1 gene were chosen (38351 and 38595) to study the effects of replacement of a single RNA residue with a 2'OMe-RNA residue at every possible position within AsCpf1 crRNAs. Given the possibility of sequence-specific tolerance to modification, it was necessary to perform this screening at two sites. A series of crRNAs were synthesized having a single 2'OMe residue at every possible position in single-base steps. The crRNAs were either 44 base or 41 base lengths. All had a 5'-end 20 base universal loop domain followed by a 3'-end 21 or 24 base protospacer target-specific domain.

An HEK cell line that stably expresses the AsCpf1 endonuclease was employed in these studies (HEK-Cpf1) (Example 2). In a reverse transfection format, anti-HPRT1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 µl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID NO:394); HPRT-low reverse primer: ACACATC-CATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. Results for HPRT1 site 38351 are shown in Table 6 below and for HRPT1 site 38595 in Table 7 below. The results demonstrate the locations of sites that reduce activity or totally kill activity of Cpf1 to cleave dsDNA when the 2'OMe modified replaced an RNA residue. The results are nearly identical whether a 24 base or 21 base protospacer domain is employed.

Sites where substitution of a 2'OMe RNA residue for an RNA residue showed loss of activity in the genome editing assay were mapped to location within the 5'-universal loop domain or the 3'-target specific protospacer domain. Results are summarized in FIG. 7. Modification of residues A2, A3, U4, U11, G15, and U20 within the universal loop domain leads to loss of activity; the same sites were identified for all 4 crRNA classes studied (Site 38351 44mer, Site 38351 41mer, Site 38595 44mer, and Site 38595 41mer). In contrast, the precise pattern of modification effects varied for sites within the protospacer domain, which is expected as it is common for modification tolerance to vary with sequence context and the protospacer domain has a different sequence for every target site. For the sequences studied, positions 5, 6, 13, 16, and 18 showed loss of activity with modification for all 4 crRNA classes and therefore are identified positions to avoid the 2'OMe RNA chemical modification.

TABLE 6

Single-base 2'OMe modification walk through HPRT1 Site 38351 AsCpf1 crRNAs

| Seq Name | Sequence 5'-3' | % Cleavage T7E1 Assay | SEQ ID NO: |
|---|---|---|---|
| 38351-44 unmod | uaauuucuacucuuguagauugugaaauggcuuauaauugcuua | 77% | 103 |
| 38351-44-L1 | uaauuucuacucuuguagauugugaaauggcuuauaauugcuua | 83% | 104 |
| 38351-44-L2 | uaauuucuacucuuguagauugugaaauggcuuauaauugcuua | 32% | 105 |
| 38351-44-L3 | uaauuucuacucuuguagauugugaaauggcuuauaauugcuua | 4% | 106 |
| 38351-44-L4 | uaauuucuacucuuguagauugugaaauggcuuauaauugcuua | 2% | 107 |
| 38351-44-L5 | uaauuucuacucuuguagauugugaaauggcuuauaauugcuua | 88% | 108 |
| 38351-44-L6 | uaauuucuacucuuguagauugugaaauggcuuauaauugcuua | 87% | 109 |
| 38351-44-L7 | uaauuucuacucuuguagauugugaaauggcuuauaauugcuua | 85% | 110 |
| 38351-44-L8 | uaauuucuacucuuguagauugugaaauggcuuauaauugcuua | 76% | 111 |
| 38351-44-L9 | uaauuucuacucuuguagauugugaaauggcuuauaauugcuua | 89% | 112 |
| 38351-44-L10 | uaauuucuacucuuguagauugugaaauggcuuauaauugcuua | 85% | 113 |
| 38351-44-L11 | uaauuucuacucuuguagauugugaaauggcuuauaauugcuua | 34% | 114 |
| 38351-44-L12 | uaauuucuacucuuguagauugugaaauggcuuauaauugcuua | 86% | 115 |
| 38351-44-L13 | uaauuucuacucuuguagauugugaaauggcuuauaauugcuua | 85% | 116 |
| 38351-44-L14 | uaauuucuacucuuguagauugugaaauggcuuauaauugcuua | 86% | 117 |
| 38351-44-L15 | uaauuucuacucuuguagauugugaaauggcuuauaauugcuua | 58% | 118 |
| 38351-44-L16 | uaauuucuacucuuguagauugugaaauggcuuauaauugcuua | 89% | 119 |
| 38351-44-L17 | uaauuucuacucuuguagauugugaaauggcuuauaauugcuua | 88% | 120 |
| 38351-44-L18 | uaauuucuacucuuguagauugugaaauggcuuauaauugcuua | 82% | 121 |
| 38351-44-L19 | uaauuucuacucuuguagauugugaaauggcuuauaauugcuua | 87% | 122 |
| 38351-44-L20 | uaauuucuacucuuguagauugugaaauggcuuauaauugcuua | 52% | 123 |
| 38351-44-T1 | uaauuucuacucuuguagauugugaaauggcuuauaauugcuua | 87% | 124 |
| 38351-44-T2 | uaauuucuacucuuguagauugugaaauggcuuauaauugcuua | 79% | 125 |
| 38351-44-T3 | uaauuucuacucuuguagauugugaaauggcuuauaauugcuua | 86% | 126 |

TABLE 6-continued

Single-base 2'OMe modification walk through HPRT1 Site 38351 AsCpf1 crRNAs

| Seq Name | Sequence 5'-3' | % Cleavage T7E1 Assay | SEQ ID NO: |
|---|---|---|---|
| 38351-44-T4 | uaauucuacucuuguagauugug<u>a</u>aauggcuuauaauugcuua | 81% | 127 |
| 38351-44-T5 | uaauucuacucuuguagauugug<u>a</u>aauggcuuauaauugcuua | 69% | 128 |
| 38351-44-T6 | uaauucuacucuuguagauuguga<u>a</u>auggcuuauaauugcuua | 57% | 129 |
| 38351-44-T7 | uaauucuacucuuguagauugugaa<u>a</u>uggcuuauaauugcuua | 84% | 130 |
| 38351-44-T8 | uaauucuacucuuguagauugugaaa<u>u</u>ggcuuauaauugcuua | 90% | 131 |
| 38351-44-T9 | uaauucuacucuuguagauugugaaau<u>g</u>gcuuauaauugcuua | 86% | 132 |
| 38351-44-T10 | uaauucuacucuuguagauugugaaaug<u>g</u>cuuauaauugcuua | 89% | 133 |
| 38351-44-T11 | uaauucuacucuuguagauugugaaaugg<u>c</u>uuauaauugcuua | 86% | 134 |
| 38351-44-T12 | uaauucuacucuuguagauugugaaauggc<u>u</u>uauaauugcuua | 90% | 135 |
| 38351-44-T13 | uaauucuacucuuguagauugugaaauggcu<u>u</u>auaauugcuua | 15% | 136 |
| 38351-44-T14 | uaauucuacucuuguagauugugaaauggcuu<u>a</u>uaauugcuua | 71% | 137 |
| 38351-44-T15 | uaauucuacucuuguagauugugaaauggcuua<u>u</u>aauugcuua | 72% | 138 |
| 38351-44-T16 | uaauucuacucuuguagauugugaaauggcuuau<u>a</u>auugcuua | 68% | 139 |
| 38351-44-T17 | uaauucuacucuuguagauugugaaauggcuuaua<u>a</u>uugcuua | 72% | 140 |
| 38351-44-T18 | uaauucuacucuuguagauugugaaauggcuuauaa<u>u</u>ugcuua | 64% | 141 |
| 38351-44-T19 | uaauucuacucuuguagauugugaaauggcuuauaau<u>u</u>gcuua | 75% | 142 |
| 38351-44-T20 | uaauucuacucuuguagauugugaaauggcuuauaauu<u>g</u>cuua | 71% | 143 |
| 38351-44-T21 | uaauucuacucuuguagauugugaaauggcuuauaauug<u>c</u>uua | 72% | 144 |
| 38351-44-T22 | uaauucuacucuuguagauugugaaauggcuuauaauugc<u>u</u>ua | 69% | 145 |
| 38351-44-T23 | uaauucuacucuuguagauugugaaauggcuuauaauugcu<u>u</u>a | 72% | 146 |
| 38351-44-T24 | uaauucuacucuuguagauugugaaauggcuuauaauugcuu<u>a</u> | 70% | 147 |
| 38351-41 unmod | uaauucuacucuuguagauugugaaauggcuuauaauugc | 77% | 148 |
| 38351-41-L1 | <u>u</u>aauucuacucuuguagauugugaaauggcuuauaauugc | 87% | 149 |
| 38351-41-L2 | u<u>a</u>auucuacucuuguagauugugaaauggcuuauaauugc | 63% | 150 |

TABLE 6-continued

Single-base 2'OMe modification walk through HPRT1 Site 38351 AsCpf1 crRNAs

| Seq Name | Sequence 5'-3' | % Cleavage T7E1 Assay | SEQ ID NO: |
|---|---|---|---|
| 38351-41-L3 | uaauuucuacucuuguagauugugaaauggcuuauaauugc | 15% | 151 |
| 38351-41-L4 | uaauuucuacucuuguagauugugaaauggcuuauaauugc | 6% | 152 |
| 38351-41-L5 | uaauuucuacucuuguagauugugaaauggcuuauaauugc | 88% | 153 |
| 38351-41-L6 | uaauuucuacucuuguagauugugaaauggcuuauaauugc | 88% | 154 |
| 38351-41-L7 | uaauuucuacucuuguagauugugaaauggcuuauaauugc | 81% | 155 |
| 38351-41-L8 | uaauuucuacucuuguagauugugaaauggcuuauaauugc | 78% | 156 |
| 38351-41-L9 | uaauuucuacucuuguagauugugaaauggcuuauaauugc | 90% | 157 |
| 38351-41-L10 | uaauuucuacucuuguagauugugaaauggcuuauaauugc | 88% | 158 |
| 38351-41-L11 | uaauuucuacucuuguagauugugaaauggcuuauaauugc | 59% | 159 |
| 38351-41-L12 | uaauuucuacucuuguagauugugaaauggcuuauaauugc | 88% | 160 |
| 38351-41-L13 | uaauuucuacucuuguagauugugaaauggcuuauaauugc | 89% | 161 |
| 38351-41-L14 | uaauuucuacucuuguagauugugaaauggcuuauaauugc | 88% | 162 |
| 38351-41-L15 | uaauuucuacucuuguagauugugaaauggcuuauaauugc | 41% | 163 |
| 38351-41-L16 | uaauuucuacucuuguagauugugaaauggcuuauaauugc | 90% | 164 |
| 38351-41-L17 | uaauuucuacucuuguagauugugaaauggcuuauaauugc | 89% | 165 |
| 38351-41-L18 | uaauuucuacucuuguagauugugaaauggcuuauaauugc | 89% | 166 |
| 38351-41-L19 | uaauuucuacucuuguagauugugaaauggcuuauaauugc | 88% | 167 |
| 38351-41-L20 | uaauuucuacucuuguagauugugaaauggcuuauaauugc | 77% | 168 |
| 38351-41-T1 | uaauuucuacucuuguagauugugaaauggcuuauaauugc | 89% | 169 |
| 38351-41-T2 | uaauuucuacucuuguagauugugaaauggcuuauaauugc | 84% | 170 |
| 38351-41-T3 | uaauuucuacucuuguagauugugaaauggcuuauaauugc | 87% | 171 |
| 38351-41-T4 | uaauuucuacucuuguagauugugaaauggcuuauaauugc | 86% | 172 |
| 38351-41-T5 | uaauuucuacucuuguagauugugaaauggcuuauaauugc | 80% | 173 |
| 38351-41-T6 | uaauuucuacucuuguagauugugaaauggcuuauaauugc | 79% | 174 |

TABLE 6-continued

Single-base 2'OMe modification walk through HPRT1 Site 38351 AsCpf1 crRNAs

| Seq Name | Sequence 5'-3' | % Cleavage T7E1 Assay | SEQ ID NO: |
|---|---|---|---|
| 38351-41-T7 | uaauucuacucuuguagauugugaaa<u>a</u>uggcuuauaauugc | 86% | 175 |
| 38351-41-T8 | uaauucuacucuuguagauugugaaau<u>g</u>gcuuauaauugc | 89% | 176 |
| 38351-41-T9 | uaauucuacucuuguagauugugaaau<u>g</u>gcuuauaauugc | 89% | 177 |
| 38351-41-T10 | uaauucuacucuuguagauugugaaaug<u>g</u>cuuauaauugc | 89% | 178 |
| 38351-41-T11 | uaauucuacucuuguagauugugaaaugg<u>c</u>uuauaauugc | 89% | 179 |
| 38351-41-T12 | uaauucuacucuuguagauugugaaauggc<u>u</u>uauaauugc | 88% | 180 |
| 38351-41-T13 | uaauucuacucuuguagauugugaaauggcu<u>u</u>auaauugc | 23% | 181 |
| 38351-41-T14 | uaauucuacucuuguagauugugaaauggcuu<u>a</u>uaauugc | 75% | 182 |
| 38351-41-T15 | uaauucuacucuuguagauugugaaauggcuua<u>u</u>aauugc | 77% | 183 |
| 38351-41-T16 | uaauucuacucuuguagauugugaaauggcuuau<u>a</u>auugc | 72% | 184 |
| 38351-41-T17 | uaauucuacucuuguagauugugaaauggcuuaua<u>a</u>uugc | 76% | 185 |
| 38351-41-T18 | uaauucuacucuuguagauugugaaauggcuuauaa<u>u</u>ugc | 71% | 186 |
| 38351-41-T19 | uaauucuacucuuguagauugugaaauggcuuauaau<u>u</u>gc | 77% | 187 |
| 38351-41-T20 | uaauucuacucuuguagauugugaaauggcuuauaauu<u>g</u>c | 75% | 188 |
| 38351-41-T21 | uaauucuacucuuguagauugugaaauggcuuauaauug<u>c</u> | 77% | 189 |

Oligonucleotide sequences are shown 5'-3'. Lowercase = RNA; Underlined lowercase = 2'-O-methyl RNA. The relative functional activity of each species is indicated by the % cleavage in a T7EI heteroduplex assay. The sequence name indicates if the crRNA is a 44mer with a 24 base target domain or a 41mer with a 21 base target domain. The position of the 2'OMe residue with either the loop domain (L) or target domain (T) is indicated.

TABLE 7

Single-base 2'OMe modification walk through HPRT1 Site 38595 AsCpf1 crRNAs

| Seq Name | Sequence 5'-3' | % Cleavage T7E1 Assay | SEQ ID NO: |
|---|---|---|---|
| 38595-44 unmod | uaauucuacucuuguagauggaaagagaauuguuuucuccuuc | 49% | 190 |
| 38595-44-L1 | <u>u</u>aauucuacucuuguagauggaaagagaauuguuuucuccuuc | 48% | 191 |
| 38595-44-L2 | u<u>a</u>auucuacucuuguagauggaaagagaauuguuuucuccuuc | 34% | 192 |

TABLE 7-continued

Single-base 2'OMe modification walk through HPRT1 Site 38595 AsCpf1 crRNAs

| Seq Name | Sequence 5'-3' | % Cleavage T7E1 Assay | SEQ ID NO: |
|---|---|---|---|
| 38595-44-L3 | uaauuucuacucuuguagauggaaagagaauuguuuucuccuuc | 6% | 193 |
| 38595-44-L4 | uaauuucuacucuuguagauggaaagagaauuguuuucuccuuc | 3% | 194 |
| 38595-44-L5 | uaauuucuacucuuguagauggaaagagaauuguuuucuccuuc | 59% | 195 |
| 38595-44-L6 | uaauuucuacucuuguagauggaaagagaauuguuuucuccuuc | 54% | 196 |
| 38595-44-L7 | uaauuucuacucuuguagauggaaagagaauuguuuucuccuuc | 56% | 197 |
| 38595-44-L8 | uaauuucuacucuuguagauggaaagagaauuguuuucuccuuc | 52% | 198 |
| 38595-44-L9 | uaauuucuacucuuguagauggaaagagaauuguuuucuccuuc | 60% | 199 |
| 38595-44-L10 | uaauuucuacucuuguagauggaaagagaauuguuuucuccuuc | 56% | 200 |
| 38595-44-L11 | uaauuucuacucuuguagauggaaagagaauuguuuucuccuuc | 23% | 201 |
| 38595-44-L12 | uaauuucuacucuuguagauggaaagagaauuguuuucuccuuc | 51% | 202 |
| 38595-44-L13 | uaauuucuacucuuguagauggaaagagaauuguuuucuccuuc | 58% | 203 |
| 38595-44-L14 | uaauuucuacucuuguagauggaaagagaauuguuuucuccuuc | 52% | 204 |
| 38595-44-L15 | uaauuucuacucuuguagauggaaagagaauuguuuucuccuuc | 33% | 205 |
| 38595-44-L16 | uaauuucuacucuuguagauggaaagagaauuguuuucuccuuc | 55% | 206 |
| 38595-44-L17 | uaauuucuacucuuguagauggaaagagaauuguuuucuccuuc | 58% | 207 |
| 38595-44-L18 | uaauuucuacucuuguagauggaaagagaauuguuuucuccuuc | 61% | 208 |
| 38595-44-L19 | uaauuucuacucuuguagauggaaagagaauuguuuucuccuuc | 54% | 209 |
| 38595-44-L20 | uaauuucuacucuuguagauggaaagagaauuguuuucuccuuc | 29% | 210 |
| 38595-44-T1 | uaauuucuacucuuguagauggaaagagaauuguuuucuccuuc | 55% | 211 |
| 38595-44-T2 | uaauuucuacucuuguagauggaaagagaauuguuuucuccuuc | 53% | 212 |
| 38595-44-T3 | uaauuucuacucuuguagauggaaagagaauuguuuucuccuuc | 49% | 213 |
| 38595-44-T4 | uaauuucuacucuuguagauggaaagagaauuguuuucuccuuc | 20% | 214 |
| 38595-44-T5 | uaauuucuacucuuguagauggaaagagaauuguuuucuccuuc | 17% | 215 |
| 38595-44-T6 | uaauuucuacucuuguagauggaaagagaauuguuuucuccuuc | 23% | 216 |

TABLE 7-continued

Single-base 2'OMe modification walk through HPRT1 Site 38595 AsCpf1 crRNAs

| Seq Name | Sequence 5'-3' | % Cleavage T7E1 Assay | SEQ ID NO: |
|---|---|---|---|
| 38595-44-T7 | uaauuucuacucuuguagauggaaagagaauuguuuucuccuuc | 47% | 217 |
| 38595-44-T8 | uaauuucuacucuuguagauggaaagagaauuguuuucuccuuc | 52% | 218 |
| 38595-44-T9 | uaauuucuacucuuguagauggaaagagaauuguuuucuccuuc | 51% | 219 |
| 38595-44-T10 | uaauuucuacucuuguagauggaaagagaauuguuuucuccuuc | 55% | 220 |
| 38595-44-T11 | uaauuucuacucuuguagauggaaagagaauuguuuucuccuuc | 53% | 221 |
| 38595-44-T12 | uaauuucuacucuuguagauggaaagagaauuguuuucuccuuc | 58% | 222 |
| 38595-44-T13 | uaauuucuacucuuguagauggaaagagaauuguuuucuccuuc | 20% | 223 |
| 38595-44-T14 | uaauuucuacucuuguagauggaaagagaauuguuuucuccuuc | 62% | 224 |
| 38595-44-T15 | uaauuucuacucuuguagauggaaagagaauuguuuucuccuuc | 60% | 225 |
| 38595-44-T16 | uaauuucuacucuuguagauggaaagagaauuguuuucuccuuc | 15% | 226 |
| 38595-44-T17 | uaauuucuacucuuguagauggaaagagaauuguuuucuccuuc | 49% | 227 |
| 38595-44-T18 | uaauuucuacucuuguagauggaaagagaauuguuuucuccuuc | 46% | 228 |
| 38595-44-T19 | uaauuucuacucuuguagauggaaagagaauuguuuucuccuuc | 64% | 229 |
| 38595-44-T20 | uaauuucuacucuuguagauggaaagagaauuguuuucuccuuc | 57% | 230 |
| 38595-44-T21 | uaauuucuacucuuguagauggaaagagaauuguuuucuccuuc | 55% | 231 |
| 38595-44-T22 | uaauuucuacucuuguagauggaaagagaauuguuuucuccuuc | 54% | 232 |
| 38595-44-T23 | uaauuucuacucuuguagauggaaagagaauuguuuucuccuuc | 56% | 233 |
| 38595-44-T24 | uaauuucuacucuuguagauggaaagagaauuguuuucuccuuc | 54% | 234 |
| 38595-41 unmod | uaauuucuacucuuguagauggaaagagaauuguuuucucc | 59% | 235 |
| 38595-41-L1 | uaauuucuacucuuguagauggaaagagaauuguuuucucc | 60% | 236 |
| 38595-41-L2 | uaauuucuacucuuguagauggaaagagaauuguuuucucc | 49% | 237 |
| 38595-41-L3 | uaauuucuacucuuguagauggaaagagaauuguuuucucc | 10% | 238 |
| 38595-41-L4 | uaauuucuacucuuguagauggaaagagaauuguuuucucc | 5% | 239 |
| 38595-41-L5 | uaauuucuacucuuguagauggaaagagaauuguuuucucc | 63% | 240 |

TABLE 7-continued

Single-base 2'OMe modification walk through HPRT1 Site 38595 AsCpf1 crRNAs

| Seq Name | Sequence 5'-3' | % Cleavage T7E1 Assay | SEQ ID NO: |
|---|---|---|---|
| 38595-41-L6 | uaauuucuacucuuguagauggaaagagaauuguuuucucc | 55% | 241 |
| 38595-41-L7 | uaauuucuacucuuguagauggaaagagaauuguuuucucc | 56% | 242 |
| 38595-41-L8 | uaauuucuacucuuguagauggaaagagaauuguuuucucc | 55% | 243 |
| 38595-41-L9 | uaauuucuacucuuguagauggaaagagaauuguuuucucc | 63% | 244 |
| 38595-41-L10 | uaauuucuacucuuguagauggaaagagaauuguuuucucc | 64% | 245 |
| 38595-41-L11 | uaauuucuacucuuguagauggaaagagaauuguuuucucc | 35% | 246 |
| 38595-41-L12 | uaauuucuacucuuguagauggaaagagaauuguuuucucc | 55% | 247 |
| 38595-41-L13 | uaauuucuacucuuguagauggaaagagaauuguuuucucc | 56% | 248 |
| 38595-41-L14 | uaauuucuacucuuguagauggaaagagaauuguuuucucc | 58% | 249 |
| 38595-41-L15 | uaauuucuacucuuguagauggaaagagaauuguuuucucc | 47% | 250 |
| 38595-41-L16 | uaauuucuacucuuguagauggaaagagaauuguuuucucc | 55% | 251 |
| 38595-41-L17 | uaauuucuacucuuguagauggaaagagaauuguuuucucc | 64% | 252 |
| 38595-41-L18 | uaauuucuacucuuguagauggaaagagaauuguuuucucc | 69% | 253 |
| 38595-41-L19 | uaauuucuacucuuguagauggaaagagaauuguuuucucc | 63% | 254 |
| 38595-41-L20 | uaauuucuacucuuguagauggaaagagaauuguuuucucc | 45% | 255 |
| 38595-41-T1 | uaauuucuacucuuguagauggaaagagaauuguuuucucc | 60% | 256 |
| 38595-41-T2 | uaauuucuacucuuguagauggaaagagaauuguuuucucc | 59% | 257 |
| 38595-41-T3 | uaauuucuacucuuguagauggaaagagaauuguuuucucc | 53% | 258 |
| 38595-41-T4 | uaauuucuacucuuguagauggaaagagaauuguuuucucc | 21% | 259 |
| 38595-41-T5 | uaauuucuacucuuguagauggaaagagaauuguuuucucc | 20% | 260 |
| 38595-41-T6 | uaauuucuacucuuguagauggaaagagaauuguuuucucc | 25% | 261 |
| 38595-41-T7 | uaauuucuacucuuguagauggaaagagaauuguuuucucc | 50% | 262 |
| 38595-41-T8 | uaauuucuacucuuguagauggaaagagaauuguuuucucc | 64% | 263 |
| 38595-41-T9 | uaauuucuacucuuguagauggaaagagaauuguuuucucc | 54% | 264 |

TABLE 7-continued

Single-base 2'OMe modification walk through HPRT1 Site 38595 AsCpf1 crRNAs

| Seq Name | Sequence 5'-3' | % Cleavage T7E1 Assay | SEQ ID NO: |
|---|---|---|---|
| 38595-41-T10 | uaauuucuacucuuguagauggaaagagaauuguuuucucc | 57% | 265 |
| 38595-41-T11 | uaauuucuacucuuguagauggaaagagaauuguuuucucc | 45% | 266 |
| 38595-41-T12 | uaauuucuacucuuguagauggaaagagaauuguuuucucc | 52% | 267 |
| 38595-41-T13 | uaauuucuacucuuguagauggaaagagaauuguuuucucc | 14% | 268 |
| 38595-41-T14 | uaauuucuacucuuguagauggaaagagaauuguuuucucc | 66% | 269 |
| 38595-41-T15 | uaauuucuacucuuguagauggaaagagaauuguuuucucc | 63% | 270 |
| 38595-41-T16 | uaauuucuacucuuguagauggaaagagaauuguuuucucc | 16% | 271 |
| 38595-41-T17 | uaauuucuacucuuguagauggaaagagaauuguuuucucc | 47% | 272 |
| 38595-41-T18 | uaauuucuacucuuguagauggaaagagaauuguuuucucc | 52% | 273 |
| 38595-41-T19 | uaauuucuacucuuguagauggaaagagaauuguuuucucc | 64% | 274 |
| 38595-41-T20 | uaauuucuacucuuguagauggaaagagaauuguuuucucc | 64% | 275 |
| 38595-41-T21 | uaauuucuacucuuguagauggaaagagaauuguuuucucc | 66% | 276 |

Oligonucleotide sequences are shown 5'-3'.
Lowercase = RNA;
Underlined lowercase = 2'-O-methyl RNA.
The relative functional activity of each species is indicated by the % cleavage in a T7EI heteroduplex assay.
The sequence name indicates if the crRNA is a 44mer with a 24 base target domain or a 41mer with a 21 base target domain.
The position of the 2'OMe residue with either the loop domain (L) or target domain (T) is indicated.

Example 6

Modification of Blocks of Sequence in AsCpf1 crRNAs.

Three sites in the human HPRT1 gene were chosen (38351, 38595, and 38104) to study the effects of replacement of a blocks of RNA residues with 2'OMe-RNA, 2'F RNA, or LNA residues within the AsCpf1 crRNA. Modification of internucleotide linkages with phosphorothioate bonds (PS) as well as non-nucleotide end-modifiers were also tested. The crRNAs were either 44 base or 41 base lengths. All had a 5'-end 20 base universal loop domain followed by a 3'-end 21 or 24 base protospacer target-specific domain.

An HEK cell line that stably expresses the AsCpf1 endonuclease was employed in these studies (HEK-Cpf1) (Example 2). In a reverse transfection format, anti-HPRT1 crRNAs were individually mixed with Lipofectamine RNAiMAX (Life Technologies) and transfected into the HEK-Cpf1 cell line. Transfections were done with 40,000 cells per well in 96 well plate format. RNAs were introduced at a final concentration of 30 nM in 0.75 µl of the lipid reagent. Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID NO:394); HPRT-low reverse primer: ACACATC-CATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. Results are shown in Table 8 below.

Large blocks of the universal 5-loop domain can be modified and retain activity (14/20 bases). However, the target-specific 3'-protospacer domain shows significant loss of activity when 2-3 consecutive 2'OMe residues replace RNA residues, even when those positions did not show any loss of activity in the single base walk (Example 5). Modification patterns in the protospacer domain are often expected to be impacted by sequence context, such that one modification pattern works well for one sequence but not for another sequence. The modification map shown in FIG. 7 displays modification patterns that range from minimal to high levels of modification that showed high performance at several sites and likely can be used regardless of sequence context.

2'F residues could be placed at any position that was tolerant of 2'OMe modification. LNA residues can also be placed within the AsCpf1 crRNA, and use of end-modifiers are shown below in Table 8. The phosphorothioate (PS) internucleotide linkage confers nuclease resistance and can be placed at the ends of the crRNA to block exonuclease attack or in the central regions to block endonuclease attack. Modification of large blocks of the crRNA (such as entire modification of the loop domain or the protospacer domain) with PS linkages are not compatible with crRNA function and significant loss of activity is seen when this modification pattern is employed. Limited use, such as 2-3 internucleotide linkages at each end, can be effectively employed, and such patterns are useful to block exonuclease attack. Non-base modifiers (such as a C3 spacer propanediol group or a ZEN modifier napthyl-azo group) can be placed at one or both ends of the crRNA without loss of activity and also block exonuclease attack.

TABLE 8

Functional impact of extensive modification of AsCpf1 crRNAs

| Seq Name | Sequence 5'-3' | % Cleavage T7E1 Assay | SEQ ID NO: |
|---|---|---|---|
| 38351-44-L | uaauuucuacucuuguagauugugaaauggcuuauaauugcuua | 51% | 277 |
| 38351-44-T | uaauuucuacucuuguagauugugaaauggcuuauaauugcuua | 1% | 278 |
| 38351-44-LT | uaauuucuacucuuguagauugugaaauggcuuauaauugcuua | 1% | 279 |
| 38351-41-L | uaauuucuacucuuguagauugugaaauggcuuauaauugc | 53% | 280 |
| 38351-41-T | uaauuucuacucuuguagauugugaaauggcuuauaauugc | 1% | 281 |
| 38351-41-LT | uaauuucuacucuuguagauugugaaauggcuuauaauugc | 1% | 282 |
| 38595-44-L | uaauuucuacucuuguagauggaaagagaauuguuuucuccuuc | 51% | 283 |
| 38595-44-T | uaauuucuacucuuguagauggaaagagaauuguuuucuccuuc | 1% | 284 |
| 38595-44-LT | uaauuucuacucuuguagauggaaagagaauuguuuucuccuuc | 1% | 285 |
| 38595-41-L | uaauuucuacucuuguagauggaaagagaauuguuuucucc | 51% | 286 |
| 38595-41-T | uaauuucuacucuuguagauggaaagagaauuguuuucucc | 1% | 287 |
| 38595-41-LT | uaauuucuacucuuguagauggaaagagaauuguuuucucc | 1% | 288 |
| 38595-41 unmod | uaauuucuacucuuguagauggaaagagaauuguuuucucc | 35% | 235 |
| 38595-41-T1-3 | uaauuucuacucuuguagauggaaagagaauuguuuucucc | 24% | 289 |
| 38595-41-T7-12 | uaauuucuacucuuguagauggaaagagaauuguuuucucc | 2% | 290 |
| 38595-41-T14-15 | uaauuucuacucuuguagauggaaagagaauuguuuucucc | 37% | 291 |
| 38595-41-T17-21 | uaauuucuacucuuguagauggaaagagaauuguuuucucc | 22% | 292 |
| 38595-41-T6-9, 18-21 | uaauuucuacucuuguagauggaaagagaauuguuuucucc | 1% | 293 |
| 38595-41-5'C3 | C3-uaauuucuacucuuguagauggaaagagaauuguuuucucc | 35% | 294 |
| 38595-41-3'C3 | uaauuucuacucuuguagauggaaagagaauuguuuucucc-C3 | 41% | 295 |
| 38595-41-2 x C3 | C3-uaauuucuacucuuguagauggaaagagaauuguuuucucc-C3 | 41% | 296 |

TABLE 8-continued

Functional impact of extensive modification of AsCpf1 crRNAs

| Seq Name | Sequence 5'-3' | % Cleavage T7E1 Assay | SEQ ID NO: |
|---|---|---|---|
| 38595-41-L1-20 | uauuucuacucuuguagauggaaagagaauuguuuucucc | 1% | 297 |
| 38595-41-L + 2 | uaauuucuacucuuguagauggaaagagaauuguuuucucc | 2% | 298 |
| 38595-41-L + 3 | uaauuucuacucuuguagauggaaagagaauuguuuucucc | 1% | 299 |
| 38595-41-L + 4 | uaauuucuacucuuguagauggaaagagaauuguuuucucc | 1% | 300 |
| 38595-41-L + 11 | uaauuucuacucuuguagauggaaagagaauuguuuucucc | 5% | 301 |
| 38595-41-L + 15 | uaauuucuacucuuguagauggaaagagaauuguuuucucc | 38% | 302 |
| 38595-41-L + 20 | uaauuucuacucuuguagauggaaagagaauuguuuucucc | 2% | 303 |
| 38595-41-61 | C3-uaauuucuacucuuguagauggaaagagaauuguuuucucc-C3 | 67% | 304 |
| 38595-41-62 | u*a*a*uuucuacucuuguagauggaaagagaauuguuuc*u*c*c | 58% | 305 |
| 38595-41-63 | u*a*a*uuucuacucuuguagauggaaagagaauuguuuc*u*c*c | 63% | 306 |
| 38595-41-64 | u*a*a*u*u*u*c*u*a*c*u*c*u*u*g*u*a*g*a*uggaaagagaauuguuuucucc | 10% | 307 |
| 38595-41-65 | uaauuucuacucuuguagau*g*g*a*a*a*g*a*g*a*a*u*u*g*u*u*u*u*c*u*c*c | 2% | 308 |
| 38595-41-66 | uaauuucuacucuuguagauggaaagagaauuguuuucucc | 57% | 309 |
| 38595-41-67 | uaauuucuacucuuguagauggaaagagaauuguuuucucc | 51% | 310 |
| 38595-41-68 | uaauuucuacucuuguagauggaaagagaauuguuuucucc | 20% | 311 |
| 38595-41-69 | uaauuucuacucuuguagauggaaagagaauuguuuucucc | 19% | 312 |
| 38595-41-70 | uaauuucuacucuuguagauggaaagagaauuguuuucucc | 27% | 313 |
| 38595-41-71 | uaauuucuacucuuguagauggaaagagaauuguuuucucc | 37% | 314 |
| 38595-41-72 | uaauuucuacucuuguagauggaaagagaauuguuuucucc | 65% | 315 |
| 38595-41-73 | uaauuucuacucuuguagauggaaagagaauuguuuucucc | 67% | 316 |
| 38595-41-74 | uaauuucuacucuuguagauggaaagagaauuguuuucucc | 65% | 317 |
| 38595-41-75 | uaauuucuacucuuguagauggaaagagaauuguuuucucc | 57% | 318 |
| 38595-41-76 | uaauuucuacucuuguagauggaaagagaauuguuuucucc | 65% | 319 |
| 38595-41-77 | uaauuucuacucuuguagauggaaagagaauuguuuucucc | 16% | 320 |
| 38595-41-78 | uaauuucuacucuuguagauggaaagagaauuguuuucucc | 49% | 321 |
| 38595-41-79 | uaauuucuacucuuguagauggaaagagaauuguuuucucc | 70% | 322 |
| 38595-41-80 | uaauuucuacucuuguagauggaaagagaauuguuuucucc | 1% | 323 |
| 38595-41-81 | uaauuucuacucuuguagauggaaagagaauuguuuucucc | 13% | 324 |
| 38595-41-82 | uaauuucuacucuuguagauggaaagagaauuguuuucucc | 51% | 325 |
| 38595-41-83 | uaauuucuacucuuguagauggaaagagaauuguuuucucc | 64% | 326 |

TABLE 8-continued

Functional impact of extensive modification of AsCpf1 crRNAs

| Seq Name | Sequence 5'-3' | % Cleavage T7E1 Assay | SEQ ID NO: |
|---|---|---|---|
| 38595-41-84 | uaau<u>uucuacucuuguaga</u>uggaaagagaauuguuu<u>uc</u>ucc | 69% | 327 |
| 38595-41-85 | uaa<u>uuucuacucuuguaga</u>uggaaagagaauuguuuuc<u>uc</u>c | 69% | 328 |
| 38595-41-86 | <u>u</u>\*a\*a\*uuucuacucuuguagauggaaagagaauuguuuc\*<u>u</u>\*<u>c</u>\*<u>c</u> | 61% | 329 |
| 38595-41-87 | +taauuucuacucuuguagauggaaagagaauuguuuucu+c+c | 60% | 330 |
| 38595-41-88 | uaau*uucuacucuuguaga*uggaaagagaauuguuuucucc | 63% | 331 |
| 38595-41-89 | uaauuucuacucuuguaga*uggaa*agagaauuguuuucucc | 34% | 332 |
| 38595-41-90 | uaauuucuacucuuguagaugga*aagagaa*uuguuuucucc | 65% | 333 |
| 38595-41-91 | uaauuucuacucuuguaga*u*ggaaagagaauuguuuucucc | 66% | 334 |
| 38595-41-92 | uaauuucuacucuuguagauggaaagagaauuguuu*ucucc* | 60% | 335 |
| 38595-41-93 | ZEN-uaauuucuacucuuguagauggaaagagaauuguuuucucc-ZEN | 61% | 336 |
| 38595-41-94 | ZEN-uaauuucuacucuuguagauggaaagagaauuguuuucucc-C3 | 59% | 337 |
| 38595-41-95 | C3-uaauuucuacucuuguagauggaaagagaauuguuuucucc-ZEN | 58% | 338 |
| 38104-41-96 | uaauuucuacucuuguagaucuugggguguguuaaaagugac | 63% | 339 |
| 38104-41-97 | C3-uaauuucuacucuuguagaucuugggguguguuaaaagugac-C3 | 63% | 340 |
| 38104-41-98 | uaa<u>uuucuacucuuguaga</u>ucuugggguguguuaaaagugac | 63% | 341 |
| 38104-41-99 | <u>u</u>\*a\*auuucuacucuuguagaucuugggguguguuaaaagu\*<u>g</u>\*<u>a</u>\*<u>c</u> | 67% | 342 |

Oligonucleotide sequences are shown 5'-3'.
Lowercase = RNA;
Underlined lowercase = 2'-O-methyl RNA;
Italics lowercase = 2'-fluoro RNA;
+a, +c, +t, +g = LNA;
C3 = C3 spacer (propanediol modifier);
\* = phosphorothioate internucleotide linkage;
ZEN - napthyl-azo modifier. The relative functional activity of each species is indicated by the % cleavage in a T7EI heteroduplex assay. The sequence name indicates if the crRNA is a 44mer with a 24 base target domain or a 41mer with a 21 base target domain and the HPRT target site is indicated (38104, 38351, or 38595).

Example 7

Use of Modified crRNAs with AsCpf1 Protein Delivered as an RNP Complex.

A site in the human HPRT1 gene (38104) was chosen to study the ability to use chemically modified crRNAs with AsCpf1 protein to perform genome editing in HEK-293 cells using electroporation to deliver the ribonucleoprotein (RNP) complex into the cells.

Purified recombinant AsCpf1 protein was employed in this example, isolated from E. coli using standard techniques. The amino-acid sequence of the recombinant protein is shown in SEQ ID NO:12.

The AsCpf1 crRNAs were heated to 95° C. for 5 minutes then allowed to cool to room temperature. The crRNAs were mixed with AsCpf1 protein at a molar ratio of 1.2:1 RNA: protein in phosphate buffered saline (PBS) (202 pmoles RNA with 168 pmoles protein in 6 μL volume, for a single transfection). The RNP complex was allowed to form at room temperature for 15 minutes. HEK293 cells were resuspended following trypsinization and washed in medium and washed a second time in PBS before use. Cells were resuspended in at a final concentration of $3.5 \times 10^5$ cells in 20 μL of Nucleofection solution. 20 μL of cell suspension was placed in the V-bottom 96-well plate and 5 μL of the Cpf1 RNP complex was added to each well (5 μM final concentration) and 3 µL of Cpf1 Electroporation Enhancer Solution was added to each well (Integrated DNA Technologies). 25 µL of the final mixture was transferred to each well of a 96 well Nucleocuvette electroporation module. Cells were electroporated using Amaxa 96 well shuttle protocol, program 96-DS-150. Following electroporation, 75 µL of medium was added to each well and 25 µL of the final cell mixture was transferred to 175 µL of pre-warmed medium in 96 well incubation plates (final volume 200 Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGT-GATGCT (SEQ ID NO:394); HPRT-low reverse primer: ACACATCCATGGGACTTCTGCCTC (SEQ ID NO:395). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)× 100. Results are shown in Table 9 below. AsCpf1 crRNAs bearing low or high levels of modification, as shown below, are compatible with delivery via electroporation as an RNP complex to mediate genome editing in mammalian cells.

age in *E. coli* cells. AsCpf1 was expressed from a plasmid. Electroporation was used to deliver both the AsCpf1 expression plasmid and chemically-synthesized crRNAs.

The AsCpf1 protein was expressed from a plasmid in this example, using a phage T7 promoter and standard *E. coli* translation elements. The amino-acid sequence of the expression construct is shown in SEQ ID NO:16).

The AsCpf1 crRNAs were heated to 95° C. for 5 minutes then allowed to cool to room temperature. The crRNAs and AsCpf1 plasmid were mixed in TE (60 femtomoles AsCpf1 plasmid with 400 pmoles RNA in 5 µL volume, for a single transformation), and added directly to 20 µL of competent *E. coli* cells). A bacterial strain where survival is linked to successful cleavage by Cpf1 was made competent by growing cells to mid-log phase, washing 3 times in ice cold 10% glycerol, and final suspension in $1:100^{th}$ volume 10% glycerol. Electroporations were performed by adding the 25 µL transformation mixture to a pre-chilled 0.1 cm electroporation cuvette and pulsing 1.8 kV exponential decay. Following electroporation, 980 µL of SOB medium was added to the electroporation cuvette with mixing and the resulting cell suspension was transferred to a sterile 15 ml culture tube. Cells were incubated with shaking (250 rpm) at 37° C. for 1.5 hours, at which time IPTG was added (1 mM) followed by further shaking incubation at 37° C. for 1 hour. Following incubation cells were plated on selective media to assess survival.

TABLE 9

Editing in mammalian cells using chemically-modified crRNAs with recombinant AsCpf1 as RNP complexes

| Seq Name | Sequence 5'-3' | % Cleavage T7E1 Assay | SEQ ID NO: |
|---|---|---|---|
| 38104-41-96 | uaauuucuacucuuguagaucuugggguguguuaaaagugac | 57% | 339 |
| 38104-41-97 | C3-uaauuucuacucuuguagaucuugggguguguuaaaagugac-C3 | 53% | 340 |
| 38104-41-98 | ua<u>auuucuacuc</u>uu<u>guaga</u>ucuugggguguguuaaaagugac | 42% | 341 |
| 38104-41-99 | <u>u</u>*a*auuucuacucuuguagaucuugggguguguuaaaagu*<u>g</u>*<u>a</u>*<u>c</u> | 43% | 342 |
| 38104-41-101 | <u>u</u>*a*au<u>uucuacuc</u>uu<u>guaga</u>ucuugggguguguuaaaagu<u>g</u>*<u>a</u>*<u>c</u> | 43% | 343 |

Oligonucleotide sequences are shown 5'-3'.
Lowercase = RNA;
Underlined = 2'-O-methyl RNA;
C3 = C3 spacer (propanediol modifier);
* = phosphorothioate internucleotide linkage.
The relative functional activity of each species is indicated by the % cleavage in a T7EI heteroduplex assay. The sequence name indicates that the crRNAs are all 41mers with a 21 base target domain.

Example 8

Use of Modified crRNAs with an AsCpf1 Expression Plasmid in *E. coli*.

A site in the human HPRT1 gene (38346) was cloned onto an *E. coli* plasmid and was used to study the ability to use chemically modified crRNAs to perform site-specific cleav- This example demonstrates that chemically-modified synthetic crRNAs can be used with Cpf1 for gene editing in bacteria. However, high efficiency is only seen using RNAs that have been more extensively modified with exonuclease-blocking PS internucleotide linkages. The modification patterns that work best in bacterial cells perform poorly in mammalian cells (Table 10).

TABLE 10

Chemically-modified crRNAs compatible with Cpf1 function in bacteria

| Seq Name | Sequence 5'-3' | % Cleavage Human | % Cleavage Bacteria | SEQ ID NO: |
|---|---|---|---|---|
| 38346-41-1 | uaauuucuacucuuguagauacauaaaacucuuuuagguua | 21% | 0% | 344 |
| 38346-41-2 | u*a*a*uuucuacucuuguagauacauaaaacucuuuuagguua | 17% | 0% | 345 |
| 38346-41-3 | u*a*a*u*u*u*cuacucuuguagauacauaaaacucuuuuagguua | 10% | 2% | 346 |
| 38346-41-4 | uaauuucuacucuuguagauacauaaaacucuuuu*a*g*g*u*u*a | 14% | 18% | 347 |
| 38346-41-5 | u*a*a*uuucuacucuuguagauacauaaaacucuuuuagg*u*u*a | 8% | 5% | 348 |
| 38346-41-6 | u*a*a*uuucuacucuuguagauacauaaaacucuuuu*a*g*g*u*u*a | 5% | 40% | 349 |
| 38346-41-7 | u*a*a*u*u*u*cuacucuuguagauacauaaaacucuuuu*a*g*g*u*u*a | 2% | 88% | 350 |
| 38346-41-8 | uaauuucuacucuuguagauacauaaaacucuuuuagg*u*u*a | 14% | 7% | 351 |
| 38346-41-9 | uaauuucuacucuuguagauacauaaaacucuuuu*a*g*g*u*u*a | 8% | 35% | 352 |
| 38346-41-10 | u*a*a*uuucuacucuuguagauacauaaaacucuuuuagg*u*u*a | 12% | 27% | 353 |
| 38346-41-11 | u*a*a*uuucuacucuuguagauacauaaaacucuuuuag*g*u*u*a | 8% | 85% | 354 |
| 38346-41-12 | u*a*a*uuucuacucuuguagauacauaaaacucuuuua*g*g*u*u*a | 5% | 92% | 355 |
| 38346-41-13 | u*a*a*uuucuacucuuguagauacauaaaacucuuuu*a*g*g*u*u*a | 4% | 100% | 356 |
| 38346-41-14 | u*a*a*u*u*u*cuacucuuguagauacauaaaacucuuuu*a*g*g*u*u*a | 1% | 90% | 357 |

Oligonucleotide sequences are shown 5'-3'.
Lowercase = RNA;
Underlined lowercase = 2'-O-methyl RNA;
C3 = C3 spacer (propanediol modifier);
* = phosphorothioate internucleotide linkage.
The relative functional activity in human cells is indicated by the % cleavage in a T7EI heteroduplex assay, and in bacteria is indicated by % survival in a Cpf1 reporter strain. The sequence name indicates that the crRNAs are all 41mers with a 21 base target domain.

Example 9

DNA and Amino Acid Sequences of Wild Type Lb Cpf1 Polypeptide, as Encoded in Isolated Nucleic Acid Vectors The list below shows wild type (WT) Lb Cpf1 nucleases expressed as polypeptide fusion proteins as described in the present invention. It will be appreciated by one with skill in the art that many different DNA sequences can encode/express the same amino acid (AA) sequence since in many cases more than one codon can encode for the same amino acid. The DNA sequences shown below only serve as examples, and other DNA sequences that encode the same protein (e.g., same amino acid sequence) are contemplated. It is further appreciated that additional features, elements or tags may be added to said sequences, such as NLS domains and the like.

Examples are shown for WT LbCpf1 showing amino acid and DNA sequences for those proteins as LbCpf1 alone and LbCpf1 fused to an N-terminal V5-tag, an N-terminal SV40 NLS domain, a C-terminal SV40 NLS domain, and a C-terminal 6×His-tag.

LbCpf1 Native DNA Sequence

SEQ ID NO: 3

ATGAGCAAACTGGAAAAATTTACGAATTGTTATAGCCTGTCCAAGACCCTGCGTTTCAAAGCCA

TCCCCGTTGGCAAAACCCAGGAGAATATTGATAATAAACGTCTGCTGGTTGAGGATGAAAAAG

AGCAGAAGACTATAAGGGAGTCAAAAAACTGCTGGATCGGTACTACCTGAGCTTTATAAATGAC

GTGCTGCATAGCATTAAACTGAAAAATCTGAATAACTATATTAGTCTGTTCCGCAAGAAAACCC

GAACAGAGAAAGAAAATAAAGAGCTGGAAAACCTGGAGATCAATCTGCGTAAAGAGATCGCAAA

AGCTTTTAAAGGAAATGAAGGTTATAAAAGCCTGTTCAAAAAAGACATTATTGAAACCATCCTG

CCGGAATTTCTGGATGATAAAGACGAGATAGCGCTCGTGAACAGCTTCAACGGGTTCACGACCG

CCTTCACGGGCTTTTTCGATAACAGGGAAAATATGTTTTCAGAGGAAGCCAAAAGCACCTCGAT

AGCGTTCCGTTGCATTAATGAAAATTTGACAAGATATATCAGCAACATGGATATTTTCGAGAAA

GTTGATGCGATCTTTGACAAACATGAAGTGCAGGAGATTAAGGAAAAAATTCTGAACAGCGATT

ATGATGTTGAGGATTTTTTCGAGGGGGAATTTTTTAACTTTGTACTGACACAGGAAGGTATAGA

TGTGTATAATGCTATTATCGGCGGGTTCGTTACCGAATCCGGCGAGAAAATTAAGGGTCTGAAT

GAGTACATCAATCTGTATAACCAAAAGACCAAACAGAAACTGCCAAAATTCAAACCGCTGTACA

AGCAAGTCCTGAGCGATCGGGAAAGCTTGAGCTTTTACGGTGAAGGTTATACCAGCGACGAGGA

GGTACTGGAGGTCTTTCGCAATACCCTGAACAAGAACAGCGAAATTTTCAGCTCCATTAAAAAG

CTGGAGAAACTGTTTAAGAATTTTGACGAGTACAGCAGCGCAGGTATTTTTGTGAAGAACGGAC

CTGCCATAAGCACCATTAGCAAGGATATTTTTGGAGAGTGGAATGTTATCCGTGATAAATGGAA

CGCGGAATATGATGACATACACCTGAAAAAGAAGGCTGTGGTAACTGAGAAATATGAAGACGAT

CGCCGCAAAAGCTTTAAAAAAATCGGCAGCTTTAGCCTGGAGCAGCTGCAGGAATATGCGGACG

CCGACCTGAGCGTGGTCGAGAAACTGAAGGAAATTATTATCCAAAAAGTGGATGAGATTTACAA

GGTATATGGTAGCAGCGAAAAACTGTTTGATGCGGACTTCGTTCTGGAAAAAAGCCTGAAAAAA

AATGATGCTGTTGTTGCGATCATGAAAGACCTGCTCGATAGCGTTAAGAGCTTTGAAAATTACA

TTAAAGCATTCTTTGGCGAGGGCAAAGAAACAAACAGAGACGAAAGCTTTTATGGCGACTTCGT

CCTGGCTTATGACATCCTGTTGAAGGTAGATCATATATATGATGCAATTCGTAATTACGTAACC

CAAAAGCCGTACAGCAAAGATAAGTTCAAACTGTATTTCCAGAACCCGCAGTTTATGGGTGGCT

GGGACAAAGACAAGGAGACAGACTATCGCGCCACTATTCTGCGTTACGGCAGCAAGTACTATCT

CGCCATCATGGACAAAAAATATGCAAAGTGTCTGCAGAAAATCGATAAGACGACGTGAACGGA

AATTACGAAAAGATTAATTATAAGCTGCTGCCAGGGCCCAACAAGATGTTACCGAAAGTATTTT

TTTCCAAAAAATGGATGGCATACTATAACCCGAGCGAGGATATACAGAAGATTTACAAAAATGG

GACCTTCAAAAAGGGGGATATGTTCAATCTGAATGACTGCCACAAACTGATCGATTTTTTTAAA

GATAGCATCAGCCGTTATCCTAAATGGTCAAACGCGTATGATTTAATTTCTCCGAAACGGAGA

AATATAAAGACATTGCTGGTTTCTATCGCGAAGTCGAAGAACAGGGTTATAAAGTTAGCTTTGA

ATCGGCCAGCAAGAAAGAGGTTGATAAACTGGTGGAGGAGGGTAAGCTGTATATGTTTCAGATT

TATAACAAAGACTTTAGCGACAAAAGCCACGGTACTCCTAATCTGCATACGATGTACTTTAAAC

TGCTGTTTGATGAGAATAACCACGGCCAAATCCGTCTCTCCGGTGGAGCAGAACTTTTTATGCG

GCGTGCGAGCCTAAAAAAGGAAGAACTGGTGGTGCATCCCGCCAACAGCCCGATTGCTAACAAA

AATCCAGATAATCCTAAGAAGACCACCACACTGTCGTACGATGTCTATAAGGATAAACGTTTCT

CGGAAGACCAGTATGAATTGCATATACCGATAGCAATTAATAAATGCCCAAAAAACATTTTCAA

AATCAACACTGAAGTTCGTGTGCTGCTGAAACATGATGATAATCCGTATGTGATCGGAATTGAC

CGTGGGGAGAGAAATCTGCTGTATATTGTAGTCGTTGATGGCAAGGGCAACATCGTTGAGCAGT

-continued

```
ATAGCCTGAATGAAATAATTAATAATTTTAACGGTATACGTATTAAAACCGACTATCATAGCCT

GCTGGATAAAAAGGAGAAAGAGCGTTTTGAGGCACGCCAAAATTGGACGAGCATCGAAAACATC

AAGGAACTGAAGGCAGGATATATCAGCCAAGTAGTCCATAAAATCTGTGAACTGGTGGAGAAGT

ACGACGCTGTCATTGCCCTGGAAGACCTCAATAGCGGCTTTAAAAACAGCCGGGTGAAGGTGGA

GAAACAGGTATACCAAAAGTTTGAAAAGATGCTCATTGATAAGCTGAACTATATGGTTGATAAA

AAGAGCAACCCGTGCGCCACTGGCGGTGCACTGAAAGGGTACCAAATTACCAATAAATTTGAAA

GCTTTAAAAGCATGAGCACGCAGAATGGGTTTATTTTTTATATACCAGCATGGCTGACGAGCAA

GATTGACCCCAGCACTGGTTTTGTCAATCTGCTGAAAACCAAATACACAAGCATTGCGGATAGC

AAAAAATTTATTTCGAGCTTCGACCGTATTATGTATGTTCCGGAGGAAGATCTGTTTGAATTTG

CCCTGGATTATAAAAACTTCAGCCGCACCGATGCAGATTATATCAAAAAATGGAAGCTGTACAG

TTATGGTAATCGTATACGTATCTTCCGTAATCCGAAGAAAAACAATGTGTTCGATTGGGAAGAG

GTCTGTCTGACCAGCGCGTATAAAGAACTGTTCAACAAGTACGGAATAAATTATCAGCAAGGTG

ACATTCGCGCACTGCTGTGTGAACAGTCAGATAAAGCATTTTATAGCAGCTTTATGGCGCTGAT

GAGCCTGATGCTCCAGATGCGCAACAGCATAACCGGTCGCACAGATGTTGACTTTCTGATCAGC

CCTGTGAAGAATAGCGACGGCATCTTCTACGATTCCAGGAACTATGAAGCACAGGAAAACGCTA

TTCTGCCTAAAAATGCCGATGCCAACGGCGCCTATAATATTGCACGGAAGGTTCTGTGGGCGAT

TGGACAGTTCAAGAAAGCGGAAGATGAGAAGCTGGATAAGGTAAAAATTGCTATTAGCAATAAG

GAATGGCTGGAGTACGCACAGACATCGGTTAAACACGCGGCCGCTTCCCTGCAGGTAATTAAAT

AA
```

LbCpf1 Native Protein Sequence

SEQ ID NO: 4

```
MLKNVGIDRLDVEKGRKNMSKLEKFTNCYSLSKTLRFKAIPVGKTQENIDNKRLLVEDEKRAED

YKGVKKLLDRYYLSFINDVLHSIKLKNLNNYISLFRKKTRTEKENKELENLEINLRKEIAKAFK

GNEGYKSLFKKDIIETILPEFLDDKDEIALVNSFNGFTTAFTGFFDNRENMFSEEAKSTSIAFR

CINENLTRYISNMDIFEKVDAIFDKHEVQEIKEKILNSDYDVEDFFEGEFFNFVLTQEGIDVYN

AIIGGFVTESGEKIKGLNEYINLYNQKTKQKLPKFKPLYKQVLSDRESLSFYGEGYTSDEEVLE

VFRNTLNKNSEIFSSIKKLEKLFKNFDEYSSAGIFVKNGPAISTISKDIFGEWNVIRDKWNAEY

DDIHLKKKAVVTEKYEDDRRKSFKKIGSFSLEQLQEYADADLSVVEKLKEIIIQKVDEIYKVYG

SSEKLFDADFVLEKSLKKNDAVVAIMKDLLDSVKSFENYIKAFFGEGKETNRDESFYGDFVLAY

DILLKVDHIYDAIRNYVTQKPYSKDKFKLYFQNPQFMGGWDKDKETDYRATILRYGSKYYLAIM

DKKYAKCLQKIDKDDVNGNYEKINYKLLPGPNKMLPKVFFSKKWMAYYNPSEDIQKIYKNGTFK

KGDMFNLNDCHKLIDFFKDSISRYPKWSNAYDFNFSETEKYKDIAGFYREVEEQGYKVSFESAS

KKEVDKLVEEGKLYMFQIYNKDFSDKSHGTPNLHTMYFKLLFDENNHGQIRLSGGAELFMRRAS

LKKEELVVHPANSPIANKNPDNPKKTTTLSYDVYKDKRFSEDQYELHIPIAINKCPKNIFKINT

EVRVLLKHDDNPYVIGIDRGERNLLYIVVVDGKGNIVEQYSLNEIINNFNGIRIKTDYHSLLDK

KEKERFEARQNWTSIENIKELKAGYISQVVHKICELVEKYDAVIALEDLNSGFKNSRVKVEKQV

YQKFEKMLIDKLNYMVDKKSNPCATGGALKGYQITNKFESFKSMSTQNGFIFYIPAWLTSKIDP

STGFVNLLKTKYTSIADSKKFISSFDRIMYVPEEDLFEFALDYKNFSRTDADYIKKWKLYSYGN

RIRIFRNPKKNNVFDWEEVCLTSAYKELFNKYGINYQQGDIRALLCEQSDKAFYSSFMALMSLM

LQMRNSITGRTDVDFLISPVKNSDGIFYDSRNYEAQENAILPKNADANGAYNIARKVLWAIGQF

KKAEDEKLDKVKIAISNKEWLEYAQTSVKH
```

E.coli optimized Lb Cpf1 DNA

SEQ ID NO: 6

ATGCTGAAAAACGTGGGTATTGATCGTCTGGATGTTGAAAAAGGTCGCAAAAATATGAGCAAACTGG

AAAAGTTCACCAACTGTTATAGCCTGAGCAAAACCCTGCGTTTTAAAGCAATTCCGGTTGGTAAAAC

CCAAGAGAACATTGATAATAAACGCCTGCTGGTCGAAGATGAAAAACGCGCTGAAGATTATAAAGGC

GTGAAAAAACTGCTGGATCGCTATTATCTGAGCTTCATTAACGATGTGCTGCACAGCATTAAACTGA

AGAACCTGAACAACTATATCAGCCTGTTTCGTAAAAAAACCCGCACCGAAAAAGAAAACAAAGAGCT

GGAAAACCTGGAAATCAATCTGCGTAAAGAAATCGCCAAAGCGTTTAAAGGTAACGAGGGTTATAAA

AGCCTGTTCAAGAAAGACATCATCGAAACCATTCTGCCGGAATTTCTGGATGATAAAGATGAAATTG

CCCTGGTGAATAGCTTTAATGGCTTTACCACCGCATTTACCGGCTTTTTTGATAATCGCGAAAACAT

GTTCAGCGAAGAAGCAAAAAGCACCAGCATTGCATTTCGCTGCATTAATGAAAATCTGACCCGCTAC

ATTAGCAACATGGATATCTTTGAAAAAGTGGACGCGATCTTCGATAAACACGAAGTGCAAGAGATCA

AAGAGAAATCCTGAACAGCGATTATGACGTCGAAGATTTTTTTGAAGGCGAGTTCTTTAACTTCGT

TCTGACCCAAGAAGGTATCGACGTTTATAACGCAATTATTGGTGGTTTTGTTACCGAAAGCGGTGAG

AAAATCAAAGGCCTGAATGAATATATCAACCTGTATAACCAGAAAACCAAACAGAAACTGCCGAAAT

TCAAACCGCTGTATAAACAGGTTCTGAGCGATCGTGAAAGCCTGAGCTTTTATGGTGAAGGTTATAC

CAGTGATGAAGAGGTTCTGGAAGTTTTTCGTAACACCCTGAATAAAAACAGCGAGATCTTTAGCAGC

ATCAAAAAGCTTGAGAAACTGTTCAAAAACTTTGATGAGTATAGCAGCGCAGGCATCTTTGTTAAAA

ATGGTCCGGCAATTAGCACCATCAGCAAAGATATTTTTGGCGAATGGAATGTGATCCGCGATAAATG

GAATGCCGAATATGATGATATCCACCTGAAAAAAAAGGCCGTGGTGACCGAGAAATATGAAGATGAT

CGTCGTAAAAGCTTCAAGAAAATTGGTAGCTTTAGCCTGGAACAGCTGCAAGAATATGCAGATGCAG

ATCTGAGCGTTGTGGAAAAACTGAAAGAAATCATCATTCAGAAGGTGGACGAGATCTATAAAGTTTA

TGGTAGCAGCGAAAAACTGTTCGATGCAGATTTTGTTCTGGAAAAAAGCCTGAAAAAGAATGATGCC

GTTGTGGCCATTATGAAAGATCTGCTGGATAGCGTTAAGAGCTTCGAGAATTACATCAAAGCCTTTT

TTGGTGAGGGCAAAGAAACCAATCGTGATGAAAGTTTCTATGGCGATTTTGTGCTGGCCTATGATAT

TCTGCTGAAAGTGGACCATATTTATGATGCCATTCGCAATTATGTTACCCAGAAACCGTATAGCAAA

GACAAGTTCAAACTGTACTTTCAGAACCCGCAGTTTATGGGTGGTTGGGATAAAGATAAAGAAACCG

ATTATCGTGCCACCATCCTGCGTTATGGTAGTAAATACTATCTGGCCATCATGGACAAAAAATACGC

AAAATGCCTGCAGAAAATCGACAAAGATGATGTGAATGGCAACTATGAAAAAATCAACTACAAACTG

CTGCCTGGTCCGAATAAAATGCTGCCGAAAGTGTTCTTTAGCAAGAAATGGATGGCCTATTATAACC

CGAGCGAGGATATTCAAAAGATCTACAAAAATGGCACCTTTAAAAAGGGCGACATGTTCAATCTGAA

CGATTGCCACAAACTGATCGATTTCTTCAAAGATTCAATTTCGCGTTATCCGAAATGGTCCAATGCC

TATGATTTTAACTTTAGCGAAACCGAAAAATACAAAGACATTGCCGGTTTTTATCGCGAAGTGGAAG

AACAGGGCTATAAAGTGAGCTTTGAAAGCGCAAGCAAAAAAGAGGTTGATAAGCTGGTTGAAGAGGG

CAAACTGTATATGTTCCAGATTTACAACAAAGATTTTAGCGACAAAAGCCATGGCACCCCGAATCTG

CATACCATGTACTTTAAACTGCTGTTCGACGAAAATAACCATGGTCAGATTCGTCTGAGCGGTGGTG

CCGAACTGTTTATGCGTCGTGCAAGTCTGAAAAAAGAAGAACTGGTTGTTCATCCGGCAAATAGCCC

GATTGCAAACAAAAATCCGGACAATCCGAAAAAAACCACGACACTGAGCTATGATGTGTATAAAGAC

AAACGTTTTAGCGAGGATCAGTATGAACTGCATATCCCGATTGCCATCAATAAATGCCCGAAAAACA

TCTTTAAGATCAACACCGAAGTTCGCGTGCTGCTGAAACATGATGATAATCCGTATGTGATTGGCAT

TGATCGTGGTGAACGTAACCTGCTGTATATTGTTGTTGTTGATGGTAAAGGCAACATCGTGGAACAG

TATAGTCTGAACGAAATTATCAACAACTTTAACGGCATCCGCATCAAAACCGACTATCATAGCCTGC

-continued

```
TGGACAAGAAAGAAAAAGAACGTTTTGAAGCACGTCAGAACTGGACCAGTATTGAAAACATCAAAGA
ACTGAAAGCCGGTTATATTAGCCAGGTGGTTCATAAAATCTGTGAGCTGGTAGAAAAATACGATGCA
GTTATTGCACTGGAAGATCTGAATAGCGGTTTCAAAAATAGCCGTGTGAAAGTCGAAAAACAGGTGT
ATCAGAAATTCGAGAAAATGCTGATCGACAAACTGAACTACATGGTCGACAAAAAAAGCAATCCGTG
TGCAACCGGTGGTGCACTGAAAGGTTATCAGATTACCAACAAATTTGAAAGCTTTAAAAGCATGAGC
ACCCAGAACGGCTTTATCTTCTATATTCCGGCATGGCTGACCAGCAAAATTGATCCGAGCACCGGTT
TTGTGAACCTGCTGAAAACAAAATATACCTCCATTGCCGACAGCAAGAAGTTTATTAGCAGCTTTGA
TCGCATTATGTATGTTCCGGAAGAGGACCTGTTTGAATTCGCACTGGATTACAAAAATTTCAGCCGT
ACCGATGCCGACTACATCAAAAAATGGAAACTGTACAGCTATGGTAACCGCATTCGCATTTTTCGCA
ACCCGAAGAAAAACAATGTGTTCGATTGGGAAGAAGTTTGTCTGACCAGCGCATATAAAGAACTTTT
CAACAAATACGGCATCAACTATCAGCAGGGTGATATTCGTGCACTGCTGTGTGAACAGAGCGATAAA
GCGTTTTATAGCAGTTTTATGGCACTGATGAGCCTGATGCTGCAGATGCGTAATAGCATTACCGGTC
GCACCGATGTGGATTTTCTGATTAGTCCGGTGAAAAATTCCGATGGCATCTTTTATGATAGCCGCAA
TTACGAAGCACAAGAAAATGCAATTCTGCCGAAAAACGCAGATGCAAATGGTGCATATAACATTGCA
CGTAAAGTTCTGTGGGCAATTGGCCAGTTTAAGAAAGCAGAAGATGAGAAGCTGGACAAAGTGAAAA
TTGCGATCAGCAATAAAGAGTGGCTGGAATACGCACAGACCAGCGTTAAACATTGA
```

E.coli optimized Lb Cpf1 AA
SEQ ID NO: 7

```
MLKNVGIDRLDVEKGRKNMSKLEKFTNCYSLSKTLRFKAIPVGKTQENIDNKRLLVEDEKRAEDYKG
VKKLLDRYYLSFINDVLHSIKLKNLNNYISLFRKKTRTEKENKELENLEINLRKEIAKAFKGNEGYK
SLFKKDIIETLPEFLDDKDEIALVNSFNGFTTAFTGFFDNRENMFSEEAKSTSIAFRCINENLTRY
ISNMDIFEKVDAIFDKHEVQEIKEKILNSDYDVEDFFEGEFFNFVLTQEGIDVYNAIIGGFVTESGE
KIKGLNEYINLYNQKTKQLPKFKPLYKQVLSDRESLSFYGEGYTSDEEVLEVFRNTLNKNSEIFSS
IKKLEKLFKNFDEYSSAGIFVKNGPAISTISKDIFGEWNVIRDKWNAEYDDIHLKKKAVVTEKYEDD
RRKSFKKIGSFSLEQLQEYADADLSVVEKLKEIIIQKVDEIYKVYGSSEKLFDADFVLEKSLKKNDA
VVAIMKDLLDSVKSFENYIKAFFGEGKETNRDESFYGDFVLAYDILLKVDHIYDAIRNYVTQKPYSK
DKFKLYFQNPQFMGGWDKDKETDYRATILRYGSKYYLAIMDKKYAKCLQKIDKDDVNGNYEKINYKL
LPGPNKMLPKVFFSKKWMAYYNPSEDIQKIYKNGTFKKGDMFNLNDCHKLIDFFKDSISRYPKWSNA
YDFNFSETEKYKDIAGFYREVEEQGYKVSFESASKKEVDKLVEEGKLYMFQTYNKDFSDKSHGTPNL
HTMYFKLLFDENNHGQIRLSGGAELFMRRASLKKEELVVHPANSPIANKNPDNPKKTTTLSYDVYKD
KRFSEDQYELHIPIAINKCPKNIFKINTEVRVLLKHDDNPYVIGIDRGERNLLYIVVVDGKGNIVEQ
YSLNEIINNFNGIRIKTDYHSLLDKKEKERFEARQNWTSIENIKELKAGYISQVVHKICELVEKYDA
VIALEDLNSGFKNSRVKVEKQVYQKFEKMLIDKLNYMVDKKSNPCATGGALKGYQITNKFESFKSMS
TQNGFIFYIPAWLTSKIDPSTGFVNLLKTKYTSIADSKKFISSFDRIMYVPEEDLFEFALDYKNFSR
TDADYIKKWKLYSYGNRIRIFRNPKKNNVFDWEEVCLTSAYKELFNKYGINYQQGDIRALLCEQSDK
AFYSSFMALMSLMLQMRNSITGRTDVDFLISPVKNSDGIFYDSRNYEAQENAILPKNADANGAYNIA
RKVLWAIGQFKKAEDEKLDKVKIAISNKEWLEYAQTSVKH
```

Hs optimized Lb Cpf1 DNA
SEQ ID NO: 9

```
ATGCTGAAGAACGTGGGCATCGACCGGCTGGACGTGGAAAAGGGCAGAAAGAACATGAGCAAGCTCG
AGAAGTTCACCAACTGCTACAGCCTGAGCAAGACCCTGCGGTTCAAGGCCATTCCTGTGGGCAAGAC
CCAAGAGAACATCGACAACAAGCGGCTGCTGGTGGAAGATGAGAAGAGAGCCGAGGACTACAAGGGC
```

-continued

```
GTGAAGAAGCTGCTGGACCGGTACTACCTGAGCTTCATCAACGACGTGCTGCACAGCATCAAGCTCA
AGAACCTGAACAACTACATCAGCCTGTTCCGGAAGAAAACCCGGACCGAGAAAGAGAACAAAGAGCT
GGAAAACCTCGAGATCAACCTGCGGAAAGAGATCGCCAAGGCCTTCAAGGGCAACGAGGGCTACAAG
AGCCTGTTCAAGAAGGACATCATCGAGACAATCCTGCCTGAGTTCCTGGACGACAAGGACGAGATCG
CCCTGGTCAACAGCTTCAACGGCTTCACAACCGCCTTCACCGGCTTTTTCGACAACCGCGAGAATAT
GTTCAGCGAGGAAGCCAAGAGCACCTCTATCGCCTTCCGGTGCATCAACGAGAATCTGACCCGGTAC
ATCAGCAACATGGATATCTTCGAGAAGGTGGACGCCATCTTCGACAAGCACGAGGTGCAAGAGATCA
AAGAAAGATCCTGAACAGCGACTACGACGTCGAGGACTTCTTCGAGGGCGAGTTCTTCAACTTCGT
GCTGACACAAGAGGGCATCGATGTGTACAACGCCATCATCGGCGGCTTCGTGACAGAGAGCGGCGAG
AAGATCAAGGGCCTGAACGAGTACATCAACCTCTACAACCAGAAAACGAAGCAGAAGCTGCCCAAGT
TCAAGCCCCTGTACAAACAGGTGCTGAGCGACAGAGAGAGCCTGTCCTTTTACGGCGAGGGCTATAC
CAGCGACGAAGAGGTGCTGGAAGTGTTCAGAAACACCCTGAACAAGAACAGCGAGATCTTCAGCTCC
ATCAAGAAGCTCGAAAAGCTGTTTAAGAACTTCGACGAGTACAGCAGCGCCGGCATCTTCGTGAAGA
ATGGCCCTGCCATCAGCACCATCTCCAAGGACATCTTCGGCGAGTGGAACGTGATCCGGGACAAGTG
GAACGCCGAGTACGACGACATCCACCTGAAGAAAAAGGCCGTGGTCACCGAGAAGTACGAGGACGAC
AGAAGAAAGAGCTTCAAGAAGATCGGCAGCTTCAGCCTGGAACAGCTGCAAGAGTACGCCGACGCCG
ATCTGAGCGTGGTGGAAAAGCTGAAAGAGATTATCATCCAGAAGGTCGACGAGATCTACAAGGTGTA
CGGCAGCAGCGAGAAGCTGTTCGACGCCGACTTTGTGCTGGAAAAGAGCCTCAAAAAGAACGACGCC
GTGGTGGCCATCATGAAGGACCTGCTGGATAGCGTGAAGTCCTTCGAGAACTATATTAAGGCCTTCT
TTGGCGAGGGCAAAGAGACAAACCGGGACGAGAGCTTCTACGGCGATTTCGTGCTGGCCTACGACAT
CCTGCTGAAAGTGGACCACATCTACGACGCCATCCGGAACTACGTGACCCAGAAGCCTTACAGCAAG
GACAAGTTTAAGCTGTACTTCCAGAATCCGCAGTTCATGGGCGGCTGGGACAAAGACAAAGAAACCG
ACTACCGGGCCACCATCCTGAGATACGGCTCCAAGTACTATCTGGCCATTATGGACAAGAAATACGC
CAAGTGCCTGCAGAAGATCGATAAGGACGACGTGAACGGCAACTACGAGAAGATTAACTACAAGCTG
CTGCCCGGACCTAACAAGATGCTGCCTAAGGTGTTCTTTAGCAAGAAATGGATGGCCTACTACAACC
CCAGCGAGGATATCCAGAAAATCTACAAGAACGGCACCTTCAAGAAAGGCGACATGTTCAACCTGAA
CGACTGCCACAAGCTGATCGATTTCTTCAAGGACAGCATCAGCAGATACCCCAAGTGGTCCAACGCC
TACGACTTCAATTTCAGCGAGACAGAGAAGTATAAGGATATCGCCGGGTTCTACCGCGAGGTGGAAG
AACAGGGCTATAAGGTGTCCTTTGAGAGCGCCAGCAAGAAAGAGGTGGACAAGCTGGTCGAAGAGGG
CAAGCTGTACATGTTCCAGATCTATAACAAGGACTTCTCCGACAAGAGCCACGGCACCCCTAACCTG
CACACCATGTACTTTAAGCTGCTGTTCGATGAGAACAACCACGGCCAGATCAGACTGTCTGGCGGAG
CCGAGCTGTTTATGAGAAGGGCCAGCCTGAAAAAAGAGGAACTGGTCGTTCACCCCGCCAACTCTCC
AATCGCCAACAAGAACCCCGACAATCCCAAGAAACCACCACACTGAGCTACGACGTGTACAAGGAT
AAGCGGTTCTCCGAGGACCAGTACGAGCTGCACATCCCTATCGCCATCAACAAGTGCCCCAAGAATA
TCTTCAAGATCAACACCGAAGTGCGGGTGCTGCTGAAGCACGACGACAACCCTTACGTGATCGGCAT
CGACAGAGGCGAGCGGAACCTGCTGTATATCGTGGTGGTGGACGGCAAGGGCAATATCGTGGAACAG
TACTCCCTGAATGAGATCATCAACAACTTCAATGGCATCCGGATCAAGACGGACTACCACAGCCTGC
TGGACAAAAAAGAGAAAGAACGCTTCGAGGCCCGGCAGAACTGGACCAGCATCGAGAACATCAAAGA
ACTGAAGGCCGGCTACATCTCCCAGGTGGTGCACAAGATCTGCGAGCTGGTTGAGAAGTATGACGCC
GTGATTGCCCTGGAAGATCTGAATAGCGGCTTTAAGAACAGCCGCGTGAAGGTCGAGAAACAGGTGT
ACCAGAAATTCGAGAAGATGCTGATCGACAAGCTGAACTACATGGTCGACAAGAAGTCTAACCCCTG
```

-continued

```
CGCCACAGGCGGAGCCCTGAAGGGATATCAGATCACCAACAAGTTCGAGTCCTTCAAGAGCATGAGC

ACCCAGAATGGCTTCATCTTCTACATCCCCGCCTGGCTGACCAGCAAGATCGATCCTAGCACCGGAT

TCGTGAACCTGCTCAAGACCAAGTACACCAGCATTGCCGACAGCAAGAAGTTCATCTCCAGCTTCGA

CCGGATTATGTACGTGCCCGAAGAGGACCTGTTCGAATTCGCCCTGGATTACAAGAACTTCAGCCGG

ACCGATGCCGACTATATCAAGAAGTGGAAGCTGTATAGCTACGGCAACCGCATCCGCATCTTCAGAA

ACCCGAAGAAAAACAACGTGTTCGACTGGGAAGAAGTGTGCCTGACCAGCGCCTACAAAGAACTCTT

CAACAAATACGGCATCAACTACCAGCAGGGCGACATCAGAGCCCTGCTGTGCGAGCAGAGCGACAAG

GCCTTTTACAGCTCCTTCATGGCCCTGATGTCCCTGATGCTGCAGATGCGGAATAGCATCACCGGCA

GGACCGACGTGGACTTCCTGATCAGCCCTGTGAAGAATTCCGACGGGATCTTCTACGACAGCAGAAA

CTACGAGGCTCAAGAGAACGCCATCCTGCCTAAGAACGCCGATGCCAACGGCGCCTATAATATCGCC

AGAAAGGTGCTGTGGGCCATCGGCCAGTTTAAGAAGGCCGAGGACGAGAAACTGGACAAAGTGAAGA

TCGCCATCTCTAACAAAGAGTGGCTGGAATACGCCCAGACCAGCGTGAAACAC
```

Hs optimized Lb Cpf1 AA

SEQ ID NO: 10

```
MLKNVGIDRLDVEKGRKNMSKLEKFTNCYSLSKTLRFKAIPVGKTQENIDNKRLLVEDEKRAEDYKG

VKKLLDRYYLSFINDVLHSIKLKNLNNYISLFRKKTRTEKENKELENLEINLRKEIAKAFKGNEGYK

SLFKKDIIETILPEFLDDKDEIALVNSFNGFTTAFTGFFDNRENMFSEEAKSTSIAFRCINENLTRY

ISNMDIFEKVDAIFDKHEVQEIKEKILNSDYDVEDFFEGEFFNFVLTQEGIDVYNAIIGGFVTESGE

KIKGLNEYINLYNQKTKQLPKFKPLYKQVLSDRESLSFYGEGYTSDEEVLEVFRNTLNKNSEIFSS

IKKLEKLFKNFDEYSSAGIFVKNGPAISTISKDIFGEWNVIRDKWNAEYDDIHLKKKAVVTEKYEDD

RRKSFKKIGSFSLEQLQEYADADLSVVEKLKEIIIQKVDEIYKVYGSSEKLFDADFVLEKSLKKNDA

VVAIMKDLLDSVKSFENYIKAFFGEGKETNRDESFYGDFVLAYDILLKVDHIYDAIRNYVTQKPYSK

DKFKLYFQNPQFMGGWDKDKETDYRATILRYGSKYYLAIMDKKYAKCLQKIDKDDVNGNYEKINYKL

LPGPNKMLPKVFFSKKWMAYYNPSEDIQKIYKNGTFKKGDMFNLNDCHKLIDFFKDSISRYPKWSNA

YDFNFSETEKYKDIAGFYREVEEQGYKVSFESASKKEVDKLVEEGKLYMFQTYNKDFSDKSHGTPNL

HTMYFKLLFDENNHGQIRLSGGAELFMRRASLKKEELVVHPANSPIANKNPDNPKKTTTLSYDVYKD

KRFSEDQYELHIPIAINKCPKNIFKINTEVRVLLKHDDNPYVIGIDRGERNLLYIVVVDGKGNIVEQ

YSLNEIINNFNGIRIKTDYHSLLDKKEKERFEARQNWTSIENIKELKAGYISQVVHKICELVEKYDA

VIALEDLNSGFKNSRVKVEKQVYQKFEKMLIDKLNYMVDKKSNPCATGGALKGYQITNKFESFKSMS

TQNGFIFYIPAWLTSKIDPSTGFVNLLKTKYTSIADSKKFISSFDRIMYVPEEDLFEFALDYKNFSR

TDADYIKKWKLYSYGNRIRIFRNPKKNNVFDWEEVCLTSAYKELFNKYGINYQQGDIRALLCEQSDK

AFYSSFMALMSLMLQMRNSITGRTDVDFLISPVKNSDGIFYDSRNYEAQENAILPKNADANGAYNIA

RKVLWAIGQFKKAEDEKLDKVKIAISNKEWLEYAQTSVKH
```

E.coli optimized Lb Cpf1 with flanking NLS's, V5 tag and
6x His - DNA

SEQ ID NO: 13

```
ATGGGTAAACCGATTCCGAATCCGCTGCTGGGTCTGGATAGCACCGCACCGAAAAAAAAACGTAAAG

TTGGTATTCATGGTGTTCCGGCAGCACTGAAAAACGTGGGTATTGATCGTCTGGATGTTGAAAAAGG

TCGCAAAAATATGAGCAAACTGGAAAAGTTCACCAACTGTTATAGCCTGAGCAAACCCTGCGTTTT

AAAGCAATTCCGGTTGGTAAAACCCAAGAGAACATTGATAATAAACGCCTGCTGGTCGAAGATGAAA

AACGCGCTGAAGATTATAAAGGCGTGAAAAAACTGCTGGATCGCTATTATCTGAGCTTCATTAACGA

TGTGCTGCACAGCATTAAACTGAAGAACCTGAACAACTATATCAGCCTGTTTCGTAAAAAAACCCGC

ACCGAAAAAGAAAACAAAGAGCTGGAAAACCTGGAAATCAATCTGCGTAAAGAAATCGCCAAAGCGT
```

-continued

TTAAAGGTAACGAGGGTTATAAAAGCCTGTTCAAGAAAGACATCATCGAAACCATTCTGCCGGAATT
TCTGGATGATAAAGATGAAATTGCCCTGGTGAATAGCTTTAATGGCTTTACCACCGCATTTACCGGC
TTTTTTGATAATCGCGAAAACATGTTCAGCGAAGAAGCAAAAAGCACCAGCATTGCATTTCGCTGCA
TTAATGAAAATCTGACCCGCTACATTAGCAACATGGATATCTTTGAAAAAGTGGACGCGATCTTCGA
TAAACACGAAGTGCAAGAGATCAAAGAGAAAATCCTGAACAGCGATTATGACGTCGAAGATTTTTTT
GAAGGCGAGTTCTTTAACTTCGTTCTGACCCAAGAAGGTATCGACGTTTATAACGCAATTATTGGTG
GTTTTGTTACCGAAAGCGGTGAGAAAATCAAAGGCCTGAATGAATATATCAACCTGTATAACCAGAA
AACCAAACAGAAACTGCCGAAATTCAAACCGCTGTATAAACAGGTTCTGAGCGATCGTGAAAGCCTG
AGCTTTTATGGTGAAGGTTATACCAGTGATGAAGAGGTTCTGGAAGTTTTTCGTAACACCCTGAATA
AAAACAGCGAGATCTTTAGCAGCATCAAAAAGCTTGAGAAACTGTTCAAAAACTTTGATGAGTATAG
CAGCGCAGGCATCTTTGTTAAAAATGGTCCGGCAATTAGCACCATCAGCAAAGATATTTTTGGCGAA
TGGAATGTGATCCGCGATAAATGGAATGCCGAATATGATGATATCCACCTGAAAAAAAAGGCCGTGG
TGACCGAGAAATATGAAGATGATCGTCGTAAAAGCTTCAAGAAAATTGGTAGCTTTAGCCTGGAACA
GCTGCAAGAATATGCAGATGCAGATCTGAGCGTTGTGGAAAAACTGAAAGAAATCATCATTCAGAAG
GTGGACGAGATCTATAAAGTTTATGGTAGCAGCGAAAAACTGTTCGATGCAGATTTTGTTCTGGAAA
AAAGCCTGAAAAAGAATGATGCCGTTGTGGCCATTATGAAAGATCTGCTGGATAGCGTTAAGAGCTT
CGAGAATTACATCAAAGCCTTTTTTGGTGAGGGCAAAGAAACCAATCGTGATGAAAGTTTCTATGGC
GATTTTGTGCTGGCCTATGATATTCTGCTGAAAGTGGACCATATTTATGATGCCATTCGCAATTATG
TTACCCAGAAACCGTATAGCAAAGACAAGTTCAAACTGTACTTTCAGAACCCGCAGTTTATGGGTGG
TTGGGATAAAGATAAAGAAACCGATTATCGTGCCACCATCCTGCGTTATGGTAGTAAATACTATCTG
GCCATCATGGACAAAAAATACGCAAAATGCCTGCAGAAAATCGACAAAGATGATGTGAATGGCAACT
ATGAAAAAATCAACTACAAACTGCTGCCTGGTCCGAATAAAATGCTGCCGAAAGTGTTCTTTAGCAA
GAAATGGATGGCCTATTATAACCCGAGCGAGGATATTCAAAAGATCTACAAAAATGGCACCTTTAAA
AAGGGCGACATGTTCAATCTGAACGATTGCCACAAACTGATCGATTTCTTCAAAGATTCAATTTCGC
GTTATCCGAAATGGTCCAATGCCTATGATTTTAACTTTAGCGAAACCGAAAAATACAAAGACATTGC
CGGTTTTTATCGCGAAGTGGAAGAACAGGGCTATAAAGTGAGCTTTGAAAGCGCAAGCAAAAAGAG
GTTGATAAGCTGGTTGAAGAGGGCAAACTGTATATGTTCCAGATTTACAACAAAGATTTTAGCGACA
AAAGCCATGGCACCCCGAATCTGCATACCATGTACTTTAAACTGCTGTTCGACGAAAATAACCATGG
TCAGATTCGTCTGAGCGGTGGTGCCGAACTGTTTATGCGTCGTGCAAGTCTGAAAAAAGAAGAACTG
GTTGTTCATCCGGCAAATAGCCCGATTGCAAACAAAAATCCGGACAATCCGAAAAAAACCACGACAC
TGAGCTATGATGTGTATAAAGACAAACGTTTTAGCGAGGATCAGTATGAACTGCATATCCCGATTGC
CATCAATAAATGCCCGAAAAACATCTTTAAGATCAACACCGAAGTTCGCGTGCTGCTGAAACATGAT
GATAATCCGTATGTGATTGGCATTGATCGTGGTGAACGTAACCTGCTGTATATTGTTGTTGTTGATG
GTAAAGGCAACATCGTGGAACAGTATAGTCTGAACGAAATTATCAACAACTTTAACGGCATCCGCAT
CAAAACCGACTATCATAGCCTGCTGGACAAGAAAGAAAAAGAACGTTTTGAAGCACGTCAGAACTGG
ACCAGTATTGAAAACATCAAAGAACTGAAAGCCGGTTATATTAGCCAGGTGGTTCATAAAATCTGTG
AGCTGGTAGAAAATACGATGCAGTTATTGCACTGGAAGATCTGAATAGCGGTTTCAAAAATAGCCG
TGTGAAAGTCGAAAAACAGGTGTATCAGAAATTCGAGAAAATGCTGATCGACAAACTGAACTACATG
GTCGACAAAAAAAGCAATCCGTGTGCAACCGGTGGTGCACTGAAAGGTTATCAGATTACCAACAAAT
TTGAAAGCTTTAAAAGCATGAGCACCCAGAACGGCTTTATCTTCTATATTCCGGCATGGCTGACCAG

-continued

```
CAAAATTGATCCGAGCACCGGTTTTGTGAACCTGCTGAAAACAAAATATACCTCCATTGCCGACAGC

AAGAAGTTTATTAGCAGCTTTGATCGCATTATGTATGTTCCGGAAGAGGACCTGTTTGAATTCGCAC

TGGATTACAAAAATTTCAGCCGTACCGATGCCGACTACATCAAAAAATGGAAACTGTACAGCTATGG

TAACCGCATTCGCATTTTTCGCAACCCGAAGAAAAACAATGTGTTCGATTGGGAAGAAGTTTGTCTG

ACCAGCGCATATAAAGAACTTTTCAACAAATACGGCATCAACTATCAGCAGGGTGATATTCGTGCAC

TGCTGTGTGAACAGAGCGATAAAGCGTTTTATAGCAGTTTTATGGCACTGATGAGCCTGATGCTGCA

GATGCGTAATAGCATTACCGGTCGCACCGATGTGGATTTTCTGATTAGTCCGGTGAAAAATTCCGAT

GGCATCTTTTATGATAGCCGCAATTACGAAGCACAAGAAAATGCAATTCTGCCGAAAAACGCAGATG

CAAATGGTGCATATAACATTGCACGTAAAGTTCTGTGGGCAATTGGCCAGTTTAAGAAAGCAGAAGA

TGAGAAGCTGGACAAAGTGAAAATTGCGATCAGCAATAAAGAGTGGCTGGAATACGCACAGACCAGC

GTTAAACATCCGAAAAAAAAACGCAAAGTGCTCGAGCACCACCACCACCACCACTGA
```

Amino acid sequence for LbCpf1 fusion, with 5'- and 3'-flanking NLS's, 5'-V5 tag and 3'-6x His, used for gene editing in both E. coli and human cells

SEQ ID NO: 14

MGKPIPNPLLGLDSTAPKKKRKVGIHGVPAALKNVGIDRLDVEKGRKNMSKLEKFTNCYSLSKTLRF

KAIPVGKTQENIDNKRLLVEDEKRAEDYKGVKKLLDRYYLSFINDVLHSIKLKNLNNYISLFRKKTR

TEKENKELENLEINLRKEIAKAFKGNEGYKSLFKKDIIETILPEFLDDKDEIALVNSFNGFTTAFTG

FFDNRENMFSEEAKSTSIAFRCINENLTRYISNMDIFEKVDAIFDKHEVQEIKEKILNSDYDVEDFF

EGEFFNFVLTQEGIDVYNAIIGGFVTESGEKIKGLNEYINLYNQKTKQKLPKFKPLYKQVLSDRESL

SFYGEGYTSDEEVLEVFRNTLNKNSEIFSSIKKLEKLFKNFDEYSSAGIFVKNGPAISTISKDIFGE

WNVIRDKWNAEYDDIHLKKKAVVTEKYEDDRRKSFKKIGSFSLEQLQEYADADLSVVEKLKEIIIQK

VDEIYKVYGSSEKLFDADFVLEKSLKKNDAVVAIMKDLLDSVKSFENYIKAFFGEGKETNRDESFYG

DFVLAYDILLKVDHIYDAIRNYVTQKPYSKDKFKLYFQNPQFMGGWDKDKETDYRATILRYGSKYYL

AIMDKKYAKCLQKIDKDDVNGNYEKINYKLLPGPNKMLPKVFFSKKWMAYYNPSEDIQKIYKNGTFK

KGDMFNLNDCHKLIDFFKDSISRYPKWSNAYDFNFSETEKYKDIAGFYREVEEQGYKVSFESASKKE

VDKLVEEGKLYMFQTYNKDFSDKSHGTPNLHTMYFKLLFDENNHGQIRLSGGAELFMRRASLKKEEL

VVHPANSPIANKNPDNPKKTTTLSYDVYKDKRFSEDQYELHIPIAINKCPKNIFKINTEVRVLLKHD

DNPYVIGIDRGERNLLYIVVVDGKGNIVEQYSLNEIINNFNGIRIKTDYHSLLDKKEKERFEARQNW

TSIENIKELKAGYISQVVHKICELVEKYDAVIALEDLNSGFKNSRVKVEKQVYQKFEKMLIDKLNYM

VDKKSNPCATGGALKGYQITNKFESFKSMSTQNGFIFYIPAWLTSKIDPSTGFVNLLKTKYTSIADS

KKFISSFDRIMYVPEEDLFEFALDYKNFSRTDADYIKKWKLYSYGNRIRIFRNPKKNNVFDWEEVCL

TSAYKELFNKYGINYQQGDIRALLCEQSDKAFYSSFMALMSLMLQMRNSITGRTDVDFLISPVKNSD

GIFYDSRNYEAQENAILPKNADANGAYNIARKVLWAIGQFKKAEDEKLDKVKIAISNKEWLEYAQTS

VKHPKKKRKVLEHHHHHH

Hs optimized Lb Cpf1 with flanking NLS's, V5 tag and 6x His - DNA

SEQ ID NO: 17

```
ATGGGCAAGCCCATTCCTAATCCTCTGCTGGGCCTCGACAGCACAGCCCCTAAGAAAAAGCGGAAAG

TGGGCATCCATGGCGTGCCAGCCGCTCTGAAGAATGTGGGCATCGACAGACTGGACGTGGAAAAGGG

CAGAAAGAACATGAGCAAGCTCGAGAAGTTCACCAACTGCTACAGCCTGAGCAAGACCCTGCGGTTC

AAGGCCATTCCTGTGGGCAAGACCCAAGAGAACATCGACAACAAGCGGCTGCTGGTGGAAGATGAGA

AGAGAGCCGAGGACTACAAGGGCGTGAAGAAGCTGCTGGACCGGTACTACCTGAGCTTCATCAACGA

CGTGCTGCACAGCATCAAGCTGAAGAACCTGAACAACTACATCAGCCTGTTCCGGAAGAAACCCGG

ACCGAGAAGAGAACAAAGAGCTGGAAAACCTCGAGATCAACCTGCGGAAAGAGATCGCCAAGGCCT
```

-continued

```
TCAAGGGCAACGAGGGCTACAAGAGCCTGTTCAAGAAGGACATCATCGAGACAATCCTGCCTGAGTT
CCTGGACGACAAGGACGAGATCGCCCTGGTCAACAGCTTCAACGGCTTCACAACCGCCTTCACCGGC
TTTTTCGACAACCGCGAGAATATGTTCAGCGAGGAAGCCAAGAGCACCTCTATCGCCTTCCGGTGCA
TCAACGAGAATCTGACCCGGTACATCAGCAACATGGATATCTTCGAGAAGGTGGACGCCATCTTCGA
CAAGCACGAGGTGCAAGAGATCAAAGAAAAGATCCTGAACAGCGACTACGACGTCGAGGACTTCTTC
GAGGGCGAGTTCTTCAACTTCGTGCTGACACAAGAGGGCATCGATGTGTACAACGCCATCATCGGCG
GCTTCGTGACAGAGAGCGGCGAGAAGATCAAGGGCCTGAACGAGTACATCAACCTCTACAACCAGAA
AACGAAGCAGAAGCTGCCCAAGTTCAAGCCCCTGTACAAACAGGTGCTGAGCGACAGAGAGAGCCTG
TCCTTTTACGGCGAGGGCTATACCAGCGACGAAGAGGTGCTGGAAGTGTTCAGAAACACCCTGAACA
AGAACAGCGAGATCTTCAGCTCCATCAAGAAGCTCGAAAAGCTGTTTAAGAACTTCGACGAGTACAG
CAGCGCCGGCATCTTCGTGAAGAATGGCCCTGCCATCAGCACCATCTCCAAGGACATCTTCGGCGAG
TGGAACGTGATCCGGGACAAGTGGAACGCCGAGTACGACGACATCCACCTGAAGAAAAAGGCCGTGG
TCACCGAGAAGTACGAGGACGACAGAAGAAAGAGCTTCAAGAAGATCGGCAGCTTCAGCCTGGAACA
GCTGCAAGAGTACGCCGACGCCGATCTGAGCGTGGTGGAAAAGCTGAAAGAGATTATCATCCAGAAG
GTCGACGAGATCTACAAGGTGTACGGCAGCAGCGAGAAGCTGTTCGACGCCGACTTTGTGCTGGAAA
AGAGCCTCAAAAAGAACGACGCCGTGGTGGCCATCATGAAGGACCTGCTGGATAGCGTGAAGTCCTT
CGAGAACTATATTAAGGCCTTCTTTGGCGAGGGCAAAGAGACAAACCGGGACGAGAGCTTCTACGGC
GATTTCGTGCTGGCCTACGACATCCTGCTGAAAGTGGACCACATCTACGACGCCATCCGGAACTACG
TGACCCAGAAGCCTTACAGCAAGGACAAGTTTAAGCTGTACTTCCAGAATCCGCAGTTCATGGGCGG
CTGGGACAAAGACAAAGAAACCGACTACCGGGCCACCATCCTGAGATACGGCTCCAAGTACTATCTG
GCCATTATGGACAAGAAATACGCCAAGTGCCTGCAGAAGATCGATAAGGACGACGTGAACGGCAACT
ACGAGAAGATTAACTACAAGCTGCTGCCCGGACCTAACAAGATGCTGCCTAAGGTGTTCTTTAGCAA
GAAATGGATGGCCTACTACAACCCCAGCGAGGATATCCAGAAAATCTACAAGAACGGCACCTTCAAG
AAAGGCGACATGTTCAACCTGAACGACTGCCACAAGCTGATCGATTTCTTCAAGGACAGCATCAGCA
GATACCCCAAGTGGTCCAACGCCTACGACTTCAATTTCAGCGAGACAGAGAAGTATAAGGATATCGC
CGGGTTCTACCGCGAGGTGGAAGAACAGGGCTATAAGGTGTCCTTTGAGAGCGCCAGCAAGAAAGAG
GTGGACAAGCTGGTCGAAGAGGGCAAGCTGTACATGTTCCAGATCTATAACAAGGACTTCTCCGACA
AGAGCCACGGCACCCCTAACCTGCACACCATGTACTTTAAGCTGCTGTTCGATGAGAACAACCACGG
CCAGATCAGACTGTCTGGCGGAGCCGAGCTGTTTATGAGAAGGGCCAGCCTGAAAAAAGAGGAACTG
GTCGTTCACCCCGCCAACTCTCCAATCGCCAACAAGAACCCCGACAATCCCAAGAAACCACCACAC
TGAGCTACGACGTGTACAAGGATAAGCGGTTCTCCGAGGACCAGTACGAGCTGCACATCCCTATCGC
CATCAACAAGTGCCCCAAGAATATCTTCAAGATCAACACCGAAGTGCGGGTGCTGCTGAAGCACGAC
GACAACCCTTACGTGATCGGCATCGATCGGGGCGAGAGAAACCTGCTGTATATCGTGGTGGTGGACG
GCAAGGGCAATATCGTGGAACAGTACTCCCTGAATGAGATCATCAACAACTTCAATGGCATCCGGAT
CAAGACGGACTACCACAGCCTGCTGGACAAAAAGAGAAAGAACGCTTCGAGGCCAGGCAGAACTGG
ACCAGCATCGAGAACATCAAAGAACTGAAGGCCGGCTACATCTCCCAGGTGGTGCACAAGATCTGCG
AGCTGGTTGAGAAGTATGACGCCGTGATTGCCCTGGAAGATCTGAATAGCGGCTTTAAGAACAGCCG
CGTGAAGGTCGAGAAACAGGTGTACCAGAAATTCGAGAAGATGCTGATCGACAAGCTGAACTACATG
GTCGACAAGAAGTCTAACCCCTGCGCCACAGGCGGAGCCCTGAAGGGATATCAGATCACCAACAAGT
TCGAGTCCTTCAAGAGCATGAGCACCCAGAATGGCTTCATCTTCTACATCCCCGCCTGGCTGACCAG
```

-continued

```
CAAGATCGATCCTAGCACCGGATTCGTGAACCTGCTCAAGACCAAGTACACCAGCATTGCCGACAGC
AAGAAGTTCATCTCCAGCTTCGACCGGATTATGTACGTGCCCGAAGAGGACCTGTTCGAATTCGCCC
TGGATTACAAGAACTTCAGCCGGACCGATGCCGACTATATCAAGAAGTGGAAGCTGTATAGCTACGG
CAACCGCATCCGCATCTTCAGAAACCCGAAGAAAAACAACGTGTTCGACTGGGAAGAAGTGTGCCTG
ACCAGCGCCTACAAAGAACTCTTCAACAAATACGGCATCAACTACCAGCAGGGCGACATCAGAGCCC
TGCTGTGCGAGCAGAGCGACAAGGCCTTTTACAGCTCCTTCATGGCCCTGATGAGCCTGATGCTGCA
GATGCGGAATAGCATCACCGGCAGAACCGACGTGGACTTCCTGATCAGCCCCGTGAAAAACTCCGAC
GGCATCTTTTACGACAGCCGGAATTACGAGGCTCAAGAGAACGCCATCCTGCCTAAGAACGCCGATG
CCAACGGCGCCTATAATATCGCCAGAAAGGTGCTGTGGGCCATCGGCCAGTTTAAGAAGGCCGAGGA
CGAGAAACTGGACAAAGTGAAGATCGCCATCTCTAACAAAGAGTGGCTGGAATACGCCCAGACCAGC
GTGAAGCACCCCAAAAAGAAACGGAAAGTGCTGGAACACCACCACCATCACCAC
```

*E.coli* optimized Lb Cpf1 with OpT NLS and 6x His - AA
SEQ ID NO: 20

```
MGDPLKNVGIDRLDVEKGRKNMSKLEKFTNCYSLSKTLRFKAIPVGKTQENIDNKRLLVEDEKRAED
YKGVKKLLDRYYLSFINDVLHSIKLKNLNNYISLFRKKTRTEKENKELENLEINLRKEIAKAFKGNE
GYKSLFKKDIIETILPEFLDDKDEIALVNSFNGFTTAFTGFFDNRENMFSEEAKSTSIAFRCINENL
TRYISNMDIFEKVDAIFDKHEVQEIKEKILNSDYDVEDFFEGEFFNFVLTQEGIDVYNAIIGGFVTE
SGEKIKGLNEYINLYNQKTKQKLPKFKPLYKQVLSDRESLSFYGEGYTSDEEVLEVFRNTLNKNSEI
FSSIKKLEKLFKNFDEYSSAGIFVKNGPAISTISKDIFGEWNVIRDKWNAEYDDIHLKKKAVVTEKY
EDDRRKSFKKIGSFSLEQLQEYADADLSVVEKLKEIIIQKVDEIYKVYGSSEKLFDADFVLEKSLKK
NDAVVAIMKDLLDSVKSFENYIKAFFGEGKETNRDESFYGDFVLAYDILLKVDHIYDAIRNYVTQKP
YSKDKFKLYFQNPQFMGGWDKDKETDYRATILRYGSKYYLAIMDKKYAKCLQKIDKDDVNGNYEKIN
YKLLPGPNKMLPKVFFSKKWMAYYNPSEDIQKIYKNGTFKKGDMFNLNDCHKLIDFFKDSISRYPKW
SNAYDFNFSETEKYKDIAGFYREVEEQGYKVSFESASKKEVDKLVEEGKLYMFQIYNKDFSDKSHGT
PNLHTMYFKLLFDENNHGQIRLSGGAELFMRRASLKKEELVVHPANSPIANKNPDNPKKTTTLSYDV
YKDKRFSEDQYELHIPIAINKCPKNIFKINTEVRVLLKHDDNPYVIGIDRGERNLLYIVVVDGKGNI
VEQYSLNEIINNFNGIRIKTDYHSLLDKKEKERFEARQNWTSIENIKELKAGYISQVVHKICELVEK
YDAVIALEDLNSGFKNSRVKVEKQVYQKFEKMLIDKLNYMVDKKSNPCATGGALKGYQITNKFESFK
SMSTQNGFIFYIPAWLTSKIDPSTGFVNLLKTKYTSIADSKKFISSFDRIMYVPEEDLFEFALDYKN
FSRTDADYIKKWKLYSYGNRIRIFRNPKKNNVFDWEEVCLTSAYKELFNKYGINYQQGDIRALLCEQ
SDKAFYSSFMALMSLMLQMRNSITGRTDVDFLISPVKNSDGIFYDSRNYEAQENAILPKNADANGAY
NIARKVLWAIGQFKKAEDEKLDKVKIAISNKEWLEYAQTSVKHGR**SSDDEATADSQHAAPPKKKRKV
LEHHHHHH**
```

*E.coli* optimized Lb Cpf1 with OpT NLS and 6x His - DNA
SEQ ID NO: 23

```
ATGGGGGATCCACTGAAAAACGTGGGTATTGATCGTCTGGATGTTGAAAAAGGTCGCAAAAATATGA
GCAAACTGGAAAAGTTCACCAACTGTTATAGCCTGAGCAAAACCCTGCGTTTTAAAGCAATTCCGGT
TGGTAAAACCCAAGAGAACATTGATAATAAACGCCTGCTGGTCGAAGATGAAAAACGCGCTGAAGAT
TATAAAGGCGTGAAAAAACTGCTGGATCGCTATTATCTGAGCTTCATTAACGATGTGCTGCACAGCA
TTAAACTGAAGAACCTGAACAACTATATCAGCCTGTTTCGTAAAAAACCCGCACCGAAAAAGAAAA
CAAAGAGCTGGAAAACCTGGAAATCAATCTGCGTAAAGAAATCGCCAAAGCGTTTAAAGGTAACGAG
GGTTATAAAAGCCTGTTCAAGAAAGACATCATCGAAACCATTCTGCCGGAATTTCTGGATGATAAAG
ATGAAATTGCCCTGGTGAATAGCTTTAATGGCTTTACCACCGCATTTACCGGCTTTTTTGATAATCG
```

```
CGAAAACATGTTCAGCGAAGAAGCAAAAAGCACCAGCATTGCATTTCGCTGCATTAATGAAAATCTG

ACCCGCTACATTAGCAACATGGATATCTTTGAAAAAGTGGACGCGATCTTCGATAAACACGAAGTGC

AAGAGATCAAAGAGAAAATCCTGAACAGCGATTATGACGTCGAAGATTTTTTTGAAGGCGAGTTCTT

TAACTTCGTTCTGACCCAAGAAGGTATCGACGTTTATAACGCAATTATTGGTGGTTTTGTTACCGAA

AGCGGTGAGAAAATCAAAGGCCTGAATGAATATATCAACCTGTATAACCAGAAAACCAAACAGAAAC

TGCCGAAATTCAAACCGCTGTATAAACAGGTTCTGAGCGATCGTGAAAGCCTGAGCTTTTATGGTGA

AGGTTATACCAGTGATGAAGAGGTTCTGGAAGTTTTTCGTAACACCCTGAATAAAAACAGCGAGATC

TTTAGCAGCATCAAAAAGCTTGAGAAACTGTTCAAAAACTTTGATGAGTATAGCAGCGCAGGCATCT

TTGTTAAAAATGGTCCGGCAATTAGCACCATCAGCAAAGATATTTTTGGCGAATGGAATGTGATCCG

CGATAAATGGAATGCCGAATATGATGATATCCACCTGAAAAAAAAGGCCGTGGTGACCGAGAAATAT

GAAGATGATCGTCGTAAAAGCTTCAAGAAAATTGGTAGCTTTAGCCTGGAACAGCTGCAAGAATATG

CAGATGCAGATCTGAGCGTTGTGGAAAAACTGAAAGAAATCATCATTCAGAAGGTGGACGAGATCTA

TAAAGTTTATGGTAGCAGCGAAAAACTGTTCGATGCAGATTTTGTTCTGGAAAAAAGCCTGAAAAAG

AATGATGCCGTTGTGGCCATTATGAAAGATCTGCTGGATAGCGTTAAGAGCTTCGAGAATTACATCA

AAGCCTTTTTTGGTGAGGGCAAAGAAACCAATCGTGATGAAAGTTTCTATGGCGATTTTGTGCTGGC

CTATGATATTCTGCTGAAAGTGGACCATATTTATGATGCCATTCGCAATTATGTTACCCAGAAACCG

TATAGCAAAGACAAGTTCAAACTGTACTTTCAGAACCCGCAGTTTATGGGTGGTTGGGATAAAGATA

AAGAAACCGATTATCGTGCCACCATCCTGCGTTATGGTAGTAAATACTATCTGGCCATCATGGACAA

AAAATACGCAAAATGCCTGCAGAAAATCGACAAAGATGATGTGAATGGCAACTATGAAAAAATCAAC

TACAAACTGCTGCCTGGTCCGAATAAAATGCTGCCGAAAGTGTTCTTTAGCAAGAAATGGATGGCCT

ATTATAACCCGAGCGAGGATATTCAAAAGATCTACAAAAATGGCACCTTTAAAAAGGGCGACATGTT

CAATCTGAACGATTGCCACAAACTGATCGATTTCTTCAAAGATTCAATTTCGCGTTATCCGAAATGG

TCCAATGCCTATGATTTTAACTTTAGCGAAACCGAAAAATACAAAGACATTGCCGGTTTTTATCGCG

AAGTGGAAGAACAGGGCTATAAAGTGAGCTTTGAAAGCGCAAGCAAAAAGAGGTTGATAAGCTGGT

TGAAGAGGGCAAACTGTATATGTTCCAGATTTACAACAAAGATTTTAGCGACAAAAGCCATGGCACC

CCGAATCTGCATACCATGTACTTTAAACTGCTGTTCGACGAAAATAACCATGGTCAGATTCGTCTGA

GCGGTGGTGCCGAACTGTTTATGCGTCGTGCAAGTCTGAAAAAAGAAGAACTGGTTGTTCATCCGGC

AAATAGCCCGATTGCAAACAAAAATCCGGACAATCCGAAAAAAACCACGACACTGAGCTATGATGTG

TATAAAGACAAACGTTTTAGCGAGGATCAGTATGAACTGCATATCCCGATTGCCATCAATAAATGCC

CGAAAAACATCTTTAAGATCAACACCGAAGTTCGCGTGCTGCTGAAACATGATGATAATCCGTATGT

GATTGGCATTGATCGTGGTGAACGTAACCTGCTGTATATTGTTGTTGATGGTAAAGGCAACATC

GTGGAACAGTATAGTCTGAACGAAATTATCAACAACTTTAACGGCATCCGCATCAAAACCGACTATC

ATAGCCTGCTGGACAAGAAAGAAAAAGAACGTTTTGAAGCACGTCAGAACTGGACCAGTATTGAAAA

CATCAAAGAACTGAAAGCCGGTTATATTAGCCAGGTGGTTCATAAAATCTGTGAGCTGGTAGAAAAA

TACGATGCAGTTATTGCACTGGAAGATCTGAATAGCGGTTTCAAAAATAGCCGTGTGAAAGTCGAAA

AACAGGTGTATCAGAAATTCGAGAAAATGCTGATCGACAAACTGAACTACATGGTCGACAAAAAAG

CAATCCGTGTGCAACCGGTGGTGCACTGAAAGGTTATCAGATTACCAACAAATTTGAAAGCTTTAAA

AGCATGAGCACCCAGAACGGCTTTATCTTCTATATTCCGGCATGGCTGACCAGCAAAATTGATCCGA

GCACCGGTTTTGTGAACCTGCTGAAAACAAAATATACCTCCATTGCCGACAGCAAGAAGTTTATTAG

CAGCTTTGATCGCATTATGTATGTTCCGGAAGAGGACCTGTTTGAATTCGCACTGGATTACAAAAAT
```

-continued

TTCAGCCGTACCGATGCCGACTACATCAAAAAATGGAAACTGTACAGCTATGGTAACCGCATTCGCA

TTTTTCGCAACCCCGAAGAAAAACAATGTGTTCGATTGGGAAGAAGTTTGTCTGACCAGCGCATATAA

AGAACTTTTCAACAAATACGGCATCAACTATCAGCAGGGTGATATTCGTGCACTGCTGTGTGAACAG

AGCGATAAAGCGTTTTATAGCAGTTTTATGGCACTGATGAGCCTGATGCTGCAGATGCGTAATAGCA

TTACCGGTCGCACCGATGTGGATTTTCTGATTAGTCCGGTGAAAAATTCCGATGGCATCTTTTATGA

TAGCCGCAATTACGAAGCACAAGAAAATGCAATTCTGCCGAAAAACGCAGATGCAAATGGTGCATAT

AACATTGCACGTAAAGTTCTGTGGGCAATTGGCCAGTTTAAGAAAGCAGAAGATGAGAAGCTGGACA

AAGTGAAAATTGCGATCAGCAATAAAGAGTGGCTGGAATACGCACAGACCAGCGTTAAACATGGTCG

TAGCAGTGATGATGAAGCAACCGCAGATAGCCAGCATGCAGCACCGCCGAAAAAAAAACGCAAAGTG

CTCGAGCACCACCACCACCACCACTGA

Hs optimized Lb Cpf1 with OpT NLS and 6x His - DNA

SEQ ID NO: 396

ATGGCTGAAGAACGTGGGCATCGACCGGCTGGACGTGGAAAAGGGCAGAAAGAACATGAGCAAGCTCG

AGAAGTTCACCAACTGCTACAGCCTGAGCAAGACCCTGCGGTTCAAGGCCATTCCTGTGGGCAAGAC

CCAAGAGAACATCGACAACAAGCGGCTGCTGGTGGAAGATGAGAAGAGAGCCGAGGACTACAAGGGC

GTGAAGAAGCTGCTGGACCGGTACTACCTGAGCTTCATCAACGACGTGCTGCACAGCATCAAGCTCA

AGAACCTGAACAACTACATCAGCCTGTTCCGGAAGAAAACCCGGACCGAGAAAGAGAACAAAGAGCT

GGAAAACCTCGAGATCAACCTGCGGAAAGAGATCGCCAAGGCCTTCAAGGGCAACGAGGGCTACAAG

AGCCTGTTCAAGAAGGACATCATCGAGACAATCCTGCCTGAGTTCCTGGACGACAAGGACGAGATCG

CCCTGGTCAACAGCTTCAACGGCTTCACCAACGCCTTCACCGGCTTTTTCGACAACCGCGAGAATAT

GTTCAGCGAGGAAGCCAAGAGCACCTCTATCGCCTTCCGGTGCATCAACGAGAATCTGACCCGGTAC

ATCAGCAACATGGATATCTTCGAGAAGGTGGACGCCATCTTCGACAAGCACGAGGTGCAAGAGATCA

AAGAAAAGATCCTGAACAGCGACTACGACGTCGAGGACTTCTTCGAGGGCGAGTTCTTCAACTTCGT

GCTGACACAAGAGGGCATCGATGTGTACAACGCCATCATCGGCGGCTTCGTGACAGAGAGCGGCGAG

AAGATCAAGGGCCTGAACGAGTACATCAACCTCTACAACCAGAAAACGAAGCAGAAGCTGCCCAAGT

TCAAGCCCCTGTACAAACAGGTGCTGAGCGACAGAGAGAGCCTGTCCTTTTACGGCGAGGGCTATAC

CAGCGACGAAGAGGTGCTGGAAGTGTTCAGAAACACCCTGAACAAGAACAGCGAGATCTTCAGCTCC

ATCAAGAAGCTCGAAAAGCTGTTTAAGAACTTCGACGAGTACAGCAGCGCCGGCATCTTCGTGAAGA

ATGGCCCTGCCATCAGCACCATCTCCAAGGACATCTTCGGCGAGTGGAACGTGATCCGGGACAAGTG

GAACGCCGAGTACGACGACATCCACCTGAAGAAAAAGGCCGTGGTCACCGAGAAGTACGAGGACGAC

AGAAGAAAGAGCTTCAAGAAGATCGGCAGCTTCAGCCTGGAACAGCTGCAAGAGTACGCCGACGCCG

ATCTGAGCGTGGTGGAAAAAGCTGAAAGAGATTATCATCCAGAAGGTCGACGAGATCTACAAGGTGTA

CGGCAGCAGCGAGAAGCTGTTCGACGCCGACTTTGTGCTGGAAAAGAGCCTCAAAAAGAACGACGCC

GTGGTGGCCATCATGAAGGACCTGCTGGATAGCGTGAAGTCCTTCGAGAACTATATTAAGGCCTTCT

TTGGCGAGGGCAAAGAGACAAACCGGGACGAGAGCTTCTACGGCGATTTCGTGCTGGCCTACGACAT

CCTGCTGAAAGTGGACCACATCTACGACGCCATCCGGAACTACGTGACCCAGAAGCCTTACAGCAAG

GACAAGTTTAAGCTGTACTTCCAGAATCCGCAGTTCATGGGCGGCTGGGACAAAGACAAAGAAACCG

ACTACCGGGCCACCATCCTGAGATACGGCTCCAAGTACTATCTGGCCATTATGGACAAGAAATACGC

CAAGTGCCTGCAGAAGATCGATAAGGACGACGTGAACGGCAACTACGAGAAGATTAACTACAAGCTG

CTGCCCGGACCTAACAAGATGCTGCCTAAGGTGTTCTTTAGCAAGAAATGGATGGCCTACTACAACC

CCAGCGAGGATATCCAGAAAATCTACAAGAACGGCACCTTCAAGAAAGGCGACATGTTCAACCTGAA

CGACTGCCACAAGCTGATCGATTTCTTCAAGGACAGCATCAGCAGATACCCCAAGTGGTCCAACGCC

-continued

```
TACGACTTCAATTTCAGCGAGACAGAGAAGTATAAGGATATCGCCGGGTTCTACCGCGAGGTGGAAG

AACAGGGCTATAAGGTGTCCTTTGAGAGCGCCAGCAAGAAAGAGGTGGACAAGCTGGTCGAAGAGGG

CAAGCTGTACATGTTCCAGATCTATAACAAGGACTTCTCCGACAAGAGCCACGGCACCCCTAACCTG

CACACCATGTACTTTAAGCTGCTGTTCGATGAGAACAACCACGGCCAGATCAGACTGTCTGGCGGAG

CCGAGCTGTTTATGAGAAGGGCCAGCCTGAAAAAAGAGGAACTGGTCGTTCACCCCGCCAACTCTCC

AATCGCCAACAAGAACCCCGACAATCCCAAGAAACCACCACACTGAGCTACGACGTGTACAAGGAT

AAGCGGTTCTCCGAGGACCAGTACGAGCTGCACATCCCTATCGCCATCAACAAGTGCCCCAAGAATA

TCTTCAAGATCAACACCGAAGTGCGGGTGCTGCTGAAGCACGACGACAACCCTTACGTGATCGGCAT

CGACAGAGGCGAGCGGAACCTGCTGTATATCGTGGTGGTGGACGGCAAGGGCAATATCGTGGAACAG

TACTCCCTGAATGAGATCATCAACAACTTCAATGGCATCCGGATCAAGACGGACTACCACAGCCTGC

TGGACAAAAAGAGAAAGAACGCTTCGAGGCCCGGCAGAACTGGACCAGCATCGAGAACATCAAAGA

ACTGAAGGCCGGCTACATCTCCCAGGTGGTGCACAAGATCTGCGAGCTGGTTGAGAAGTATGACGCC

GTGATTGCCCTGGAAGATCTGAATAGCGGCTTTAAGAACAGCCGCGTGAAGGTCGAGAAACAGGTGT

ACCAGAAATTCGAGAAGATGCTGATCGACAAGCTGAACTACATGGTCGACAAGAAGTCTAACCCCTG

CGCCACAGGCGGAGCCCTGAAGGGATATCAGATCACCAACAAGTTCGAGTCCTTCAAGAGCATGAGC

ACCCAGAATGGCTTCATCTTCTACATCCCCGCCTGGCTGACCAGCAAGATCGATCCTAGCACCGGAT

TCGTGAACCTGCTCAAGACCAAGTACACCAGCATTGCCGACAGCAAGAAGTTCATCTCCAGCTTCGA

CCGGATTATGTACGTGCCCGAAGAGGACCTGTTCGAATTCGCCCTGGATTACAAGAACTTCAGCCGG

ACCGATGCCGACTATATCAAGAAGTGGAAGCTGTATAGCTACGGCAACCGCATCCGCATCTTCAGAA

ACCCGAAGAAAAACAACGTGTTCGACTGGGAAGAAGTGTGCCTGACCAGCGCCTACAAAGAACTCTT

CAACAAATACGGCATCAACTACCAGCAGGGCGACATCAGAGCCCTGCTGTGCGAGCAGAGCGACAAG

GCCTTTTACAGCTCCTTCATGGCCCTGATGTCCCTGATGCTGCAGATGCGGAATAGCATCACCGGCA

GGACCGACGTGGACTTCCTGATCAGCCCTGTGAAGAATTCCGACGGGATCTTCTACGACAGCAGAAA

CTACGAGGCTCAAGAGAACGCCATCCTGCCTAAGAACGCCGATGCCAACGGCGCCTATAATATCGCC

AGAAAGGTGCTGTGGGCCATCGGCCAGTTTAAGAAGGCCGAGGACGAGAAACTGGACAAAGTGAAGA

TCGCCATCTCTAACAAAGAGTGGCTGGAATACGCCCAGACCAGCGTGAAGCACGGCAGATCTAGTGA

CGATGAGGCCACCGCCGATAGCCAGCATGCAGCCCCTCCAAAGAAAAAGCGGAAAGTGCTGGAACAC

CACCACCATCACCAC
```

Hs optimized Lb Cpf1 with OpT NLS and 6x His - AA

SEQ ID NO: 24

```
MLKNVGIDRLDVEKGRKNMSKLEKFTNCYSLSKTLRFKAIPVGKTQENIDNKRLLVEDEKRAEDYKG

VKKLLDRYYLSFINDVLHSIKLKNLNNYISLFRKKTRTEKENKELENLEINLRKEIAKAFKGNEGYK

SLFKKDIIETILPEFLDDKDEIALVNSFNGFTTAFTGFFDNRENMFSEEAKSTSIAFRCINENLTRY

ISNMDIFEKVDAIFDKHEVQEIKEKILNSDYDVEDFFEGEFFNFVLTQEGIDVYNAIIGGFVTESGE

KIKGLNEYINLYNQKTKQKLPKFKPLYKQVLSDRESLSFYGEGYTSDEEVLEVFRNTLNKNSEIFSS

IKKLEKLFKNFDEYSSAGIFVKNGPAISTISKDIFGEWNVIRDKWNAEYDDIHLKKKAVVTEKYEDD

RRKSFKKIGSFSLEQLQEYADADLSVVEKLKEIIIQKVDEIYKVYGSSEKLFDADFVLEKSLKKNDA

VVAIMKDLLDSVKSFENYIKAFFGEGKETNRDESFYGDFVLAYDILLKVDHIYDAIRNYVTQKPYSK

DKFKLYFQNPQFMGGWDKDKETDYRATILRYGSKYYLAIMDKKYAKCLQKIDKDDVNGNYEKINYKL

LPGPNKMLPKVFFSKKWMAYYNPSEDIQKIYKNGTFKKGDMFNLNDCHKLIDFFKDSISRYPKWSNA

YDFNFSETEKYKDIAGFYREVEEQGYKVSFESASKKEVDKLVEEGKLYMFQTYNKDFSDKSHGTPNL
```

-continued

```
HTMYFKLLFDENNHGQIRLSGGAELFMRRASLKKEELVVHPANSPIANKNPDNPKKTTTLSYDVYKD

KRFSEDQYELHIPIAINKCPKNIFKINTEVRVLLKHDDNPYVIGIDRGERNLLYIVVVDGKGNIVEQ

YSLNEIINNFNGIRIKTDYHSLLDKKEKERFEARQNWTSIENIKELKAGYISQVVHKICELVEKYDA

VIALEDLNSGFKNSRVKVEKQVYQKFEKMLIDKLNYMVDKKSNPCATGGALKGYQITNKFESFKSMS

TQNGFIFYIPAWLTSKIDPSTGFVNLLKTKYTSIADSKKFISSFDRIMYVPEEDLFEFALDYKNFSR

TDADYIKKWKLYSYGNRIRIFRNPKKNNVFDWEEVCLTSAYKELFNKYGINYQQGDIRALLCEQSDK

AFYSSFMALMSLMLQMRNSITGRTDVDFLISPVKNSDGIFYDSRNYEAQENAILPKNADANGAYNIA

RKVLWAIGQFKKAEDEKLDKVKIAISNKEWLEYAQTSVKHGRSSDDEATADSQHAAPPKKKRKVLEH

HHHHH
```

Example 10

Use of Modified crRNAs with LbCpf1 Protein Delivered as an RNP Complex.

Twelve sites in the human HPRT1 gene, 38094-S(SEQ ID No. 358), 38104-S (SEQ ID No. 361), 38115-AS (SEQ ID No. 364), 38146-AS (SEQ ID No. 367), 38164-AS (SEQ ID No. 370), 38164-5 (SEQ ID No. 372), 38186-5 (SEQ ID No. 376), 38228-5 (SEQ ID No. 379), 38330-AS (SEQ ID No. 382), 38343-5 (SEQ ID No. 385), 38455-5 (SEQ ID No. 388) and 38486-S(SEQ ID No. 391) (where A and AS represent the sense and antisense strand, respectively), were chosen to study the target editing activity of LbCpf1, as compared to that of AsCpf1 and SpyCas9. Studies were done comparing the ability to use chemically modified crRNAs with LbCpf1 protein to perform genome editing in HEK-293 cells using electroporation to deliver the ribonucleoprotein protein (RNP) complexes into cells.

Purified recombinant LbCpf1 protein was employed in this example, isolated from *E. coli* using standard techniques. The amino-acid sequence of the recombinant protein is shown in SEQ ID NO:14.

Figure 9:
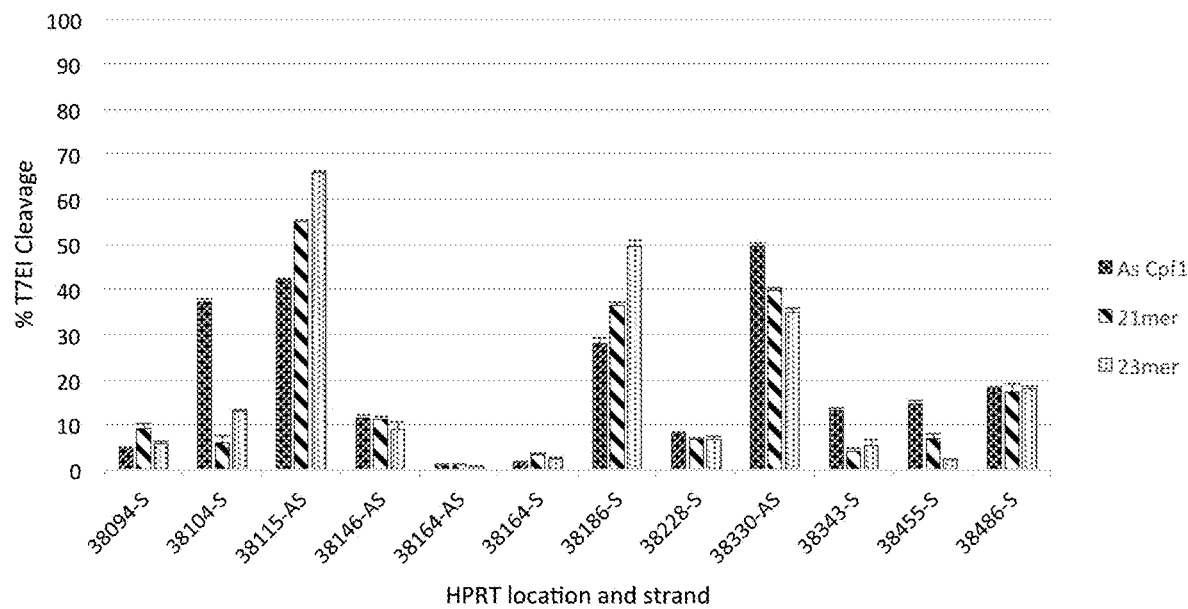
FIG. 9 depicts exemplary results that compare the target editing activity of LbCpf1 with that of AsCpf1 and SpyCas9 for 12 regions of the HPRT gene with low GC content via T7EI mismatch endonuclease assay. In this study, all enzymes and crRNA were delivered as RNP complexes (5 into HEK293 cells by nucleofection using the Amaxa system from Lonza, and DNA was extracted after 48 hr. Percent editing was determined by T7E1 mismatch endonuclease assay. Error bars represent standard errors of the means. Of note, the crRNA's for LbCpf1 were tested at the native 23mer nucleotide length as well as the previously optimized AsCpf1 length of 21 bases.

The LbCpf1 crRNAs, and AsCpf1 control crRNAs, were heated to 95° C. for 5 minutes then allowed to cool to room temperature. The crRNAs were mixed with LbCpf1, or AsCpf1, at a molar ratio of 1:1 RNA:protein in PBS (5 µM RNP complex in 10 µL volume, for a single transfection). The RNP complex was allowed to form at room temperature for 15 minutes. HEK293 cells were resuspended following trypsinization and washed in medium and washed a second time in PBS before use. Cells were resuspended in at a final concentration of $3.5 \times 10^5$ cells in 20 µL of Nucleofection solution. 20 µL of cell suspension was placed in the V-bottom 96-well plate and 5 µL of the Cpf1 RNP complex was added to each well (5 µM final concentration) and 3 µM of Cpf1 Electroporation Enhancer Solution was added to each well (Integrated DNA Technologies). 25 µL of the final mixture was transferred to each well of a 96 well Nucleocuvette electroporation module. Cells were electroporated using Amaxa 96 well shuttle protocol, program 96-DS-150. Following electroporation, 75 µL of medium was added to each well and 25 µL of the final cell mixture was transferred to 175 µL of pre-warmed medium in 96 well incubation plates (final volume 200 Cells were incubated at 37° C. for 48 hours. Genomic DNA was isolated using QuickExtract solution (Epicentre). Genomic DNA was amplified with KAPA HiFi DNA Polymerase (Roche) and primers targeting the HPRT region of interest (HPRT-low forward primer: AAGAATGTTGTGATAAAAGGTGATGCT (SEQ ID No. 394); HPRT-low reverse primer: ACACATC-CATGGGACTTCTGCCTC (SEQ ID No. 395)). PCR products were melted and re-annealed in NEB buffer 2 (New England Biolabs) to allow for heteroduplex formation followed by digestion with 2 units of T7 endonuclease 1 (T7EI; New England Biolabs) for 1 hour at 37° C. The digested products were visualized on a Fragment Analyzer (Advanced Analytical Technologies). Percent cleavage of targeted DNA was calculated as the average molar concentration of the cut products/(average molar concentration of the cut products+molar concentration of the uncut band)×100. The sequences are shown in Table 10, and the results are graphically represented in FIG. 9.

TABLE 10

Sequences of modified AsCpf1 and LbCpf1 crRNAs tested

| Seq Name | Sequence 5'-3' | SEQ ID NO: |
| --- | --- | --- |
| 38094-S-Control | C3-uaauuucuacucuuguagauauagucuuuccuuggguguguu-C3 | 358 |
| 38094-S-21 | C3-uaauuucuacuaaguguagauauagucuuuccuuggguguguu-C3 | 359 |
| 38094-S-23 | C3-uaauuucuacuaaguguagauauagucuuuccuuggguguguua-C3 | 360 |
| 38104-S-Cpf1 | C3-uaauuucuacucuuguagaucuugggguguguuaaaagugac-C3 | 361 |
| 38104-S-4197 | C3-uaauuucuacuaaguguagaucuugggguguguuaaaagugac-C3 | 362 |

TABLE 10-continued

Sequences of modified AsCpf1 and LbCpf1 crRNAs tested

| Seq Name | Sequence 5'-3' | SEQ ID NO: |
|---|---|---|
| 38104-S-23 | C3-uaauuucuacuaaguguagaucuuggguguguuaaaagugacca-C3 | 363 |
| 38115-AS-Cpf1 | C3-uaauuucuacucuuguagauacacacccaaggaaagacuau-C3 | 364 |
| 38115-AS-21 | C3-uaauuucuacuaaguguagauacacacccaaggaaagacuau-C3 | 365 |
| 38115-AS-23 | C3-uaauuucuacuaaguguagauacacacccaaggaaagacuauga-C3 | 366 |
| 38146-AS-Cpf1 | C3-uaauuucuacucuuguagauauccgugcugaguguaccaug-C3 | 367 |
| 38146-AS-21 | C3-uaauuucuacuaaguguagauauccgugcugaguguaccaug-C3 | 368 |
| 38146-AS-23 | C3-uaauuucuacuaaguguagauauccgugcugaguguaccaugca-C3 | 369 |
| 38164-AS-Cpf1 | C3-uaauuucuacucuuguagauuaaacacuguuucauuucauc-C3 | 370 |
| 38164-AS-21 | C3-uaauuucuacuaaguguagauuaaacacuguuucauuucauc-C3 | 371 |
| 38164-AS-23 | C3-uaauuucuacuaaguguagauuaaacacuguuucauuucauccg-C3 | 372 |
| 38164-S-Cpf1 | C3-uaauuucuacucuuguagaugaaacgucagucuucucuuuu-C3 | 373 |
| 38164-S-21 | C3-uaauuucuacuaaguguagaugaaacgucagucuucucuuuu-C3 | 374 |
| 38164-S-23 | C3-uaauuucuacuaaguguagaugaaacgucagucuucucuuuugu-C3 | 375 |
| 38186-S-Cpf1 | C3-uaauuucuacucuuguagauuaaugcccuguagucucucug-C3 | 376 |
| 38186-S-21 | C3-uaauuucuacuaaguguagauuaaugcccuguagucucucug-C3 | 377 |
| 38186-S-23 | C3-uaauuucuacuaaguguagauuaaugcccuguagucucucugua-C3 | 378 |
| 38228-S-Cpf1 | C3-uaauuucuacucuuguagauuaauuaacagcuugcuggugu-C3 | 379 |
| 38228-S-21 | C3-uaauuucuacuaaguguagauuaauuaacagcuugcuggugu-C3 | 380 |
| 38228-S-23 | C3-uaauuucuacuaaguguagauuaauuaacagcuugcuggugaaa-C3 | 381 |
| 38330-AS-Cpf1 | C3-uaauuucuacucuuguagaugguuaaagaugguuaaaugau-C3 | 382 |
| 38330-AS-21 | C3-uaauuucuacuaaguguagaugguuaaagaugguuaaaugau-C3 | 383 |
| 38330-AS-23 | C3-uaauuucuacuaaguguagaugguuaaagaugguuaaaugauug-C3 | 384 |
| 38343-S-Cpf1 | C3-uaauuucuacucuuguagauugugaaauggcuuauaauugc-C3 | 385 |
| 38343-S-21 | C3-uaauuucuacuaaguguagauugugaaauggcuuauaauugc-C3 | 386 |
| 38343-S-23 | C3-uaauuucuacuaaguguagauugugaaauggcuuauaauugcuu-C3 | 387 |
| 38455-S-Cpf1 | C3-uaauuucuacucuuguagauguuguuggauuugaaauucca-C3 | 388 |
| 38455-S-21 | C3-uaauuucuacuaaguguagauguuguuggauuugaaauucca-C3 | 389 |
| 38455-S-23 | C3-uaauuucuacuaaguguagauguuguuggauuugaaauuccaga-C3 | 390 |

TABLE 10-continued

Sequences of modified AsCpf1 and LbCpf1 crRNAs tested

| Seq Name | Sequence 5'-3' | SEQ ID NO: |
|---|---|---|
| 38486-S-Cpf1 | C3-uaauuucuacucuuguagauuuguaggauaugcccuugacu-C3 | 391 |
| 38486-S-21 | C3-uaauuucuacuaaguguagauuuguaggauaugcccuugacu-C3 | 392 |
| 38486-S-23 | C3-uaauuucuacuaaguguagauuuguaggauaugcccuugacuau-C3 | 393 |

RNA bases are shown 5'-3' orientation, RNA bases are shown in lower case.
Locations are specified within the human HPRT1 gene with orientation relative to the sense coding strand indicated (S = sense, AS = antisense).
C3 = C3 spacer (propanediol modifier).
Cpf1 = Cpf1 crRNA control.
21 and 23 represent the length of the 3/ protospacer for each crRNA.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated polypeptide encoding a wild-type AsCpf1 protein, wherein the isolated polypeptide comprises SEQ ID NO: 12.

2. An isolated CRISPR/Cpf1 endonuclease system, comprising:
   an AsCpf1 polypeptide, and
   an AsCpf1 crRNA,
   wherein the AsCpf1 polypeptide comprises SEQ ID NO:12.

3. The isolated CRISPR/Cpf1 endonuclease system of claim 2, wherein the AsCpf1 crRNA is selected from a length-truncated AsCpf1 crRNA or a chemically-modified AsCpf1 crRNA, or an AsCpf1 crRNA comprising both length truncations and chemical modifications.

4. An isolated CRISPR/Cpf1 endonuclease system, comprising: a human cell line expressing an AsCpf1 polypeptide and an AsCpf1 crRNA,
   wherein the AsCpf1 polypeptide comprises SEQ ID NO:12.

5. The isolated CRISPR/Cpf1 endonuclease system of claim 4, wherein the AsCpf1 crRNA is selected from a length-truncated AsCpf1 crRNA or a chemically-modified AsCpf1 crRNA, or an AsCpf1 crRNA comprising both length truncations and chemical modifications.

6. The isolated CRISPR/Cpf1 endonuclease system of claim 4, wherein the AsCpf1 crRNA is a length-truncated AsCpf1 crRNA comprising a 5'-universal loop domain of 19 to 20 nucleotides in length and a 3'-target specific protospacer domain of 19 to 21 nucleotides in length.

7. The isolated CRISPR/Cpf1 endonuclease system of claim 2, wherein the AsCpf1 crRNA is a length-truncated AsCpf1 crRNA comprising a 5'-universal loop domain of 19 to 20 nucleotides in length and a 3'-target specific protospacer domain of 19 to 21 nucleotides in length.

8. The CRISPR/Cpf1 endonuclease system of claim 2, wherein the AsCpf1 crRNA comprises both a length truncation and a chemical modification.

9. The CRISPR/Cpf1 endonuclease system of claim 8, wherein the chemical modification of the AsCpf1 crRNA is selected from the group consisting of an end-group modification, 2'OMe modification, 2'-fluoro modification and LNA modification.

10. A method of performing gene editing, comprising: contacting a candidate editing target site locus with an active CRISPR/Cpf1 endonuclease system having a wild-type AsCpf1 polypeptide and an AsCpf1 crRNA, wherein the wild-type AsCpf1 polypeptide is SEQ ID NO: 12.

11. The method of claim 10, wherein the AsCpf1 crRNA is selected from a length-truncated AsCpf1 crRNA, a chemically-modified AsCpf1 crRNA, or an AsCpf1 crRNA comprising both length truncations and chemical modifications.

* * * * *